United States Patent
Ahmed et al.

(10) Patent No.: US 10,287,286 B2
(45) Date of Patent: May 14, 2019

(54) COMPOUNDS

(71) Applicant: Takeda Pharmaceutical Company Limited, Osaka (JP)

(72) Inventors: Saleh Ahmed, Cambridge (GB); Gregory Barker, Cambridge (GB); Hannah Canning, Cambridge (GB); Richard Davenport, Cambridge (GB); David Harrison, Cambridge (GB); Kerry Jenkins, Cambridge (GB); David Livermore, Cambridge (GB); Susanne Wright, Cambridge (GB); Natasha Kinsella, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/558,824

(22) PCT Filed: Mar. 17, 2016

(86) PCT No.: PCT/JP2016/059782
§ 371 (c)(1),
(2) Date: Sep. 15, 2017

(87) PCT Pub. No.: WO2016/148306
PCT Pub. Date: Sep. 22, 2016

(65) Prior Publication Data
US 2018/0072714 A1    Mar. 15, 2018

(30) Foreign Application Priority Data
Mar. 18, 2015 (GB) .................. 1504565.1

(51) Int. Cl.
*C07D 471/04* (2006.01)
*C07D 487/04* (2006.01)
*C07D 519/00* (2006.01)

(52) U.S. Cl.
CPC ......... *C07D 471/04* (2013.01); *C07D 487/04* (2013.01); *C07D 519/00* (2013.01)

(58) Field of Classification Search
CPC ... C07D 471/04; C07D 487/04; C07D 519/00
See application file for complete search history.

(56) References Cited

U.S. PATENT DOCUMENTS

| 4,209,621 A | 6/1980 | Dusza et al. |
| 2011/0077267 A1* | 3/2011 | Mitani ................. C07D 471/04 514/303 |
| 2015/0239889 A1 | 8/2015 | Nakajima et al. |

FOREIGN PATENT DOCUMENTS

| EP | 0121341 A1 | 10/1984 |
| WO | WO 2002/002563 | 1/2002 |
| WO | WO 2010/018853 | 2/2010 |
| WO | WO 2010/018868 | 2/2010 |
| WO | WO/2011/090127 A1 | 6/2011 |
| WO | WO/2014/030716 A1 | 2/2014 |

OTHER PUBLICATIONS

Aurora Screening Library, published Jan. 1, 2015, Order No. Cat. K08.258.458, CAS Registry No. 1223747-97-4.

* cited by examiner

*Primary Examiner* — Erich A Leeser
(74) *Attorney, Agent, or Firm* — Matthew J. Russo

(57) ABSTRACT

The present invention provides compounds of formula (I) and pharmaceutically acceptable salts thereof,

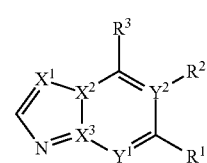

(I)

wherein $X^1$, $X^2$, $X^3$, $Y^1$, $Y^2$, $R^1$, $R^2$ and $R^3$ are as defined in the specification, processes for their preparation, pharmaceutical compositions containing them and their use in therapy.

13 Claims, No Drawings

COMPOUNDS

CROSS-REFERENCE TO RELATED APPLICATIONS

This application is the U.S. National Stage entry under 35 U.S.C. § 371(c) of International Application PCT/JP2016/059782, filed Mar. 17, 2016, which claims the benefit of United Kingdom application GB 1504565.1, filed Mar. 18, 2015.

TECHNICAL FIELD

The present invention relates to pyridyl and pyrimidinyl derivatives, processes for their preparation, pharmaceutical compositions containing them and their use in therapy. In particular, the invention relates to compounds and compositions that are capable of decreasing HIF prolyl hydroxylase (HPH) enzyme activity, also referred to as prolyl hydroxylase domain (PHD) protein, thereby increasing the stability and/or activity and/or to levels of hypoxia inducible factor (HIF) and/or altering other hypoxia-induced reactions independent of HIF.

BACKGROUND OF THE INVENTION

HIF mediates changes in gene expression in response to changes in cellular oxygen concentration. HIF is a heterodimer having an oxygen-regulated subunit (HIF-α) and a constitutively expressed subunit (HIF-β). In cells with adequate oxygen, HIF-α is hydroxylated at conserved proline residues by prolyl-hydroxylase (PHD) resulting in its rapid degradation. In cells with inadequate oxygen (hypoxia), there is a rapid accumulation of HIF-α which triggers an increase in glycolysis to compensate for energy loss due to reduced oxidative phosphorylation and upregulation of erythropoiesis and angiogenesis to achieve more efficient oxygen utilization. Other HIF-independent signalling pathways also respond to hypoxia and contribute to oxygen availability increase. PHD exists in three isoforms referred to as PHD1, PHD2 and PHD3 which function as oxygen sensors and in the regulation of cell metabolism in response to oxygen content in cells. Due to the central role of PHD in oxygen sensing, PHD inhibitors would be expected to be useful in treating cardiovascular disorders such as ischemic events, hematological disorders such as anemia, pulmonary disorders, brain disorders, and kidney disorders.

Studies using genetically engineered knockout mice or siRNA have identified that the three PHD isoforms differ in the way that they regulate HIF. It would appear that PHD inhibitors with an activity profile showing selectivity towards PHD1 may be most advantageous as unwanted side effects can arise from significant inhibition of PHD2.

Patent Document 1 describes certain triazolopyrimidine derivative compounds that are said to be useful as pest control agents.

Patent Document 2 describes certain pyridyl triazolopyrimidine derivative compounds that are said to be useful as harmful organism control agents.

Patent Document 3 describes triazolopyrimidine compounds that are said to be useful for treating of inhibiting the growth of cancerous tumour cells and associated diseases.

Patent Document 4 describes certain triazolopyrimidine compounds that are said to be useful as anxiolytic agents.

Non-Patent Documents 1 and 2 describe triazolopyrimidine compounds.

DOCUMENT LIST

Patent Documents

Patent Document 1: WO2010/018868
Patent Document 2: WO2010/018853
Patent Document 3: WO02/02563
Patent Document 4: U.S. Pat. No. 4,209,621

Non-Patent Documents

Non-Patent Document 1: Aurora Screening Library January 2015 Cat. K08.258.458
Non-Patent Document 2: Ambinter Stock Screening Collection September 2014 Cat. Amb 11195313 (Cas Reg. No. 1223747-97-4)

SUMMARY OF THE INVENTION

Problems to be Solved by the Invention

There is a need for treatment of the above conditions and others described herein with compounds that are PHD inhibitors. The present invention provides inhibitors of PHD.

Means of Solving the Problems

In accordance with the present invention, there is provided a compound of formula (I)

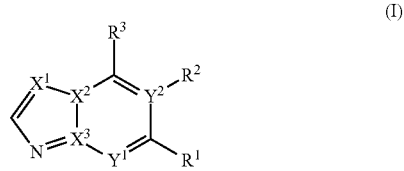

(I)

wherein
$X^1$, $X^2$, $X^3$ and $Y^1$ each independently represent C, CH or N, provided that (i) at least one of $X^1$, $X^2$, $X^3$ and $Y^1$ represents N, and (ii) if $Y^1$ represents N, then $X^3$ represents C;
$R^1$ represents hydrogen, halogen, $C_1$-$C_6$ alkyl, $C_3$-$C_6$ cycloalkyl,
$C_1$-$C_6$ alkoxy$C_1$-$C_6$ alkyl,
$C_1$-$C_6$ hydroxyalkyl, —$OR^4$, —$SR^4$, —$C(O)R^4$, —$C(O)OR^4$, —$(CH_2)_m NHC(O)R^4$, —$(CH_2)_m NH$ $C(O)OR^4$, —$NHC(O)NHR^4$, —$NHSO_2 R^4$, —$C(O)NR^5 R^6$, —$(CH_2)_m NR^5 R^6$, —$SO_2 NR^5 R^6$ or a 4- to 9-membered heterocyclyl (unsubstituted, or substituted by at least one substituent to independently selected from oxo, $C_1$-$C_6$ alkyl, $C_1$-$C_6$ alkylcarbonyl, $C_1$-$C_6$ alkoxy, $C_3$-$C_6$ cycloalkyl, $C_1$-$C_6$ alkoxycarbonyl, —$(CH_2)_p NR^7 R^8$ and $C(O)NR^7 R^8$);
m is 0 or 1;
p is 0 or 1;
$R^4$ represents hydrogen, $C_1$-$C_6$ alkyl (unsubstituted, or substituted by at least one substituent independently selected from halogen, hydroxyl, $C_1$-$C_6$ haloalkyl, $C_1$-$C_6$ alkoxy, $C_3$-$C_6$ cycloalkyl, $C_6$-$C_{10}$ aryl, $NR^9 R^{10}$, oxetanyl, oxolanyl and oxanyl), $C_3$-$C_6$ cycloalkyl (unsubstituted, or substituted by at least one substituent independently selected from halogen, cyano and $C_1$-$C_6$ alkyl), $C_6$-$C_{10}$ aryl, or a 4- to 7-membered heterocyclyl (unsubstituted, or substituted by at least one $C_1$-$C_6$ alkyl);

$R^5$ and $R^6$ each independently represent hydrogen, $C_1$-$C_6$ alkyl (unsubstituted, or substituted by at least one substituent independently selected from halogen, hydroxyl, $C_1$-$C_6$ alkoxy, $C_3$-$C_6$ cycloalkyl, $NR^{11}R^{12}$, $C_6$-$C_{10}$ aryl, 5- to 10-membered heteroaryl and 4- to 7-membered heterocyclyl, each of the aryl, heteroaryl and heterocyclyl substituents being optionally substituted with at least one substituent independently selected from halogen, oxo, $C_1$-$C_6$ alkyl, $C_1$-$C_6$ alkoxy, $C_1$-$C_6$ alkoxycarbonyl, and phenyl), $C_1$-$C_6$ alkylcarbonyl, $C_3$-$C_6$ cycloalkyl, $C_6$-$C_{10}$ aryl, 5- to 10-membered heteroaryl, 4- to 7-membered heterocyclyl, each of the aryl, heteroaryl and heterocyclyl groups being optionally substituted with at least one substituent independently selected from halogen, $C_1$-$C_6$ alkyl, $C_1$-$C_6$ alkoxy, and $C_1$-$C_6$ alkylcarbonyl, or $R^5$ and $R^6$ may together with the nitrogen atom to which they are attached form a 4- to 7-membered saturated heterocyclic ring unsubstituted, or substituted by at least one substituent independently selected from halogen, hydroxyl, oxo and $C_1$-$C_6$ alkoxy;

$R^7$ and $R^8$ each independently represent a hydrogen atom or a $C_1$-$C_6$ alkyl or $C_3$-$C_6$ cycloalkyl group, or R and R may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;

$R^9$ and $R^{10}$ each independently represent a hydrogen atom or a $C_1$-$C_6$ alkyl or $C_3$-$C_6$ cycloalkyl group, or $R^9$ and $R^{10}$ may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;

$R^{11}$ and $R^{12}$ each independently represent a hydrogen atom or a $C_1$-$C_6$ alkyl or $C_3$-$C_6$ cycloalkyl group;

$Y^2$ represents C or N;

when $Y^2$ represents C, $R^2$ represents a hydrogen or halogen atom, or a $C_1$-$C_3$ alkyl or amino ($NH_2$) group; when $Y^2$ represents N, $R^2$ is absent;

$R^3$ represents a group of formula (II) to (VIII)

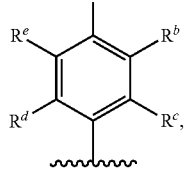

(II)

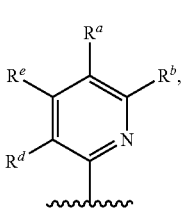

(III)

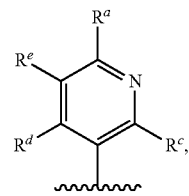

(IV)

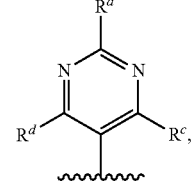

(V)

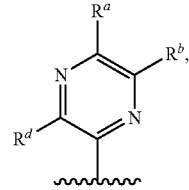

(VI)

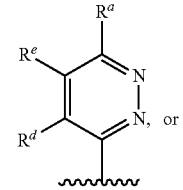

(VII)

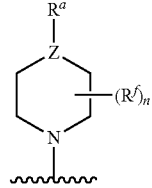

(VIII)

wherein in formulae (II) to (VIII), n is 0 or an integer from 1 to 4, Z represents CH or N, $R^a$ represents halogen, cyano, $C_1$-$C_6$ alkyl, $C_2$-$C_6$ alkenyl, $C_2$-$C_6$ alkynyl or $C_3$-$C_6$ cycloalkyl, each of $R^b$, $R^c$, $R^d$ and $R^e$ independently represents hydrogen, halogen, $C_1$-$C_6$ alkyl, $C_1$-$C_6$ alkoxy, $C_1$-$C_6$ haloalkyl, $C_3$-$C_6$ cycloalkyl or $NR^{13}R^{14}$, and each $R^f$ independently represents halogen, $C_1$-$C_6$ alkyl, $C_1$-$C_6$ alkoxy, $C_1$-$C_6$ haloalkyl, $C_3$-$C_6$ cycloalkyl or $NR^{13}R^{14}$; and $R^{13}$ and $R^{14}$ each independently represent a hydrogen atom or a $C_1$-$C_6$ alkyl or $C_3$-$C_6$ cycloalkyl group, or $R^{13}$ and $R^{14}$ may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;

provided that when $X^1$, $X^2$ and $Y^1$ represent N, $X^3$ represents C, $Y^2$ represents C, $R^1$ and $R^2$ both represent hydrogen, $R^3$ represents a group of formula (II) and $R^a$ represents fluoro or chloro, then at least one of $R^b$, $R^c$, $R^d$ and $R^e$ is other than a hydrogen atom;

or a pharmaceutically acceptable salt thereof.

In the context of the present specification, unless otherwise stated, an "alkyl", "alkenyl" or "alkynyl" substituent group or an "alkyl", "alkenyl" or "alkynyl" moiety in a substituent group may be linear or branched.

Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, tert-butyl, n-pentyl, and n-hexyl.

An "alkenyl" substituent group or an alkenyl moiety in a substituent group refers to an unsaturated alkyl group or moiety having one or more carbon-carbon double bonds. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl.

An "alkynyl" substituent group or an alkynyl moiety in a substituent group refers to an unsaturated alkyl group or moiety having one or more carbon-carbon triple bonds. Examples of $C_2$-$C_6$ alkynyl groups/moieties include ethynyl, 2-propynyl, 1-butynyl, 2-butynyl, 1-pentynyl and 1-hexynyl.

A "cycloalkyl" substituent group or a "cycloalkyl" moiety in a substituent group refers to a saturated hydrocarbyl ring containing, for example, from 3 to 8 carbon atoms, examples of which include cyclopropyl, cyclobutyl, cyclopentyl and cyclohexyl.

A "haloalkyl" substituent group or a "haloalkyl" moiety in a substituent group refers to an alkyl group or moiety in which one or more, e.g. one, two, three, four or five, hydrogen atoms are replaced independently by halogen atoms, i.e. by fluorine, chlorine, bromine or iodine atoms. Examples of haloalkyl groups/moieties include fluoromethyl, difluoromethyl, trifluoromethyl and 2,2,2-trifluoroethyl.

A "hydroxyalkyl" substituent group or a "hydroxyalkyl" moiety in a substituent group refers to an alkyl group or moiety in which one or more, e.g. one, two or three hydrogen atoms are replaced by hydroxyl groups, examples of which include —$CH_2OH$, —$CH_2CH_2OH$, —$CH_2CH_2CH_2OH$, —$CH(OH)CH_2OH$, —$CH_2CH(OH)CH_2OH$, —$CH(CH_3)OH$ and —$CH(CH_2OH)_2$.

The term "oxo" refers to an oxygen atom doubly bonded to the carbon atom to which it is attached to form the carbonyl of a ketone or aldehyde.

The term "halogen" includes fluorine, chlorine, bromine and iodine.

A "heterocyclyl" substituent group or a "heterocyclyl" moiety in a substituent group refers to a 4- to 9-membered ring system which may be monocyclic or bicyclic (in which the two rings are fused, bridged or spiro), wherein the ring system is saturated and contains from 1 to 4 ring heteroatoms independently selected from, nitrogen, oxygen and sulphur. It should be understood that a heterocyclyl group/moiety can be attached to the rest of the molecule through any suitable ring carbon or ring nitrogen atom. Examples of heterocyclyl groups include azetidinyl, pyrrolidinyl, piperidinyl, piperazinyl, morpholinyl, thiomorpholinyl, oxazolidinyl, oxetanyl, oxolanyl (tetrahydrofuranyl), oxanyl (tetrahydropyranyl), pyrazolidinyl, oxazolidinyl, imidazolidinyl, thiazolidinyl, dioxolanyl, 1,4-dioxanyl, 1,4-diazepanyl, azepanyl, azabicyclo[3.2.1]octyl, azabicyclo[2.2.1]heptanyl, azaspiro[3.5]nonanyl, 2,6-diazaspiro[3.3]heptanyl, 2-oxa-6-azaspiro[3.3]heptanyl and oxaspiro[4.4]nonanyl.

An "aryl" substituent group or an "aryl" moiety in a substituent group refers to a monocyclic or bicyclic aromatic hydrocarbon ring, examples of which include phenyl and naphthyl.

A "heteroaryl" substituent group or a "heteroaryl" moiety in a substituent group refers to an aryl group in which from 1 to 4 ring carbon atoms are replaced by heteroatoms independently selected from nitrogen, oxygen and sulphur. The heteroaryl group/moiety can be attached to the rest of the molecule through any suitable ring carbon or ring nitrogen atom. Examples of heteroaryl groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl, tetrazinyl, quinoxalinyl, benzothiazolyl, benzoxazolyl, quinolinyl, quinazolinyl, indolyl, 7-azaindolyl, indolizinyl, indazolyl, imidazo[1,2-a]pyridinyl, 1,3-thiazolo[5,4-b]pyridinyl, 1,3-thiazolo[5,4-c]pyridinyl and 7H-pyrrolo[2,3-d]pyrimidinyl.

For the avoidance of doubt, with respect to the heterocyclyl, aryl and heteroaryl groups, it should be understood that the invention does not encompass any unstable ring structures or any O—O, O—S or S—S bonds and that if the heterocyclyl, aryl or heteroaryl group is substituted, the substituent may be attached to any suitable ring atom.

When any of $R^5$ and $R^6$, or $R^7$ and $R^8$, or $R^9$ and $R^{10}$, or $R^{13}$ and $R^{14}$, together with the nitrogen atom to which they are attached form a 4- to 7-membered saturated heterocyclic ring, the heterocyclic ring may contain one or more (e.g. one or two) further ring heteroatoms (e.g. nitrogen, oxygen or sulphur atoms) in addition to the nitrogen atom to which $R^5$ and $R^6$ or $R^7$ and $R^8$, or $R^9$ and $R^{10}$, or $R^{13}$ and $R^{14}$, are attached. However, it will be appreciated that the invention does not encompass any unstable ring structures or any O—O, O—S or S—S bonds. If a substituent is present on the ring, it may be attached to any suitable ring atom. Examples of such heterocyclic rings include azetidinyl, pyrrolidinyl, piperidinyl, morpholinyl, thiomorpholinyl, piperazinyl, azepanyl and 1,4-oxaazepanyl.

For the purposes of the present invention, where a combination of moieties is referred to as one group, for example, alkoxyalkyl, alkylcarbonyl or, alkoxycarbonyl, the last mentioned moiety contains the atom by which the group is attached to the rest of the molecule. An example of an alkoxyalkyl group is 3-methoxypropyl (—$CH_2CH_2CH_2OCH_3$).

When any chemical group or moiety in formula (I) is described as being optionally substituted, it will be appreciated that the group or moiety may be either unsubstituted or substituted by one or more of the specified substituents. It will be appreciated that the number and nature of substituents will be selected so as to avoid sterically undesirable combinations.

$X^1$, $X^2$, $X^3$ and $Y^1$ each independently represent C, CH or N, provided that (i) at least one of $X^1$, $X^2$, $X^3$ and $Y^1$ represents N, and (ii) if $Y^1$ represents N, then $X^3$ represents C.

In an embodiment of the invention, at least two of $X^1$, $X^2$, $X^3$ and $Y^1$ represent N. For example, $X^1$ and $X^2$ both represent N, $X^3$ represents C and $Y^1$ represents CH.

In another embodiment, at least three of $X^1$, $X^2$, $X^3$ and $Y^1$ represent N. For example, each of $X^1$, $X^2$ and $Y^1$ represents N and $X^3$ represents C.

$R^1$ represents one of the following groups:
(i) hydrogen,
(ii) halogen (e.g. fluorine, chlorine, bromine or iodine),
(iii) $C_1$-$C_6$, or $C_1$-$C_4$, or $C_1$-$C_2$ alkyl, (iv) $C_3$-$C_6$ or $C_3$-$C_5$ cycloalkyl,
(v) $C_1$-$C_6$ alkoxy$C_1$-$C_6$ alkyl (e.g. $C_1$-$C_3$ alkoxy$C_1$-$C_6$ alkyl or $C_1$-$C_3$ alkoxy$C_1$-$C_4$ alkyl),
(vi) $C_1$-$C_6$, or $C_1$-$C_4$, or $C_1$-$C_2$ hydroxyalkyl,
(vii) —OR$^4$,
(viii) —SR$^4$,
(ix) —C(O)R$^4$,
(x) —C(O)OR$^4$,
(xi) —(CH$_2$)$_m$NHC(O)R$^4$,
(xii) —(CH$_2$)$_m$NHC(O)OR$^4$,
(xiii) —NHC(O)NHR$^4$,
(xiv) —NHSO$_2$R$^4$,
(xv) —C(O)NR$^5$R$^6$,
(xvi) —(CH$_2$)$_m$NR$^5$R$^6$,
(xvii) —SO$_2$NR$^5$R$^6$, or
(xviii) a 4- to 5-, 6-, 7-, 8- or 9-membered heterocyclyl which is either unsubstituted or is substituted by at least one substituent (e.g. one, two, three or four substituents) independently selected from oxo, $C_1$-$C_6$, or $C_1$-$C_4$, or $C_1$-$C_2$ alkyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkoxy, $C_3$-$C_6$ cycloalkyl, $C_1$-$C_6$, or $C_1$-$C_4$, or $C_1$-$C_2$ alkoxycarbonyl, —(CH$_2$)$_p$NR$^7$R$^8$ and C(O)NR$^7$R$^8$.

In an embodiment of the invention, R$^1$ represents:
(i) hydrogen,
(ii) fluorine or chlorine,
(iii) $C_1$-$C_4$, or $C_1$-$C_3$, or $C_1$-$C_2$ alkyl,
(iv) $C_3$-$C_5$ cycloalkyl,
(v) $C_1$-$C_2$ alkoxy$C_1$-$C_2$ alkyl,
(vi) $C_1$-$C_2$ hydroxyalkyl,
(vii) —OR$^4$,
(viii) —SR$^4$,
(ix) —C(O)R$^4$,
(x) —C(O)OR$^4$,
(xi) —(CH$_2$)$_m$NHC(O)R$^4$,
(xii) —(CH$_2$)$_m$NHC(O)OR$^4$,
(xiii) —NHC(O)NHR$^4$,
(xiv) —NHSO$_2$R$^4$,
(xv) —C(O)NR$^5$R$^6$,
(xvi) —(CH$_2$)$_m$NR$^5$R$^6$,
(xvii) —SO$_2$NR$^5$R$^6$, or
(xviii) a 4- to 5-, 6-, 7-, 8- or 9-membered heterocyclyl comprising one or two ring heteroatoms independently selected from nitrogen, oxygen and sulphur which is either unsubstituted or is substituted by at least one substituent (e.g. one, two, three or four substituents) independently selected from oxo, $C_1$-$C_4$, or $C_1$-$C_3$, or $C_1$-$C_2$ alkyl, $C_1$-$C_2$ alkylcarbonyl, $C_1$-$C_2$ alkoxy, $C_3$-$C_5$ cycloalkyl, $C_1$-$C_4$, or $C_1$-$C_3$, or $C_1$-$C_2$ alkoxycarbonyl, —(CH$_2$)$_p$NR$^7$R$^8$ and C(O)NR$^7$R$^8$.

In another embodiment of the invention, R$^1$ represents:
(i) hydrogen,
(ii) chlorine,
(iii) methyl,
(iv) cyclopropyl,
(v) methoxymethyl,
(vi) hydroxymethyl,
(vii) —OR$^4$,
(viii) —SR$^4$,
(ix) —C(O)R$^4$,
(x) —C(O)OR$^4$,
(xi) —(CH$_2$)$_m$NHC(O)R$^4$,
(xii) —(CH$_2$)$_m$NHC(O)OR$^4$,
(xiii) —NHC(O)NHR$^4$,
(xiv) —NHSO$_2$R$^4$,
(xv) —C(O)NR$^5$R$^6$,
(xvi) —(CH$_2$)$_m$NR$^5$R$^6$,
(xvii) —SO$_2$NR$^5$R$^6$, or
(xviii) a 4- to 5-, 6-, 7-, 8- or 9-membered heterocyclyl comprising one or two ring heteroatoms independently selected from nitrogen and oxygen which is either unsubstituted or is substituted by one or two substituents independently selected from oxo, $C_1$-$C_4$, or $C_1$-$C_3$, or $C_1$-$C_2$ alkyl (e.g. methyl, ethyl, n-propyl or n-butyl), $C_1$-$C_2$ alkylcarbonyl, $C_1$-$C_2$ alkoxy, cyclopropyl, $C_1$-$C_4$, or $C_1$-$C_3$, or $C_1$-$C_2$ alkoxycarbonyl (e.g tert-butyloxycarbonyl), —(CH$_2$)$_p$NR$^7$R$^8$ and C(O)NR$^7$R$^8$.

In one aspect of the invention, the R$^1$ heterocyclyl group is selected from azetidinyl, pyrrolidinyl, piperidinyl, morpholinyl, oxazolidinyl, piperazinyl, azaspiro[3.5]nonanyl, 2-oxa-6-azaspiro[3.3]heptanyl and 2,6-diazaspiro[3.3]heptanyl.

R$^4$ represents hydrogen, $C_1$-$C_6$, or $C_1$-$C_4$, or $C_1$-$C_2$ alkyl (unsubstituted, or substituted by at least one substituent, e.g. one, two, three or four substituents, independently selected from halogen, hydroxyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_3$-$C_6$ or $C_3$-$C_5$ cycloalkyl, $C_6$-$C_{10}$ aryl, NR$^9$R$^{10}$, oxetanyl, oxolanyl and oxanyl), $C_3$-$C_6$ cycloalkyl (unsubstituted, or substituted by at least one substituent, e.g. one, two, three or four substituents, independently selected from halogen, cyano and $C_1$-$C_6$, or $C_1$-$C_4$, or $C_1$-$C_2$ alkyl), $C_6$-$C_{10}$ aryl, or a 4- to 7-membered heterocyclyl (unsubstituted, or substituted by at least one, e.g. one, two, three or four independently selected, $C_1$-$C_6$, or $C_1$-$C_4$, or $C_1$-$C_2$ alkyl groups).

In an embodiment of the invention, R$^4$ represents hydrogen, $C_1$-$C_4$, or $C_1$-$C_3$, or $C_1$-$C_2$ alkyl (unsubstituted, or substituted by at least one substituent, e.g. one, two, three or four substituents, independently selected from fluorine, chlorine, hydroxyl, trifluoromethyl, $C_1$-$C_2$ alkoxy, cyclopropyl, phenyl, NR$^9$R$^{10}$, oxetanyl, oxolanyl and oxanyl), $C_3$-$C_5$ cycloalkyl (unsubstituted, or substituted by at least one substituent, e.g. one, two, three or four substituents, independently selected from fluorine, chlorine, cyano and $C_1$-$C_2$ alkyl), phenyl, or a 4- to 7-membered heterocyclyl (unsubstituted, or substituted by at least one, e.g. one, two, three or four independently selected, $C_1$-$C_6$, or $C_1$-$C_4$, or $C_1$-$C_2$ alkyl groups).

In one aspect of the invention, the R$^4$ heterocyclyl group represents a 4- to 6-membered heterocyclyl comprising one or two ring heteroatoms independently selected from nitrogen, oxygen and sulphur. In a preferred aspect, the 4- to 6-membered heterocyclyl comprises a single ring nitrogen or a single ring oxygen atom, examples of which include pyrrolidinyl, oxetanyl, oxolanyl and oxanyl.

In a further embodiment of the invention, R$^4$ represents hydrogen, $C_1$-$C_3$ alkyl (unsubstituted, or substituted by at least one substituent, e.g. one, two or three substituents, independently selected from fluorine, hydroxyl, trifluoromethyl, $C_1$-$C_2$ alkoxy, cyclopropyl, phenyl, NR$^9$R$^{10}$, oxetanyl, oxolanyl and oxanyl), $C_3$-$C_4$ cycloalkyl (unsubstituted, or substituted by at least one substituent, e.g. one or two substituents, independently selected from fluorine, cyano and $C_1$-$C_2$ alkyl), phenyl, or a 4- to 6-membered heterocyclyl (unsubstituted, or substituted by one or two $C_1$-$C_6$ alkyl, particularly methyl, groups which may be the same or different).

R$^5$ and R$^6$ each independently represent
(i) hydrogen,
(ii) $C_1$ to $C_2$, $C_3$, $C_4$, $C_5$ or $C_6$ alkyl (unsubstituted, or substituted by at least one substituent, e.g. one, two, three or four substituents, independently selected from halogen, hydroxyl, $C_1$-$C_6$, or $C_1$-$C_4$, or $C_1$-$C_2$ alkoxy, $C_3$-$C_6$ cycloalkyl, NR$^{11}$R$^{12}$, $C_6$-$C_{10}$ aryl, 5- to 6-, 7-, 8-, 9- or 10-membered heteroaryl and 4- to 6- or 7-membered heterocyclyl, each of the aryl, heteroaryl and heterocyclyl substituents being optionally substituted with at least one substituent, e.g. one, two, three, or four substituents, independently selected from halogen, oxo, $C_1$-$C_6$, or $C_1$-$C_4$, or $C_1$-$C_2$ alkyl, $C_1$-$C_6$, or $C_1$-$C_4$, or $C_1$-$C_2$ alkoxy, $C_1$-$C_6$, or $C_1$-$C_4$, or $C_1$-$C_2$ alkoxycarbonyl, and phenyl),
(iii) $C_1$-$C_6$, or $C_1$-$C_4$, or $C_1$-$C_2$ alkylcarbonyl,
(iv) $C_3$-$C_6$ cycloalkyl,
(v) $C_6$-$C_{10}$ aryl,
(vi) 5- to 6-, 7-, 8-, 9- or 10-membered heteroaryl,
(vii) 4- to 6- or 7-membered heterocyclyl, each of the aryl, heteroaryl and heterocyclyl groups (groups (v), (vi) and (vii) above) being optionally substituted with at least one substituent, e.g. one, two, three or four substituents, independently selected from halogen, $C_1$-$C_6$, or $C_1$-$C_4$, or $C_1$-$C_2$ alkyl, $C_1$-$C_6$, or $C_1$-$C_4$, or $C_1$-$C_2$ alkoxy, and $C_1$-$C_6$, or $C_1$-$C_4$, or $C_1$-$C_2$ alkylcarbonyl, or $R^5$ and $R^6$ may together with the nitrogen atom to which they are attached form a 4- to 6- or 7-membered saturated heterocyclic ring unsubstituted, or substituted by at least one substituent, e.g. one, two, three or four substituents, independently selected from halogen, hydroxyl, oxo and $C_1$-$C_6$, or $C_1$-$C_4$, or $C_1$-$C_2$ alkoxy.

In one aspect of the invention, the $R^5$ or $R^6$ heteroaryl groups or moieties are 5- to 6-membered monocyclic rings comprising one or two ring heteroatoms independently selected from nitrogen, oxygen and sulphur.

In another aspect, the $R^5$ or $R^6$ heteroaryl groups or moieties are 5- to 6-membered monocyclic rings comprising one or two ring nitrogen atoms, examples of which include imidazolyl, pyrazolyl, pyridazinyl and pyrimidinyl.

In a further aspect of the invention, the $R^5$ or $R^6$ heterocyclyl groups or moieties are 4- to 6-membered monocyclic rings comprising one or two ring heteroatoms independently selected from nitrogen, oxygen and sulphur.

In yet another aspect, the $R^5$ or $R^6$ heterocyclyl groups or moieties are 4- to 6-membered monocyclic rings comprising one or two ring heteroatoms independently selected from nitrogen and oxygen, examples of which include azetidinyl, pyrrolidinyl, piperidinyl, piperazinyl, morpholinyl, oxetanyl, oxolanyl and oxanyl.

In one embodiment, $R^5$ and $R^6$ each independently represent
(i) hydrogen,
(ii) $C_1$ to $C_2$, $C_3$, $C_4$ or $C_5$ alkyl (unsubstituted, or substituted by at least one substituent, e.g. one, two, three or four substituents, independently selected from fluorine, chlorine, hydroxyl, $C_1$-$C_2$ alkoxy, cyclopropyl, $NR^{11}R^{12}$, phenyl, 5- to 6-, 7-, 8-, 9- or 10-membered heteroaryl and 4- to 6-membered heterocyclyl, each of the aryl, heteroaryl and heterocyclyl substituents being optionally substituted with at least one substituent, e.g. one, two, three, or four substituents, independently selected from fluorine, chlorine, oxo, $C_1$-$C_2$ alkyl, $C_1$-$C_2$ alkoxy, $C_1$-$C_4$, or $C_1$-$C_2$ alkoxycarbonyl, and phenyl),
(iii) $C_1$-$C_2$ alkylcarbonyl,
(iv) cyclopropyl,
(v) phenyl,
(vi) 5- to 6-, 7-, 8-, 9- or 10-membered heteroaryl,
(vii) 4- to 6-membered heterocyclyl, each of the aryl, heteroaryl and heterocyclyl groups (groups (v), (vi) and (vii) above) being optionally substituted with at least one substituent, e.g. one, two, three or four substituents, independently selected from fluorine, chlorine, $C_1$-$C_2$ alkyl, $C_1$-$C_2$ alkoxy, and $C_1$-$C_2$ alkylcarbonyl.

In another embodiment, $R^5$ and $R^6$ each independently represent
(i) hydrogen,
(ii) $C_1$ to $C_2$, $C_3$, $C_4$ or $C_5$ alkyl (unsubstituted, or substituted by at least one substituent, e.g. one, two, three or four substituents, independently selected from fluorine, hydroxyl, methoxy, cyclopropyl, $NR^{11}R^{12}$, phenyl, 5- to 6-membered heteroaryl and 4- to 6-membered heterocyclyl, each of the aryl, heteroaryl and heterocyclyl substituents being optionally substituted with at least one substituent, e.g. one, two, three, or four substituents, independently selected from fluorine, chlorine, oxo, methyl, methoxy, $C_1$-$C_4$ alkoxycarbonyl, and phenyl),
(iii) methylcarbonyl,
(iv) cyclopropyl,
(v) phenyl,
(vi) 5- to 6-membered heteroaryl,
(vii) 4- to 6-membered heterocyclyl, each of the aryl, heteroaryl and heterocyclyl groups (groups (v), (vi) and (vii) above) being optionally substituted with at least one substituent, e.g. one, two, three or four substituents, independently selected from methyl, methoxy, and $C_1$-$C_2$ alkylcarbonyl.

In an alternative embodiment, $R^5$ and $R^6$ together with the nitrogen atom to which they are attached form a 4- to 6-membered saturated heterocyclic ring unsubstituted, or substituted by at least one substituent, e.g. one, two, three or four substituents, independently selected from fluorine, chlorine, hydroxyl, oxo and $C_1$-$C_2$ alkoxy.

In one aspect, the saturated heterocyclic ring may contain a single ring heteroatom (being the nitrogen atom to which $R^5$ and $R^6$ are attached).

In a second aspect, the saturated heterocyclic ring may contain a second ring heteroatom selected from nitrogen or oxygen.

In a further embodiment, $R^5$ and $R^6$ together with the nitrogen atom to which they are attached form an azetidinyl or pyrrolidinyl ring optionally substituted by one or two substituents independently selected from fluorine, hydroxyl and methoxy.

In a still further embodiment, $R^5$ and $R^6$ together with the nitrogen atom to which they are attached form an azetidinyl ring substituted by a methoxy group.

$R^7$ and $R^8$ each independently represent a hydrogen atom or a $C_1$-$C_6$, or $C_1$-$C_4$, or $C_1$-$C_2$ alkyl or $C_3$-$C_6$ cycloalkyl group, or R and R may together with the nitrogen atom to which they are attached form a 4- to 7-membered saturated heterocyclic ring optionally substituted by at least one substituent (e.g. one, two, three or four substituents) independently selected from halogen, hydroxyl, oxo and $C_1$-$C_6$, or $C_1$-$C_4$, or $C_1$-$C_2$ alkoxy.

In one aspect, the saturated heterocyclic ring may contain a single ring heteroatom (being the nitrogen atom to which $R^7$ and $R^8$ are attached).

In a second aspect, the saturated heterocyclic ring may contain a second ring heteroatom selected from nitrogen or oxygen.

In one embodiment, $R^7$ and $R^8$ each independently represent a hydrogen atom or a $C_1$-$C_6$, or $C_1$-$C_4$, or $C_1$-$C_2$ alkyl, particularly methyl, group.

In another embodiment, $R^7$ and $R^8$ together with the nitrogen atom to which they are attached form a pyrrolidinyl ring which is unsubstituted or substituted as hereinbefore described.

$R^9$ and $R^{10}$ each independently represent a hydrogen atom or a $C_1$-$C_6$, or $C_1$-$C_4$, or $C_1$-$C_2$ alkyl or $C_3$-$C_6$ cycloalkyl group, or $R^9$ and $R^{10}$ may together with the nitrogen atom to which they are attached form a 4- to 6- or 7-membered saturated heterocyclic ring optionally substituted by at least one substituent (e.g. one, two, three or four substituents) independently selected from halogen, hydroxyl, oxo and $C_1$-$C_6$, or $C_1$-$C_4$, or $C_1$-$C_2$ alkoxy.

In one aspect, the saturated heterocyclic ring may contain a single ring heteroatom (being the nitrogen atom to which $R^9$ and $R^{10}$ are attached).

In a second aspect, the saturated heterocyclic ring may contain a second ring heteroatom selected from nitrogen or oxygen.

In one embodiment, $R^9$ and $R^{10}$ each independently represent a hydrogen atom or a $C_1$-$C_6$, or $C_1$-$C_4$, or $C_1$-$C_2$ alkyl group. In another embodiment, $R^9$ and $R^{10}$ both represent a methyl group.

In a further embodiment, $R^9$ and $R^{10}$ together with the nitrogen atom to which they are attached form a 4- to 6-membered saturated heterocyclic ring (e.g. azetidinyl, pyrrolidinyl or piperidinyl) optionally substituted by at least one substituent (e.g. one, two, three or four substituents) independently selected from fluorine, chlorine, hydroxyl, oxo and $C_1$-$C_2$ alkoxy.

In a still further embodiment, $R^9$ and $R^{10}$ together with the nitrogen atom to which they are attached form a 4- to 6-membered saturated heterocyclic ring (e.g. azetidinyl, pyrrolidinyl or piperidinyl) optionally substituted by one or two substituents independently selected from fluorine, chlorine, hydroxyl, oxo and methoxy, in particular oxo.

$R^{11}$ and $R^{12}$ each independently represent a hydrogen atom or a $C_1$-$C_6$, or $C_1$-$C_4$, or $C_1$-$C_2$ alkyl or $C_3$-$C_6$ cycloalkyl group.

In one embodiment, $R^{11}$ and $R^{12}$ each independently represent a hydrogen atom or a $C_1$-$C_6$, or $C_1$-$C_4$, or $C_1$-$C_2$ alkyl group. In another embodiment, $R^{11}$ and $R^{12}$ both represent a methyl group.

In an embodiment of the invention, $Y^2$ represents C and $R^2$ represents a hydrogen or halogen atom (e.g. fluorine or chlorine), or a $C_1$-$C_3$ alkyl (e.g. methyl) or amino ($NH_2$) group.

In another embodiment, $Y^2$ represents C and $R^2$ represents a hydrogen or fluorine atom or a methyl or amino group.

In an embodiment of the invention, $Y^2$ represents N and $R^2$ is absent.

$R^3$ represents a group of formula (II) to (VIII)

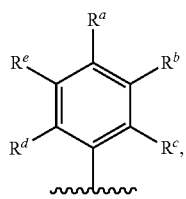
(II)

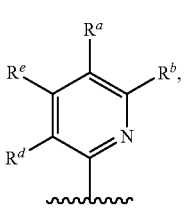
(III)

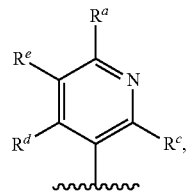
(IV)

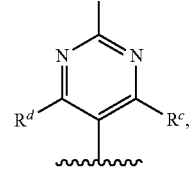
(V)

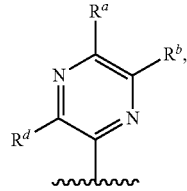
(VI)

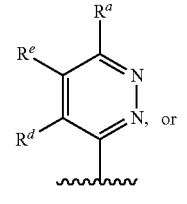
(VII)

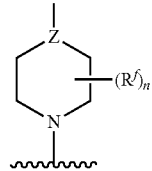
(VIII)

wherein in formulae (II) to (VIII), n is 0 or an integer 1, 2, 3 or 4, Z represents CH or N, $R^a$ represents halogen, cyano, $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl or $C_3$-$C_6$ cycloalkyl, each of $R^b$, $R^c$, $R^d$ and $R^e$ independently represents hydrogen, halogen, $C_1$-$C_6$, or $C_1$-$C_4$, or $C_1$-$C_2$ alkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkyl, $C_3$-$C_6$ cycloalkyl or $NR^{13}R^{14}$, and each $R^f$ independently represents halogen, $C_1$-$C_6$, or $C_1$-$C_4$, or $C_1$-$C_2$ alkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkyl, $C_3$-$C_6$ cycloalkyl or $NR_{13}R_{14}$.

It will be appreciated that if there is more than one $NR^{13}R^{14}$ substituent present in any of formulae (II) to (VIII), they may be the same or different.

In an embodiment of the invention, $R^a$ represents halogen, cyano or $C_2$-$C_6$ or $C_2$-$C_4$ alkynyl.

In another embodiment, $R^a$ represents fluorine, chlorine, cyano or $C_2$-$C_4$ alkynyl.

In yet another embodiment, $R^a$ represents chlorine, cyano or ethynyl.

In one embodiment of the invention, each of $R^b$, $R^c$, $R^d$ and $R^e$ independently represents hydrogen, halogen, $C_1$-$C_2$ alkyl, $C_1$-$C_2$ alkoxy, $C_1$-$C_2$ haloalkyl (e.g. trifluoromethyl) or $NR^{13}R^{14}$.

In a further embodiment, each of $R^b$, $R^c$, $R^d$ and $R^e$ independently represents hydrogen, fluorine, chlorine, bromine, $C_1$-$C_2$ alkyl, methoxy, trifluoromethyl or $NR^{13}R^{14}$.

In one embodiment of the invention, each $R^f$ independently represents halogen, $C_1$-$C_2$ alkyl, $C_1$-$C_2$ alkoxy, $C_1$-$C_2$ haloalkyl (e.g. trifluoromethyl) or $NR^{13}R^{14}$.

In a further embodiment, each $R^f$ independently represents fluorine, chlorine, bromine, $C_1$-$C_2$ alkyl, methoxy, trifluoromethyl or $NR^{13}R^{14}$.

In another embodiment, n is 0 in formula (VIII) so that $R^f$ is absent.

In an embodiment of the invention, $R^3$ represents a group of formula (II) in which $R^a$, $R^b$, $R^c$, $R^d$ and $R^e$ are as hereinbefore defined.

In a further embodiment, $R^3$ represents a group of formula (II) in which $R^a$ represents cyano and each of $R^b$, $R^c$, $R^d$ and $R^e$ independently represents hydrogen, fluorine, chlorine, bromine, $C_1$-$C_2$ alkyl, methoxy, trifluoromethyl or $NR^{13}R^{14}$.

In a still further embodiment, $R^3$ represents a group of formula (II) in which $R^a$ represents cyano, $R^c$ represents methyl, and each of $R^b$, $R^d$ and $R^e$ independently represents hydrogen, fluorine or methyl.

In yet another embodiment, $R^3$ represents a group of formula (II) in which $R^a$ represents cyano, $R^c$ represents methyl, and each of $R^b$, $R^d$ and $R^e$ represents hydrogen.

$R^{13}$ and $R^{14}$ each independently represent a hydrogen atom or a $C_1$-$C_6$, or $C_1$-$C_4$, or $C_1$-$C_2$ alkyl or $C_3$-$C_6$ cycloalkyl group, or $R^{13}$ and $R^{14}$ may together with the nitrogen atom to which they are attached form a 4- to 6- or 7-membered saturated heterocyclic ring optionally substituted by at least one substituent (e.g. one, two, three or four substituents) independently selected from halogen, hydroxyl, oxo and $C_1$-$C_6$, or $C_1$-$C_4$, or $C_1$-$C_2$ alkoxy.

In one aspect, the saturated heterocyclic ring may contain a single ring heteroatom (being the nitrogen atom to which $R^{13}$ and $R^{14}$ are attached).

In a second aspect, the saturated heterocyclic ring may contain a second ring heteroatom selected from nitrogen or oxygen.

In one embodiment, $R^{13}$ and $R^{14}$ each independently represent a hydrogen atom or a $C_1$-$C_6$, or $C_1$-$C_4$, or $C_1$-$C_2$ alkyl group. In another embodiment, $R^{13}$ and $R^{14}$ each independently represent a hydrogen atom or a methyl group. In yet another embodiment, $R^{13}$ and $R^{14}$ both represent a hydrogen atom.

In one embodiment, the invention provides compounds of formula (Ia)

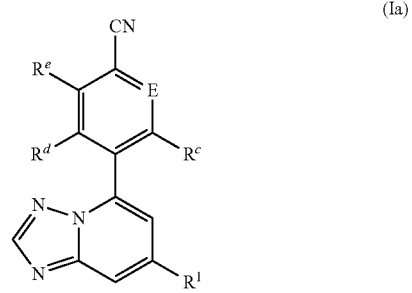

(Ia)

in which $R^1$ represents $NHC(O)R^4$ or $NR^5R^6$;
E is a nitrogen atom or $CR^b$;
$R^b$ and $R^e$ each independently represent a hydrogen or fluorine atom;

$R^c$ and $R^d$ each independently represent a hydrogen, fluorine or chlorine atom or a methyl group; and
$R^4$, $R^5$ and $R^6$ are as defined above.

In one aspect, $R^1$ in formula (Ia) represents $NHC(O)R^4$ in which $R^4$ represents a $C_1$-$C_3$ alkyl or $C_3$-$C_6$ cycloalkyl group.

In another aspect, $R^1$ in formula (Ia) represents $NR^5R^6$ in which $R^5$ and $R^6$ each represent a hydrogen atom.

Examples of compounds of the invention include:
5-(2,4-dichlorophenyl)-[1,2,4]triazolo[1,5-a]pyridine;
5-(4-chlorophenyl)-[1,2,4]triazolo[1,5-a]pyridine;
4-{[1,2,4]triazolo[1,5-a]pyridin-5-yl}benzonitrile;
4-{7-methyl-[1,2,4]triazolo[1,5-a]pyridin-5-yl}benzonitrile;
2-fluoro-4-{[1,2,4]triazolo[1,5-a]pyridin-5-yl}benzonitrile;
2,6-difluoro-4-{[1,2,4]triazolo[1,5-a]pyridin-5-yl}benzonitrile;
3-fluoro-4-{[1,2,4]triazolo[1,5-a]pyridin-5-yl}benzonitrile;
3-methyl-4-{[1,2,4]triazolo[1,5-a]pyridin-5-yl}benzonitrile;
5-(4-chloro-2-fluorophenyl)-[1,2,4]triazolo[1,5-a]pyridine;
2-chloro-4-{[1,2,4]triazolo[1,5-a]pyridin-5-yl}benzonitrile;
4-{[1,2,4]triazolo[1,5-a]pyridin-5-yl}-2-(trifluoromethyl)benzonitrile;
5-(4-chloro-3-fluorophenyl)-[1,2,4]triazolo[1,5-a]pyridine;
2-methyl-4-{[1,2,4]triazolo[1,5-a]pyridin-5-yl}benzonitrile;
6-{[1,2,4]triazolo[1,5-a]pyridin-5-yl}pyridine-3-carbonitrile;
5-{[1,2,4]triazolo[1,5-a]pyridin-5-yl}pyridine-2-carbonitrile;
4-{[1,2,4]triazolo[1,5-c]pyrimidin-5-yl}benzonitrile;
2-fluoro-4-{[1,2,4]triazolo[1,5-c]pyrimidin-5-yl}benzonitrile;
4-{6-methyl-[1,2,4]triazolo[1,5-a]pyridin-5-yl}benzonitrile;
2-fluoro-4-{6-methyl-[1,2,4]triazolo[1,5-a]pyridin-5-yl}benzonitrile;
5-{7-chloro-[1,2,4]triazolo[1,5-a]pyridin-5-yl}-6-methyl-pyridine-2-carbonitrile;
5-{[1,2,4]triazolo[1,5-a]pyridin-5-yl}pyrimidine-2-carbonitrile;
5-{[1,2,4]triazolo[1,5-a]pyridin-5-yl}pyrazine-2-carbonitrile;
2,3-difluoro-4-{[1,2,4]triazolo[1,5-a]pyridin-5-yl}benzonitrile;
3-fluoro-5-{[1,2,4]triazolo[1,5-a]pyridin-5-yl}pyridine-2-carbonitrile;
4-methyl-5-{[1,2,4]triazolo[1,5-a]pyridin-5-yl}pyridine-2-carbonitrile;
3,5-dimethyl-4-{[1,2,4]triazolo[1,5-a]pyridin-5-yl}benzonitrile;
6-{[1,2,4]triazolo[1,5-a]pyridin-5-yl}pyridazine-3-carbonitrile;
6-methyl-5-{[1,2,4]triazolo[1,5-a]pyridin-5-yl}pyridine-2-carbonitrile;
2-fluoro-5-methyl-4-{[1,2,4]triazolo[1,5-a]pyridin-5-yl}benzonitrile;
3-chloro-4-{[1,2,4]triazolo[1,5-a]pyridin-5-yl}benzonitrile;
3-methoxy-4-{[1,2,4]triazolo[1,5-a]pyridin-5-yl}benzonitrile;
5-methyl-6-{[1,2,4]triazolo[1,5-a]pyridin-5-yl}pyridine-3-carbonitrile;
3-ethyl-4-{[1,2,4]triazolo[1,5-a]pyridin-5-yl}benzonitrile;
3-fluoro-5-methyl-4-{[1,2,4]triazolo[1,5-a]pyridin-5-yl}benzonitrile;
3-amino-4-{[1,2,4]triazolo[1,5-a]pyridin-5-yl}benzonitrile;

3-bromo-4-{[1,2,4]triazolo[1,5-a]pyridin-5-yl}benzonitrile;
1-{[1,2,4]triazolo[1,5-a]pyridin-5-yl}piperidine-4-carbonitrile;
4-{[1,2,4]triazolo[1,5-a]pyrimidin-7-yl}benzonitrile;
4-[7-(hydroxymethyl)-[1,2,4]triazolo[1,5-a]pyridin-5-yl]benzonitrile;
methyl 5-(4-cyanophenyl)-[1,2,4]triazolo[1,5-a]pyridine-7-carboxylate;
5-(4-cyanophenyl)-[1,2,4]triazolo[1,5-a]pyridine-7-carboxylic acid;
4-{7-cyclopropyl-[1,2,4]triazolo[1,5-a]pyridin-5-yl}benzonitrile;
4-[7-(pyrrolidine-1-carbonyl)-[1,2,4]triazolo[1,5-a]pyridin-5-yl]benzonitrile;
5-(4-cyanophenyl)-N-(2-methoxyethyl)-[1,2,4]triazolo[1,5-a]pyridine-7-carboxamide;
4-{7-[(2S)-2-methylpyrrolidine-1-carbonyl]-[1,2,4]triazolo[1,5-a]pyridin-5-yl}benzonitrile;
4-[7-(3-methylpyrrolidine-1-carbonyl)-[1,2,4]triazolo[1,5-a]pyridin-5-yl]benzonitrile;
5-(4-cyanophenyl)-N-(3-methoxyphenyl)-[1,2,4]triazolo[1,5-a]pyridine-7-carboxamide;
N-[2-(3-chlorophenyl)ethyl]-5-(4-cyanophenyl)-[1,2,4]triazolo[1,5-a]pyridine-7-carboxamide;
N-[2-(4-chlorophenyl)ethyl]-5-(4-cyanophenyl)-[1,2,4]triazolo[1,5-a]pyridine-7-carboxamide;
5-(4-cyanophenyl)-N-[2-(3-methoxyphenyl)ethyl]-[1,2,4]triazolo[1,5-a]pyridine-7-carboxamide;
N-(3-chlorophenyl)-5-(4-cyanophenyl)-[1,2,4]triazolo[1,5-a]pyridine-7-carboxamide;
N-(4-chlorophenyl)-5-(4-cyanophenyl)-[1,2,4]triazolo[1,5-a]pyridine-7-carboxamide;
5-(4-cyanophenyl)-N-(6-methylpyridazin-3-yl)-[1,2,4]triazolo[1,5-a]pyridine-7-carboxamide;
5-(4-cyanophenyl)-N-(2-methylpyrimidin-5-yl)-[1,2,4]triazolo[1,5-a]pyridine-7-carboxamide;
N-[(3-chlorophenyl)methyl]-5-(4-cyanophenyl)-[1,2,4]triazolo[1,5-a]pyridine-7-carboxamide;
N-[(4-chlorophenyl)methyl]-5-(4-cyanophenyl)-[1,2,4]triazolo[1,5-a]pyridine-7-carboxamide;
5-(4-cyanophenyl)-N-[(3-methoxyphenyl)methyl]-[1,2,4]triazolo[1,5-a]pyridine-7-carboxamide;
5-(4-cyanophenyl)-[1,2,4]triazolo[1,5-a]pyridine-7-carboxamide;
5-(4-cyanophenyl)-N-methyl-[1,2,4]triazolo[1,5-a]pyridine-7-carboxamide;
N-butyl-5-(4-cyanophenyl)-[1,2,4]triazolo[1,5-a]pyridine-7-carboxamide;
5-(4-cyanophenyl)-N-[(1-methyl-1H-imidazol-4-yl)methyl]-[1,2,4]triazolo[1,5-a]pyridine-7-carboxamide;
5-(4-cyanophenyl)-N-[(1-methyl-1H-pyrazol-4-yl)methyl]-[1,2,4]triazolo[1,5-a]pyridine-7-carboxamide;
tert-butyl 3-({[5-(4-cyanophenyl)-[1,2,4]triazolo[1,5-a]pyridin-7-yl]formamido}methyl)azetidine-1-carboxylate;
5-(4-cyanophenyl)-N-[2-(morpholin-4-yl)ethyl]-[1,2,4]triazolo[1,5-a]pyridine-7-carboxamide;
5-(4-cyanophenyl)-N-[2-(4-methylpiperazin-1-yl)ethyl]-[1,2,4]triazolo[1,5-a]pyridine-7-carboxamide;
5-(4-cyanophenyl)-N-(propan-2-yl)-[1,2,4]triazolo[1,5-a]pyridine-7-carboxamide;
5-(4-cyanophenyl)-N-(cyclopropylmethyl)-[1,2,4]triazolo[1,5-a]pyridine-7-carboxamide;
5-(4-cyanophenyl)-N-(oxetan-3-yl)-[1,2,4]triazolo[1,5-a]pyridine-7-carboxamide;
5-(4-cyanophenyl)-N-(oxetan-3-ylmethyl)-[1,2,4]triazolo[1,5-a]pyridine-7-carboxamide;
5-(4-cyanophenyl)-N-(1-methylazetidin-3-yl)-[1,2,4]triazolo[1,5-a]pyridine-7-carboxamide;
5-(4-cyanophenyl)-N-(2-hydroxyethyl)-[1,2,4]triazolo[1,5-a]pyridine-7-carboxamide;
4-(5-{[2-(dimethylamino)ethyl]amino}-[1,2,4]triazolo[1,5-a]pyrimidin-7-yl)benzonitrile;
4-{5-[3-(dimethylamino)pyrrolidin-1-yl]-[1,2,4]triazolo[1,5-a]pyrimidin-7-yl}benzonitrile;
1-[7-(4-cyanophenyl)-[1,2,4]triazolo[1,5-a]pyrimidin-5-yl]-N-methylpyrrolidine-2-carboxamide;
4-{5-[(2S)-2-(pyrrolidin-1-ylmethyl)pyrrolidin-1-yl]-[1,2,4]triazolo[1,5-a]pyrimidin-7-yl}benzonitrile;
4-{5-[3-(pyrrolidin-1-yl)piperidin-1-yl]-[1,2,4]triazolo[1,5-a]pyrimidin-7-yl}benzonitrile;
4-{5-[(1-methylpiperidin-4-yl)amino]-[1,2,4]triazolo[1,5-a]pyrimidin-7-yl}benzonitrile;
4-{5-[(1-methylpiperidin-3-yl)amino]-[1,2,4]triazolo[1,5-a]pyrimidin-7-yl}benzonitrile;
4-{5-[(1-acetylpiperidin-3-yl)amino]-[1,2,4]triazolo[1,5-a]pyrimidin-7-yl}benzonitrile;
4-(5-{[(1-methylpiperidin-4-yl)methyl]amino}-[1,2,4]triazolo[1,5-a]pyrimidin-7-yl)benzonitrile;
4-(5-{[2-(2-oxopyrrolidin-1-yl)ethyl]amino}-[1,2,4]triazolo[1,5-a]pyrimidin-7-yl)benzonitrile;
4-[5-(dimethylamino)-[1,2,4]triazolo[1,5-a]pyrimidin-7-yl]benzonitrile;
4-[5-(pyrrolidin-1-yl)-[1,2,4]triazolo[1,5-a]pyrimidin-7-yl]benzonitrile;
4-{5-[(cyclopropylmethyl)amino]-[1,2,4]triazolo[1,5-a]pyrimidin-7-yl}benzonitrile;
4-{5-[(cyclopropylmethyl)(methyl)amino]-[1,2,4]triazolo[1,5-a]pyrimidin-7-yl}benzonitrile;
4-(5-{[2-(pyrrolidin-1-yl)ethyl]amino}-[1,2,4]triazolo[1,5-a]pyrimidin-7-yl)benzonitrile;
4-(5-{[2-(dimethylamino)ethyl](methyl)amino}-[1,2,4]triazolo[1,5-a]pyrimidin-7-yl)benzonitrile;
4-(5-{[3-(dimethylamino)propyl]amino}-[1,2,4]triazolo[1,5-a]pyrimidin-7-yl)benzonitrile;
4-[5-(2-methylpyrrolidin-1-yl)-[1,2,4]triazolo[1,5-a]pyrimidin-7-yl]benzonitrile;
4-[5-(3-methylpyrrolidin-1-yl)-[1,2,4]triazolo[1,5-a]pyrimidin-7-yl]benzonitrile;
4-[5-(2,5-dimethylpyrrolidin-1-yl)-[1,2,4]triazolo[1,5-a]pyrimidin-7-yl]benzonitrile;
4-[5-(3,3-dimethylpyrrolidin-1-yl)-[1,2,4]triazolo[1,5-a]pyrimidin-7-yl]benzonitrile;
4-[5-(2-cyclopropylpyrrolidin-1-yl)-[1,2,4]triazolo[1,5-a]pyrimidin-7-yl]benzonitrile;
4-{5-[2-(2-methylpropyl)pyrrolidin-1-yl]-[1,2,4]triazolo[1,5-a]pyrimidin-7-yl}benzonitrile;
4-{5-[(3-methylbutyl)amino]-[1,2,4]triazolo[1,5-a]pyrimidin-7-yl}benzonitrile;
4-[5-(cyclopropylamino)-[1,2,4]triazolo[1,5-a]pyrimidin-7-yl]benzonitrile;
4-{5-[3-(2-methylpropyl)pyrrolidin-1-yl]-[1,2,4]triazolo[1,5-a]pyrimidin-7-yl}benzonitrile;
4-(5-{7-azaspiro[3.5]nonan-7-yl}-[1,2,4]triazolo[1,5-a]pyrimidin-7-yl)benzonitrile;
4-[5-cyclopropyl(methyl)amino]-[1,2,4]triazolo[1,5-a]pyrimidin-7-yl}benzonitrile;
4-{7-amino-[1,2,4]triazolo[1,5-a]pyridin-5-yl}benzonitrile;
4-{7-[(cyclopropylmethyl)amino]-[1,2,4]triazolo[1,5-a]pyridin-5-yl}benzonitrile;
4-{7-[(2-methoxyethyl)amino]-[1,2,4]triazolo[1,5-a]pyridin-5-yl}benzonitrile;
4-[7-(ethylamino)-[1,2,4]triazolo[1,5-a]pyridin-5-yl]benzonitrile;

4-{7-[(oxan-4-ylmethyl)amino]-[1,2,4]triazolo[1,5-a]pyridin-5-yl}benzonitrile;
4-{7-[(oxolan-3-ylmethyl)amino]-[1,2,4]triazolo[1,5-a]pyridin-5-yl}benzonitrile;
4-{7-[(2,2-difluoroethyl)amino]-[1,2,4]triazolo[1,5-a]pyridin-5-yl}benzonitrile;
4-{7-[(oxetan-3-ylmethyl)amino]-[1,2,4]triazolo[1,5-a]pyridin-5-yl}benzonitrile;
4-{7-[(3,3,3-trifluoropropyl)amino]-[1,2,4]triazolo[1,5-a]pyridin-5-yl}benzonitrile;
4-(7-{[3-(morpholin-4-yl)propyl]amino}-[1,2,4]triazolo[1,5-a]pyridin-5-yl)benzonitrile;
4-{7-[(2-hydroxy-2-methylpropyl)amino]-[1,2,4]triazolo[1,5-a]pyridin-5-yl}benzonitrile;
4-{7-[(3-methoxypropyl)amino]-[1,2,4]triazolo[1,5-a]pyridin-5-yl}benzonitrile;
4-{7-[(oxolan-2-ylmethyl)amino]-[1,2,4]triazolo[1,5-a]pyridin-5-yl}benzonitrile;
4-(7-{[2-(dimethylamino)ethyl]amino}-[1,2,4]triazolo[1,5-a]pyridin-5-yl)benzonitrile;
4-[7-(benzylamino)-[1,2,4]triazolo[1,5-a]pyridin-5-yl]benzonitrile;
4-(7-{[(2-fluorophenyl)methyl]amino}-[1,2,4]triazolo[1,5-a]pyridin-5-yl)benzonitrile;
4-(7-{[(3-fluorophenyl)methyl]amino}-[1,2,4]triazolo[1,5-a]pyridin-5-yl)benzonitrile;
4-(7-{[(4-fluorophenyl)methyl]amino}-[1,2,4]triazolo[1,5-a]pyridin-5-yl)benzonitrile;
4-[7-(cyclopropylmethoxy)-[1,2,4]triazolo[1,5-a]pyridin-5-yl]benzonitrile;
4-[7-(benzyloxy)-[1,2,4]triazolo[1,5-a]pyridin-5-yl]benzonitrile;
tert-butyl N-[5-(4-cyanophenyl)-[1,2,4]triazolo[1,5-a]pyridin-7-yl]carbamate;
N-[5-(4-cyanophenyl)-[1,2,4]triazolo[1,5-a]pyridin-7-yl]acetamide;
N-[5-(4-cyanophenyl)-[1,2,4]triazolo[1,5-a]pyridin-7-yl]cyclopropanecarboxamide;
N-[5-(4-cyanophenyl)-[1,2,4]triazolo[1,5-a]pyridin-7-yl]benzamide;
tert-butyl N-[5-(4-cyano-3-fluorophenyl)-[1,2,4]triazolo[1,5-a]pyridin-7-yl]carbamate;
2-fluoro-4-{7-[(oxetan-3-ylmethyl)amino]-[1,2,4]triazolo[1,5-a]pyridin-5-yl}benzonitrile;
2-fluoro-4-{7-[(3,3,3-trifluoropropyl)amino]-[1,2,4]triazolo[1,5-a]pyridin-5-yl}benzonitrile;
2-fluoro-4-(7-{[(3-methyl oxetan-3-yl)methyl]amino}-[1,2,4]triazolo[1,5-a]pyridin-5-yl)benzonitrile;
2-fluoro-4-(7-{[(3-phenyloxetan-3-yl)methyl]amino}-[1,2,4]triazolo[1,5-a]pyridin-5-yl)benzonitrile;
4-{7-[2-(dimethylamino)ethoxy]-[1,2,4]triazolo[1,5-a]pyridin-5-yl}-2-fluorobenzonitrile;
2-fluoro-4-{7-[2-(pyrrolidin-1-yl)ethoxy]-[1,2,4]triazolo[1,5-a]pyridin-5-yl}benzonitrile;
2-fluoro-4-[7-(oxolan-2-ylmethoxy)-[1,2,4]triazolo[1,5-a]pyridin-5-yl]benzonitrile;
2-fluoro-4-{7-[2-(2-oxopyrrolidin-1-yl)ethoxy]-[1,2,4]triazolo[1,5-a]pyridin-5-yl}benzonitrile;
2-fluoro-4-[7-(oxolan-3-ylmethoxy)-[1,2,4]triazolo[1,5-a]pyridin-5-yl]benzonitrile;
2-fluoro-4-[7-(2-oxopyrrolidin-1-yl)-[1,2,4]triazolo[1,5-a]pyridin-5-yl]benzonitrile;
2-fluoro-4-[7-(2-oxo-1,3-oxazolidin-3-yl)-[1,2,4]triazolo[1,5-a]pyridin-5-yl]benzonitrile;
N-[5-(4-cyano-3-fluorophenyl)-[1,2,4]triazolo[1,5-a]pyridin-7-yl]-N-methylacetamide;
2-fluoro-4-[7-(morpholin-4-yl)-[1,2,4]triazolo[1,5-a]pyridin-5-yl]benzonitrile;
2-fluoro-4-[7-(3-methoxyazetidin-1-yl)-[1,2,4]triazolo[1,5-a]pyridin-5-yl]benzonitrile;
N-[5-(4-cyano-3-fluorophenyl)-[1,2,4]triazolo[1,5-a]pyridin-7-yl]acetamide;
4-[7-(3-methoxyazetidin-1-yl)-[1,2,4]triazolo[1,5-a]pyridin-5-yl]benzonitrile;
4-(7-{2-oxa-6-azaspiro[3.3]heptan-6-yl}-[1,2,4]triazolo[1,5-a]pyridin-5-yl)benzonitrile;
N-[5-(4-cyano-2-methylphenyl)-[1,2,4]triazolo[1,5-a]pyridin-7-yl]acetamide;
tert-butyl 4-[5-(4-cyanophenyl)-[1,2,4]triazolo[1,5-a]pyridin-7-yl]piperazine-1-carboxylate;
tert-butyl 6-[5-(4-cyanophenyl)-[1,2,4]triazolo[1,5-a]pyridin-7-yl]-2,6-diazaspiro[3.3]heptane-2-carboxylate;
methyl N-[5-(4-cyano-2-methylphenyl)-[1,2,4]triazolo[1,5-a]pyridin-7-yl]carbamate;
4-{7-amino-[1,2,4]triazolo[1,5-a]pyridin-5-yl}-2-fluorobenzonitrile;
4-{6-fluoro-[1,2,4]triazolo[1,5-a]pyridin-5-yl}benzonitrile;
N-[5-(4-cyano-3-fluorophenyl)-[1,2,4]triazolo[1,5-a]pyridin-7-yl]cyclopropanesulfonamide;
N-[5-(4-cyano-3-fluorophenyl)-[1,2,4]triazolo[1,5-a]pyridin-7-yl]benzenesulfonamide;
3-[5-(4-cyano-3-fluorophenyl)-[1,2,4]triazolo[1,5-a]pyridin-7-yl]-1-phenylurea;
N-[5-(4-cyanophenyl)-[1,2,4]triazolo[1,5-a]pyridin-7-yl]-3-methoxypropanamide;
N-[5-(4-cyanophenyl)-[1,2,4]triazolo[1,5-a]pyridin-7-yl]-2-phenylacetamide;
N-[5-(4-cyano-3-fluorophenyl)-[1,2,4]triazolo[1,5-a]pyridin-7-yl]-3,3,3-trifluoropropanamide;
N-[5-(4-cyano-3-fluorophenyl)-[1,2,4]triazolo[1,5-a]pyridin-7-yl]-2-methoxyacetamide;
N-[5-(4-cyano-3-fluorophenyl)-[1,2,4]triazolo[1,5-a]pyridin-7-yl]cyclobutanecarboxamide;
N-[5-(4-cyano-3-fluorophenyl)-[1,2,4]triazolo[1,5-a]pyridin-7-yl]-2-(oxan-4-yl)acetamide;
N-[5-(4-cyano-3-fluorophenyl)-[1,2,4]triazolo[1,5-a]pyridin-7-yl]-2-methylcyclopropane-1-carboxamide;
N-[5-(4-cyano-3-fluorophenyl)-[1,2,4]triazolo[1,5-a]pyridin-7-yl]-2-(piperidin-1-yl)acetamide;
(2S)—N-[5-(4-cyano-3-fluorophenyl)-[1,2,4]triazolo[1,5-a]pyridin-7-yl]oxolane-2-carboxamide;
(2R)—N-[5-(4-cyano-3-fluorophenyl)-[1,2,4]triazolo[1,5-a]pyridin-7-yl]oxolane-2-carboxamide;
N-[5-(4-cyano-3-fluorophenyl)-[1,2,4]triazolo[1,5-a]pyridin-7-yl]-2-(dimethylamino)acetamide;
N-[5-(4-cyano-3-fluorophenyl)-[1,2,4]triazolo[1,5-a]pyridin-7-yl]oxolane-3-carboxamide;
N-[5-(4-cyano-3-fluorophenyl)-[1,2,4]triazolo[1,5-a]pyridin-7-yl]-1-methylcyclopropane-1-carboxamide;
N-[5-(4-cyano-3-fluorophenyl)-[1,2,4]triazolo[1,5-a]pyridin-7-yl]oxane-3-carboxamide;
N-[5-(4-cyano-3-fluorophenyl)-[1,2,4]triazolo[1,5-a]pyridin-7-yl]-4-methyloxane-4-carboxamide;
N-[5-(4-cyano-3-fluorophenyl)-[1,2,4]triazolo[1,5-a]pyridin-7-yl]-3-methyloxetane-3-carboxamide;
N-[5-(4-cyano-3-fluorophenyl)-[1,2,4]triazolo[1,5-a]pyridin-7-yl]oxetane-3-carboxamide;
N-[5-(4-cyano-3-fluorophenyl)-[1,2,4]triazolo[1,5-a]pyridin-7-yl]-2,2-difluorocyclopropane-1-carboxamide;
N-[5-(4-cyano-3-fluorophenyl)-[1,2,4]triazolo[1,5-a]pyridin-7-yl]-2-cyclopropylacetamide;
N-[5-(4-cyano-3-fluorophenyl)-[1,2,4]triazolo[1,5-a]pyridin-7-yl]-2-methoxy-2-methylpropanamide;

1-cyano-N-[5-(4-cyano-3-fluorophenyl)-[1,2,4]triazolo[1,5-a]pyridin-7-yl]cyclopropane-1-carboxamide;
N-[5-(4-cyano-3-fluorophenyl)-[1,2,4]triazolo[1,5-a]pyridin-7-yl]-3-fluorocyclobutane-1-carboxamide;
N-[5-(4-cyano-3-fluorophenyl)-[1,2,4]triazolo[1,5-a]pyridin-7-yl]-2-(oxetan-3-yl)acetamide;
N-[5-(4-cyano-3-fluorophenyl)-[1,2,4]triazolo[1,5-a]pyridin-7-yl]cyclopropanecarboxamide;
N-[5-(4-cyano-2-methylphenyl)-[1,2,4]triazolo[1,5-a]pyridin-7-yl]-3,3,3-trifluoropropanamide;
4-[7-(benzylsulfanyl)-[1,2,4]triazolo[1,5-a]pyridin-5-yl]benzonitrile;
5-(4-cyanophenyl)-N-(cyclopropylmethyl)-[1,2,4]triazolo[1,5-a]pyridine-7-sulfonamide;
5-(4-cyanophenyl)-N-[2-(dimethylamino)ethyl]-[1,2,4]triazolo[1,5-a]pyridine-7-sulfonamide;
5-(4-cyanophenyl)-N-[2-(dimethylamino)ethyl]-[1,2,4]triazolo[1,5-a]pyridine-7-sulfonamide;
2-(azetidin-1-yl)-N-[5-(4-cyanophenyl)-[1,2,4]triazolo[1,5-a]pyridin-7-yl]acetamide;
4-{7-amino-6-fluoro-[1,2,4]triazolo[1,5-a]pyridin-5-yl}benzonitrile;
5-(4-ethynylphenyl)-[1,2,4]triazolo[1,5-a]pyridine;
4-(7-{[(propan-2-yl)amino]methyl}-[1,2,4]triazolo[1,5-a]pyridin-5-yl)benzonitrile;
4-(7-{[(2,2,2-trifluoroethyl)amino]methyl}-[1,2,4]triazolo[1,5-a]pyridin-5-yl)benzonitrile;
4-(7-{[(oxetan-3-yl)amino]methyl}-[1,2,4]triazolo[1,5-a]pyridin-5-yl)benzonitrile;
4-(7-{[(oxetan-3-ylmethyl)amino]methyl}-[1,2,4]triazolo[1,5-a]pyridin-5-yl)benzonitrile;
4-(7-{[(2,2-difluoroethyl)amino]methyl}-[1,2,4]triazolo[1,5-a]pyridin-5-yl)benzonitrile;
4-[7-({[(3-chlorophenyl)methyl]amino}methyl)-[1,2,4]triazolo[1,5-a]pyridin-5-yl]benzonitrile;
4-(7-{[(cyclopropylmethyl)amino]methyl}-[1,2,4]triazolo[1,5-a]pyridin-5-yl)benzonitrile;
4-[7-({[(3-methoxyphenyl)methyl]amino}methyl)-[1,2,4]triazolo[1,5-a]pyridin-5-yl]benzonitrile;
4-{7-[(3-methoxyazetidin-1-yl)methyl]-[1,2,4]triazolo[1,5-a]pyridin-5-yl}benzonitrile;
4-(7-{[(oxolan-3-yl)amino]methyl}-[1,2,4]triazolo[1,5-a]pyridin-5-yl)benzonitrile;
4-(7-{[(oxolan-3-ylmethyl)amino]methyl}-[1,2,4]triazolo[1,5-a]pyridin-5-yl)benzonitrile;
4-{7-[(cyclopropylamino)methyl]-[1,2,4]triazolo[1,5-a]pyridin-5-yl}benzonitrile;
cyclopropylmethyl N-[5-(4-cyano-3-fluorophenyl)-[1,2,4]triazolo[1,5-a]pyridin-7-yl]carbamate;
2-methoxyethyl N-[5-(4-cyano-3-fluorophenyl)-[1,2,4]triazolo[1,5-a]pyridin-7-yl]carbamate;
1-methylpiperidin-4-yl N-[5-(4-cyano-3-fluorophenyl)-[1,2,4]triazolo[1,5-a]pyridin-7-yl]carbamate;
3-(dimethylamino)propyl N-[5-(4-cyano-3-fluorophenyl)-[1,2,4]triazolo[1,5-a]pyridin-7-yl]carbamate;
2-(dimethylamino)ethyl N-[5-(4-cyano-3-fluorophenyl)-[1,2,4]triazolo[1,5-a]pyridin-7-yl]carbamate;
oxolan-3-yl N-[5-(4-cyano-3-fluorophenyl)-[1,2,4]triazolo[1,5-a]pyridin-7-yl]carbamate;
2-fluoro-4-{[1,2,4]triazolo[1,5-a]pyrimidin-7-yl}benzonitrile;
2,6-difluoro-4-{[1,2,4]triazolo[1,5-a]pyrimidin-7-yl}benzonitrile;
3-fluoro-4-{[1,2,4]triazolo[1,5-a]pyrimidin-7-yl}benzonitrile;
3-methyl-4-{[1,2,4]triazolo[1,5-a]pyrimidin-7-yl}benzonitrile;
3-chloro-4-{[1,2,4]triazolo[1,5-a]pyrimidin-7-yl}benzonitrile;
3-fluoro-5-{[1,2,4]triazolo[1,5-a]pyrimidin-7-yl}pyridine-2-carbonitrile;
2,3-difluoro-4-{[1,2,4]triazolo[1,5-a]pyrimidin-7-yl}benzonitrile;
2-fluoro-5-methyl-4-{[1,2,4]triazolo[1,5-a]pyrimidin-7-yl}benzonitrile;
4-{7-amino-[1,2,4]triazolo[1,5-a]pyridin-5-yl}-3-methylbenzonitrile;
4-{7-amino-[1,2,4]triazolo[1,5-a]pyridin-5-yl}-3-fluorobenzonitrile;
4,6-dimethyl-5-{[1,2,4]triazolo[1,5-a]pyridin-5-yl}pyrimidine-2-carbonitrile;
5-{7-amino-[1,2,4]triazolo[1,5-a]pyridin-5-yl}-6-methylpyridine-2-carbonitrile;
5-(4-chloro-3-methoxyphenyl)-[1,2,4]triazolo[1,5-a]pyridine;
2-fluoro-4-{6-fluoro-[1,2,4]triazolo[1,5-a]pyridin-5-yl}benzonitrile;
4-{6-fluoro-[1,2,4]triazolo[1,5-a]pyridin-5-yl}-3-methylbenzonitrile;
3-fluoro-4-{6-fluoro-[1,2,4]triazolo[1,5-a]pyridin-5-yl}benzonitrile;
4-{5-amino-[1,2,4]triazolo[1,5-a]pyrimidin-7-yl}benzonitrile;
4-{7-hydroxy-[1,2,4]triazolo[1,5-a]pyridin-5-yl}benzonitrile;
2-fluoro-4-{7-hydroxy-[1,2,4]triazolo[1,5-a]pyridin-5-yl}benzonitrile;
4-{7-amino-[1,2,4]triazolo[1,5-a]pyridin-5-yl}-2-fluoro-5-methylbenzonitrile;
4-{[1,2,4]triazolo[1,5-a]pyridin-5-yl}piperazine-1-carbonitrile;
3,5-difluoro-4-{[1,2,4]triazolo[1,5-a]pyridin-5-yl}benzonitrile;
2-fluoro-3-methyl-4-{[1,2,4]triazolo[1,5-a]pyridin-5-yl}benzonitrile;
4-[7-(methoxymethyl)-[1,2,4]triazolo[1,5-a]pyridin-5-yl]benzonitrile;
N-{[5-(4-cyanophenyl)-[1,2,4]triazolo[1,5-a]pyridin-7-yl]methyl}acetamide;
N-{[5-(4-cyanophenyl)-[1,2,4]triazolo[1,5-a]pyridin-7-yl]methyl}cyclopropanecarboxamide;
4-{6-amino-[1,2,4]triazolo[1,5-a]pyridin-5-yl}benzonitrile;
4-{7-amino-[1,2,4]triazolo[1,5-a]pyridin-5-yl}-2-fluoro-3-methylbenzonitrile hydrochloride;
5-{6-fluoro-[1,2,4]triazolo[1,5-a]pyridin-5-yl}-6-methylpyridine-2-carbonitrile;
4-[7-(piperazin-1-yl)-[1,2,4]triazolo[1,5-a]pyridin-5-yl]benzonitrile;
4-[7-(4-acetylpiperazin-1-yl)-[1,2,4]triazolo[1,5-a]pyridin-5-yl]benzonitrile;
4-{7-[(2,3-dihydroxypropyl)amino]-[1,2,4]triazolo[1,5-a]pyridin-5-yl}-3-methylbenzonitrile;
N-[5-(4-cyano-fluoro-2-methylphenyl)-[1,2,4]triazolo[1,5-a]pyridin-7-yl]acetamide;
4-{7-chloro-[1,2,4]triazolo[1,5-a]pyridin-5-yl}-2,3-difluorobenzonitrile;
4-{7-chloro-[1,2,4]triazolo[1,5-a]pyridin-5-yl}-2-fluoro-5-methylbenzonitrile;
N-[5-(4-cyano-3-fluorophenyl)-[1,2,4]triazolo[1,5-a]pyridin-7-yl]formamide;
6-amino-5-{[1,2,4]triazolo[1,5-a]pyridin-5-yl}pyridine-2-carbonitrile;
N-[5-(4-Cyano-2-methylphenyl)-[1,2,4]triazolo[1,5-a]pyridin-7-yl]-2-hydroxyacetamide;

N-[5-(4-Cyano-2-methylphenyl)-[1,2,4]triazolo[1,5-a]pyridin-7-yl]-3,3,3-trifluoro-2-hydroxypropanamide;
N-[5-(4-Cyano-2-methylphenyl)-[1,2,4]triazolo[1,5-a]pyridin-7-yl]-2-hydroxy-2-methylpropanamide;
N-[5-(6-Cyano-2-methylpyridin-3-yl)-[1,2,4]triazolo[1,5-a]pyridin-7-yl]acetamide;
tert-Butyl N-[5-(4-cyano-2-fluorophenyl)-[1,2,4]triazolo[1,5-a]pyridin-7-yl]carbamate;
N-[5-(4-Cyano-3-fluorophenyl)-[1,2,4]triazolo[1,5-a]pyridin-7-yl]oxetane-2-carboxamide;
N-[5-(4-Cyano-2-fluorophenyl)-[1,2,4]triazolo[1,5-a]pyridin-7-yl]acetamide;
N-[5-(4-Cyano-2-fluorophenyl)-[1,2,4]triazolo[1,5-a]pyridin-7-yl]cyclopropanecarboxamide;
3-Fluoro-4-{7-[(2-methoxyethyl)amino]-[1,2,4]triazolo[1,5-a]pyridin-5-yl}benzonitrile;
N-[5-(6-Cyano-4-methylpyridin-3-yl)-[1,2,4]triazolo[1,5-a]pyridin-7-yl]acetamide;
5-{7-Amino-[1,2,4]triazolo[1,5-a]pyridin-5-yl}-4-methylpyridine-2-carbonitrile;
4-{7-Hydroxy-[1,2,4]triazolo[1,5-a]pyridin-5-yl}-3-methylbenzonitrile;
N-[5-(4-Cyano-2-methylphenyl)-[1,2,4]triazolo[1,5-a]pyridin-7-yl]cyclopropanecarboxamide;
5-{7-Hydroxy-[1,2,4]triazolo[1,5-a]pyridin-5-yl}-6-methylpyridine-2-carbonitrile;
3-Methyl-4-(7-{2-oxa-6-azaspiro[3.3]heptan-6-yl}-[1,2,4]triazolo[1,5-a]pyridin-5-yl)benzonitrile;
N-[5-(6-Cyano-2-methylpyridin-3-yl)-[1,2,4]triazolo[1,5-a]pyridin-7-yl]cyclopropanecarboxamide;
4-{5-Amino-[1,2,4]triazolo[1,5-a]pyrimidin-7-yl}-2-fluoro-5-methylbenzonitrile;
4-{7-Amino-[1,2,4]triazolo[1,5-a]pyridin-5-yl}-3,5-difluorobenzonitrile;
4-{5-[(Cyclopropylmethyl)amino]-[1,2,4]triazolo[1,5-a]pyrimidin-7-yl}-3-methylbenzonitrile;
4-{5-Amino-[1,2,4]triazolo[1,5-a]pyrimidin-7-yl}-3-methylbenzonitrile;
N-[5-(4-Cyano-2-methylphenyl)-[1,2,4]triazolo[1,5-a]pyridin-7-yl]-2,2-difluorocyclopropane-1-carboxamide;
4-{7-Amino-[1,2,4]triazolo[1,5-a]pyridin-5-yl}-3-chlorobenzonitrile;
4-{7-Amino-[1,2,4]triazolo[1,5-a]pyridin-5-yl}-2,3-difluorobenzonitrile;
N-[5-(2-Chloro-4-cyanophenyl)-[1,2,4]triazolo[1,5-a]pyridin-7-yl]acetamide;
N-[5-(4-Cyano-5-fluoro-2-methylphenyl)-[1,2,4]triazolo[1,5-a]pyridin-7-yl]acetamide;
and pharmaceutically acceptable salts thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises
(i) when $R^3$ represents a group of formula (II) to (VII), reacting a compound of formula (X)

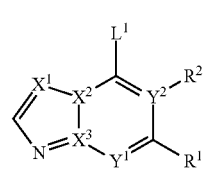

(X)

wherein $L^1$ represents a leaving group (e.g. a halogen atom, tributyl stannyl, boronic acid (—B(OH)$_2$) or boronic ester or trimethylsilane) and $X^1$, $X^2$, $X^3$, $Y^1$, $Y^2$, $R^1$ and $R^2$ are as defined above, with a compound of formula (XI), $R^3$-$L^2$ wherein $L^2$ represents a boronic acid or boronic ester moiety or a halogen atom and $R^3$ is as defined above, in the presence of a palladium catalyst (e.g. palladium (II) chloride, palladium (II) acetate, bis(dibenzylideneacetone)palladium(0) or tetrakis(triphenylphosphine)palladium) and a base (e.g. sodium carbonate, potassium carbonate, potassium phosphate and the like); or
(ii) when $R^3$ represents a group of formula (VIII), reacting a compound of formula (X) as defined in (i) above with a compound of formula (XII)

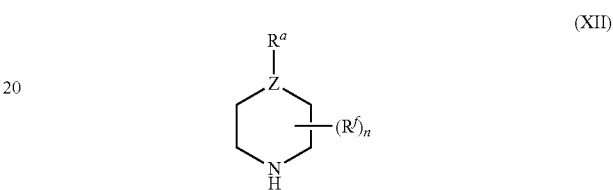

(XII)

wherein n, Z, $R^a$ and $R^f$ are as defined above;
and optionally thereafter carrying out one or more of the following procedures:
converting a compound of formula (I) into another compound of formula (I)
removing any protecting groups
forming a pharmaceutically acceptable salt.

Process (i) is conveniently carried out under a nitrogen atmosphere, in an organic solvent such as dioxane, tetrahydrofuran, acetonitrile or N-methylpyrrolidone and at a temperature in the range of, for example, 20° C. to 120° C.

Process (ii) is conveniently carried out in an organic solvent such as dimethylsulphoxide, N-methylpyrrolidone, ethanol, isopropyl alcohol, acetonitrile or tetrahydrofuran and at a temperature in the range of, for example, 20° C. to 180° C.

Compounds of formulae (X), (XI) and (XII) are either commercially available, are well known in the literature or may be prepared using known techniques.

In one embodiment, a compound of formula (I) may be converted into another compound of formula (I). For example, a compound of formula (I) in which $R^1$ represents an alkoxy carbonyl group, —C(O)OR$^4$, may be converted into a corresponding compound of formula (I) in which $R^1$ represents a hydroxymethyl group by reacting the former with a reducing agent such as lithium borohydride in the presence of a polar solvent such as tetrahydrofuran at a temperature in the range from 0° C. to 200 or 25° C.

Alternatively, a compound of formula (I) in which $R^1$ represents a carboxyl group may be converted into a corresponding compound of formula (I) in which $R^1$ represents an amide group, —C(O)NR$^5$R$^6$, by reacting the former with an amine of formula (XX), HNR$^5$R$^6$, where $R^5$ and $R^6$ are as hereinbefore defined,
(a) in the presence of a known coupling reagent such as EDC (1-ethyl-3-(3-dimethylaminopropyl)carbodiimide) or HOAt (7-aza-1-hydroxybenzotriazole), or
(b) with HATU (1-[bis(dimethylamino)methylene]-1H-1,2,3-triazolo[4,5-b]pyridinium 3-oxid hexafluorophosphate) in the presence of a base such as N,N-diisopropylethylamine.

A compound of formula (I) in which $R^1$ represents a halogen atom may be converted to a corresponding compound of formula (I) in which R¹ represents —NR⁵R⁶, by reacting the former with an amine of formula (XX), HNR⁵R⁶, (a) in a polar solvent such as ethanol under a nitrogen atmosphere and at elevated temperature, e.g. in the range from 70° C. to 180° C., or (b) in the presence of an organopalladium catalyst, e.g. tris(dibenzylideneacetone)dipalladium(0), and dicyclohexyl(2',4',6'-triisopropyl-[1,1'-biphenyl]-2-yl)phosphine with a base such as caesium carbonate in a polar solvent such as dioxane and at elevated temperature, e.g. in the range from 90° C. to 150° C.

A compound of formula (I) in which R¹ represents a halogen atom may be converted to a corresponding compound of formula (I) in which R¹ represents a group, —OR⁴, by reacting the former with an alcohol of formula (XXIa), R⁴OH, where R⁴ is as hereinbefore defined, in the presence of palladium (II) acetate and [1,1'-binaphthalen]-2-yldi-tert-butylphosphine in a hydrocarbon solvent such as toluene under a nitrogen atmosphere and at elevated temperature, e.g. in the range from 100° C. to 130° C.

A compound of formula (I) in which R¹ represents a halogen atom may be converted to a corresponding compound of formula (I) in which R¹ represents —SR⁴, by reacting the former with a thiol of formula (XXIb), NaSR⁴, in a polar solvent such as dimethylformamide under a nitrogen atmosphere and at room temperature (20° to 25° C.).

A compound of formula (I) in which R¹ represents a halogen atom may be converted to a corresponding compound of formula (I) in which R¹ represents a group, —NHC(O)R⁴, by reacting the former with a compound of formula (XXII), R⁴C(O)NH₂, where R⁴ is as hereinbefore defined, in the presence of caesium carbonate, an organopalladium catalyst, e.g. tris(dibenzylideneacetone)dipalladium(0), and dicyclohexyl(2',4',6'-triisopropyl-[1,1'-biphenyl]-2-yl)phosphine in a polar solvent such as dioxane and under a nitrogen atmosphere.

Alternatively, compounds of formula (I) in which R¹ represents a group, —NHC(O)R⁴, may be prepared by reacting compounds of formula (I) in which R¹ represents an amino group with compounds of formula (XXIII), R⁴C(O)L³, where L³ represent a halogen, e.g. chlorine, atom and R⁴ is as hereinbefore defined in the presence of a catalytic amount of N,N-dimethylformamide.

As another alternative, compounds of formula (I) in which R¹ represents a group, —NHC(O)R⁴, may be prepared by reacting compounds of formula (I) in which R¹ represents an amino group with compounds of formula (XXIV), R⁴C(O)OH, in which R⁴ is as hereinbefore defined,
(a) in the presence of a known coupling reagent such as EDC (1-ethyl-3-(3-dimethylaminopropyl)carbodiimide) or HOAt (7-aza-1-hydroxybenzotriazole), or
(b) with HATU (1-[bis(dimethylamino)methylene]-1H-1,2,3-triazolo[4,5-b]pyridinium 3-oxid hexafluorophosphate) in the presence of a base such as N,N-diisopropylethylamine, or
(c) with propylphosphonic anhydride solution in the presence of a base such as triethylamine. It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the introduction and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate orp-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses ¹H, ²H and ³H. Similarly carbon atoms are to be understood to include ¹²C, ¹³C and ¹⁴C, nitrogen atoms are to be understood to include ¹⁴N and ¹⁵N, and oxygen atoms are to be understood to include ¹⁶O, ¹⁷O and ¹⁸O.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also forms an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals and may be used for the treatment of conditions associated with hypoxia inducible factor (HIF) and/or other hypoxia-induced alterations independent of HIF.

Thus, the present invention provides a compound of formula (I) or a pharmaceutically acceptable salt thereof as hereinbefore defined for use in therapy, in particular for the treatment of conditions associated with hypoxia inducible factor and/or other hypoxia-induced alterations independent of HIF.

The present invention also provides the use of a compound of formula (I) or a pharmaceutically acceptable salt thereof as hereinbefore defined for the preparation of a medicament for the treatment of conditions associated with hypoxia inducible factor and/or other hypoxia-induced alterations independent of HIF.

The present invention still further provides a method of treating a condition associated with hypoxia inducible factor and/or other hypoxia-induced alterations independent of HIF which comprises administering to a patient in need thereof a therapeutically effective amount of a compound of formula (I) or a pharmaceutically acceptable salt thereof as hereinbefore defined.

Examples of preferred embodiments of the present invention are as described below.

[1] A compound of formula (I)

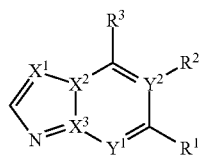

(I)

wherein
- $X^1$ represents N; $X^2$ represents N; $X^3$ represents C; $Y^1$ represents CH;
- $R^1$ represents hydrogen, halogen, $C_1$-$C_6$ alkyl, $C_3$-$C_6$ cycloalkyl, $C_1$-$C_6$ alkoxy$C_1$-$C_6$ alkyl, $C_1$-$C_6$ hydroxyalkyl, —$OR^4$, —$SR^4$, —$C(O)R^4$, —$C(O)OR^4$, —$(CH_2)_mNHC(O)R^4$, —$(CH_2)_mNH$ $C(O)OR^4$, —$NHC(O)NHR^4$, —$NHSO_2R^4$, —$C(O)NR^5R^6$, —$(CH_2)_mNR^5R^6$, —$SO_2NR^5R^6$ or a 4- to 9-membered heterocyclyl (unsubstituted, or substituted by at least one substituent independently selected from oxo, $C_1$-$C_6$ alkyl, $C_1$-$C_6$ alkylcarbonyl, $C_1$-$C_6$ alkoxy, $C_3$-$C_6$ cycloalkyl, $C_1$-$C_6$ alkoxycarbonyl, —$(CH_2)_pNR^7R^8$ and $C(O)NR^7R^8$);
- m is 0 or 1;
- p is 0 or 1;
- $R^4$ represents hydrogen, $C_1$-$C_6$ alkyl (unsubstituted, or substituted by at least one substituent independently selected from halogen, hydroxyl, $C_1$-$C_6$ haloalkyl, $C_1$-$C_6$ alkoxy, $C_3$-$C_6$ cycloalkyl, $C_6$-$C_{10}$ aryl, $NR^9R^{10}$, oxetanyl, oxolanyl and oxanyl), $C_3$-$C_6$ cycloalkyl (unsubstituted, or substituted by at least one substituent independently selected from halogen, cyano and $C_1$-$C_6$ alkyl), $C_6$-$C_{10}$ aryl, or a 4- to 7-membered heterocyclyl (unsubstituted, or substituted by at least one $C_1$-$C_6$ alkyl);
- $R^5$ and $R^6$ each independently represent hydrogen, $C_1$-$C_6$ alkyl (unsubstituted, or substituted by at least one substituent independently selected from halogen, hydroxyl, $C_1$-$C_6$ alkoxy, $C_3$-$C_6$ cycloalkyl, $NR^{11}R^{12}$, $C_6$-$C_{10}$ aryl, 5- to 10-membered heteroaryl and 4- to 7-membered heterocyclyl, each of the aryl, heteroaryl and heterocyclyl substituents being optionally substituted with at least one substituent independently selected from halogen, oxo, $C_1$-$C_6$ alkyl, $C_1$-$C_6$ alkoxy, $C_1$-$C_6$ alkoxycarbonyl, and phenyl), $C_1$-$C_6$ alkylcarbonyl, $C_3$-$C_6$ cycloalkyl, $C_6$-$C_{10}$ aryl, 5- to 10-membered heteroaryl, 4- to 7-membered heterocyclyl, each of the aryl, heteroaryl and heterocyclyl groups being optionally substituted with at least one substituent independently selected from halogen, $C_1$-$C_6$ alkyl, $C_1$-$C_6$ alkoxy, and $C_1$-$C_6$ alkylcarbonyl,
or $R^5$ and $R^6$ may together with the nitrogen atom to which they are attached form a 4- to 7-membered saturated heterocyclic ring unsubstituted, or substituted by at least one substituent independently selected from halogen, hydroxyl, oxo and $C_1$-$C_6$ alkoxy;
- $R^7$ and $R^8$ each independently represent a hydrogen atom or a $C_1$-$C_6$ alkyl or $C_3$-$C_6$ cycloalkyl group, or R and R may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;
- $R^9$ and $R^{10}$ each independently represent a hydrogen atom or a $C_1$-$C_6$ alkyl or $C_3$-$C_6$ cycloalkyl group, or $R^9$ and $R^{10}$ may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;
- $R^{11}$ and $R^{12}$ each independently represent a hydrogen atom or a $C_1$-$C_6$ alkyl or $C_3$-$C_6$ cycloalkyl group;
- $Y^2$ represents C or N;
- when $Y^2$ represents C, $R^2$ represents a hydrogen or halogen atom, or a $C_1$-$C_3$ alkyl or amino group;
- when $Y^2$ represents N, $R^2$ is absent;
- $R^3$ represents a group of formula (II) to (VIII)

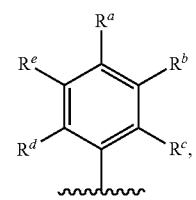

(II)

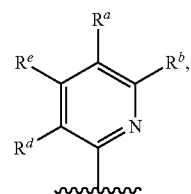

(III)

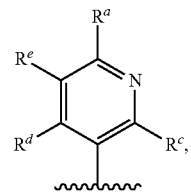

(IV)

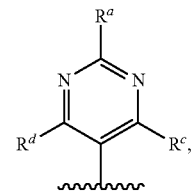

(V)

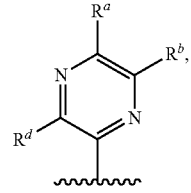

(VI)

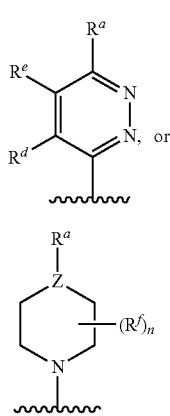

wherein in formulae (II) to (VIII), n is 0 or an integer from 1 to 4, Z represents CH or N, $R^a$ represents halogen, cyano, $C_1$-$C_6$ alkyl, $C_2$-$C_6$ alkenyl, $C_2$-$C_6$ alkynyl or $C_3$-$C_6$ cycloalkyl, each of $R^b$, $R^c$, $R^d$ and $R^e$ independently represents hydrogen, halogen, $C_1$-$C_6$ alkyl, $C_1$-$C_6$ alkoxy, $C_1$-$C_6$ haloalkyl, $C_3$-$C_6$ cycloalkyl or $NR^{13}R^{14}$, and each $R^f$ independently represents halogen, $C_1$-$C_6$ alkyl, $C_1$-$C_6$ alkoxy, $C_1$-$C_6$ haloalkyl, $C_3$-$C_6$ cycloalkyl or $NR^{13}R^{14}$; and $R^{13}$ and $R^{14}$ each independently represent a hydrogen atom or a $C_1$-$C_6$ alkyl or $C_3$-$C_6$ cycloalkyl group, or $R^{13}$ and $R^{14}$ may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;

or a pharmaceutically acceptable salt thereof.

[2] A compound according to the above [1], wherein $R^1$ represents (i) hydrogen,
(ii) chlorine,
(iii) methyl,
(iv) cyclopropyl,
(v) methoxymethyl,
(vi) hydroxymethyl,
(vii) —$OR^4$,
(viii) —$SR^4$,
(ix) —$C(O)R^4$,
(x) —$C(O)OR^4$,
(xi) —$(CH_2)_m NHC(O)R^4$,
(xii) —$(CH_2)_m NHC(O)OR^4$,
(xiii) —$NHC(O)NHR^4$,
(xiv) —$NHSO_2R^4$,
(xv) —$C(O)NR^5R^6$,
(xvi) —$(CH_2)_m NR^5R^6$,
(xvii) —$SO_2NR^5R^6$, or
(xviii) a 4- to 9-membered heterocyclyl comprising one or two ring heteroatoms independently selected from nitrogen and oxygen which is either unsubstituted or is substituted by one or two substituents independently selected from oxo, $C_1$-$C_4$ alkyl, $C_1$-$C_2$ alkylcarbonyl, $C_1$-$C_2$ alkoxy, cyclopropyl, $C_1$-$C_4$ alkoxycarbonyl, —$(CH_2)_p NR^7R^8$ and $C(O)NR^7R^8$.

[3] A compound according to the above [1], wherein $R^1$ represents —$(CH_2)_m NHC(O)R^4$ or —$(CH_2)_m NR^5R^6$ and m is 0.

[4] A compound according to the above [1], [2] or [3], wherein $R^4$ represents hydrogen, $C_1$-$C_3$ alkyl (unsubstituted, or substituted by one, two or three substituents independently selected from fluorine, hydroxyl, trifluoromethyl, $C_1$-$C_2$ alkoxy, cyclopropyl, phenyl, $NR^9R^{10}$, oxetanyl, oxolanyl and oxanyl), $C_3$-$C_4$ cycloalkyl (unsubstituted, or substituted by one or two substituents independently selected from fluorine, cyano and $C_1$-$C_2$ alkyl), phenyl, or a 4- to 6-membered heterocyclyl (unsubstituted, or substituted by one or two $C_1$-$C_6$ alkyl groups).

[5] A compound according to the above [1], [2], [3] or [4], wherein $R^5$ and $R^6$ each independently represent
(i) hydrogen,
(ii) $C_1$ to $C_5$ alkyl (unsubstituted, or substituted by one, two, three or four substituents independently selected from fluorine, hydroxyl, methoxy, cyclopropyl, $NR^{11}R^{12}$, phenyl, 5- to 6-membered heteroaryl and 4- to 6-membered heterocyclyl, each of the aryl, heteroaryl and heterocyclyl substituents being optionally substituted with one, two, three, or four substituents independently selected from fluorine, chlorine, oxo, methyl, methoxy, $C_1$-$C_4$ alkoxycarbonyl, and phenyl),
(iii) methylcarbonyl,
(iv) cyclopropyl,
(v) phenyl,
(vi) 5- to 6-membered heteroaryl, or
(vii) 4- to 6-membered heterocyclyl, each of the aryl, heteroaryl and heterocyclyl groups (groups (v), (vi) and (vii) above) being optionally substituted with one, two, three or four substituents independently selected from methyl, methoxy, and $C_1$-$C_2$ alkylcarbonyl.

[6] A compound according to the above [1], [2], [3], [4] or [5], wherein $R^3$ represents a group of formula (II) or a group of formula (IV).

[7] A compound according to the above [1], [2], [3], [4], [5] or [6], wherein $R^a$ represents cyano.

[8] A compound according to the above [1], [2], [3], [4] or [5], wherein $R^3$ represents a group of formula (II) in which $R^a$ represents cyano, $R^c$ represents methyl, and each of $R^b$, $R^d$ and $R^e$ independently represents hydrogen, fluorine or methyl.

[9] A compound according to the above [1] of formula (Ia)

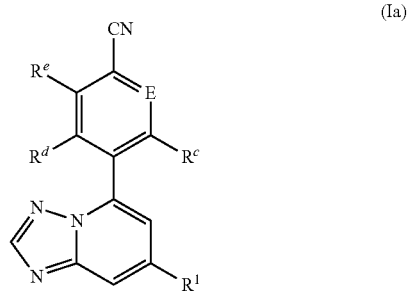

in which $R^1$ represents $NHC(O)R^4$ or $NR^5R^6$;
E is a nitrogen atom or $CR^b$;
$R^b$ and $R^e$ each independently represent a hydrogen or fluorine atom;
$R^c$ and $R^d$ each independently represent a hydrogen, fluorine or chlorine atom or a methyl group;
$R^4$ represents a $C_1$-$C_3$ alkyl or $C_3$-$C_6$ cycloalkyl group; and
$R^5$ and $R^6$ each represent a hydrogen atom.

[10] A compound of formula (I) as defined in the above [1] which is:
5-(2,4-dichlorophenyl)-[1,2,4]triazolo[1,5-a]pyridine;
5-(4-chlorophenyl)-[1,2,4]triazolo[1,5-a]pyridine;
4-{[1,2,4]triazolo[1,5-a]pyridin-5-yl}benzonitrile;

4-{7-methyl-[1,2,4]triazolo[1,5-a]pyridin-5-yl}benzonitrile;
2-fluoro-4-{[1,2,4]triazolo[1,5-a]pyridin-5-yl}benzonitrile;
2,6-difluoro-4-{[1,2,4]triazolo[1,5-a]pyridin-5-yl}benzonitrile;
3-fluoro-4-{[1,2,4]triazolo[1,5-a]pyridin-5-yl}benzonitrile;
3-methyl-4-{[1,2,4]triazolo[1,5-a]pyridin-5-yl}benzonitrile;
5-(4-chloro-2-fluorophenyl)-[1,2,4]triazolo[1,5-a]pyridine;
2-chloro-4-{[1,2,4]triazolo[1,5-a]pyridin-5-yl}benzonitrile;
4-{[1,2,4]triazolo[1,5-a]pyridin-5-yl}-2-(trifluoromethyl)benzonitrile;
5-(4-chloro-3-fluorophenyl)-[1,2,4]triazolo[1,5-a]pyridine;
2-methyl-4-{[1,2,4]triazolo[1,5-a]pyridin-5-yl}benzonitrile;
6-{[1,2,4]triazolo[1,5-a]pyridin-5-yl}pyridine-3-carbonitrile;
5-{[1,2,4]triazolo[1,5-a]pyridin-5-yl}pyridine-2-carbonitrile;
4-{[1,2,4]triazolo[1,5-c]pyrimidin-5-yl}benzonitrile;
2-fluoro-4-{[1,2,4]triazolo[1,5-c]pyrimidin-5-yl}benzonitrile;
4-{6-methyl-[1,2,4]triazolo[1,5-a]pyridin-5-yl}benzonitrile;
2-fluoro-4-{6-methyl-[1,2,4]triazolo[1,5-a]pyridin-5-yl}benzonitrile;
5-{7-chloro-[1,2,4]triazolo[1,5-a]pyridin-5-yl}-6-methylpyridine-2-carbonitrile;
5-{[1,2,4]triazolo[1,5-a]pyridin-5-yl}pyrimidine-2-carbonitrile;
5-{[1,2,4]triazolo[1,5-a]pyridin-5-yl}pyrazine-2-carbonitrile;
2,3-difluoro-4-{[1,2,4]triazolo[1,5-a]pyridin-5-yl}benzonitrile;
3-fluoro-5-{[1,2,4]triazolo[1,5-a]pyridin-5-yl}pyridine-2-carbonitrile;
4-methyl-5-{[1,2,4]triazolo[1,5-a]pyridin-5-yl}pyridine-2-carbonitrile;
3,5-dimethyl-4-{[1,2,4]triazolo[1,5-a]pyridin-5-yl}benzonitrile;
6-{[1,2,4]triazolo[1,5-a]pyridin-5-yl}pyridazine-3-carbonitrile;
6-methyl-5-{[1,2,4]triazolo[1,5-a]pyridin-5-yl}pyridine-2-carbonitrile;
2-fluoro-5-methyl-4-{[1,2,4]triazolo[1,5-a]pyridin-5-yl}benzonitrile;
3-chloro-4-{[1,2,4]triazolo[1,5-a]pyridin-5-yl}benzonitrile;
3-methoxy-4-{[1,2,4]triazolo[1,5-a]pyridin-5-yl}benzonitrile;
5-methyl-6-{[1,2,4]triazolo[1,5-a]pyridin-5-yl}pyridine-3-carbonitrile;
3-ethyl-4-{[1,2,4]triazolo[1,5-a]pyridin-5-yl}benzonitrile;
3-fluoro-5-methyl-4-{[1,2,4]triazolo[1,5-a]pyridin-5-yl}benzonitrile;
3-amino-4-{[1,2,4]triazolo[1,5-a]pyridin-5-yl}benzonitrile;
3-bromo-4-{[1,2,4]triazolo[1,5-a]pyridin-5-yl}benzonitrile;
1-{[1,2,4]triazolo[1,5-a]pyridin-5-yl}piperidine-4-carbonitrile;
4-{7-(hydroxymethyl)-[1,2,4]triazolo[1,5-a]pyridin-5-yl}benzonitrile;
methyl 5-(4-cyanophenyl)-[1,2,4]triazolo[1,5-a]pyridine-7-carboxylate;
5-(4-cyanophenyl)-[1,2,4]triazolo[1,5-a]pyridine-7-carboxylic acid;
4-{7-cyclopropyl-[1,2,4]triazolo[1,5-a]pyridin-5-yl}benzonitrile;
4-[7-(pyrrolidine-1-carbonyl)-[1,2,4]triazolo[1,5-a]pyridin-5-yl]benzonitrile;
5-(4-cyanophenyl)-N-(2-methoxyethyl)-[1,2,4]triazolo[1,5-a]pyridine-7-carboxamide;
4-{7-[(2S)-2-methylpyrrolidine-1-carbonyl]-[1,2,4]triazolo[1,5-a]pyridin-5-yl}benzonitrile;
4-[7-(3-methylpyrrolidine-1-carbonyl)-[1,2,4]triazolo[1,5-a]pyridin-5-yl]benzonitrile;
5-(4-cyanophenyl)-N-(3-methoxyphenyl)-[1,2,4]triazolo[1,5-a]pyridine-7-carboxamide;
N-[2-(3-chlorophenyl)ethyl]-5-(4-cyanophenyl)-[1,2,4]triazolo[1,5-a]pyridine-7-carboxamide;
N-[2-(4-chlorophenyl)ethyl]-5-(4-cyanophenyl)-[1,2,4]triazolo[1,5-a]pyridine-7-carboxamide;
5-(4-cyanophenyl)-N-[2-(3-methoxyphenyl)ethyl]-[1,2,4]triazolo[1,5-a]pyridine-7-carboxamide;
N-(3-chlorophenyl)-5-(4-cyanophenyl)-[1,2,4]triazolo[1,5-a]pyridine-7-carboxamide;
N-(4-chlorophenyl)-5-(4-cyanophenyl)-[1,2,4]triazolo[1,5-a]pyridine-7-carboxamide;
5-(4-cyanophenyl)-N-(6-methylpyridazin-3-yl)-[1,2,4]triazolo[1,5-a]pyridine-7-carboxamide;
5-(4-cyanophenyl)-N-(2-methylpyrimidin-5-yl)-[1,2,4]triazolo[1,5-a]pyridine-7-carboxamide;
N-[(3-chlorophenyl)methyl]-5-(4-cyanophenyl)-[1,2,4]triazolo[1,5-a]pyridine-7-carboxamide;
N-[(4-chlorophenyl)methyl]-5-(4-cyanophenyl)-[1,2,4]triazolo[1,5-a]pyridine-7-carboxamide;
5-(4-cyanophenyl)-N-[(3-methoxyphenyl)methyl]-[1,2,4]triazolo[1,5-a]pyridine-7-carboxamide;
5-(4-cyanophenyl)-[1,2,4]triazolo[1,5-a]pyridine-7-carboxamide;
5-(4-cyanophenyl)-N-methyl-[1,2,4]triazolo[1,5-a]pyridine-7-carboxamide;
N-butyl-5-(4-cyanophenyl)-[1,2,4]triazolo[1,5-a]pyridine-7-carboxamide;
5-(4-cyanophenyl)-N-[(1-methyl-1H-imidazol-4-yl)methyl]-[1,2,4]triazolo[1,5-a]pyridine-7-carboxamide;
5-(4-cyanophenyl)-N-[(1-methyl-1H-pyrazol-4-yl)methyl]-[1,2,4]triazolo[1,5-a]pyridine-7-carboxamide;
tert-butyl 3-({[5-(4-cyanophenyl)-[1,2,4]triazolo[1,5-a]pyridin-7-yl]formamido}methyl)azetidine-1-carboxylate;
5-(4-cyanophenyl)-N-[2-(morpholin-4-yl)ethyl]-[1,2,4]triazolo[1,5-a]pyridine-7-carboxamide;
5-(4-cyanophenyl)-N-[2-(4-methylpiperazin-1-yl)ethyl]-[1,2,4]triazolo[1,5-a]pyridine-7-carboxamide;
5-(4-cyanophenyl)-N-(propan-2-yl)-[1,2,4]triazolo[1,5-a]pyridine-7-carboxamide;
5-(4-cyanophenyl)-N-(cyclopropylmethyl)-[1,2,4]triazolo[1,5-a]pyridine-7-carboxamide;
5-(4-cyanophenyl)-N-(oxetan-3-yl)-[1,2,4]triazolo[1,5-a]pyridine-7-carboxamide;
5-(4-cyanophenyl)-N-(oxetan-3-ylmethyl)-[1,2,4]triazolo[1,5-a]pyridine-7-carboxamide;
5-(4-cyanophenyl)-N-(1-methylazetidin-3-yl)-[1,2,4]triazolo[1,5-a]pyridine-7-carboxamide;
5-(4-cyanophenyl)-N-(2-hydroxyethyl)-[1,2,4]triazolo[1,5-a]pyridine-7-carboxamide;
4-{7-amino-[1,2,4]triazolo[1,5-a]pyridin-5-yl}benzonitrile;
4-{7-[(cyclopropylmethyl)amino]-[1,2,4]triazolo[1,5-a]pyridin-5-yl}benzonitrile;
4-{7-[(2-methoxyethyl)amino]-[1,2,4]triazolo[1,5-a]pyridin-5-yl}benzonitrile;
4-[7-(ethyl amino)-[1,2,4]triazolo[1,5-a]pyridin-5-yl]benzonitrile;
4-{7-[(oxan-4-ylmethyl)amino]-[1,2,4]triazolo[1,5-a]pyridin-5-yl}benzonitrile;

4-{7-[(oxolan-3-ylmethyl)amino]-[1,2,4]triazolo[1,5-a]pyridin-5-yl}benzonitrile;
4-{7-[(2,2-difluoroethyl)amino]-[1,2,4]triazolo[1,5-a]pyridin-5-yl}benzonitrile;
4-{7-[(oxetan-3-ylmethyl)amino]-[1,2,4]triazolo[1,5-a]pyridin-5-yl}benzonitrile;
4-{7-[(3,3,3-trifluoropropyl)amino]-[1,2,4]triazolo[1,5-a]pyridin-5-yl}benzonitrile;
4-(7-{[3-(morpholin-4-yl)propyl]amino}-[1,2,4]triazolo[1,5-a]pyridin-5-yl)benzonitrile;
4-{7-[(2-hydroxy-2-methylpropyl)amino]-[1,2,4]triazolo[1,5-a]pyridin-5-yl}benzonitrile;
4-{7-[(3-methoxypropyl)amino]-[1,2,4]triazolo[1,5-a]pyridin-5-yl}benzonitrile;
4-{7-[(oxolan-2-ylmethyl)amino]-[1,2,4]triazolo[1,5-a]pyridin-5-yl}benzonitrile;
4-(7-{[2-(dimethylamino)ethyl]amino}-[1,2,4]triazolo[1,5-a]pyridin-5-yl)benzonitrile;
4-[7-(benzylamino)-[1,2,4]triazolo[1,5-a]pyridin-5-yl]benzonitrile;
4-(7-{[(2-fluorophenyl)methyl]amino}-[1,2,4]triazolo[1,5-a]pyridin-5-yl)benzonitrile;
4-(7-{[(3-fluorophenyl)methyl]amino}-[1,2,4]triazolo[1,5-a]pyridin-5-yl)benzonitrile;
4-(7-{[(4-fluorophenyl)methyl]amino}-[1,2,4]triazolo[1,5-a]pyridin-5-yl)benzonitrile;
4-[7-(cyclopropylmethoxy)-[1,2,4]triazolo[1,5-a]pyridin-5-yl]benzonitrile;
4-[7-(benzyloxy)-[1,2,4]triazolo[1,5-a]pyridin-5-yl]benzonitrile;
tert-butyl N-[5-(4-cyanophenyl)-[1,2,4]triazolo[1,5-a]pyridin-7-yl]carbamate;
N-[5-(4-cyanophenyl)-[1,2,4]triazolo[1,5-a]pyridin-7-yl]acetamide;
N-[5-(4-cyanophenyl)-[1,2,4]triazolo[1,5-a]pyridin-7-yl]cyclopropanecarbxamide;
N-[5-(4-cyanophenyl)-[1,2,4]triazolo[1,5-a]pyridin-7-yl]benzamide;
tert-butyl N-[5-(4-cyano-3-fluorophenyl)-[1,2,4]triazolo[1,5-a]pyridin-7-yl]carbamate;
2-fluoro-4-{7-[(oxetan-3-ylmethyl)amino]-[1,2,4]triazolo[1,5-a]pyridin-5-yl}benzonitrile;
2-fluoro-4-{7-[(3,3,3-trifluoropropyl)amino]-[1,2,4]triazolo[1,5-a]pyridin-5-yl}benzonitrile;
2-fluoro-4-(7-{[(3-methyloxetan-3-yl)methyl]amino}-[1,2,4]triazolo[1,5-a]pyridin-5-yl)benzonitrile;
2-fluoro-4-(7-{[(3-phenyloxetan-3-yl)methyl]amino}-[1,2,4]triazolo[1,5-a]pyridin-5-yl)benzonitrile;
4-{7-[2-(dimethylamino)ethoxy]-[1,2,4]triazolo[1,5-a]pyridin-5-yl}-2-fluorobenzonitrile;
2-fluoro-4-{7-[2-(pyrrolidin-1-yl)ethoxy]-[1,2,4]triazolo[1,5-a]pyridin-5-yl}benzonitrile;
2-fluoro-4-[7-(oxolan-2-ylmethoxy)-[1,2,4]triazolo[1,5-a]pyridin-5-yl]benzonitrile;
2-fluoro-4-{7-[2-(2-oxopyrrolidin-1-yl)ethoxy]-[1,2,4]triazolo[1,5-a]pyridin-5-yl}benzonitrile;
2-fluoro-4-[7-(oxolan-3-ylmethoxy)-[1,2,4]triazolo[1,5-a]pyridin-5-yl]benzonitrile;
2-fluoro-4-[7-(2-oxopyrrolidin-1-yl)-[1,2,4]triazolo[1,5-a]pyridin-5-yl]benzonitrile;
2-fluoro-4-[7-(2-oxo-1,3-oxazolidin-3-yl)-[1,2,4]triazolo[1,5-a]pyridin-5-yl]benzonitrile;
N-[5-(4-cyano-3-fluorophenyl)-[1,2,4]triazolo[1,5-a]pyridin-7-yl]-N-methylacetamide;
2-fluoro-4-[7-(morpholin-4-yl)-[1,2,4]triazolo[1,5-a]pyridin-5-yl]benzonitrile;
2-fluoro-4-[7-(3-methoxyazetidin-1-yl)-[1,2,4]triazolo[1,5-a]pyridin-5-yl]benzonitrile;
N-[5-(4-cyano-3-fluorophenyl)-[1,2,4]triazolo[1,5-a]pyridin-7-yl]acetamide;
4-[7-(3-methoxyazetidin-1-yl)-[1,2,4]triazolo[1,5-a]pyridin-5-yl]benzonitrile;
4-(7-{2-oxa-6-azaspiro[3.3]heptan-6-yl}-[1,2,4]triazolo[1,5-a]pyridin-5-yl)benzonitrile;
N-[5-(4-cyano-2-methylphenyl)-[1,2,4]triazolo[1,5-a]pyridin-7-yl]acetamide;
tert-butyl 4-[5-(4-cyanophenyl)-[1,2,4]triazolo[1,5-a]pyridin-7-yl]piperazine-1-carboxylate;
tert-butyl 6-[5-(4-cyanophenyl)-[1,2,4]triazolo[1,5-a]pyridin-7-yl]-2,6-diazaspiro[3.3]heptane-2-carboxylate;
methyl N-[5-(4-cyano-2-methylphenyl)-[1,2,4]triazolo[1,5-a]pyridin-7-yl]carbamate;
4-{7-amino-[1,2,4]triazolo[1,5-a]pyridin-5-yl}-2-fluorobenzonitrile;
4-{6-fluoro-[1,2,4]triazolo[1,5-a]pyridin-5-yl}benzonitrile;
N-[5-(4-cyano-3-fluorophenyl)-[1,2,4]triazolo[1,5-a]pyridin-7-yl]cyclopropanesulfonamide;
N-[5-(4-cyano-3-fluorophenyl)-[1,2,4]triazolo[1,5-a]pyridin-7-yl]benzenesulfonamide;
3-[5-(4-cyano-3-fluorophenyl)-[1,2,4]triazolo[1,5-a]pyridin-7-yl]-1-phenylurea;
N-[5-(4-cyanophenyl)-[1,2,4]triazolo[1,5-a]pyridin-7-yl]-3-methoxypropanamide;
N-[5-(4-cyanophenyl)-[1,2,4]triazolo[1,5-a]pyridin-7-yl]-2-phenylacetamide;
N-[5-(4-cyano-3-fluorophenyl)-[1,2,4]triazolo[1,5-a]pyridin-7-yl]-3,3,3-trifluoropropanamide;
N-[5-(4-cyano-3-fluorophenyl)-[1,2,4]triazolo[1,5-a]pyridin-7-yl]-2-methoxyacetamide;
N-[5-(4-cyano-3-fluorophenyl)-[1,2,4]triazolo[1,5-a]pyridin-7-yl]cyclobutanecarboxamide;
N-[5-(4-cyano-3-fluorophenyl)-[1,2,4]triazolo[1,5-a]pyridin-7-yl]-2-(oxan-4-yl)acetamide;
N-[5-(4-cyano-3-fluorophenyl)-[1,2,4]triazolo[1,5-a]pyridin-7-yl]-2-methylcyclopropane-1-carboxamide;
N-[5-(4-cyano-3-fluorophenyl)-[1,2,4]triazolo[1,5-a]pyridin-7-yl]-2-(piperidin-1-yl)acetamide;
(2S)—N-[5-(4-cyano-3-fluorophenyl)-[1,2,4]triazolo[1,5-a]pyridin-7-yl]oxolane-2-carboxamide;
(2R)—N-[5-(4-cyano-3-fluorophenyl)-[1,2,4]triazolo[1,5-a]pyridin-7-yl]oxolane-2-carboxamide;
N-[5-(4-cyano-3-fluorophenyl)-[1,2,4]triazolo[1,5-a]pyridin-7-yl]-2-(dimethylamino)acetamide;
N-[5-(4-cyano-3-fluorophenyl)-[1,2,4]triazolo[1,5-a]pyridin-7-yl]oxolane-3-carboxamide;
N-[5-(4-cyano-3-fluorophenyl)-[1,2,4]triazolo[1,5-a]pyridin-7-yl]-1-methylcyclopropane-1-carboxamide;
N-[5-(4-cyano-3-fluorophenyl)-[1,2,4]triazolo[1,5-a]pyridin-7-yl]oxane-3-carboxamide;
N-[5-(4-cyano-3-fluorophenyl)-[1,2,4]triazolo[1,5-a]pyridin-7-yl]-4-methyloxane-4-carboxamide;
N-[5-(4-cyano-3-fluorophenyl)-[1,2,4]triazolo[1,5-a]pyridin-7-yl]-3-methyloxetane-3-carboxamide;
N-[5-(4-cyano-3-fluorophenyl)-[1,2,4]triazolo[1,5-a]pyridin-7-yl]oxetane-3-carboxamide;
N-[5-(4-cyano-3-fluorophenyl)-[1,2,4]triazolo[1,5-a]pyridin-7-yl]-2,2-difluorocyclopropane-1-carboxamide;
N-[5-(4-cyano-3-fluorophenyl)-[1,2,4]triazolo[1,5-a]pyridin-7-yl]-2-cyclopropylacetamide;
N-[5-(4-cyano-3-fluorophenyl)-[1,2,4]triazolo[1,5-a]pyridin-7-yl]-2-methoxy-2-methylpropanamide;
1-cyano-N-[5-(4-cyano-3-fluorophenyl)-[1,2,4]triazolo[1,5-a]pyridin-7-yl]cyclopropane-1-carboxamide;

N-[5-(4-cyano-3-fluorophenyl)-[1,2,4]triazolo[1,5-a]pyridin-7-yl]-3-fluorocyclobutane-1-carboxamide;
N-[5-(4-cyano-3-fluorophenyl)-[1,2,4]triazolo[1,5-a]pyridin-7-yl]-2-(oxetan-3-yl)acetamide;
N-[5-(4-cyano-3-fluorophenyl)-[1,2,4]triazolo[1,5-a]pyridin-7-yl]cyclopropanecarboxamide;
N-[5-(4-cyano-2-methylphenyl)-[1,2,4]triazolo[1,5-a]pyridin-7-yl]-3,3,3-trifluoropropanamide;
4-[7-(benzylsulfanyl)-[1,2,4]triazolo[1,5-a]pyridin-5-yl]benzonitrile;
5-(4-cyanophenyl)-N-(cyclopropylmethyl)-[1,2,4]triazolo[1,5-a]pyridine-7-sulfonamide;
5-(4-cyanophenyl)-N-[2-(dimethylamino)ethyl]-[1,2,4]triazolo[1,5-a]pyridine-7-sulfonamide;
5-(4-cyanophenyl)-N-[2-(dimethylamino)ethyl]-[1,2,4]triazolo[1,5-a]pyridine-7-sulfonamide;
2-(azetidin-1-yl)-N-[5-(4-cyanophenyl)-[1,2,4]triazolo[1,5-a]pyridin-7-yl]acetamide;
4-{7-amino-6-fluoro-[1,2,4]triazolo[1,5-a]pyridin-5-yl}benzonitrile;
5-(4-ethynylphenyl)-[1,2,4]triazolo[1,5-a]pyridine;
4-(7-{[(propan-2-yl)amino]methyl}-[1,2,4]triazolo[1,5-a]pyridin-5-yl)benzonitrile;
4-(7-{[(2,2,2-trifluoroethyl)amino]methyl}-[1,2,4]triazolo[1,5-a]pyridin-5-yl)benzonitrile;
4-(7-{[(oxetan-3-yl)amino]methyl}-[1,2,4]triazolo[1,5-a]pyridin-5-yl)benzonitrile;
4-(7-{[(oxetan-3-ylmethyl)amino]methyl}-[1,2,4]triazolo[1,5-a]pyridin-5-yl)benzonitrile;
4-(7-{[(2,2-difluoroethyl)amino]methyl}-[1,2,4]triazolo[1,5-a]pyridin-5-yl)benzonitrile;
4-[7-({[(3-chlorophenyl)methyl]amino}methyl)-[1,2,4]triazolo[1,5-a]pyridin-5-yl]benzonitrile;
4-(7-{[(cyclopropylmethyl)amino]methyl}-[1,2,4]triazolo[1,5-a]pyridin-5-yl)benzonitrile;
4-[7-({[(3-methoxyphenyl)methyl]amino}methyl)-[1,2,4]triazolo[1,5-a]pyridin-5-yl]benzonitrile;
4-{7-[(3-methoxyazetidin-1-yl)methyl]-[1,2,4]triazolo[1,5-a]pyridin-5-yl}benzonitrile;
4-(7-{[(oxolan-3-yl)amino]methyl}-[1,2,4]triazolo[1,5-a]pyridin-5-yl)benzonitrile;
4-(7-{[(oxolan-3-ylmethyl)amino]methyl}-[1,2,4]triazolo[1,5-a]pyridin-5-yl)benzonitrile;
4-{7-[(cyclopropylamino)methyl]-[1,2,4]triazolo[1,5-a]pyridin-5-yl}benzonitrile;
cyclopropylmethyl N-[5-(4-cyano-3-fluorophenyl)-[1,2,4]triazolo[1,5-a]pyridin-7-yl]carbamate;
2-methoxyethyl N-[5-(4-cyano-3-fluorophenyl)-[1,2,4]triazolo[1,5-a]pyridin-7-yl]carbamate;
1-methylpiperidin-4-yl N-[5-(4-cyano-3-fluorophenyl)-[1,2,4]triazolo[1,5-a]pyridin-7-yl]carbamate;
3-(dimethylamino)propyl N-[5-(4-cyano-3-fluorophenyl)-[1,2,4]triazolo[1,5-a]pyridin-7-yl]carbamate;
2-(dimethylamino)ethyl N-[5-(4-cyano-3-fluorophenyl)-[1,2,4]triazolo[1,5-a]pyridin-7-yl]carbamate;
oxolan-3-yl N-[5-(4-cyano-3-fluorophenyl)-[1,2,4]triazolo[1,5-a]pyridin-7-yl]carbamate;
4-{7-amino-[1,2,4]triazolo[1,5-a]pyridin-5-yl}-3-methylbenzonitrile;
4-{7-amino-[1,2,4]triazolo[1,5-a]pyridin-5-yl}-3-fluorobenzonitrile;
4,6-dimethyl-5-{[1,2,4]triazolo[1,5-a]pyridin-5-yl}pyrimidine-2-carbonitrile;
5-{7-amino-[1,2,4]triazolo[1,5-a]pyridin-5-yl}-6-methylpyridine-2-carbonitrile;
5-(4-chloro-3-methoxyphenyl)-[1,2,4]triazolo[1,5-a]pyridine;
2-fluoro-4-{6-fluoro-[1,2,4]triazolo[1,5-a]pyridin-5-yl}benzonitrile;
4-{6-fluoro-[1,2,4]triazolo[1,5-a]pyridin-5-yl}-3-methylbenzonitrile;
3-fluoro-4-{6-fluoro-[1,2,4]triazolo[1,5-a]pyridin-5-yl}benzonitrile;
4-{7-hydroxy-[1,2,4]triazolo[1,5-a]pyridin-5-yl}benzonitrile;
2-fluoro-4-{7-hydroxy-[1,2,4]triazolo[1,5-a]pyridin-5-yl}benzonitrile;
4-{7-amino-[1,2,4]triazolo[1,5-a]pyridin-5-yl}-2-fluoro-5-methylbenzonitrile;
4-{[1,2,4]triazolo[1,5-a]pyridin-5-yl}piperazine-1-carbonitrile;
3,5-difluoro-4-{[1,2,4]triazolo[1,5-a]pyridin-5-yl}benzonitrile;
2-fluoro-3-methyl-4-{[1,2,4]triazolo[1,5-a]pyridin-5-yl}benzonitrile;
4-[7-(methoxymethyl)-[1,2,4]triazolo[1,5-a]pyridin-5-yl]benzonitrile;
N-{[5-(4-cyanophenyl)-[1,2,4]triazolo[1,5-a]pyridin-7-yl]methyl}acetamide;
N-{[5-(4-cyanophenyl)-[1,2,4]triazolo[1,5-a]pyridin-7-yl]methyl}cyclopropanecarboxamide;
4-{6-amino-[1,2,4]triazolo[1,5-a]pyridin-5-yl}benzonitrile;
4-{7-amino-[1,2,4]triazolo[1,5-a]pyridin-5-yl}-2-fluoro-3-methylbenzonitrile hydrochloride;
5-{6-fluoro-[1,2,4]triazolo[1,5-a]pyridin-5-yl}-6-methylpyridine-2-carbonitrile;
4-[7-(piperazin-1-yl)-[1,2,4]triazolo[1,5-a]pyridin-5-yl]benzonitrile;
4-[7-(4-acetylpiperazin-1-yl)-[1,2,4]triazolo[1,5-a]pyridin-5-yl]benzonitrile;
4-{7-[(2,3-dihydroxypropyl)amino]-[1,2,4]triazolo[1,5-a]pyridin-5-yl}-3-methylbenzonitrile;
N-[5-(4-cyano-3-fluoro-2-methylphenyl)-[1,2,4]triazolo[1,5-a]pyridin-7-yl]acetamide;
4-{7-chloro-[1,2,4]triazolo[1,5-a]pyridin-5-yl}-2,3-difluorobenzonitrile;
4-{7-chloro-[1,2,4]triazolo[1,5-a]pyridin-5-yl}-2-fluoro-5-methylbenzonitrile;
N-[5-(4-cyano-3-fluorophenyl)-[1,2,4]triazolo[1,5-a]pyridin-7-yl]formamide;
6-amino-5-{[1,2,4]triazolo[1,5-a]pyridin-5-yl}pyridine-2-carbonitrile;
N-[5-(4-Cyano-2-methylphenyl)-[1,2,4]triazolo[1,5-a]pyridin-7-yl]-2-hydroxyacetamide;
N-[5-(4-Cyano-2-methylphenyl)-[1,2,4]triazolo[1,5-a]pyridin-7-yl]-3,3,3-trifluoro-2-hydroxypropanamide;
N-[5-(4-Cyano-2-methylphenyl)-[1,2,4]triazolo[1,5-a]pyridin-7-yl]-2-hydroxy-2-methylpropanamide;
N-[5-(6-Cyano-2-methylpyridin-3-yl)-[1,2,4]triazolo[1,5-a]pyridin-7-yl]acetamide;
tert-Butyl N-[5-(4-cyano-2-fluorophenyl)-[1,2,4]triazolo[1,5-a]pyridin-7-yl]carbamate;
N-[5-(4-Cyano-3-fluorophenyl)-[1,2,4]triazolo[1,5-a]pyridin-7-yl]oxetane-2-carboxamide;
N-[5-(4-Cyano-2-fluorophenyl)-[1,2,4]triazolo[1,5-a]pyridin-7-yl]acetamide;
N-[5-(4-Cyano-2-fluorophenyl)-[1,2,4]triazolo[1,5-a]pyridin-7-yl]cyclopropanecarboxamide;
3-Fluoro-4-{7-[(2-methoxyethyl)amino]-[1,2,4]triazolo[1,5-a]pyridin-5-yl}benzonitrile;
N-[5-(6-Cyano-4-methylpyridin-3-yl)-[1,2,4]triazolo[1,5-a]pyridin-7-yl]acetamide;
5-{7-Amino-[1,2,4]triazolo[1,5-a]pyridin-5-yl}-4-methylpyridine-2-carbonitrile;

4-{7-Hydroxy-[1,2,4]triazolo[1,5-a]pyridin-5-yl}-3-methylbenzonitrile;
N-[5-(4-Cyano-2-methylphenyl)-[1,2,4]triazolo[1,5-a]pyridin-7-yl]cyclopropanecarboxamide;
5-{7-Hydroxy-[1,2,4]triazolo[1,5-a]pyridin-5-yl}-6-methylpyridine-2-carbonitrile;
3-Methyl-4-(7-{2-oxa-6-azaspiro[3.3]heptan-6-yl}-[1,2,4]triazolo[1,5-a]pyridin-5-yl)benzonitrile;
N-[5-(6-Cyano-2-methylpyridin-3-yl)-[1,2,4]triazolo[1,5-a]pyridin-7-yl]cyclopropanecarboxamide;
4-{7-Amino-[1,2,4]triazolo[1,5-a]pyridin-5-yl}-3,5-difluorobenzonitrile;
N-[5-(4-Cyano-2-methylphenyl)-[1,2,4]triazolo[1,5-a]pyridin-7-yl]-2,2-difluorocyclopropane-1-carboxamide;
4-{7-Amino-[1,2,4]triazolo[1,5-a]pyridin-5-yl}-3-chlorobenzonitrile;
4-{7-Amino-[1,2,4]triazolo[1,5-a]pyridin-5-yl}-2,3-difluorobenzonitrile;
N-[5-(2-Chloro-4-cyanophenyl)-[1,2,4]triazolo[1,5-a]pyridin-7-yl]acetamide; or
N-[5-(4-Cyano-5-fluoro-2-methylphenyl)-[1,2,4]triazolo[1,5-a]pyridin-7-yl]acetamide;
or a pharmaceutically acceptable salt thereof.

[11] A pharmaceutical composition comprising a compound of formula (I) or a pharmaceutically acceptable salt thereof, as defined in the above[1], in association with a pharmaceutically acceptable adjuvant, diluent or carrier, and optionally one or more other therapeutic agents.

[12] The pharmaceutical composition of the above [11], which is a PHD inhibitor.

[13] The pharmaceutical composition of the above [11], which is an agent for the treatment of acute kidney injury, chronic kidney disease, acute decompensated heart failure, heart failure following a heart attack or peripheral artery disease.

[14] A compound of formula (I) or a pharmaceutically acceptable salt thereof, as defined in the above [1], for use in therapy.

[15] A compound of formula (I) or a pharmaceutically acceptable salt thereof, as defined in the above [1], for use in treating acute kidney injury, chronic kidney disease, acute decompensated heart failure, heart failure following a heart attack or peripheral artery disease.

[16] A method for inhibiting PHD in a patient, comprising administering to a patient in need thereof a therapeutically effective amount of a compound of formula (I) or a pharmaceutically acceptable salt thereof, as defined in the above [1].

[17] A method for treating acute kidney injury, chronic kidney disease, acute decompensated heart failure, heart failure following a heart attack or peripheral artery disease which comprises administering to a patient in need thereof a therapeutically effective amount of a compound of formula (I) or a pharmaceutically acceptable salt thereof, as defined in the above [1].

[18] Use of a compound of formula (I) or a pharmaceutically acceptable salt thereof, as defined in the above [1], for the preparation of a medicament for the treatment of acute kidney injury, chronic kidney disease, acute decompensated heart failure, heart failure following a heart attack or peripheral artery disease.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

The terms "treat", "treatment" and "treating" include improvement of the conditions described herein. The terms "treat", "treatment" and "treating" include all processes providing slowing, interrupting, arresting, controlling, or stopping of the state or progression is of the conditions described herein, but does not necessarily indicate a total elimination of all symptoms or a cure of the condition. The terms "treat", "treatment," and "treating" are intended to include therapeutic as well as prophylactic treatment of such conditions.

As used herein the terms "condition," "disorder," and "disease" relate to any unhealthy or abnormal state. The term "conditions associated with hypoxia inducible factor and/or other hypoxia-induced alterations independent of HIF" includes conditions, disorders and diseases in which the inhibition of PHD, in particular PHD1, provides a therapeutic benefit, such as hypoxic or ischaemic conditions, examples of which include:

(1) Cardiovascular and Metabolic disorders: stroke; myocardial infarction including acute myocardial infarction; congestive heart failure; atherosclerosis; chronic venous insufficiency; cardiac cirrhosis; diabetes; acute decompensated heart failure; heart failure following a heart attack; peripheral artery disease; and occlusive artery disease;

(2) Haematological disorders: anaemia;

(3) Pulmonary disorders: chronic obstructive pulmonary disease; pulmonary embolism; mountain sickness; acute respiratory failure; and interstitial lung diseases (ILD) including idiopathic ILD, such as idiopathic pulmonary fibrosis, desquamative interstitial pneumonia, nonspecific interstitial pneumonia, cryptogenic organizing pneumonia, respiratory bronchiolitis-associated interstitial lung disease, acute interstitial pneumonia or lymphoid interstitial pneumonia;

(4) Kidney disorders: acute kidney failure; acute kidney injury; chronic kidney disease; and renal ischaemia reperfusion injury;

(5) Cancer: leukaemia (chronic myelogenous leukaemia and chronic lymphocytic leukaemia); breast cancer; genitourinary cancer; skin cancer; bone cancer; prostate cancer; liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumour, islet cell tumour, acute and chronic lymphocytic and granulocytic tumours; hairy-cell tumour, adenoma, medullary carcinoma, pheochromocytoma, mucosal neuromas, intestinal ganglioneuromas, hyperplastic corneal nerve tumuor, marfanoid habitus tumuor, Wilms' tumuor, seminoma, ovarian tumuor, leiomyomater tumuor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas; and (6) Liver disorders: hepatic ischemia reperfusion injury.

The compound may be useful for preventing or treating, for example, such diseases as cardiac diseases (cardiac hypertrophy, acute heart failure and chronic heart failure including congestive heart failure, cardiomyopathy, angina, myocarditis, arrhythmia, tachycardia, myocardial infarction, etc.), myocardial ischemia, venous insufficiency, post-myocardial infarction transition to heart failure, hypertension, cor pulmonale, arteriosclerosis including atherosclerosis (aneurysm, coronary arterial sclerosis, cerebral arterial sclerosis, peripheral arterial sclerosis, etc.), intervention (percutaneous coronary angioplasty, stent placement, coronary angioscopy, intravascular ultrasound, coronary thrombolytic therapy, etc.)—and heart transplantation-related vascular thickening/occlusion/organ damages, vascular reocclusion/restenosis after bypass surgery, respiratory diseases (cold syndrome, pneumonia, asthma, pulmonary hypertension, pulmonary thrombus/pulmonary embolism, etc.), bone disorders (nonmetabolic bone disorders such as bone fracture, refracture, bone malformation/spondylosis deformans, osteosarcoma, myeloma, dysostosis and scoliosis, bone defect, osteoporosis, osteomalacia, rickets, osteitis fibrosis, renal osteodystrophy, Paget's disease of bone, myelitis with rigidity, chronic rheumatoid arthritis, gonarthrosis and articular tissue destruction in similar disorders thereof, etc.), inflammatory diseases (retinopathy, nephropathy, nerve damage, arthritis such as chronic rheumatoid arthritis, osteoarthritis, rheumatoid myelitis and periostitis, inflammation after surgery/trauma, reduction of swelling, pharyngitis, cystitis, atopic dermatitis, inflammatory enteric diseases such as Crohn's disease and ulcerative colitis, meningitis, inflammatory eye diseases, inflammatory pulmonary diseases such as pneumonia, silicosis, pulmonary sarcoidosis and pulmonary tuberculosis, etc.), allergic diseases (allergic rhinitis, conjunctivitis, gastrointestinal allergy, pollen allergy, anaphylaxis, etc.), drug dependence, neurodegenerative diseases (Alzheimer's disease, Parkinson's disease, amyotrophic lateral sclerosis, AIDS encephalopathy, etc.), central nervous system damage (disorders such as cerebral hemorrhage and cerebral infarction and aftereffects and complications thereof, head injury, spinal damage, cerebral edema, etc.), dementia, disturbed memory, disturbed consciousness, amnesia, anxiety symptoms, nervous symptoms, unpleasant condition, mental disorders (depression, epilepsy, alcohol dependency, etc.), ischemic peripheral circulatory disorder, deep-vein thrombosis, occlusive peripheral circulatory disorder, arteriosclerosis obliterans (ASO), occlusive thromboangiitis, diabetes (type 1 diabetes, type 2 diabetes, type 1.5 diabetes (LADA (Latent Autoimmune Diabetes in Adults)), pregnancy diabetes, diabetes with impaired insulin secretion, obese diabetes, impaired glucose tolerance (IGT), IFG (Impaired Fasting Glucose), IFG (Impaired Fasting Glycaemia), etc.), diabetic complications (nerve damage, nephropathy, retinopathy, cataract, macroangiopathy, osteopenia, diabetic hyperosmolar diabetic coma, infectious diseases (respiratory infection, urinary infection, digestive tract infection, skin and soft tissue infection, lower limb infection, etc.), diabetic gangrene, xerostomia, deterioration in hearing, cerebrovascular damage, peripheral circulatory disorder, etc.), urinary incontinence, metabolic/nutritional disorders (obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, hyperlipidemia, hypercholesterolemia, impaired glucose tolerance, etc.), insulin resistant syndrome, syndrome X, vesceral obesity syndrome, male or female sexual dysfunction, cerebrovascular damage (asymptomatic cerebrovascular damage, transient cerebral ischemia attack, stroke, cerebrovascular dementia, hypertensive encephalopathy, cerebral infarction, etc.), cerebral edema, cerebral circulatory disturbance, recurrence and aftereffects of cerebrovascular damages (neurological symptoms, mental symptoms, subjective symptoms, impairment of activities of daily living, etc.), kidney diseases (nephritis, glomerulonephritis, glomerulosclerosis, renal failure, thrombotic microangiopathy, diabetic nephropathy, nephrotic syndrome, hypertensive nephrosclerosis, complications of dialysis, organ damage including nephropathy by irradiation, etc.), ocular disorders (glaucoma, ocular hypertension, etc.), thrombosis, multiple organ failure, endothelial dysfunction, other circulatory diseases (ischemic cerebral circulatory disturbance, Raynaud's disease, Buerger's disease, etc.), chronic occlusive pulmonary diseases, interstitial pneumonia, carinii pneumonia, connective tissue disorders (e.g., systemic erythematosus, scleroderma, polyarteritis, etc.), liver disorders (hepatitis and cirrhosis including chronic types, etc.), digestive disorders (gastritis, gastric ulcer, gastric cancer, disorder after gastric surgery, poor digestion, esophageal ulcer, pancreatitis, colon polyp, cholelithiasis, hemorrhoidal problem, esophageal and gastric variceal rupture, etc.), hematological/hematopoietic disorders (erythrocytosis, vascular purpura, autoimmune hemolytic anemia, disseminated intravascular coagulation syndrome, multiple myelosis, etc.), solid tumor, tumors (malignant melanoma, malignant lymphoma, digestive organs (e.g., stomach, intestine, etc.) cancers, etc.), cancers and cachexia associated therewith, cancer metastases, endocrine disorders (Addison's disease, Cushing's syndrome, pheochromocytoma, primary aldosteronism, etc.), urological/male genital diseases (cystitis, prostatic enlargement, prostate cancer, sexually transmitted diseases, etc.), gynecological disorders (menopausal disorders, pregnancy toxemia, endometriosis, uterine fibroid, ovarian diseases, mammary gland diseases, sexually transmitted diseases, etc.), infectious diseases (viral infectious diseases of, for example, cytomegalovirus, influenza virus and herpesvirus, rickettsial infectious diseases, bacterial infectious diseases, etc.), toxemia (septicemia, septic shock, endotoxic shock, gram-negative septicemia, toxin shock syndrome, etc.), cutaneous diseases (keloid, hemangioma, psoriasis, etc.).

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (g/kg) to 100 micrograms per kilogram body weight (g/kg). Alternatively, if the compound is administered orally, then the daily dosage of the compound of the invention may be in the range from 0.01 micrograms per kilogram body weight (g/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The present invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of inj ectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents for the treatment of one or more of the conditions previously indicated. Such therapeutic agents may be selected from the following:

(i) Angiotensin II receptor blockers such as Candesartan, Losartan, Valsartan, Irbesartan, Telmisartan, Olmisartan or Azilsartan;
(ii) Diuretics;
(iii) ACE and Renin inhibitors;
(iv) Adrenergic alpha receptor antagonists; and
(v) Vasodilators.

Such combination products employ the compounds of this invention within the dosage range described herein and the other pharmaceutically active agent within approved dosage ranges.

The present invention will now be further explained by reference to the following illustrative examples, in which the starting materials and reagents used are available from commercial suppliers or prepared via literature procedures.

Nuclear magnetic resonance (NMR) spectra were recorded at 400 MHz or 300 MHz as stated and at 300.3K unless otherwise stated; the chemical shifts (δ) are reported in parts per million. Spectra were recorded using a Bruker 400 AVANCE instrument fitted with a 5 mm BBFO probe with instrument controlled by Bruker TopSpin 2.1 software, or by a Bruker 400 AVANCE-III instrument fitted with a 5 mm BBFO probe with instrument controlled by Bruker TopSpin 3.0 software, or by a Bruker 300 MHz AVANCE II instrument fitted with a 5 mm DUL probe with instrument controlled by Bruker TopSpin 1.3 software.

Purity was assessed using one or more of the following:
- UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.1% formic acid or 0.025% ammonia. Mass spectra were recorded with a Waters SQD single quadrupole mass spectrometer using atmospheric pressure ionisation.
- UPLC with UV (photodiode array) detection over a wide range of wavelengths, normally 200-500 nm, using a Waters Acquity H-Class UPLC system controlled by Empower-2 software. Mass spectra were recorded with a Waters SQD single quadrupole mass spectrometer using electrospray ionization. Mobile phase consisted of 5 mM ammonium acetate or 0.1% formic acid in water and acetonitrile using Acquity UPLC BEH or HSS C18 columns (2.1 mm id×50 mm long).
- LCMS with UV (photodiode array) detection over a wide range of wavelengths, normally 200-500 nm and the detection was also observed at a wavelength 260 nm and 80 bandwidth, using Shimandzu Nexera LCMS-2020 system controlled by Lab Solution software. Mass spectra were recorded with a single quadrupole mass spectrometer using electrospray ionization. Mobile phase consisted of 20 mM ammonium acetate mixed with water and methanol using Waters X-bridge column (C18, 5 m, 4.6 mm id×150 mm).
- LCMS with UV (photodiode array) detection over a wide range of wavelengths, normally 200-500 nm, using Waters ZQ-2000 system controlled by Empower-1 software. Mass spectra were recorded with a Waters ZQ single quadrupole mass spectrometer using electrospray ionization. Mobile phases consisted of 0.1% ammonia mixed with water and acetonitrile using Waters X-bridge column (C18, 5 μm, 4.6 mm id×150 mm).

Compounds were purified using normal phase chromatography on silica, using Biotage or Isolute KP-Sil cartridges or Kinesis Telos Silica cartridges, or on basic silica, using Biotage or Isolute KP-NH cartridges, or by reverse phase chromatographic methods, using Biotage or Isolute KP-C18-HS cartridges or by SCX-2 or Strata catch-release cartridges, or by preparative HPLC.

Preparative HPLC was performed using one or more of the following:
- Agilent Technologies 1100 Series system or a Waters autopurification LC/MS system typically using Waters 19 mm id×250 mm long C18 columns such as XBridge or SunFire 5 m materials at rt.
- Shimadzu Preparative HPLC system typically using 19 mm id×150 mm long C18 columns 5 μm or 20 mm id×250 mm long C8 columns 5 μm materials at rt. The Shimadzu Preparative HPLC system was controlled by LC-Solution software.

Mobile phases typically consisted of acetonitrile or methanol mixed with water containing either 0.1% formic acid or 0.1% ammonia, unless stated otherwise.

Rt in the following examples means the temperature ranging from 20° C. to 25° C.

Abbreviations

Ac acetyl
AcOH acetic acid
app. apparent (spectral)
aq aqueous
Bn, Bzl benzyl
BOC, Boc tert-butoxycarbonyl
bp boiling point,
br broad (spectral)
Bu, n-Bu normal (primary) butyl
t-Bu tert-butyl
Bz benzoyl
CBZ, Cbz benzyloxycarbonyl
$CD_2Cl_2$ deuterated dichloromethane
$CDCl_3$ deuterated chloroform
$CD_3CN$ deuterated acetonitrile
m-CPBA meta-chloroperoxybenzoic acid
Cy cyclohexyl
δ chemical shift in ppm downfield from tetramethylsilane
d day(s); doublet (spectral);
dba dibenzylideneacetone
DCM dichloromethane
DCM-$d_2$ deuterated dichloromethane
DIAD Diisopropylazodicarboxylate
dioxane 1,4-dioxane
DIPEA N,N-diisopropylethylamine
DMA dimethylacetamide
DMF dimethylformamide
DMF-DMA N,N-dimethylformamide dimethyl acetal
DMSO dimethyl sulfoxide
DMSO-$d_6$ perdeuterated dimethyl sulfoxide
DPPA Diphenylphosphoryl azide
dppf 1,1'-bis(diphenylphosphanyl) ferrocene
Eaton's reagent 7.7 wt % phosphorus pentoxide solution in methanesulfonic acid
ES electrospray
Et ethyl
EtOAc ethyl acetate
EtOH ethanol
h hour(s)
HATU 1-[bis(dimethylamino)methylene]-1H-1,2,3-triazolo[4,5-b]pyridinium-3-oxid hexafluorophosphate
HBTU N,N,N',N'-tetramethyl-O-(1H-benzotriazol-1-yl)uronium hexafluorophosphate
HPLC high-performance liquid chromatography
Hz hertz
IPA iso-propyl alcohol
L liter(s)
LDA lithium diisopropylamide
μ micro
m multiplet (spectral); meter(s); milli
M molar (moles per liter); mega
Me methyl
MeOH methanol
Methanol-$d_4$ deuterated methanol
mg milligram
min minute(s); minimum
mL milliliter
mmol millimoles
mmolar millimolar (millimoles per liter, mM)
mol mole(s); molecular (e.g. in mol. wt.)
mp melting point
Ms, mesyl methylsulfonyl
MS mass spectrometry
MTBE methyl tert-butyl ether
MW molecular weight
m/z mass-to-charge ratio
NaHMDS sodium hexamethyldisilazane
NBS N-bromosuccinimde
NCS N-chlorosuccinimide nm nanometer(s)
NMP N-methylpyrrolidone
NMR nuclear magnetic resonance
[(Cinnamyl)PdCl]$_2$ Bis[cinnamyl palladium(II) chloride]
obsc. obscured peak (spectral)
petrol petroleum ether boiling range 40-60° C.
Ph phenyl
Phase Separator Biotage Phase Separator (Part #120-1908-F)
PMB p-methoxybenzyl
ppm part(s) per million
ppt precipitate
Pr, n-Pr propan-1-yl
iPr isopropyl
PTFE polytetrafluoroethylene
q quartet (spectral)
rt room temperature
s singlet (spectral); second(s)
sat. saturated
SCX strong cation exchange resin
STAB sodium triacetoxy borohydride
t triplet (spectral)
t time; temperature in units of degrees Celsius (° C.)
TEA triethylamine
Tf, trifyl trifluoromethanesulfonyl
TFA trifluoroacetic acid
TFAA trifluoroacetic anhydride
THF tetrahydrofuran
tlc thin layer chromatography
TMEDA N,N,N',N'-tetramethyl-1,2-ethylenediamine
TMS trimethylsilyl
Ts, tosyl para-toluenesulfonyl
UV ultraviolet
Xantphos 4,5-Bis(diphenylphosphino)-9,9-dimethylxanthene
X-Phos 2-dicyclohexylphosphino-2',4',6'-triisopropylbiphenyl

1. INTERMEDIATES

Intermediate 1 5-(Tetramethyl-1,3,2-dioxaborolan-2-yl)-[1,2,4]triazolo[1,5-a]pyridine

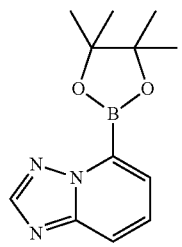 [SMILES: CC1(C)OB(c2cccc3ncnn23)OC1(C)C]

A stirred solution of 5-bromo-[1,2,4]triazolo[1,5-a]pyridine (CAS 143329-58-2, 0.25 g, 1.262 mmol), bis(pinacolato)diboron (0.401 g, 1.578 mmol) and potassium acetate (0.248 g, 2.52 mmol) in dry DMF (6.31 mL) was evacuated and purged with nitrogen. To this was added PdCl$_2$(dppf) (0.052 g, 0.063 mmol). The reaction was heated at 100° C. under nitrogen for 20 h. The reaction was diluted with EtOAc and filtered through celite. The celite was washed with EtOAc and the filtrate concentrated to give a brown oil. This was then taken on to the next stage without purification.
MS ES$^+$: 246

Scheme 1

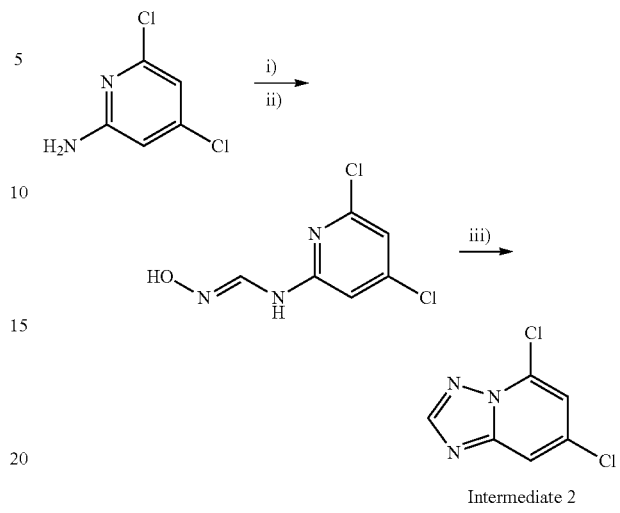

Reagents: i) DMF—DMA, IPA ii) NH$_2$OH·HCl, MeOH iii) Eatons reagent

Intermediate 2 5,7-Dichloro-[1,2,4]triazolo[1,5-a]pyridine

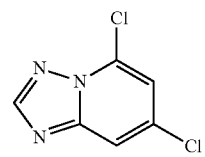 [SMILES: Clc1cc(Cl)n2ncnc2c1]

Step 1:
DMF-DMA (5.13 mL, 38.3 mmol) was added to a solution of 4,6-dichloropyridin-2-amine (CAS 116632-24-7, 5 g, 30.7 mmol) in EtOH (150 mL). The reaction was heated to 85° C. for 75 min. The reaction mixture was allowed to cool to rt then solvent was removed in vacuo to give (E)-N'-(4,6-dichloropyridin-2-yl)-N,N-dimethylmethanimidamide as a brown oil which was taken on to the next step without purification.

Step 2:
Hydroxylamine hydrochloride (2.99 g, 43.0 mmol) was added to a solution of (E)-N'-(4,6-dichloropyridin-2-yl)-N,N-dimethylmethanimidamide (6.70 g, 30.7 mmol) in MeOH (133 mL) under nitrogen. The reaction was stirred at rt for 1 h and then concentrated in vacuo. The residue was triturated with water and the solid collected by filtration, washing with water. The solid was dried under vacuum overnight to afford (E)-N-(4,6-dichloropyridin-2-yl)-N'-hydroxymethanimidamide.

$^1$H NMR (400 MHz, DMSO-d$_6$) δ ppm 7.13 (s, 2H) 7.68 (d, J=10 Hz, 1H) 9.89 (d, J=10 Hz, 1H) 10.44 (s, 1H)

Step 3:
(E)-N-(4,6-dichloropyridin-2-yl)-N'-hydroxymethanimidamide (6.12 g, 29.7 mmol) and Eaton's reagent (30 mL) were combined and heated to 105° C. for 20 min. The reaction mixture was allowed to cool to rt, diluted with ice water and basified with solid K$_2$CO$_3$ to pH 8. The resulting solution was extracted twice with EtOAc, and the organic layers were combined and dried over MgSO$_4$, filtered, and concentrated to give a brown solid. The solid was crystallised from MTBE to afford the title compound.

¹H NMR (300 MHz, DMSO-d$_6$) δ ppm 7.76 (d, J=2 Hz, 1H) 8.16 (d, J=2 Hz, 1H) 8.66 (s, 1H)

MS ES⁺: 188

Scheme 2

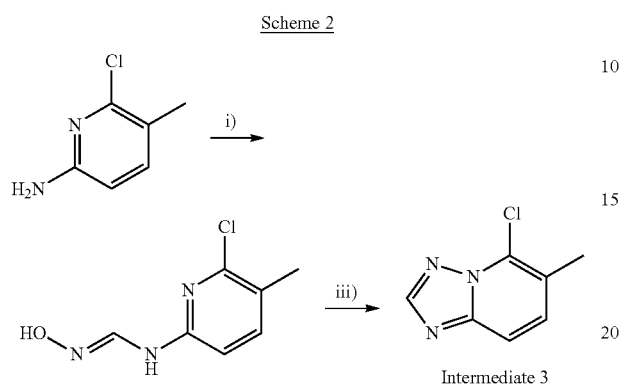

Reagents: i) DMF—DMA, IPA then NH$_2$OH•HCl ii) TFAA

Intermediate 3 5-Chloro-6-methyl-[1,2,4]triazolo[1,5-a]pyridine

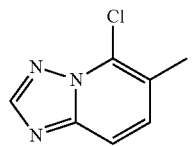

Step 1:

A solution of 6-chloro-5-methylpyridin-2-amine (CAS 442129-37-5, 1 g, 7.01 mmol) in IPA (10 mL) was treated with DMF-DMA (1.315 mL, 9.82 mmol). The mixture was heated to reflux for 2 h. The reaction was removed from the heat, treated with hydroxylamine hydrochloride (0.682 g, 9.82 mmol) and heated to 50° C. for 2 h. The reaction was concentrated in vacuo and the residue was purified by flash chromatography (0-100% EtOAc in petrol) to afford N'-(6-chloro-5-methylpyridin-2-yl)-N-hydroxymethanimidamide.

¹H NMR (400 MHz, DMSO-d$_6$) δ ppm 2.20 (s, 3H) 6.91-7.03 (m, 1H) 7.55-7.61 (m, 1H) 7.63-7.69 (m, 1H) 9.43-9.53 (m, 1H) 10.17 (s, 1H)

MS ES⁺: 186

Step 2:

A suspension of N'-(6-chloro-5-methylpyridin-2-yl)-N-hydroxymethanimidamide (0.5 g, 2.69 mmol) in THF (7 mL) was treated with TFAA (0.419 mL, 2.96 mmol) and heated to 40° C. for 2.5 h. The reaction was cooled to rt, quenched with sat. NaHCO$_3$ and extracted with EtOAc (×2). The organic phases were combined, dried (phase separator) and concentrated in vacuo. The residue was purified by flash chromatography (0-40% EtOAc in petrol on silica) to afford the title compound.

¹H NMR (400 MHz, DMSO-d$_6$) δ ppm 2.46 (s, 3H) 7.65-7.75 (m, 1H) 7.78-7.85 (m, 1H) 8.55 (s, 1H)

MS ES⁺: 168

Scheme 3

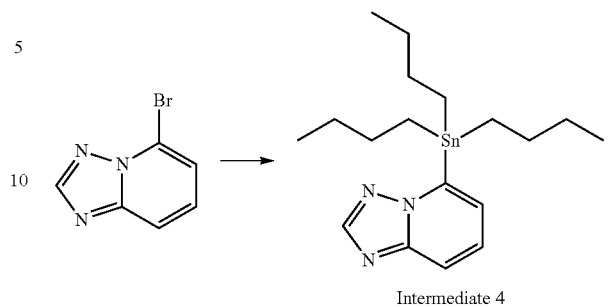

Intermediate 4 5-(Tributylstannyl)-[1,2,4]triazolo[1,5-a]pyridine

To a stirred solution of 5-bromo-[1,2,4]triazolo[1,5-a]pyridine (CAS 143329-58-2, 2 g, 10.1 mmol) in THF (40 mL) at −78° C. under a nitrogen atmosphere was added n-BuLi [2.5M in hexanes] (4.85 mL, 12.1 mmol) drop wise over 5 min. The reaction was stirred at −78° C. for 20 min. To the stirred reaction mixture was added tri-n-butyltin chloride (3.29 mL, 12.1 mmol) over 5 min via syringe addition. The reaction was stirred at −78° C. for a further 45 min. The reaction was quenched at −78° C. with sat. (aq.) NaHCO$_3$. The reaction mixture was allowed to warm to room temperature and was partitioned between EtOAc and water. The organic phase was washed with water and brine then dried over Na$_2$SO$_4$. The crude product was absorbed onto diatomaceous earth and was purified by column chromatography on basic silica (0-20% EtOAc/petrol) to afford the title compound.

¹H NMR (400 MHz, DMSO-d$_6$) δ ppm 0.75-0.90 (m, 9H) 1.19-1.33 (m, 12H) 1.45-1.63 (m, 6H) 7.11-7.22 (m, 1H) 7.50-7.63 (m, 1H) 7.72-7.80 (m, 1H) 8.46 (s, 1H)

MS ES⁺: 410

Scheme 4

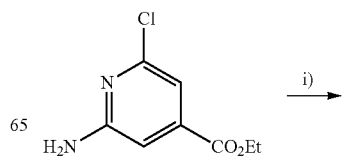

-continued

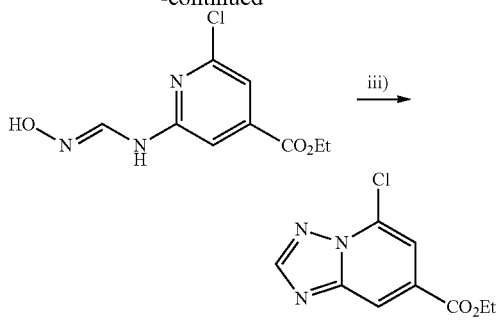

Intermediate 5

Reagents: i) DMF—DMA, IPA then NH$_2$OH•HCl ii) TFAA

Intermediate 5 Ethyl 5-chloro-[1,2,4]triazolo[1,5-a]pyridine-7-carboxylate

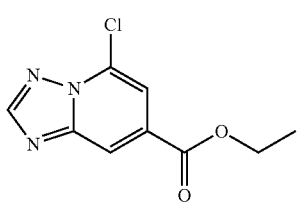

Prepared as described for 5-chloro-6-methyl-[1,2,4]triazolo[1,5-a]pyridine (Intermediate 3) from ethyl 2-amino-6-chloropyridine-4-carboxylate (CAS 28056-05-5) to afford the title compound.

$^1$H NMR (400 MHz, DMSO-d$_6$) δ ppm 1.32-1.44 (m, 3H) 4.34-4.45 (m, 2H) 7.78 (s, 1H) 8.37 (s, 1H) 8.79 (s, 1H)

MS ES$^+$: 226

Scheme 5

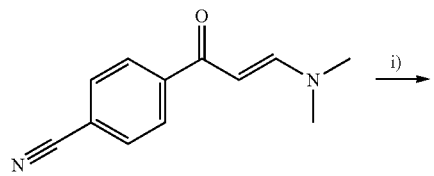

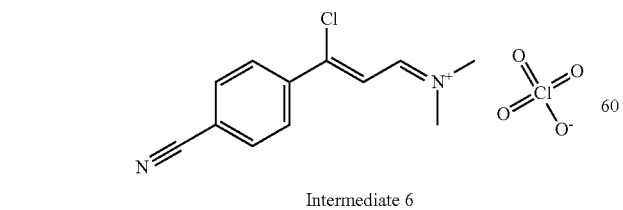

Intermediate 6

Reagents: i) POCl$_3$, DCM

Intermediate 6 [(2Z)-3-Chloro-3-(4-cyanophenyl)prop-2-en-1-ylidene]dimethylazanium perchlorate

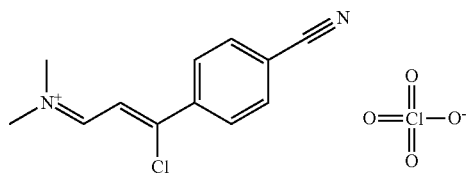

POCl$_3$ (0.512 mL, 5.49 mmol) was slowly added to a solution of 4-[(2E)-3-(dimethylamino)prop-2-enoyl]benzonitrile (CAS 96604-38-5, 1.1 g, 5.49 mmol) in DCM (5.5 mL) at 0° C. under nitrogen. The reaction was stirred at rt for 6 h. The reaction mixture was poured into an ice-cold solution of lithium perchlorate (1.753 g, 16.48 mmol) in water (14 mL) and the solid formed was collected by filtration, then washed with water and cold diethyl ether to afford the title compound.

$^1$H NMR (400 MHz, DMSO-d$_6$) δ ppm 3.70 (s, 3H) 3.81 (s, 3H) 7.81-7.89 (m, 1H) 8.07-8.15 (m, 2H) 8.20-8.29 (m, 2H) 9.01-9.09 (m, 1H)

Scheme 6

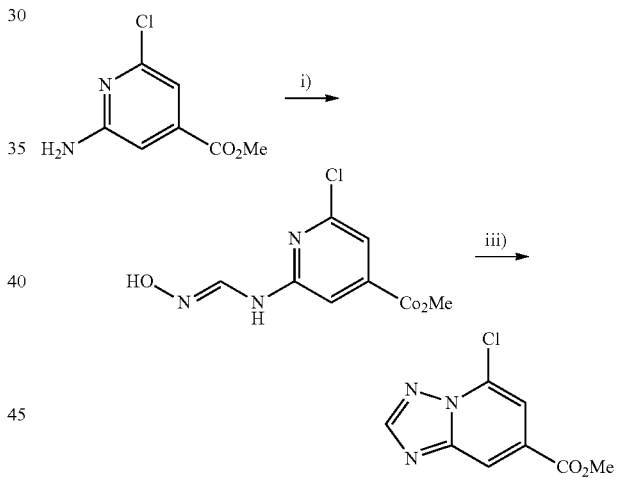

Intermediate 7

Reagents: i) DMF—DMA, IPA then NH$_2$OH•HCl ii) TFAA

Intermediate 7 Methyl 5-chloro-[1,2,4]triazolo[1,5-a]pyridine-7-carboxylate

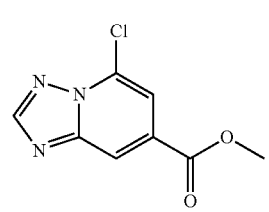

Prepared as described for 5-chloro-6-methyl-[1,2,4]triazolo[1,5-a]pyridine (Intermediate 3) from methyl 2-amino-6-chloropyridine-4-carboxylate (CAS 1005508-80-4) to afford the title compound.

$^1$H NMR (400 MHz, DMSO-d$_6$) δ ppm 3.95 (s, 3H) 7.80-7.85 (m, 1H) 8.37-8.44 (m, 1H) 8.81 (s, 1H)

MS ES$^+$: 212

Intermediate 8 4-{7-Chloro-[1,2,4]triazolo[1,5-a]pyridin-5-yl}benzonitrile

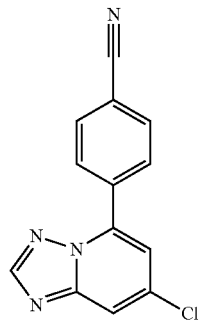 [SMILES: N#Cc1ccc(-c2cc(Cl)cc3ncnn23)cc1]

A suspension of 5,7-dichloro-[1,2,4]triazolo[1,5-a]pyridine (Intermediate 2, 1.5 g, 7.98 mmol), (4-cyanophenyl)boronic acid (CAS 126747-14-6, 1.231 g, 8.38 mmol), PdCl$_2$(dppf) (0.292 g, 0.399 mmol) and Na$_2$CO$_3$ (0.888 g, 8.38 mmol) in dioxane (22 mL) and water (4.4 mL) was de-gassed and refilled with N$_2$. The reaction was heated to reflux for 2 h. The reaction was poured into water and extracted twice with EtOAc. The organics were combined, dried (phase separator) and concentrated in vacuo. The resulting residue was purified by flash chromatography (0-100% EtOAc in petrol on basic silica) to afford the title compound.

$^1$H NMR (400 MHz, DMSO-d$_6$) δ ppm 7.61-7.68 (m, 1H) 8.03-8.13 (m, 2H) 8.15-8.20 (m, 1H) 8.21-8.27 (m, 2H) 8.57-8.67 (m, 1H)

MS ES$^+$: 255

Intermediate 9 4-{5-Chloro-[1,2,4]triazolo[1,5-a]pyrimidin-7-yl}benzonitrile

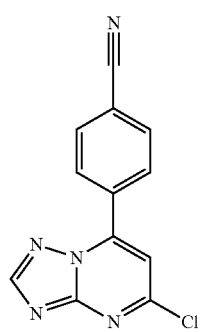 [SMILES: N#Cc1ccc(-c2cc(Cl)nc3ncnn23)cc1]

Water (35 mL) was added to a stirred suspension of 5,7-dichloro-[1,2,4]triazolo[1,5-a]pyrimidine (CAS 78706-26-0, 2 g, 10.58 mmol), PdCl$_2$(dppf) (0.774 g, 1.058 mmol), Na$_2$CO$_3$ (1.178 g, 11.11 mmol) and (4-cyanophenyl)boronic acid (CAS 126747-14-6, 1.555 g, 10.58 mmol) in dioxane (176 mL) under nitrogen. The reaction was heated to 60° C. for 2 h. The reaction mixture was diluted with water and extracted with DCM (3×). The organic extracts were combined and concentrated. The crude product was loaded onto a cation exchange cartridge, washed with MeOH then eluted with 2M ammonia/MeOH solution. Concentration in vacuo afforded the title compound.

MS ES$^+$: 256

Intermediate 10 4-{7-Chloro-[1,2,4]triazolo[1,5-a]pyridin-5-yl}-2-fluorobenzonitrile

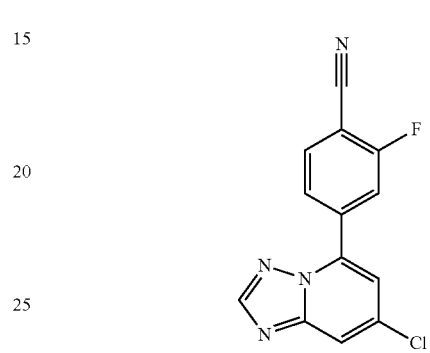

Prepared as described for 4-{7-chloro-[1,2,4]triazolo[1,5-a]pyridin-5-yl}benzonitrile (Intermediate 8) from 5-chloro-6-methyl-[1,2,4]triazolo[1,5-a]pyridine (Intermediate 3) and (4-cyano-3-fluorophenyl)boronic acid (CAS 843663-18-3) to afford the title compound.

$^1$H NMR (400 MHz, DMSO-d$_6$) δ ppm 7.74 (1H, d, J=2 Hz) 8.13-8.19 (2H, m) 8.21-8.28 (2H, m) 8.63 (1H, s)

MS ES$^+$: 273

Intermediate 11 tert-Butyl N-[5-(4-cyano-3-fluorophenyl)-[1,2,4]triazolo[1,5-a]pyridin-7-yl]carbamate

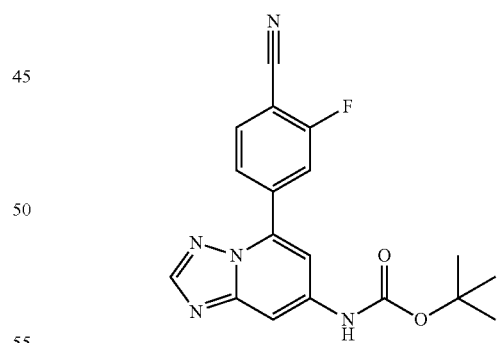

A solution of 4-(7-chloro-[1,2,4]triazolo[1,5-a]pyridin-5-yl)-2-fluorobenzonitrile (Intermediate 10, 3.55 g, 9.11 mmol), tert-butyl carbamate (CAS 4248-19-5, 1.281 g, 10.94 mmol), Pd$_2$(dba)$_3$ (0.835 g, 0.911 mmol), dicyclohexyl(2',4',6'-triisopropyl-[1,1'-biphenyl]-2-yl)phosphine (0.230 g, 0.483 mmol) and Cs$_2$CO$_3$ (8.91 g, 27.3 mmol) in dioxane (30 mL) was de-gassed and refilled with N$_2$ three times. The reaction was heated under N$_2$ to 100° C. overnight. The reaction was poured into EtOAc and washed with brine, the organic phase was separated, dried (phase separator) and concentrated in vacuo. The resulting residue was absorbed onto MgSO₄ and purified by flash chromatography (0-100% EtOAc in petrol on basic silica) to afford the title compound.

¹H NMR (300 MHz, DMSO-d₆) δ ppm 1.53 (s, 9H) 7.51 (s, 1H) 7.90-7.98 (m, 2H) 8.10-8.23 (m, 2H) 8.42 (s, 1H) 10.09 (s, 1H)

MS ES⁺: 354

Scheme 7

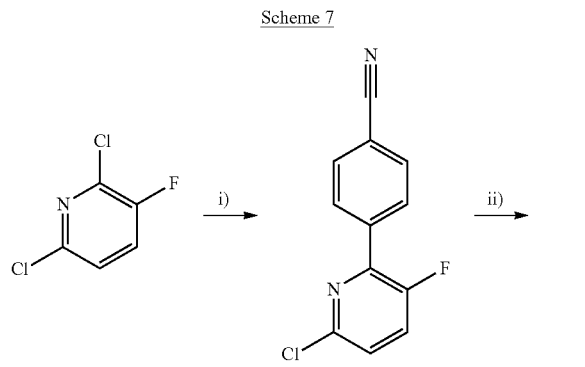

i) Tetrakis K₂CO₃, 4-cyanoboronic acid, ii) Pd₂(dba)₃, Cs₂CO₃, tert-butyl carbamate, dicyclohexyl(2',4',6'-triisopropyl-[1,1'-biphenyl]-2-yl)phosphine, iii) HCl, dioxane, iv) DMF—DMA, IPA, NH₂OH·HCl Intermediate 12 (E)-N-[6-(4-Cyanophenyl)-5-fluoro-pyridin-2-yl]-N'-hydroxymethanimidamide

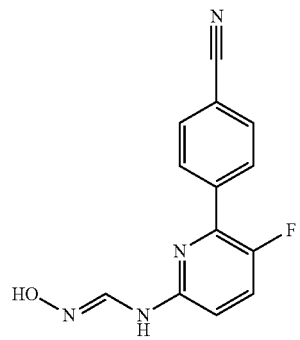 [SMILES: N#Cc1ccc(-c2nc(N/C=N/O)ccc2F)cc1]

Step 1:
A suspension of 2,6-dichloro-3-fluoropyridine (CAS 52208-50-1, 0.5 g, 3.01 mmol), (4-cyanophenyl)boronic acid (CAS 126747-14-6, 0.487 g, 3.31 mmol), tetrakis(triphenylphosphine)palladium(0) (0.139 g, 0.120 mmol) and K₂CO₃ (0.833 g, 6.02 mmol) in THF (6 mL) and water (3 mL) was flushed with N₂ and stirred at rt over the weekend. The reaction mixture was poured into water and extracted with EtOAc. The organic phase was separated, dried (phase separator) and concentrated in vacuo. The resulting residue was purified by flash chromatography (0-100% DCM in petrol on SiO₂) to afford 4-(6-chloro-3-fluoropyridin-2-yl)benzonitrile.

¹H NMR (400 MHz, DMSO-d₆) δ ppm 7.65-7.75 (m, 1H) 7.92-8.13 (m, 5H)

MS ES⁺: 233

Step 2:
A flask containing a suspension of 4-(6-chloro-3-fluoro-pyridin-2-yl)benzonitrile (0.300 g, 1.290 mmol), tert-butyl carbamate (0.181 g, 1.547 mmol), dicyclohexyl(2',4',6'-triisopropyl-[1,1'-biphenyl]-2-yl)phosphine (0.031 g, 0.064 mmol), Pd₂(dba)₃ (0.118 g, 0.129 mmol) and Cs₂CO₃ (1.26 g, 3.87 mmol) in dioxane (5 mL) was evacuated and refilled with N₂. The reaction was heated in a microwave reactor at 100° C. for 30 min. The reaction was poured into water and extracted with EtOAc. The organic was collected, dried (phase separator) and concentrated in vacuo. The resulting residue was purified by flash chromatography (0-100% DCM in petrol then 0-50% EtOAc in DCM) to afford tert-butyl N-[6-(4-cyanophenyl)-5-fluoropyridin-2-yl]carbamate.

MS ES⁻=312

Step 3:
A solution of tert-butyl [6-(4-cyanophenyl)-5-fluoropyridin-2-yl]carbamate (0.325 g, 0.519 mmol) and HCl (4M in dioxane, 0.648 mL, 2.59 mmol) was stirred at rt for 2 h. More HCl (0.648 mL, 2.59 mmol) was added and the reaction was heated to 50° C. for 4 h. The reaction was concentrated in vacuo and the resulting residue was purified by SCX-2, loading and washing with MeOH then eluting with 2M NH₃ in MeOH. The appropriate fractions were collected and concentrated in vacuo to afford 4-(6-amino-3-fluoropyridin-2-yl)benzonitrile.

¹H NMR (400 MHz, DCM-d₂) δ ppm 4.63 (br. s., 2H) 6.53-6.65 (m, 1H) 7.33-7.43 (m, 1H) 7.72-7.83 (m, 2H) 8.07-8.20 (m, 2H)

MS ES⁺: 214

Step 4:

A solution of 4-(6-amino-3-fluoropyridin-2-yl)benzonitrile (0.160 g, 0.750 mmol) and DMF-DMA (0.141 mL, 1.05 mmol) in IPA (2.5 mL) was heated to reflux for 2 h. The temperature was reduced to 50° C. and hydroxylamine hydrochloride (73.0 mg, 1.05 mmol) was added. The reaction was stirred at 50° C. for 30 min then the reaction mixture was conccentrated in vacuo and the resulting residue was triturated with EtOH, filtered and dried to afford the title compound.

$^1$H NMR (300 MHz, DMSO-$d_6$) δ ppm 7.09-7.26 (m, 1H) 7.66-7.85 (m, 1H) 7.87-8.06 (m, 3H) 8.11-8.23 (m, 2H) 9.57-9.65 (m, 1H) 10.18 (s, 1H)

MS ES$^+$=257

Intermediate 13 2-Chloro-N-(5-(4-cyanophenyl)-[1,2,4]triazolo[1,5-a]pyridin-7-yl)acetamide A solution of TEA (0.308 mL, 2.208 mmol) and the HCl salt of 4-(7-amino-[1,2,4]triazolo[1,5-a]pyridin-5-yl)benzonitrile (Example 100) (200 mg, 0.736 mmol) in DMF (2.5 mL) was cooled to 0° C. and chloroacetyl chloride (CAS 79-04-9, 0.088 mL, 1.104 mmol) was added. The reaction was stirred at 0° C. for 0.5 hrs. The reaction was diluted with brine and extracted with EtOAc. The organic phase was washed with brine, dried (phase separator) and concentrated in vacuo. The crude product was purified by flash chromatography (0-100% EtOAc in petrol on SiO$_2$) to afford the title compound.

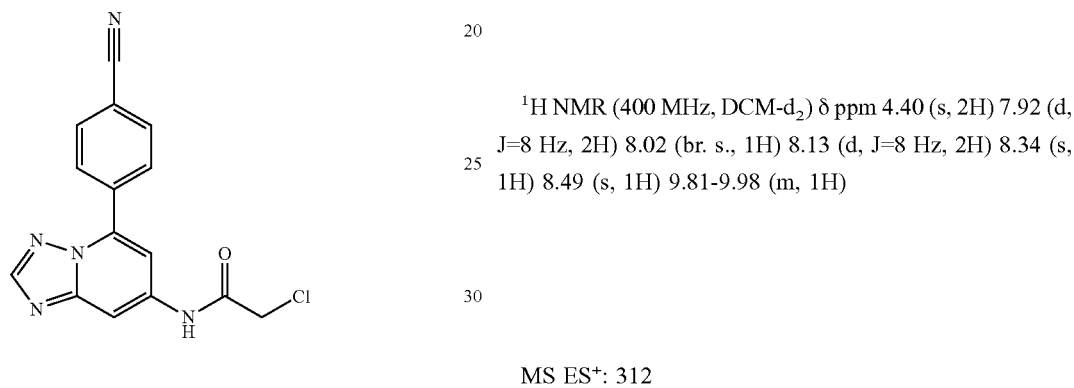

$^1$H NMR (400 MHz, DCM-$d_2$) δ ppm 4.40 (s, 2H) 7.92 (d, J=8 Hz, 2H) 8.02 (br. s., 1H) 8.13 (d, J=8 Hz, 2H) 8.34 (s, 1H) 8.49 (s, 1H) 9.81-9.98 (m, 1H)

MS ES$^+$: 312

Scheme 8

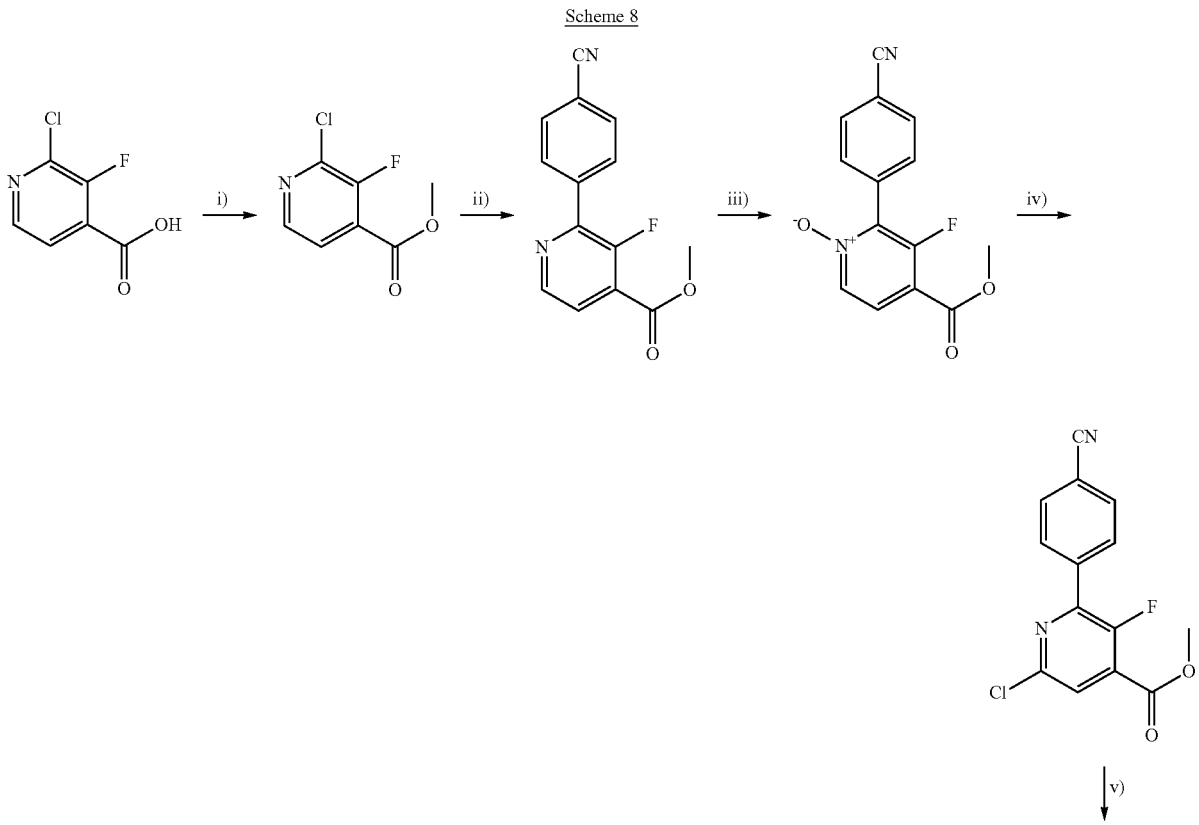

-continued

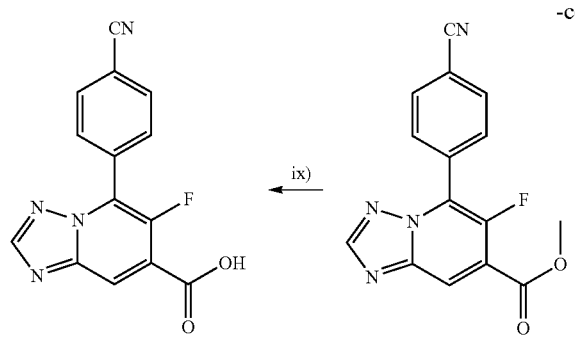 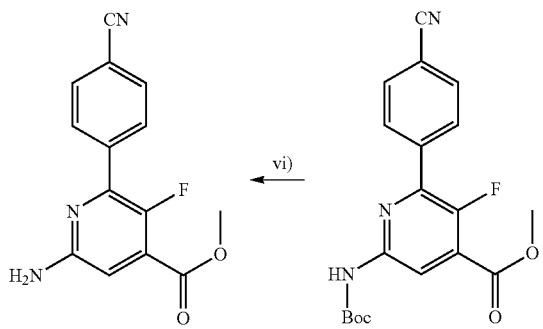

Reagents: i) TMS-diazomethane, MeOH, DCM ii) (4-cyanophenyl) boronic acid, PdCl₂(dppf), NaCO₃, dioxane, water iii) m-CPBA, DCM, iv) POCl₃, v) tert-butyl carbamate, Pd₂(dba)₃, dicyclohexyl(2′,4′,6′-triisopropyl-[1,1′-biphenyl]-2-yl)phosphine, Cs₂CO₃, dioxane, vi) HCl, dioxane, vii) DMF—DMA, TEA, IPA then hydroxylamine hydrochloride, viii) TFAA, THF, ix) LiOH, MeOH, THF Intermediate 14 5-(4-Cyanophenyl)-6-fluoro-[1,2,4]triazolo[1,5-a]pyridine-7-carboxylic acid

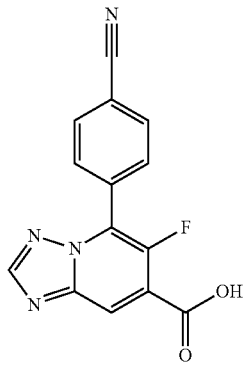 [SMILES: N#Cc1ccc(-c2c(F)c(C(=O)O)cc3ncnn23)cc1]

Step 1:

A suspension of 2-chloro-3-fluoropyridine-4-carboxylic acid (CAS 628691-93-0, 2 g, 11.39 mmol) in MeOH (7 mL) and DCM (21 mL) at 0° C. was treated with TMS-Diazomethane (5.70 mL, 11.39 mmol) in a drop wise fashion. The reaction was stirred at 0° C. for 0.5 h. The reaction was quenched with AcOH (0.5 mL) and concentrated in vacuo. The residue was purified by flash chromatography (0-100% EtOAc in petrol on SiO₂) to afford methyl 2-chloro-3-fluoropyridine-4-carboxylate.

¹H NMR (300 MHz, Methanol-d₄) δ ppm 3.97 (s, 3H) 7.76-7.86 (m, 1H) 8.29-8.40 (m, 1H)

Step 2:

A suspension of methyl 2-chloro-3-fluoropyridine-4-carboxylate (1.7 g, 8.97 mmol), (4-cyanophenyl)boronic acid (CAS 126747-14-6, 1.384 g, 9.42 mmol), PdCl₂(dppf)-CH₂Cl₂ adduct (0.366 g, 0.448 mmol) and Na₂CO₃ (0.998 g, 9.42 mmol) in dioxane (25 mL) and water (5 mL) was flushed with N₂ and heated to 100° C. for 1 h. The reaction was cooled to rt and partitioned between EtOAc and water. The organic was collected, dried (phase separator) and concentrated in vacuo. The residue was purified by flash chromatography (0-100% DCM in petrol on SiO₂) to afford methyl 2-(4-cyanophenyl)-3-fluoropyridine-4-carboxylate.

¹H NMR (300 MHz, Methanol-d₄) δ ppm 4.01 (s, 3H) 7.83-7.99 (m, 3H) 8.08-8.20 (m, 2H) 8.64-8.72 (m, 1H)

MS ES⁺: 257

Step 3:

A solution of methyl 2-(4-cyanophenyl)-3-fluoropyridine-4-carboxylate (1.27 g, 4.96 mmol) in DCM (20 mL) was treated with m-CPBA (1.326 g, 7.68 mmol). The mixture was stirred at rt for 4 days. The reaction was diluted with DCM, washed with sat. bicarb. solution, dried (phase separator) and concentrated in vacuo to afford 2-(4-cyanophenyl)-3-fluoro-4-(methoxycarbonyl)pyridine 1-oxide, which was used in the next step without purification ¹H NMR (300 MHz, Methanol-d₄) δ ppm 3.98 (s, 3H) 7.50-7.57 (m, 1H) 7.65-7.74 (m, 1H) 7.79-7.86 (m, 2H) 7.86-7.93 (m, 2H)

MS ES⁺: 273

Step 4:

A solution of 2-(4-cyanophenyl)-3-fluoro-4-(methoxycarbonyl)pyridine 1-oxide (1.35 g, 4.96 mmol) in POCl₃ (9.24 mL, 99 mmol) was heated to 60° C. for 24 h. The reaction was concentrated in vacuo and the resulting residue was purified by flash chromatography (0-50% EtOAc in petrol on SiO₂) to afford methyl 6-chloro-2-(4-cyanophenyl)-3-fluoropyridine-4-carboxylate.

¹H NMR (400 MHz, Methanol-d₄) δ ppm 4.01 (s, 3H) 7.85-7.96 (m, 3H) 8.10-8.19 (m, 2H)

MS ES⁺: 291

Step 5:

A flask was charged with methyl 6-chloro-2-(4-cyanophenyl)-3-fluoropyridine-4-carboxylate (1.03 g, 3.54 mmol), tert-butyl carbamate (0.830 g, 7.09 mmol), dicyclohexyl(2′,4′,6′-triisopropyl-[1,1′-biphenyl]-2-yl)phosphine (0.068 g, 0.142 mmol), Cs₂CO₃ (2.309 g, 7.09 mmol) and Pd₂(dba)₃ (0.065 g, 0.071 mmol). The flask was evacuated and refilled with N₂ three times. Dioxane (12 mL) was added and the mixture was heated to 90° C. for 1 h. The reaction was cooled to rt and partitioned between EtOAc and water. The organic phase was washed with brine, dried (phase separator) and concentrated in vacuo to afford methyl 6-((tert-butoxycarbonyl)amino)-2-(4-cyanophenyl)-3-fluoropyridine-4-carboxylate, which was used in the next step without further purification.

¹H NMR (400 MHz, Methanol-d₄) δ ppm 1.55 (s, 9H) 3.98 (s, 3H) 7.78-7.91 (m, 2H) 8.13 (s, 2H) 8.29-8.42 (m, 1H)

MS ES⁺: 316 (M-ᵗBu)

Step 6:

A solution of methyl 6-((tert-butoxycarbonyl)amino)-2-(4-cyanophenyl)-3-fluoropyridine-4-carboxylate (1.37 g, 3.69 mmol) and HCl (4M in dioxane, 4.61 mL, 18.45 mmol) in dioxane (15 mL) was heated to 50° C. overnight. More HCl (4M in dioxane, 4.61 mL, 18.45 mmol) was added and the reaction was heated to 60° C. for a further 2 h. The mixture was concentrated in vacuo to afford crude methyl 6-amino-2-(4-cyanophenyl)-3-fluoropyridine-4-carboxylate hydrochloride, which was used in the next step without purification.

MS ES+: 272

Step 7:

A solution of methyl 6-amino-2-(4-cyanophenyl)-3-fluoropyridine-4-carboxylate hydrochloride (1.1 g, 3.57 mmol), TEA (0.498 mL, 3.57 mmol) and DMF-DMA (0.766 mL, 5.72 mmol) in IPA (10 mL) was heated to 80° C. for 1 hr. More TEA (0.498 mL, 3.57 mmol) and DMF-DMA (0.766 mL, 5.72 mmol) was added and the reaction was heated overnight at 80° C. More TEA (0.498 mL, 3.57 mmol) and DMF-DMA (0.766 mL, 5.72 mmol) was added and the reaction was heated for a further 3 h. The reaction was cooled to 50° C. and hydroxylamine hydrochloride (0.397 g, 5.72 mmol) was added. The reaction was stirred at 50° C. for a further 30 min. More hydroxylamine hydrochloride (0.397 g, 5.72 mmol) was added and the reaction was heated for a further 30 min. The reaction was concentrated in vacuo and the resulting residue was absorbed onto MgSO4 and purified by flash chromatography (0-100% EtOAc in petrol then 0-20% MeOH in EtOAc on basic silica) to afford methyl 2-(4-cyanophenyl)-3-fluoro-6-[(E)-N-hydroxyimidamido]pyridine-4-carboxylate.

MS ES+: 315

Step 8:

A solution of methyl 2-(4-cyanophenyl)-3-fluoro-6-[(E)-N-hydroxyimidamido]pyridine-4-carboxylate (1.1 g, 3.50 mmol) in THF (15 mL) was treated with TFAA (1.978 mL, 14.00 mmol) and heated to 40° C. for 1 hr. The reaction was basified with sat. NaHCO3 and partitioned between DCM and water. The organic was collected, dried (phase separator) and concentrated in vacuo. The resulting residue was triturated with EtOH, filtered and dried to afford methyl 5-(4-cyanophenyl)-6-fluoro-[1,2,4]triazolo[1,5-a]pyridine-7-carboxylate.

¹H NMR (400 MHz, DMSO-d6) δ ppm 3.93-4.03 (m, 3H) 7.99-8.06 (m, 2H) 8.08-8.15 (m, 2H) 8.44-8.53 (m, 1H) 8.67-8.71 (m, 1H)

MS ES+: 297

Step 9:

A solution of methyl 5-(4-cyanophenyl)-6-fluoro-[1,2,4]triazolo[1,5-a]pyridine-7-carboxylate (220 mg, 0.743 mmol) and LiOH (2M in water, 3.71 mL, 7.43 mmol) in THF (4 mL) and MeOH (4 mL) was stirred at rt for 1 h. 2N HCl (3.71 mL) was added and the mixture was partitioned between EtOAc and water. The organic phase was collected, dried (phase separator) and concentrated in vacuo to afford 5-(4-cyanophenyl)-6-fluoro-[1,2,4]triazolo[1,5-a]pyridine-7-carboxylic acid (Intermediate 14)

¹H NMR (400 MHz, DMSO-d6) δ ppm 7.95-8.03 (m, 2H) 8.07-8.17 (m, 2H) 8.35-8.47 (m, 1H) 8.67 (s, 1H) 14.01-14.19 (m, 1H)

MS ES+ 237 (M-CO2H)

Scheme 9

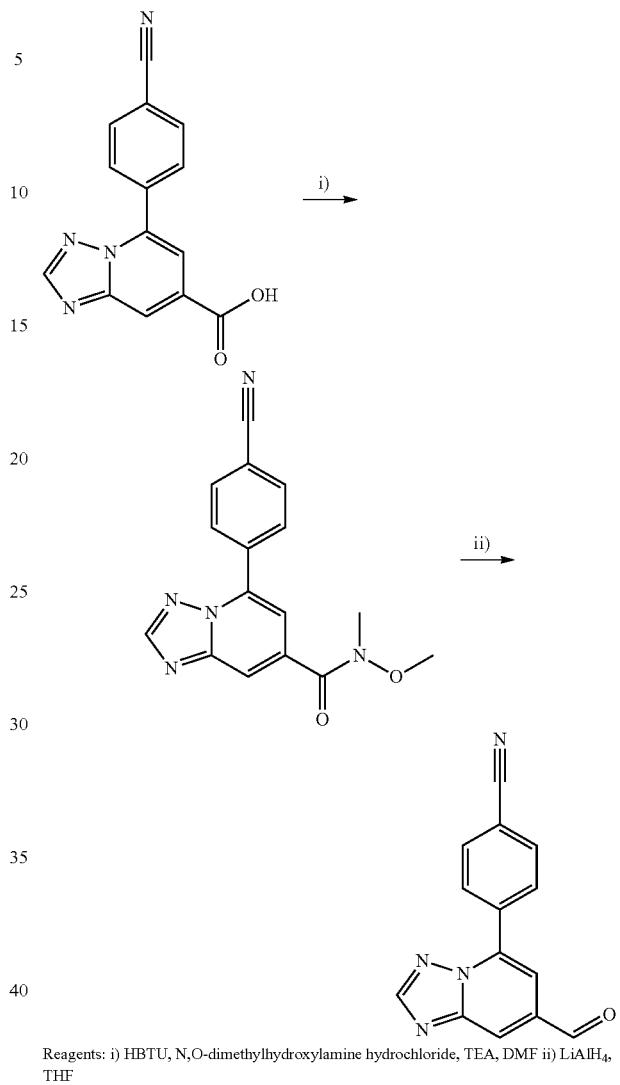

Reagents: i) HBTU, N,O-dimethylhydroxylamine hydrochloride, TEA, DMF ii) LiAlH4, THF Intermediate 15 4-(7-Formyl-[1,2,4]triazolo[1,5-a]pyridin-5-yl)benzonitrile

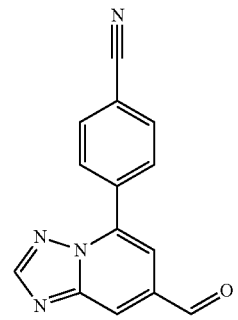 [SMILES: N#Cc1ccc(-c2cc(C=O)cc3ncnn23)cc1]

Step 1:

HBTU (19.6 g, 50 mmol) in DMF (50 mL) was added to a stirred suspension of 5-(4-cyanophenyl)-[1,2,4]triazolo[1, 5-a]pyridine-7-carboxylic acid (Example 41, 12.40 g, 47 mmol), N,O-dimethylhydroxylamine hydrochloride (6.9 g, 70 mmol) and TEA (16.3 mL, 117 mmol) in dry DMF (150 mL) and was held at room temperature for 1 hr. The reaction mixture was poured into EtOAc and washed with water (×3). The organic phase was concentrated and the residue was purified by flash chromatography (0-10% MeOH in EtOAc on $SiO_2$) to give 5-(4-cyanophenyl)-N-methoxy-N-methyl-[1,2,4]triazolo[1,5-a]pyridine-7-carboxamide.

$^1$H NMR (300 MHz, $CDCl_3$) δ ppm 3.40 (s, 3H) 3.64 (s, 3H) 7.53 (m, 1H) 7.85 (m, 2H) 8.12 (m, 2H) 8.24 (m, 1H) 8.46 (s, 1H).

MS ES$^+$: 308.

Step 2:

1M $LiAlH_4$ in THF (0.72 mL, 0.72 mmol) was added drop wise to a stirred solution of 5-(4-cyanophenyl)-N-methoxy-N-methyl-[1,2,4]triazolo[1,5-a]pyridine-7-carboxamide (300 mg, 0.98 mmol) in dry THF (10 mL) at −10° C. After 30 min, 1 M HCl (aq) (5 mL) was added and stirring was continued at room temperature for 15 min. The reaction mixture was extracted with EtOAc, then the organic phase was washed with brine, dried over $MgSO_4$ and concentrated to afford 4-(7-formyl-[1,2,4]triazolo[1,5-a]pyridin-5-yl)benzonitrile.

$^1$H NMR (400 MHz, $CDCl_3$) δ ppm 7.67 (m, 1H) 7.88-7.90 (m, 2H) 8.13-8.15 (m, 2H) 8.31-8.33 (m, 1H) 8.55 (s, 1H) 10.18 (s, 1H),

MS ES$^+$: 249 for 1 h. The cooled reaction mixture was poured into a mixture of water and crushed ice. The pH was adjusted to 10 using 10N NaOH, and the solution was concentrated in vacuo. The resulting slurry was filtered, washed once with cold water and dried in vacuo at 50° C. to afford [1,2,4]triazolo[1,5-a]pyrimidin-7-ol.

$^1$H NMR (300 MHz, DMSO-$d_6$) δ ppm 5.82-5.84 (d, J=7 Hz, 1H), 7.91-7.93 (d, J=7 Hz, 1H) and 8.13 (s, 1H).

MS ES$^+$: 155

Step 2:

A stirred mixture of phosphoryl trichloride (85 mL, 917 mmol, 13 eq.), [1,2,4]triazol[1,5-a]pyrimidin-7-ol (9.6 g, 70.53 mmol, 1 eq.) and tetraethylammonium chloride (584 mg, 3.53 mmol, 0.05 eq.) was heated under reflux for 16 h. Excess phosphoryl trichloride was removed under vacuum and the residue was treated with EtOAc and 2 N $K_2CO_3$ (aq). Once the vigorous effervescence had ceased, the mixture was filtered under vacuum. The filter-cake was washed with water and then dried by azeotroping with MeCN to afford 7-chloro-[1,2,4]triazolo[1,5-a]pyrimidine. A second crop of 7-chloro-[1,2,4]triazolo[1,5-a]pyrimidine was obtained by extraction of the filtrates with EtOAc. Both crops of material were of sufficient quality to be used without further purification.

$^1$H NMR (300 MHz, DMSO-$d_6$) δ ppm 7.69-7.7 (m, 1H) 8.76 (s, 1H) 8.82-8.84 (m, 1H).

MS ES$^+$: 155

Scheme 10

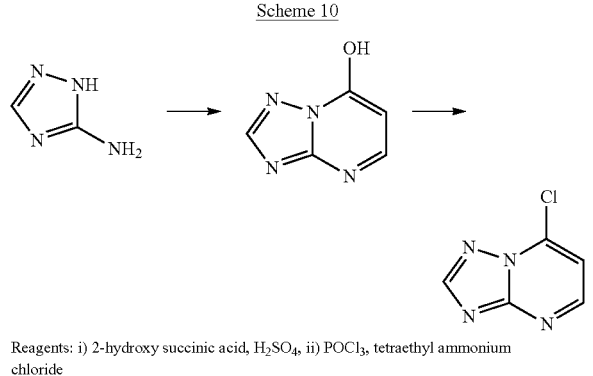

Reagents: i) 2-hydroxy succinic acid, $H_2SO_4$, ii) $POCl_3$, tetraethyl ammonium chloride Intermediate 16 7-Chloro-[1,2,4]triazolo[1,5-a]pyrimidine Step 1:

2-Hydroxysuccinic acid (CAS 97-67-6, 33.5 g, 250 mmol, 1.05 eq.) was added as a powder to ice-cold stirred concentrated sulfuric acid (95 mL). 1H-1,2,4-triazol-5-amine (CAS 61-82-5, 20 g, 238 mmol) was added at a rate such that the temperature remained below 10° C. throughout. The reaction mixture was then allowed to warm to room temperature and stirred for 12 h, and then heated at 100° C.

Scheme 11

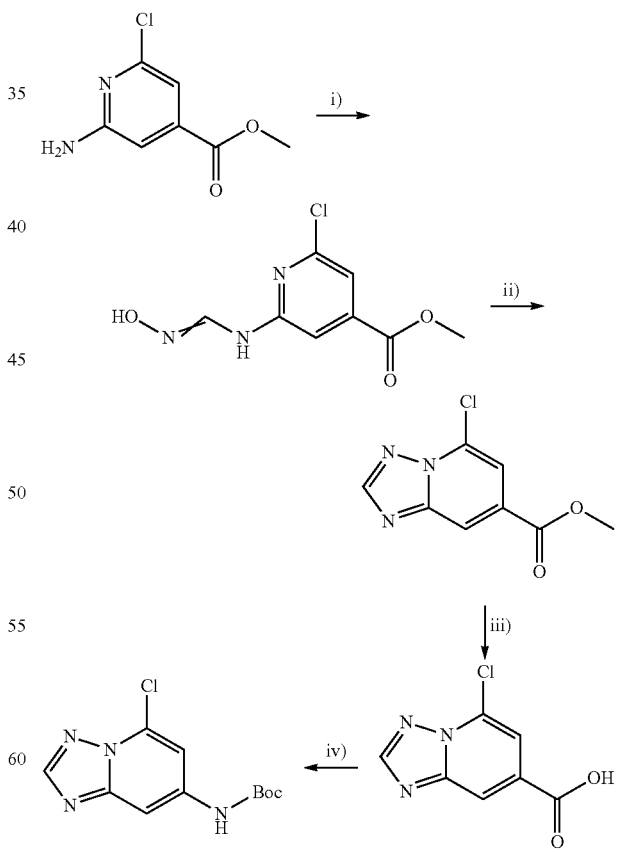

Reagents: i) DMF—DMA, IPA then $NH_2OH·HCl$, ii) TFAA, iii) LiOH, THF, MeOH, iv) diphenyl phosphorazidate, TEA, tert-butanol, Toluene

Intermediate 17 tert-Butyl N-(5-chloro-[1,2,4]triazolo[1,5-a]pyridin-7-yl)carbamate

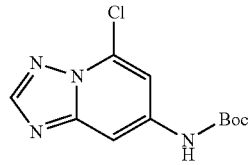 [SMILES: CC(C)(C)OC(=O)Nc1cc(Cl)n2ncnc2c1]

Step 1:

A solution of methyl 2-amino-6-chloropyridine-4-carboxylate (CAS 1005508-80-4, 10 g, 53.6 mmol) and DMF-DMA (7.18 mL, 53.6 mmol) was heated to 70° C. for 2 h. More DMF-DMA (7.18 mL, 53.6 mmol) was added and the reaction was heated for a further 4 h. The reaction was cooled to 50° C. and hydroxylamine hydrochloride (3.72 g, 53.6 mmol) was added. The reaction was stirred at 50° C. for 2 h. The reaction was concentrated in vacuo and the resulting residue was triturated with EtOH. The solid was filtered and dried under vacuum to afford methyl 2-chloro-6-(N-hydroxyimidamido)pyridine-4-carboxylate.

$^1$H NMR (400 MHz, DMSO-$d_6$) δ ppm 3.32 (s, 3H), 7.22-7.26 (m, 1H), 7.57-7.61 (m, 1H) 7.69-7.74 (m, 1H), 10.00-10.04 (m, 1H), 10.40 (s, 1H)

MS ES$^+$: 230

Step 2:

A solution of methyl 2-chloro-6-(N-hydroxyimidamido)pyridine-4-carboxylate (12 g, 52.3 mmol) in THF (100 mL) was treated with TFAA (14.76 mL, 105 mmol). The reaction was heated to 40° C. for 7 h then maintained at rt overnight. The reaction was quenched and basified with NaHCO$_3$ (aq) and partitioned between EtOAc and water. The organic phase was collected, dried (phase separator) and concentrated in vacuo. The resulting residue was purified by flash chromatography (0-100% EtOAc in petrol on SiO$_2$) to afford methyl 5-chloro-[1,2,4]triazolo[1,5-a]pyridine-7-carboxylate.

$^1$H NMR (400 MHz, Methanol-$d_4$) δ ppm 4.03 (s, 3H) 7.84-7.90 (m, 1H) 8.40-8.49 (m, 1H) 8.66 (s, 1H)

MS ES$^+$: 212

Step 3:

A solution of methyl 5-chloro-[1,2,4]triazolo[1,5-a]pyridine-7-carboxylate (6.44 g, 30.4 mmol) in MeOH (50 mL) and THF (50 mL) was treated with LiOH (2M aq, 30.4 mL, 60.9 mmol). The reaction was stirred at rt for 1 h. The reaction was acidified with 2N HCl (30 mL) and the resulting precipitate was filtered, washed with MeOH and dried to afford 5-chloro-[1,2,4]triazolo[1,5-a]pyridine-7-carboxylic acid.

$^1$H NMR (400 MHz, DMSO-$d_6$) δ ppm 7.74-7.83 (m, 1H) 8.29-8.40 (m, 1H) 8.79 (s, 1H) 13.98 (s, 1H)

MS ES$^+$: 198

Step 4:

A suspension of 5-chloro-[1,2,4]triazolo[1,5-a]pyridine-7-carboxylic acid (4 g, 20.25 mmol) in toluene (100 mL) was treated sequentially with TEA (4.23 mL, 30.4 mmol), tert-butanol (2.90 mL, 30.4 mmol) and diphenyl phosphorazidate (4.36 mL, 20.25 mmol). The reaction was heated to 90° C. under N$_2$ for 30 min. The reaction was concentrated in vacuo and the resulting residue was purified by flash chromatography (0-100% EtOAc in petrol on SiO$_2$) to afford the title compound.

$^1$H NMR (400 MHz, DCM-$d_2$) δ ppm 1.53 (s, 9H) 7.18 (s, 1H) 7.36-7.47 (m, 1H) 7.67-7.74 (m, 1H) 8.26 (s, 1H)

MS ES$^+$: 213 (M-$^t$Bu)

Scheme 12

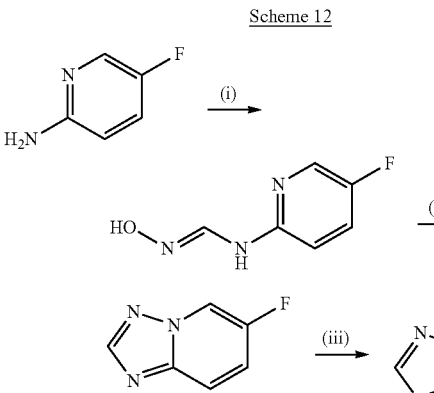

Reagents: i) DMF—DMA, IPA then NH$_2$OH•HCl, ii) TFAA, THF iii) lithium magnesium 2,2,6,6-tetramethylpiperidin-1-ide dichloride, Iodine, THF

Intermediate 18 6-Fluoro-5-iodo-[1,2,4]triazolo[1,5-a]pyridine

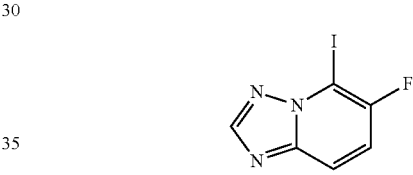

Step 1:

A solution of 5-fluoropyridin-2-amine (CAS 21717-96-4, 10 g, 89 mmol) and DMF-DMA (19.11 mL, 143 mmol) in IPA (100 mL) was heated to 70° C. overnight. The reaction was cooled to ~50° C. and hydroxylamine hydrochloride (9.92 g, 143 mmol) was added. The reaction was heated at 50° C. for a further 30 min. The reaction was cooled and concentrated in vacuo. The resulting residue was triturated with a minimum amount of IPA with a few drops of water. The precipitate was filtered and dried to afford N-(5-fluoropyridin-2-yl)-N'-hydroxyformimidamide.

$^1$H NMR (300 MHz, DMSO-$d_6$) δ ppm 7.00-7.15 (m, 1H) 7.51-7.66 (m, 1H) 7.75 (d, J=10 Hz, 1H) 8.04-8.16 (m, 1H) 9.41 (d, J=10 Hz, 1H) 10.07 (s, 1H)

MS ES$^+$: 156

Step 2:

A solution of N-(5-fluoropyridin-2-yl)-N'-hydroxymethanimidamide (13.8 g, 89 mmol) in THF (148 mL) was treated with TFAA (25.1 mL, 178 mmol). The reaction was heated to 40° C. for 1 h. The reaction was diluted with water, basified with solid NaHCO$_3$ and extracted with EtOAc. The organic phase was collected, dried (phase separator) and concentrated in vacuo. The resulting residue was purified by flash chromatography (0-60% EtOAc in petrol on SiO$_2$) to afford 6-fluoro-[1,2,4]triazolo[1,5-a]pyridine $^1$H NMR (400 MHz, Methanol-$d_4$) δ ppm 7.65-7.77 (m, 1H) 7.81-7.89 (m, 1H) 8.45 (s, 1H) 8.90-9.04 (m, 1H)

MS ES$^+$: 138

Step 3:

Lithium magnesium 2,2,6,6-tetramethylpiperidin-1-ide dichloride (1M THF/toluene) (8.75 mL, 8.75 mmol) was added drop wise to a solution of 6-fluoro-[1,2,4]triazolo[1,5-a]pyridine (1 g, 7.29 mmol) in THF (25 mL) at −20° C. under argon. The reaction was stirred at −20° C. for 1 h. A solution of iodine (2.221 g, 8.75 mmol) in THF (20 mL) was added drop wise over 30 min at −20° C. and the reaction was allowed to warm to rt for 1 h. The reaction was quenched and diluted with water. The resulting precipitate was filtered and dried to afford the title compound.

$^1$H NMR (300 MHz, DMSO-$d_6$) δ ppm 7.71-7.83 (m, 1H) 7.84-7.97 (m, 1H) 8.60 (s, 1H)

MS ES$^+$: 264

Scheme 13

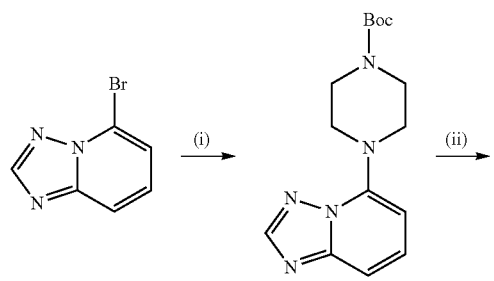

Reagents: i) N-Boc piperazine, NMP ii) HCl, NMP

Intermediate 19 1-{[1,2,4]Triazolo[1,5-a]pyridin-5-yl}piperazine

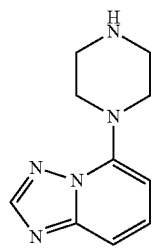 [SMILES: c1cc(N2CCNCC2)n2ncnc2c1]

Step 1:

A mixture of 5-bromo-[1,2,4]triazolo[1,5-a]pyridine (0.2 g, 1.010 mmol) and tert-butyl piperazine-1-carboxylate (CAS 57260-71-6, 0.752 g, 4.04 mmol) in NMP (2 mL) was degassed with nitrogen before being irradiated in a microwave reactor at 120° C. for 40 mins. The reaction was diluted with HCl (3% aqueous) and extracted with DCM. The organic phases were combined, dried (phase separator) and concentrated in vacuo. The crude product was absorbed onto silica and was purified by flash chromatography (0-100% EtOAc in petrol on SiO$_2$) to afford tert-butyl 4-([1,2,4]triazolo[1,5-a]pyridin-5-yl)piperazine-1-carboxylate.

MS ES$^+$: 304

Step 2:

To a stirred solution of tert-butyl 4-([1,2,4]triazolo[1,5-a]pyridin-5-yl)piperazine-1-carboxylate (0.306 mg, 1.01 mmol) in NMP (0.5 mL) was added HCl [4.0 M in dioxane] (2.53 mL, 10.10 mmol) and the reaction was stirred at rt for 1 h. The reaction mixture was concentrated in vacuo to remove excess HCl and the residue was treated with 7N methanolic ammonia (5-10 mL) and was again concentrated in vacuo to remove excess ammonia. The sample was purified by SCX-2, loading and washing with MeOH and eluting with 1M NH$_3$ in MeOH to afford the title compound.

$^1$H NMR (400 MHz, DMSO-$d_6$) δ ppm 3.20-3.35 (m, 4H) 3.56-3.71 (m, 4H) 6.67 (d, J=7 Hz, 1H) 7.48 (d, J=9 Hz, 1H) 7.58-7.71 (m, 1H) 8.49 (s, 1H) 8.60-9.06 (m, 1H)

MS ES$^+$: 204

Intermediate 20 5-(Trimethylstannyl)-[1,2,4]triazolo[1,5-a]pyridine

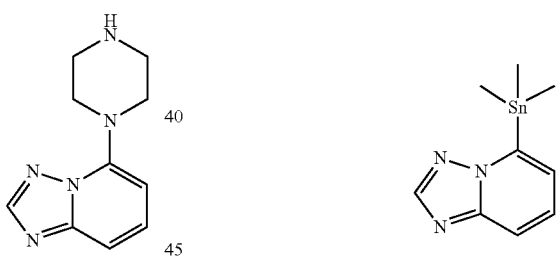

To a stirred solution of 5-bromo-[1,2,4]triazolo[1,5-a]pyridine (2 g, 10.10 mmol) in THF (40 mL) at −60° C. under a nitrogen atmosphere was added n-BuLi [2.5M in hexanes] (4.85 mL, 12.12 mmol) drop wise over 5 min. The temperature was reduced to −78° C. and the reaction was stirred at −78° C. for 1 h. To the stirred reaction mixture was added chlorotrimethylstannane [1.0M in THF] (12.12 mL, 12.12 mmol) over 5 min. The reaction was stirred at −78° C. for a further 1 h. The reaction was quenched at −78° C. with sat. (aq.) NaHCO$_3$ and allowed to warm to room temperature. The reaction was partitioned between EtOAc and water. The organic phase was washed with water and brine then concentrated in vacuo. The crude product was absorbed onto diatomaceous earth and purified by flash chromatography (0-40% EtOAc in petrol on basic silica) to afford the title compound.

$^1$H NMR (400 MHz, DMSO-$d_6$) δ ppm 0.40-0.50 (m, 9H) 7.12-7.19 (m, 1H) 7.49-7.60 (m, 1H) 7.71-7.78 (m, 1H) 8.45 (s, 1H)

MS ES$^+$: 284

Intermediate 21 4-(7-(Aminomethyl)-[1,2,4]triazolo[1,5-a]pyridin-5-yl)benzonitrile

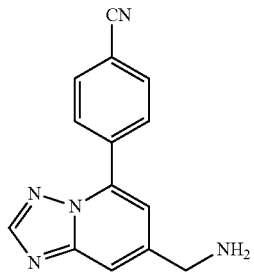 [SMILES: N#Cc1ccc(-c2cc(CN)cc3ncnn23)cc1]

Step 1:
A solution of 4-(7-(hydroxymethyl)-[1,2,4]triazolo[1,5-a]pyridin-5-yl)benzonitrile (Example 39, 0.180 g, 0.719 mmol), phthalimide (0.138 g, 0.935 mmol) and triphenylphosphine (0.245 g, 0.935 mmol) in dry THF (3 mL) was treated with DIAD (0.182 mL, 0.935 mmol). The mixture was stirred at rt for 3 h. The mixture was partitioned between EtOAc, 2-methyl-THF, and brine, separated, dried (phase separator) and concentrated in vacuo. The resulting solid was purified by flash chromatography (0-100% ethyl acetate in petrol on basic silica) to afford 4-(7-((1,3-dioxo-2,3-dihydro-1H-isoindol-2-yl)methyl]-[1,2,4]triazolo[1,5-a]pyridin-5-yl}benzonitrile
MS ES$^+$: 380
Step 2:
To a suspension of 4-(7-((1,3-dioxo-2,3-dihydro-1H-isoindol-2-yl)methyl]-[1,2,4]triazolo[1,5-a]pyridin-5-yl}benzonitrile (0.100 g, 0.264 mmol) in EtOH (2 mL) was added methanamine, 40% aq. (600 µL, 6.93 mmol). The reaction was stirred at rt for 20 h. The reaction was diluted with brine and extracted twice with EtOAc. The organic phases were combined, dried (phase separator) and concentrated in vacuo to afford the title compound.
MS ES$^+$: 250

Intermediate 22 6-Methyl-5-(tetramethyl-1,3,2-dioxaborolan-2-yl)pyridine-2-carbonitrile

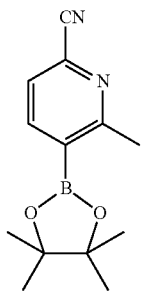

A suspension of 5-bromo-6-methylpyridine-2-carbonitrile (CAS 1173897-86-3, 0.195 g, 0.990 mmol), PdCl$_2$(dppf) (0.072 g, 0.099 mmol), bis(pinocolato)diboron (0.352 g, 1.386 mmol) and potassium acetate (0.194 g, 1.979 mmol) in dry DMSO (1.979 mL) was degassed (vacuum/nitrogen cycles) and heated in a sealed tube at 90° C. for 4 h. The mixture was diluted with EtOAc, washed sequentially with water and brine, dried (phase separator) and concentrated in vacuo. The resulting residue was purified by flash chromatography (0-30% EtOAc in petrol on SiO$_2$) to afford the title compound.
MS ES$^+$: 245

Intermediate 22 Ethyl 5-(4-cyanophenyl)-[1,2,4]triazolo[1,5-a]pyridine-7-carboxylate

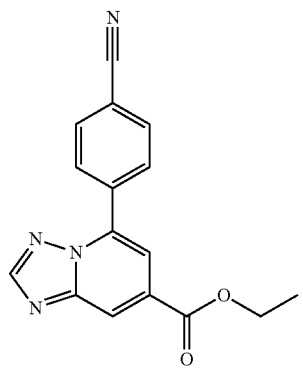 [SMILES: CCOC(=O)c1cc(-c2ccc(C#N)cc2)n2ncnc2c1]

Prepared as described for 4-{7-chloro-[1,2,4]triazolo[1,5-a]pyridin-5-yl}benzonitrile (Intermediate 8) from ethyl 5-chloro-[1,2,4]triazolo[1,5-a]pyridine-7-carboxylate (Intermediate 5, 1.23 g, 5.45 mmol) and (4-cyanophenyl)boronic acid (CAS 126747-14-6, 0.961 g, 6.54 mmol) to afford the title compound.
$^1$H NMR (400 MHz, DMSO-d$_6$) δ ppm 1.33-1.45 (m, 3H) 4.36-4.49 (m, 2H) 7.75-7.83 (m, 1H) 8.04-8.13 (m, 2H) 8.20-8.28 (m, 2H) 8.43-8.50 (m, 1H) 8.75 (s, 1H)
MS ES$^+$: 293

Intermediate 24 4-{7-Chloro-[1,2,4]triazolo[1,5-a]pyridin-5-yl}-3-methylbenzonitrile

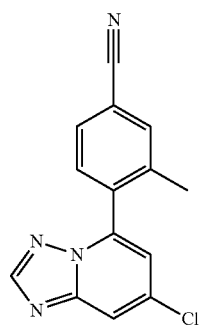 [SMILES: Cc1cc(C#N)ccc1-c1cc(Cl)cc2ncnn12]

Prepared as described for 4-{7-chloro-[1,2,4]triazolo[1,5-a]pyridin-5-yl}benzonitrile (Intermediate 8) from 5,7-dichloro-[1,2,4]triazolo[1,5-a]pyridine (Intermediate 2) and (4-cyano-2-methylphenyl)boronic acid (CAS 313546-18-8) to afford the title compound.
MS ES$^+$: 269

Intermediate 25 tert-Butyl N-[5-(tributylstannyl)-[1,2,4]triazolo[1,5-a]pyridin-7-yl]carbamate

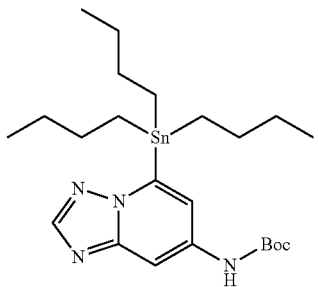 [SMILES: CCC[CH2][Sn]([CH2]CCC)([CH2]CCC)[c]1cc(NC(=O)OC(C)(C)C)cc2ncnn12]

To a solution of tert-Butyl N-(5-chloro-[1,2,4]triazolo[1,5-a]pyridin-7-yl)carbamate (Intermediate 17, 9.0 g, 33.58 mmol) in dioxane (220 mL) was added bis(tributyltin) (23.37 g, 40.29 mmol), LiCl (11.88 g, 198.0 mmol) and degassed for 10 mins using $N_2$ atmosphere and tricylohexylphosphine (0.92 g, 3.3 mmol), $Pd_2(dba)_3$ (1.51 g, 1.65 mmol) were added. The reaction mixture was stirred at 110° C. for 15 h. After completion, reaction mixture was allowed to cool to room temperature then was diluted with water and extracted with EtOAc. The combined organic layer was dried over $Na_2SO_4$ and solvent was concentrated in vacuo. The crude compound was purified by flash chromatography (0-10% EtOAc in hexanes on $SiO_2$) to afford the title compound.

$^1$H NMR (400 MHz DMSO-$d_6$) δ ppm 0.80-0.84 (m, 10H), 1.17-1.32 (m, 15H), 1.48-1.57 (m, 11H), 7.16-7.23 (m, 1H), 7.83-7.83 (m, 1H), 8.22-8.28 (s, 1H), 9.87 (s, 1H) MS ES+: 525

2. EXAMPLES

The following Examples 1 to 20 were made by one of the procedures 1, 2 or 3 as described. Boronate esters may be substituted for boronic acids in each case.

Procedure 1

$PdCl_2(dppf)$ (0.018 g, 0.025 mmol) was added to a degassed suspension of an aryl halide (0.252 mmol), an appropriate boronic acid (0.379 mmol) and $K_2CO_3$ (0.174 g, 1.262 mmol) in dioxane (2 mL) and water (0.5 mL) under nitrogen. The reaction was degassed, sealed and then heated in a microwave reactor at 140° C. for 0.5 h. The reaction mixture was diluted with EtOAc and water, and then filtered through a thiol cartridge. The filtrate was passed through a phase separator and solvent removed in vacuo. The crude product was purified by reverse phase preparative HPLC eluting with acetonitrile/water (with 0.1% ammonia) to afford the title compound.

Procedure 2

A mixture of an aryl halide (0.505 mmol), a boronic acid (0.757 mmol), potassium phosphate (0.536 g, 2.52 mmol) and $PdCl_2(dppf)$ (0.037 g, 0.050 mmol) in dioxane (4 mL) and water (1 mL) was purged with nitrogen. The reaction mixture was heated in a microwave reactor at 120° C. for 45 min. The reaction mixture was concentrated in vacuo and the crude product was purified by reverse phase preparative HPLC eluting with acetonitrile/water (with 0.1% ammonia) to afford the title compound.

For example, the compound of Example 8 (3-methyl-4-{[1,2,4]triazolo[1,5-a]pyridin-5-yl}benzonitrile) was prepared according to Procedure 2 as follows: $PdCl_2(dppf)$ (5.53 g, 7.574 mmol) was added to a degassed suspension of 5-bromo-[1,2,4]triazolo[1,5-a]pyridine (CAS 143329-58-2, 30 g, 151.4 mmol), (4-cyano-2-methylphenyl)boronic acid (CAS 313546-18-8), 26.82 g, 166 mmol) and potassium phosphate (96.35 g, 454.4 mmol) in 1,4-dioxane (24 mL) and water (6.00 mL) under nitrogen. The reaction was degassed, sealed and then heated to 90° C. for 2 h. The reaction mixture was diluted with water and extracted with EtOAc. The organic layer was washed with brine, dried over $Na_2SO_4$, filtered and solvent removed in vacuum to give title crude compound. The crude compound was purified by flash chromatography (0-50% EtOAc in hexane on $SiO_2$). The resulting reisude was dissolved in minimal hot (70° C.) ethanol allowed to cool to room temperature with stirring. The crystals were filtered and dried under vacuum to afford the title compound.

$^1$H NMR (400 MHz, DMSO-$d_6$) δ ppm 2.09 (s, 3H) 7.22-7.30 (m, 1H) 7.62-7.71 (m, 1H) 7.76-7.89 (m, 2H) 7.91-8.02 (m, 2H) 8.49 (s, 1H)

Procedure 3

Tetrakis(triphenylphosphine)palladium (0) (0.073 g, 0.063 mmol) was added to a degassed to suspension of an aryl halide (1.262 mmol), a boronic acid (1.515 mmol) and $Cs_2CO_3$ (0.823 g, 2.52 mmol) in dioxane (2.8 mL) and water (1.4 mL) under nitrogen. The reaction was degassed, sealed and then heated thermally to 100° C. for 6 h. The reaction mixture was diluted with DCM and filtered through a pad of celite. The filtrate was washed with brine, dried ($MgSO_4$), filtered and concentrated in vacuo. The crude product was purified by reverse phase preparative HPLC eluted with acetonitrile/water (with 0.1% ammonia) to afford the title compound.

| Ex. No. | Compound name | Structure | Starting aryl halide | Starting boronic acid | Method | MS ES+ $^1$H NMR data δ ppm |
|---|---|---|---|---|---|---|
| 1 | 5-(2,4-dichlorophenyl)-[1,2,4]triazolo[1,5-a]pyridine | 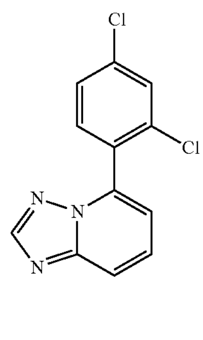 [SMILES: Clc1ccc(-c2cccc3ncnn23)c(Cl)c1] | 5-bromo-[1,2,4]triazolo[1,5-a]pyridine (CAS 143329-58-2) | (2,4-dichlorophenyl)boronic acid (CAS 68716-47-2) | 1 | 264 $^1$H NMR (400 MHz, DCM-$d_2$) δ ppm 7.20-7.24 (m, 1 H) 7.52 (app. s, 2 H) 7.68 (s, 1 H) 7.77-7.83 (m, 1 H) 7.98-8.04 (m, 1 H) 8.42 (s, 1 H) |

-continued

| Ex. No. | Compound name | Structure | Starting aryl halide | Starting boronic acid | Method | MS ES+ | 1H NMR data δ ppm |
|---|---|---|---|---|---|---|---|
| 2 | 5-(4-chloro-phenyl)-[1,2,4]triazolo[1,5-a]pyridine | 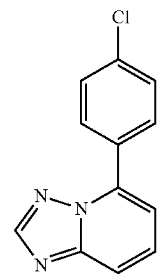 [SMILES: Clc1ccc(-c2cccc3ncnn23)cc1] | 5-bromo-[1,2,4]triazolo[1,5-a]pyridine (CAS 143329-58-2) | (4-chlorophenyl)boronic acid (CAS 1679-18-1) | 1 | 230 | 1H NMR (400 MHz, DMSO-d6) δ ppm 7.40-7.45 (m, 1 H) 7.64-7.69 (m, 2 H) 7.75-7.82 (m, 1 H) 7.87-7.93 (m, 1 H) 8.03-8.09 (m, 2 H) 8.55 (s, 1 H) |
| 3 | 4-{[1,2,4]triazolo[1,5-a]pyridin-5-yl}benzonitrile | 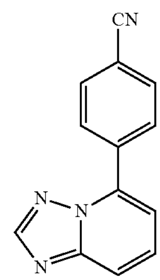 [SMILES: N#Cc1ccc(-c2cccc3ncnn23)cc1] | 5-bromo-[1,2,4]triazolo[1,5-a]pyridine (CAS 143329-58-2) | (4-cyanophenyl)boronic acid (CAS 126747-14-6) | 1 | 221 | 1H NMR (400 MHz, DMSO-d6) δ ppm 7.49-7.53 (m, 1 H) 7.78-7.85 (m, 1 H) 7.94-7.99 (m, 1 H) 8.05-8.09 (m, 2 H) 8.21-8.26 (m, 2 H) 8.57 (s, 1 H) |
| 4 | 4-{7-methyl-[1,2,4]triazolo[1,5-a]pyridin-5-yl}benzonitrile | 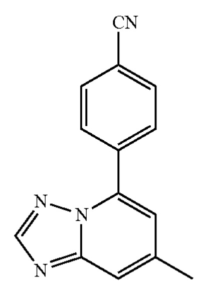 [SMILES: Cc1cc(-c2ccc(C#N)cc2)n2ncnc2c1] | 5-chloro-7-methyl-[1,2,4]triazolo[1,5-a]pyridine (CAS 878259-99-5) | (4-cyanophenyl)boronic acid (CAS 126747-14-6) | 1 | 235 | 1H NMR (400 MHz, DMSO-d6) δ ppm 7.41 (s, 1 H) 7.75 (s, 1 H) 8.03-8.10 (m, 2 H) 8.19-8.27 (m, 2 H) 8.48 (s, 1 H) 2.50 (obsc., 3H) |
| 5 | 2-fluoro-4-{[1,2,4]triazolo[1,5-a]pyridin-5-yl}benzonitrile | 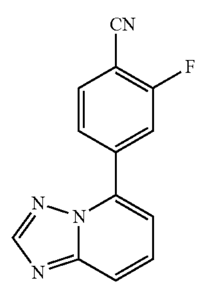 [SMILES: N#Cc1ccc(-c2cccc3ncnn23)cc1F] | 5-bromo-[1,2,4]triazolo[1,5-a]pyridine (CAS 143329-58-2) | (4-cyano-3-fluorophenyl)boronic acid (CAS 843663-18-3) | 3 | 239 | 1H NMR (400 MHz, DMSO-d6) δ ppm 7.56-7.62 (m, 1 H) 7.79-7.86 (m, 1 H) 7.97-8.03 (m, 1 H) 8.08-8.13 (m, 1 H) 8.14-8.20 (m, 1 H) 8.24-8.30 (m, 1 H) 8.60 (s, 1 H) |
| 6 | 2,6-difluoro-4-{[1,2,4]triazolo[1,5-a]pyridin-5-yl}benzonitrile | 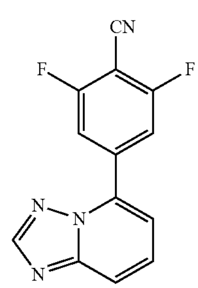 [SMILES: N#Cc1c(F)cc(-c2cccc3ncnn23)cc1F] | 5-bromo-[1,2,4]triazolo[1,5-a]pyridine (CAS 143329-58-2) | 2,6-difluoro-4-(4,4,5,5-tetramethyl-1,3,2-dioxaborolan-2-yl)benzonitrile (CAS 1003298-73-4) | 2 | 257 | 1H NMR (400 MHz, DMSO-d6) δ ppm 7.63-7.68 (m, 1 H) 7.81-7.88 (m, 1 H) 8.00-8.06 (m, 1 H) 8.18-8.24 (m, 2 H) 8.63 (s, 1 H) |

| Ex. No. | Compound name | Structure | Starting aryl halide | Starting boronic acid | Method | MS ES+ | ¹H NMR data δ ppm |
|---|---|---|---|---|---|---|---|
| 7 | 3-fluoro-4-{[1,2,4]triazolo[1,5-a]pyridin-5-yl}benzonitrile | 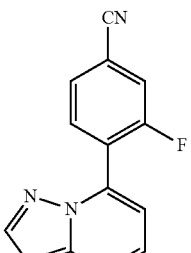 | 5-bromo-[1,2,4]triazolo[1,5-a]pyridine (CAS 143329-58-2) | (4-cyano-2-fluorophenyl)boronic acid (CAS 1150114-77-4) | 2 | 239 | ¹H NMR (400 MHz, DMSO-d₆) δ ppm 7.41-7.47 (m, 1 H) 7.79-7.86 (m, 1 H) 7.92-8.05 (m, 3 H) 8.12-8.18 (m, 1 H) 8.53 (s, 1 H) |
| 8 | 3-methyl-4-{[1,2,4]triazolo[1,5-a]pyridin-5-yl}benzonitrile | 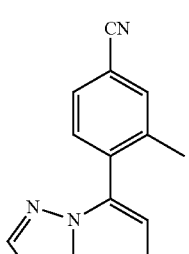 | 5-bromo-[1,2,4]triazolo[1,5-a]pyridine (CAS 143329-58-2) | (4-cyano-2-methylphenyl)boronic acid (CAS 313546-18-8) | 2 | 235 | ¹H NMR (400 MHz, DMSO-d₆) δ ppm 2.09 (s, 3 H) 7.22-7.30 (m, 1 H) 7.62-7.71 (m, 1 H) 7.76-7.89 (m, 2 H) 7.91-8.02 (m, 2 H) 8.49 (s, 1 H) |
| 9 | 5-(4-chloro-2-fluorophenyl)-[1,2,4]triazolo[1,5-a]pyridine | 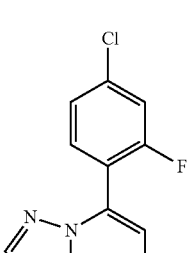 | 5-bromo-[1,2,4]triazolo[1,5-a]pyridine (CAS 143329-58-2) | (4-chloro-2-fluorophenyl)boronic acid (CAS 160591-91-3) | 2 | 248 | ¹H NMR (400 MHz, DMSO-d₆) δ ppm 7.36 (d, J = 7 Hz, 1 H) 7.49-7.58 (m, 1 H) 7.66-7.74 (m, 1 H) 7.75-7.85 (m, 2 H) 7.92-8.00 (m, 1 H) 8.51 (s, 1 H) |
| 10 | 2-chloro-4-{[1,2,4]triazolo[1,5-a]pyridin-5-yl}benzonitrile | 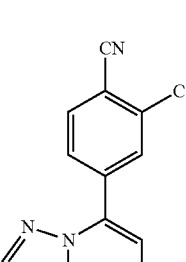 | 5-bromo-[1,2,4]triazolo[1,5-a]pyridine (CAS 143329-58-2) | (3-chloro-4-cyanophenyl)boronic acid (CAS 1008415-02-8) | 2 | 255 | ¹H NMR (400 MHz, DMSO-d₆) δ ppm 7.59 (d, J = 7 Hz, 1 H) 7.76-7.85 (m, 1 H) 7.99 (d, J = 9 Hz, 1 H) 8.20 (app. s, 2 H) 8.46 (s, 1 H) 8.60 (s, 1 H) |
| 11 | 4-{[1,2,4]triazolo[1,5-a]pyridin-5-yl}-2-(trifluoromethyl)benzonitrile | 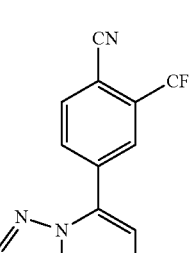 | 5-bromo-[1,2,4]triazolo[1,5-a]pyridine (CAS 143329-58-2) | (4-cyano-3-(trifluoromethyl)phenyl)boronic acid (CAS 915299-32-0) | 2 | 289 | ¹H NMR (300 MHz, DMSO-d₆) δ ppm 7.59-7.71 (m, 1 H), 7.77-7.91 (m, 1 H), 7.96-8.07 (m, 1 H), 8.32-8.47 (m, 1 H), 8.49-8.65 (m, 2 H), 8.70 (s, 1 H) |

-continued

| Ex. No. | Compound name | Structure | Starting aryl halide | Starting boronic acid | Method | MS ES+ | 1H NMR data δ ppm |
|---|---|---|---|---|---|---|---|
| 12 | 5-(4-chloro-3-fluorophenyl)-[1,2,4]triazolo[1,5-a]pyridine | 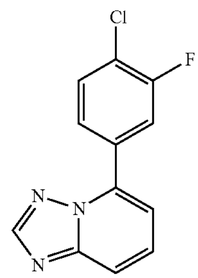 [SMILES: Fc1cc(-c2cccc3ncnn23)ccc1Cl] | 5-bromo-[1,2,4]triazolo[1,5-a]pyridine (CAS 143329-58-2) | (4-chloro-3-fluorophenyl)boronic acid (CAS 137504-86-0) | 2 | 248 | 1H NMR (400 MHz, DMSO-d6) δ ppm 7.51 (d, J = 7 Hz, 1 H) 7.73-7.85 (m, 2 H) 7.87-7.98 (m, 2 H) 8.10-8.21 (m, 1 H) 8.58 (s, 1 H) |
| 13 | 2-methyl-4-{[1,2,4]triazolo[1,5-a]pyridin-5-yl}benzonitrile | 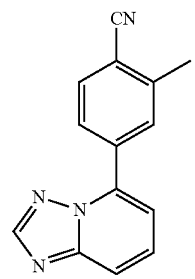 [SMILES: Cc1cc(-c2cccc3ncnn23)ccc1C#N] | 5-bromo-[1,2,4]triazolo[1,5-a]pyridine (CAS 143329-58-2) | (4-cyano-3-methylphenyl)boronic acid (CAS 856255-58-8) | 2 | 235 | 1H NMR (400 MHz, DMSO-d6) δ ppm 2.60 (s, 3 H) 7.48 (d, J = 7 Hz, 1 H) 7.72-7.86 (m, 1 H) 7.87-8.05 (m, 3 H) 8.11 (s, 1 H) 8.57 (s, 1 H) |
| 14 | 6-{[1,2,4]triazolo[1,5-a]pyridin-5-yl}pyridine-3-carbonitrile | 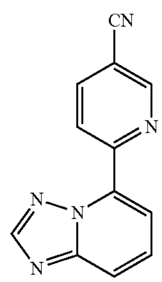 [SMILES: N#Cc1ccc(-c2cccc3ncnn23)nc1] | 6-bromonicotinonitrile (CAS 139585-70-9) | 5-(tetramethyl-1,3,2-dioxaborolan-2-yl)-[1,2,4]triazolo[1,5-a]pyridine (Intermediate 1) | 2 | 222 | 1H NMR (400 MHz, DMSO-d6) δ ppm 7.86-7.92 (m, 1 H) 8.04-8.11 (m, 2 H) 8.58-8.63 (m, 1 H) 8.69 (s, 1 H) 9.04-9.10 (m, 1 H) 9.23-9.28 (m, 1 H) |
| 15 | 5-{[1,2,4]triazolo[1,5-a]pyridin-5-yl}pyridine-2-carbonitrile | 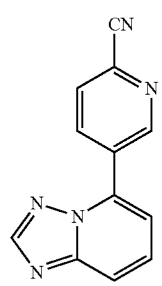 [SMILES: N#Cc1ccc(-c2cccc3ncnn23)cn1] | 5-bromopicolinonitrile (CAS 97483-77-7) | 5-(tetramethyl-1,3,2-dioxaborolan-2-yl)-[1,2,4]triazolo[1,5-a]pyridine (Intermediate 1) | 2 | 222 | 1H NMR (400 MHz, Methanol-d4) δ ppm 7.58 (d, J = 6 Hz, 1 H) 7.81-7.91 (m, 1 H) 7.91-7.97 (m, 1 H) 8.10 (d, J = 8 Hz, 1 H) 8.51 (s, 1 H) 8.68-8.76 (m, 1 H) 9.37 (d, J = 2 Hz, 1 H) |
| 16 | 4-{[1,2,4]triazolo[1,5-c]pyrimidin-5-yl}benzonitrile | 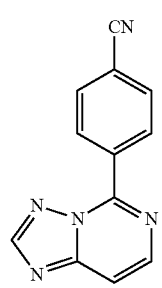 [SMILES: N#Cc1ccc(-c2nccc3ncnn23)cc1] | 5-chloro-[1,2,4]triazolo[1,5-c]pyrimidine (CAS 76044-36-5) | (4-cyanophenyl)boronic acid (CAS 126747-14-6) | 1 | 222 | 1H NMR (400 MHz, DMSO-d6) δ ppm 7.96-8.05 (m, 1 H) 8.10-8.18 (m, 2 H) 8.48-8.56 (m, 1 H) 8.64-8.74 (m, 2 H) 8.79 (s, 1 H) |

-continued

| Ex. No. | Compound name | Structure | Starting aryl halide | Starting boronic acid | Method | MS ES+ | $^1$H NMR data δ ppm |
|---|---|---|---|---|---|---|---|
| 17 | 2-fluoro-4-{[1,2,4]triazolo[1,5-c]pyrimidin-5-yl}benzonitrile | 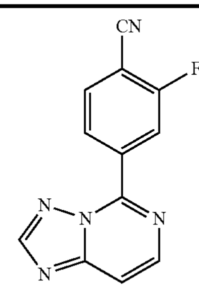 | 5-chloro-[1,2,4]triazolo[1,5-c]pyrimidine (CAS 76044-36-5) | (4-cyano-3-fluorophenyl)boronic acid (CAS 843663-18-3) | 1 | 240 | $^1$H NMR (400 MHz, DMSO-d$_6$) δ ppm 8.02-8.11 (m, 1 H) 8.18-8.27 (m, 1 H) 8.49-8.57 (m, 2 H) 8.59-8.64 (m, 1 H) 8.82 (s, 1 H) |
| 18 | 4-{6-methyl-[1,2,4]triazolo[1,5-a]pyridin-5-yl}benzonitrile | 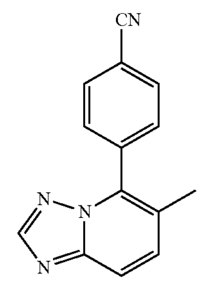 [SMILES: Cc1ccc2ncnn2c1-c1ccc(C#N)cc1] | 5-chloro-6-methyl-[1,2,4]triazolo[1,5-a]pyridine (Intermediate 3) | (4-cyanophenyl)boronic acid (CAS 126747-14-6) | 1 | 235 | $^1$H NMR (400 MHz, DCM-d$_2$) δ ppm 2.28 (s, 3 H) 7.54-7.68 (m, 3 H) 7.74-7.81 (m, 1 H) 7.83-7.92 (m, 2 H) 8.22 (s, 1 H) |
| 19 | 2-fluoro-4-{6-methyl-[1,2,4]triazolo[1,5-a]pyridin-5-yl}benzonitrile | 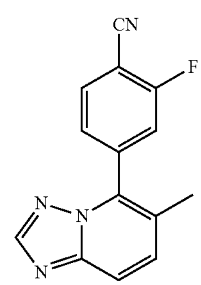 [SMILES: Cc1ccc2ncnn2c1-c1ccc(C#N)c(F)c1] | 5-chloro-6-methyl-[1,2,4]triazolo[1,5-a]pyridine (Intermediate 3) | (4-cyano-3-fluorophenyl)boronic acid (CAS 843663-18-3) | 1 | 253 | $^1$H NMR (400 MHz, DCM-d$_2$) δ ppm 2.29 (s, 3 H) 7.38-7.49 (m, 2 H) 7.53-7.62 (m, 1 H) 7.76-7.81 (m, 1 H) 7.83-7.89 (m, 1 H) 8.22 (s, 1 H) |
| 20 | 5-{7-chloro-[1,2,4]triazolo[1,5-a]pyridin-5-yl}-6-methylpyridine-2-carbonitrile | 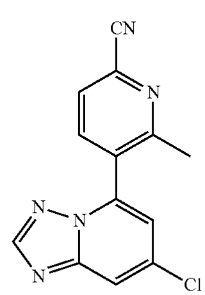 [SMILES: Cc1nc(C#N)ccc1-c1cc(Cl)cc2ncnn12] | 5,7-dichloro-[1,2,4]triazolo[1,5-a]pyridine (Intermediate 2) | 6-methyl-5-(tetramethyl-1,3,2-dioxaborolan-2-yl)pyridine-2-carbonitrile (Intermediate 22) | 1 | 270 | $^1$H NMR (300 MHz, CD$_3$CN-d$_3$) δ ppm 2.39 (s, 3 H) 7.24 (d, J = 2 Hz, 1 H) 7.87 (d, J = 8 Hz, 1 H) 7.94-8.04 (m, 2 H) 8.35 (s, 1 H) |

The following Examples 21 to 36 were made by the following procedure:

To a vial containing 5-(tributylstannyl)-[1,2,4]triazolo[1,5-a]pyridine (Intermediate 4, 0.080 g, 0.196 mmol), copper (I) iodide (1.866 mg, 9.80 μmol) and tetrakis(triphenylphosphine)palladium (0) (0.011 g, 9.80 μmol) in THF (1 mL) was added an aryl or heteroaryl halide (0.216 mmol). The vial was degassed and purged with nitrogen, sealed and irradiated in a microwave reactor at 120° C. for 20 min. The reaction was concentrated in vacuo and the resulting residue was purified by reverse phase preparative HPLC eluting with acetonitrile/water (with 0.1% ammonia) to afford the title compound.

| Ex. No. | Compound name | Structure | Starting aryl stannane | Starting halide | MS ES+ | 1H NMR data δ ppm |
|---|---|---|---|---|---|---|
| 21 | 5-{[1,2,4]triazolo[1,5-a]pyridin-5-yl}pyrimidine-2-carbonitrile | 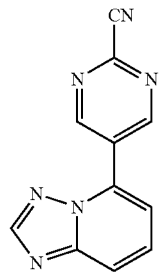 [SMILES: N#Cc1ncc(-c2cccc3ncnn23)cn1] | 5-(tributylstannyl)-[1,2,4]triazolo[1,5-a]pyridine (Intermediate 4) | 5-bromo-pyrimidine-2-carbonitrile (CAS 38275-57-9) | 223 | 1H NMR (400 MHz, DMSO-d6) δ ppm 7.76 (d, J = 7 Hz, 1 H) 7.84-7.93 (m, 1 H) 8.04 (d, J = 8 Hz, 1 H) 8.64 (s, 1 H) 9.70 (s, 2 H) |
| 22 | 5-{[1,2,4]triazolo[1,5-a]pyridin-5-yl}pyrazine-2-carbonitrile | 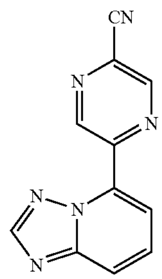 [SMILES: N#Cc1cnc(-c2cccc3ncnn23)cn1] | 5-(tributylstannyl)-[1,2,4]triazolo[1,5-a]pyridine (Intermediate 4) | 5-bromo-pyrazine-2-carbonitrile (CAS 221295-04-1) | 223 | 1H NMR (400 MHz, DMSO-d6) δ ppm 7.86-8.00 (m, 1 H) 8.07 (d, J = 7 Hz, 1 H) 8.14 (d, J = 8 Hz, 1 H) 8.74 (s, 1 H) 9.45 (s, 1 H) 10.15 (s, 1 H) |
| 23 | 2,3-difluoro-4-{[1,2,4]triazolo[1,5-a]pyridin-5-yl}benzonitrile | 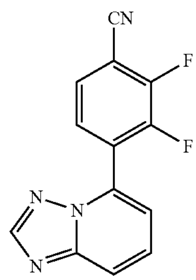 [SMILES: N#Cc1ccc(-c2cccc3ncnn23)c(F)c1F] | 5-(tributylstannyl)-[1,2,4]triazolo[1,5-a]pyridine (Intermediate 4) | 4-bromo-2,3-difluoro-benzonitrile (CAS 126163-58-4) | 257 | 1H NMR (400 MHz, DMSO-d6) δ ppm 7.38-7.56 (m, 1 H) 7.73-7.94 (m, 2 H) 7.96-8.14 (m, 2 H) 8.56 (s, 1 H) |
| 24 | 3-fluoro-5-{[1,2,4]triazolo[1,5-a]pyridin-5-yl}pyridine-2-carbonitrile | 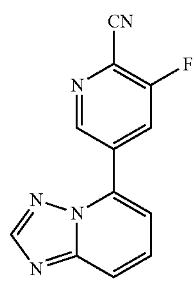 [SMILES: N#Cc1ncc(-c2cccc3ncnn23)cc1F] | 5-(tributylstannyl)-[1,2,4]triazolo[1,5-a]pyridine (Intermediate 4) | 5-bromo-3-fluoropicolino-nitrile (CAS 886373-28-0) | 240 | 1H NMR (400 MHz, DMSO-d6) δ ppm 7.72 (d, J = 7 Hz, 1 H) 7.81-7.90 (m, 1 H) 8.04 (d, J = 9 Hz, 1 H) 8.63 (s, 1 H) 8.85 (d, J = 10 Hz, 1 H) 9.29 (s, 1 H) |
| 25 | 4-methyl-5-{[1,2,4]triazolo[1,5-a]pyridin-5-yl}pyridine-2-carbonitrile | 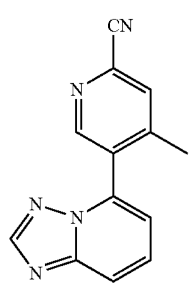 [SMILES: Cc1cc(C#N)ncc1-c1cccc2ncnn12] | 5-(tributylstannyl)-[1,2,4]triazolo[1,5-a]pyridine (Intermediate 4) | 5-bromo-4-methylpico-linonitrile (CAS 886364-86-9) | 236 | 1H NMR (400 MHz, DMSO-d6) δ ppm 7.39 (d, J = 7 Hz, 1 H) 7.79-7.87 (m, 1 H) 7.98-8.05 (m, 1 H) 8.21 (s, 1 H) 8.52 (s, 1 H) 8.82 (s, 1 H) |

| Ex. No. | Compound name | Structure | Starting aryl stannane | Starting halide | MS ES+ | 1H NMR data δ ppm |
|---|---|---|---|---|---|---|
| 26 | 3,5-dimethyl-4-{[1,2,4]triazolo[1,5-a]pyridin-5-yl}benzonitrile | 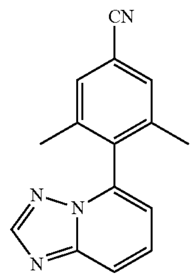 [SMILES: Cc1cc(C#N)cc(C)c1-c1cccc2ncnn12] | 5-(tributylstannyl)-[1,2,4]triazolo[1,5-a]pyridine (Intermediate 4) | 4-bromo-3,5-dimethylbenzonitrile (CAS 75344-77-3) | 249 | 1H NMR (400 MHz, Methanol-d4) δ ppm 2.05 (s, 6 H) 7.20 (d, J = 7 Hz, 1 H) 7.63 (s, 2 H) 7.81-7.98 (m, 2 H) 8.41 (s, 1 H) |
| 27 | 6-{[1,2,4]triazolo[1,5-a]pyridin-5-yl}pyridazine-3-carbonitrile | 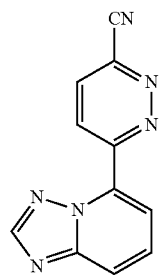 [SMILES: N#Cc1ccc(-c2cccc3ncnn23)nn1] | 5-(tributylstannyl)-[1,2,4]triazolo[1,5-a]pyridine (Intermediate 4) | 6-chloropyridazine-3-carbonitrile (CAS 35857-89-7) | 223 | 1H NMR (400 MHz, DMSO-d6) δ ppm 7.89-7.98 (m, 1 H) 8.10-8.19 (m, 2 H) 8.57-8.66 (m, 1 H) 8.70 (s, 1 H) 9.13-9.23 (m, 1 H) |
| 28 | 6-methyl-5-{[1,2,4]triazolo[1,5-a]pyridin-5-yl}pyridine-2-carbonitrile | 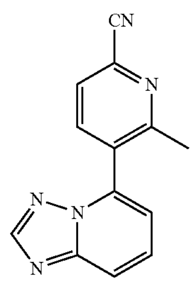 [SMILES: Cc1nc(C#N)ccc1-c1cccc2ncnn12] | 5-(tributylstannyl)-[1,2,4]triazolo[1,5-a]pyridine (Intermediate 4) | 5-bromo-6-methylpicolinonitrile (CAS 1173897-86-3) | 236 | 1H NMR (400 MHz, CD3CN-d3) δ ppm 2.37 (s, 3 H) 7.12-7.22 (m, 1 H) 7.71-7.80 (m, 1 H) 7.83-7.94 (m, 2 H) 7.97-8.04 (m, 1 H) 8.34 (s, 1 H) |
| 29 | 2-fluoro-5-methyl-4-{[1,2,4]triazolo[1,5-a]pyridin-5-yl}benzonitrile | 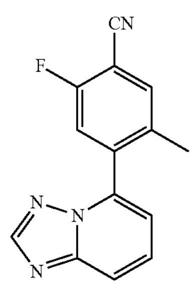 [SMILES: Cc1cc(C#N)c(F)cc1-c1cccc2ncnn12] | 5-(tributylstannyl)-[1,2,4]triazolo[1,5-a]pyridine (Intermediate 4) | 4-bromo-2-fluoro-5-methylbenzonitrile (CAS 916792-13-7) | 253 | 1H NMR (400 MHz, CD3CN-d3) δ ppm 2.11 (s, 3 H) 7.08-7.17 (m, 1 H) 7.42-7.48 (m, 1 H) 7.70-7.84 (m, 2 H) 7.86-7.92 (m, 1 H) 8.33 (s, 1 H) |
| 30 | 3-chloro-4-{[1,2,4]triazolo[1,5-a]pyridin-5-yl}benzonitrile | 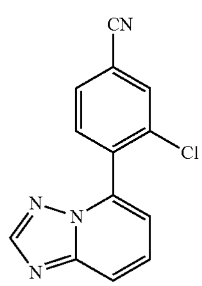 [SMILES: N#Cc1ccc(-c2cccc3ncnn23)c(Cl)c1] | 5-(tributylstannyl)-[1,2,4]triazolo[1,5-a]pyridine (Intermediate 4) | 4-bromo-3-chlorobenzonitrile (CAS 57418-97-0) | 255 | 1H NMR (400 MHz, DMSO-d6) δ ppm 7.29-7.41 (m, 1 H) 7.77-7.85 (m, 1 H) 7.87-7.93 (m, 1 H) 7.97-8.10 (m, 2 H) 8.30-8.36 (m, 1 H) 8.50 (s, 1 H) |

| Ex. No. | Compound name | Structure | Starting aryl stannane | Starting halide | MS ES+ | 1H NMR data δ ppm |
|---|---|---|---|---|---|---|
| 31 | 3-methoxy-4-{[1,2,4]triazolo[1,5-a]pyridin-5-yl}benzonitrile | 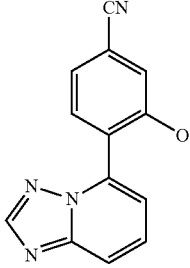 | 5-(tributylstannyl)-[1,2,4]triazolo[1,5-a]pyridine (Intermediate 4) | 4-bromo-3-Methoxy-benzonitrile (CAS 120315-65-3) | 251 | 1H NMR (400 MHz, DMSO-d6) δ ppm 3.78 (s, 3 H) 7.26 (d, J = 7 Hz, 1 H) 7.61 (d, J = 8 Hz, 1 H) 7.67-7.81 (m, 3 H) 7.93 (d, J = 9 Hz, 1 H) 8.44 (s, 1 H) |
| 32 | 5-methyl-6-{[1,2,4]triazolo[1,5-a]pyridin-5-yl}pyridine-3-carbonitrile | 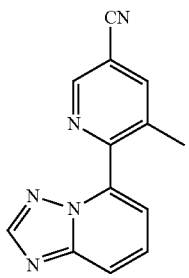 [SMILES: Cc1cc(C#N)cnc1-c1cccc2ncnn12] | 5-(tributylstannyl)-[1,2,4]triazolo[1,5-a]pyridine (Intermediate 4) | (6-chloro-5-methyl-pyridine-3-carbonitrile (CAS 66909-33-9) | 236 | 1H NMR (400 MHz, DMSO-d6) δ ppm 2.12 (s, 3 H) 7.38 (d, J = 7 Hz, 1 H) 7.81-7.92 (m, 1 H) 8.04 (d, J = 9 Hz, 1 H) 8.44-8.56 (m, 2 H) 9.05 (s, 1 H) |
| 33 | 3-ethyl-4-{[1,2,4]triazolo[1,5-a]pyridin-5-yl}benzonitrile | 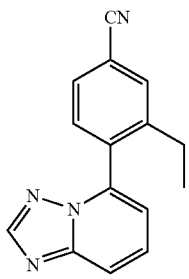 [SMILES: CCc1cc(C#N)ccc1-c1cccc2ncnn12] | 5-(tributylstannyl)-[1,2,4]triazolo[1,5-a]pyridine (Intermediate 4) | 4-bromo-3-ethyl-benzonitrile (CAS 170230-29-2) | 249 | 1H NMR (400 MHz, Methanol-d4) δ ppm 1.08 (t, J = 8 Hz, 3 H) 2.39-2.57 (m, 2 H) 7.20-7.26 (m, 1 H) 7.55-7.60 (m, 1 H) 7.72-7.78 (m, 1 H) 7.82-7.88 (m, 2 H) 7.89-7.95 (m, 1 H) 8.40 (s, 1 H) |
| 34 | 3-fluoro-5-methyl-4-{[1,2,4]triazolo[1,5-a]pyridin-5-yl}benzonitrile | 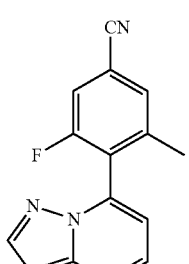 | 5-(tributylstannyl)-[1,2,4]triazolo[1,5-a]pyridine (Intermediate 4) | 3-fluoro-4-iodo-5-methyl-benzonitrile (CAS 1465326-81-1) | 253 | 1H NMR (400 MHz, CD3CN-d3) δ ppm 2.12 (s, 3 H) 7.09-7.21 (m, 1 H) 7.48-7.57 (m, 1 H) 7.63 (s, 1 H) 7.68-7.78 (m, 1 H) 7.83-7.92 (m, 1 H) 8.29 (s, 1 H) |
| 35 | 3-amino-4-{[1,2,4]triazolo[1,5-a]pyridin-5-yl}benzonitrile | 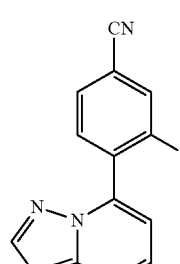 | 5-(tributylstannyl)-[1,2,4]triazolo[1,5-a]pyridine (Intermediate 4) | 3-amino-4-iodoben-zonitrile (CAS 665033-21-6) | 236 | 1H NMR (400 MHz, DMSO-d6) δ ppm 5.53 (s, 2 H) 7.00-7.06 (m, 1 H) 7.10-7.16 (m, 1 H) 7.18-7.24 (m, 1 H) 7.34-7.40 (m, 1 H) 7.70-7.76 (m, 1 H) 7.86-7.96 (m, 1 H) 8.45 (s, 1 H) |

| Ex. No. | Compound name | Structure | Starting aryl stannane | Starting halide | MS ES+ 1H NMR data δ ppm |
|---|---|---|---|---|---|
| 36 | 3-bromo-4-{[1,2,4]triazolo[1,5-a]pyridin-5-yl}benzonitrile | 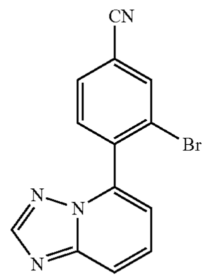 | 5-(tributylstannyl)-[1,2,4]triazolo[1,5-a]pyridine (Intermediate 4) | 3-bromo-4-iodobenzonitrile (CAS 1000577-94-5) | 299 1H NMR (400 MHz, Methanol-d4) δ 7.29 (d, J = 6 Hz, 1 H) 7.72-7.80 (m, 1 H) 7.82-7.90 (m, 1 H) 7.92-7.98 (m, 2 H) 8.23-8.29 (m, 1 H) 8.42 (s, 1 H) |

Example 37: 1-{[1,2,4]Triazolo[1,5-a]pyridin-5-yl}piperidine-4-carbonitrile

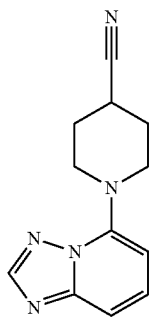 [SMILES: N#CC1CCN(c2cccc3ncnn23)CC1]

Piperidine-4-carbonitrile (44.5 mg, 0.404 mmol) was added to a solution of 5-bromo [1,2,4]triazolo[1,5-a]pyridine (CAS 143329-58-2, 0.080 g, 0.404 mmol) and DIPEA (0.353 mL, 2.020 mmol) in DMSO (1.5 mL). The reaction mixture was heated in a microwave reactor at 150° C. for 20 min. The crude reaction mixture was purified directly by reverse phase preparative HPLC eluted with acetonitrile/water (with 0.1% ammonia) to afford the title compound.

1H NMR (400 MHz, DCM-d2) δ ppm 2.07-2.31 (m, 4H) 2.92-3.09 (m, 1H) 3.36-3.52 (m, 2H) 3.60-3.76 (m, 2H) 6.39-6.50 (m, 1H) 7.36-7.48 (m, 1H) 7.49-7.61 (m, 1H) 8.31 (s, 1H)
MS ES+: 228

Example 38: 4-{[1,2,4]Triazolo[1,5-a]pyrimidin-7-yl}benzonitrile

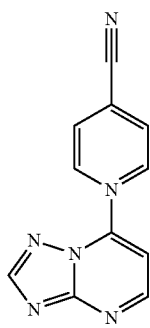

1H-1,2,4-triazol-5-amine (CAS 61-82-5, 0.848 g, 10.09 mmol) was added to a suspension of sodium hydride (0.242 g, 10.09 mmol) in DMF (16 mL) under nitrogen. The mixture was stirred at rt for 10 min. A solution of (E)-N-(3-chloro-3-(4-cyanophenyl)allylidene)-N-methylmethanaminium perchlorate (Intermediate 6, 1.61 g, 5.04 mmol) in DMF (16 mL) was added and the mixture was heated at 100° C. for 12 h, then allowed to cool to rt. The precipitate was collected by filtration, washed with water, EtOH and Et2O and dried in vacuo to afford the title compound.

1H NMR (400 MHz, DMSO-d6) δ ppm 7.70-7.75 (m, 1H) 8.10-8.18 (m, 2H) 8.33-8.40 (m, 2H) 8.77 (s, 1H) 8.99-9.04 (m, 1H)
MS ES+: 222

Example 39: 4-[7-(Hydroxymethyl)-[1,2,4]triazolo[1,5-a]pyridin-5-yl]benzonitrile

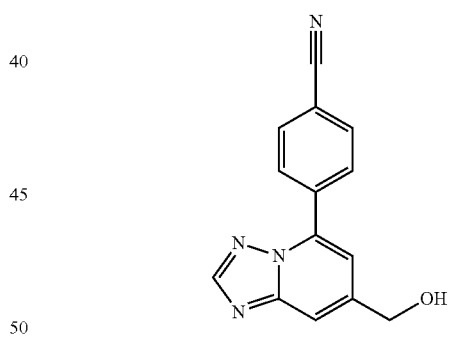

Step 1:
Ethyl 5-(4-cyanophenyl)-[1,2,4]triazolo[1,5-a]pyridine-7-carboxylate was prepared as described for 4-{7-chloro-[1,2,4]triazolo[1,5-a]pyridin-5-yl}benzonitrile (Intermediate 8) from ethyl 5-chloro-[1,2,4]triazolo[1,5-a]pyridine-7-carboxylate (Intermediate 5) and (4-cyanophenyl) boronic acid.

1H NMR (400 MHz, DMSO-d6) δ ppm 1.33-1.45 (m, 3H) 4.36-4.49 (m, 2H) 7.75-7.83 (m, 1H) 8.04-8.13 (m, 2H) 8.20-8.28 (m, 2H) 8.43-8.50 (m, 1H) 8.75 (s, 1H)
MS ES+: 293
Step 2:
To a suspension of ethyl 5-(4-cyanophenyl)-[1,2,4]triazolo[1,5-a]pyridine-7-carboxylate (0.063 g, 0.216 mmol) in dry THF (2 mL) cooled to 0° C. under nitrogen was added drop wise lithium borohydride solution (2M in THF, 0.1 mL, 0.200 mmol). The reaction mixture was stirred at 0° C. for 1 h, then at rt for 2 h. Further lithium borohydride solution (2M in THF, 0.1 mL, 0.200 mmol) was added and the reaction mixture stirred at rt for 1 h. The reaction was quenched with water, extracted twice with EtOAc, dried (phase separator) and concentrated in vacuo. The crude product was purified by reverse phase preparative HPLC eluting with acetonitrile/water (with 0.1% ammonia) to afford the title compound.

$^1$H NMR (400 MHz, Methanol-$d_4$) δ ppm 4.73 (s, 2H) 7.30 (s, 1H) 7.69-7.74 (m, 1H) 7.80-7.87 (m, 2H) 8.06-8.15 (m, 2H) 8.32 (s, 1H)

MS ES$^+$: 251

Example 40: Methyl 5-(4-cyanophenyl)-[1,2,4]triazolo[1,5-a]pyridine-7-carboxylate

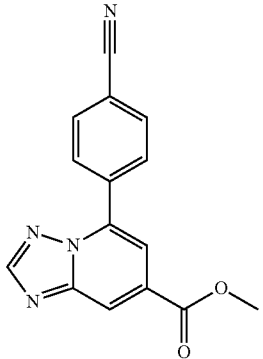 [SMILES: COC(=O)c1cc(-c2ccc(C#N)cc2)n2ncnc2c1]

Prepared as described for 4-{7-chloro-[1,2,4]triazolo[1,5-a]pyridin-5-yl}benzonitrile (Intermediate 8) from methyl 5-chloro-[1,2,4]triazolo[1,5-a]pyridine-7-carboxylate (Intermediate 7, 8.48 g, 40.1 mmol) and (4-cyanophenyl)boronic acid (CAS 126747-14-6, 7.07 g, 48.1 mmol to afford the title compound.

$^1$H NMR (400 MHz, DMSO-$d_6$) δ ppm 3.97 (s, 3H) 7.76-7.82 (m, 1H) 8.05-8.12 (m, 2H) 8.20-8.28 (m, 2H) 8.44-8.50 (m, 1H) 8.75 (s, 1H)

MS ES$^+$: 279

Example 41: 5-(4-Cyanophenyl)-[1,2,4]triazolo[1,5-a]pyridine-7-carboxylic acid

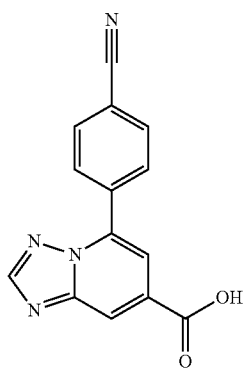 [SMILES: N#Cc1ccc(-c2cc(C(=O)O)cc3ncnn23)cc1]

A mixture of methyl 5-(4-cyanophenyl)-[1,2,4]triazolo[1,5-a]pyridine-7-carboxylate (Example 40, 3.8 g, 13.66 mmol), 2M aqueous LiOH (50 mL, 100 mmol), THF (75 ml) and MeOH (75 ml) was stirred at rt for 20 h. The organic solvents were removed in vacuo and the resulting aqueous suspension was diluted with water and EtOAc. The suspension was filtered and the phases separated. The aqueous phase was washed with EtOAc then acidified to pH~2 with 2M HCl. The aqueous phase was then extracted with EtOAc (×2), and these extracts were dried (Na$_2$SO$_4$), combined and concentrated in vacuo to give afford the title compound.

$^1$H NMR (300 MHz, DMSO-$d_6$) δ ppm 3.65-4.05 (obsc., 1H) 7.78 (s, 1H) 8.01 (d, J=8 Hz, 2H) 8.18 (d, J=8 Hz, 2H) 8.22 (s, 1H) 8.57 (s, 1H).

MS ES$^+$: 265

Example 42: 4-{7-Cyclopropyl-[1,2,4]triazolo[1,5-a]pyridin-5-yl}benzonitrile

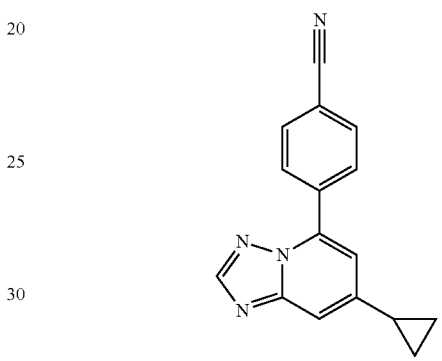

A microwave vial was charged with 4-(7-chloro-[1,2,4]triazolo[1,5-a]pyridin-5-yl)benzonitrile (Intermediate 8, 75 mg, 0.294 mmol), cyclopropylboronic acid (CAS 411235-57-9, 76 mg, 0.883 mmol), PdCl$_2$(dppf) (21.55 mg, 0.029 mmol) and potassium carbonate (122 mg, 0.883 mmol). The vial was sealed, evacuated and refilled with N$_2$ twice. Dioxane (0.8 mL) and water (0.15 mL) was added and the reaction was heated thermally to 100° C. overnight. The reaction was poured into water and extracted with DCM. The organic phase was collected, dried (phase separator) and concentrated in vacuo. The resulting residue was purified by flash chromatography (0-100% EtOAc in petrol on basic silica). The residue was further purified by reverse phase preparative HPLC eluting with acetonitrile/water (with 0.1% ammonia) to afford the title compound.

$^1$H NMR (300 MHz, DCM-$d_2$) δ ppm 0.88-1.02 (m, 2H) 1.15-1.29 (m, 2H) 2.05-2.19 (m, 1H) 6.98 (s, 1H) 7.56 (s, 1H) 7.79-7.88 (m, 2H) 8.02-8.13 (m, 2H) 8.34 (s, 1H)

MS ES$^+$: 261

The following Examples 43 to 71 were made by one of the procedures described below.

Procedure 1:

A mixture of 5-(4-cyanophenyl)-[1,2,4]triazolo[1,5-a]pyridine-7-carboxylic acid (Example 41, 0.0488 g, 0.184 mmol), HATU (0.105 g, 0.277 mmol) and N-methylmorpholine (0.03 mL, 0.277 mmol) in NMP (1.25 mL) was stirred at rt for 15 min. An amine (0.369 mmol) was added and the reaction mixture stirred at rt for 3 h. The reaction was diluted with DMSO (0.4 mL) and the crude product was purified by reverse phase preparative HPLC eluting with acetonitrile/water (with 0.1% formic acid) to afford the title compound.

Procedure 2:

A mixture of 5-(4-cyanophenyl)-[1,2,4]triazolo[1,5-a]pyridine-7-carboxylic acid (Example 41, 0.1 g, 0.38 mmol), HATU (173 mg, 0.45 mmol) and DIPEA (0.117 g, 0.90 mmol) in dry DMF (3 mL) was added to the amine (0.42 mmol) in DMF (0.8 mL) and shaken at room temperature for 2 hr. Dilution with water (4 mL) and filtration of the resulting precipitate afforded the title compound.

| Ex. No. | Compound name | Structure | Starting Amine | Method | MS $^1$H NMR data ES$^+$ δ ppm |
|---|---|---|---|---|---|
| 43 | 4-[7-(pyrrolidine-1-carbonyl)-[1,2,4]triazolo[1,5-a]pyridin-5-yl]benzonitrile | 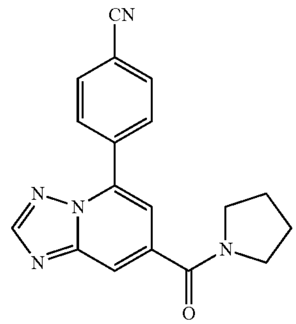 [SMILES: N#Cc1ccc(-c2cc(C(=O)N3CCCC3)cc3ncnn23)cc1] | Pyrrolidine (CAS 123-75-1) | 1 | 318 $^1$H NMR (400 MHz, DMSO-d$_6$) δ ppm 1.79-1.97 (m, 4 H) 3.17 (s, 2 H) 3.46-3.55 (m, 2 H) 7.54-7.60 (m, 1 H) 8.02-8.12 (m, 3 H) 8.20-8.31 (m, 2 H) 8.65 (s, 1 H) |
| 44 | 5-(4-cyanophenyl)-N-(2-methoxyethyl)-[1,2,4]triazolo[1,5-a]pyridine-7-carboxamide | 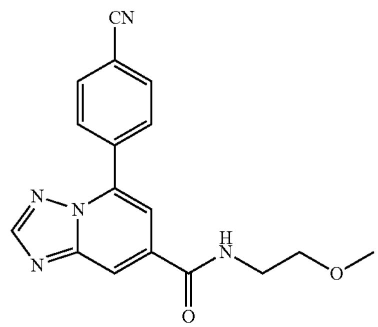 [SMILES: COCCNC(=O)c1cc(-c2ccc(C#N)cc2)n2ncnc2c1] | 2-methoxyethanamine (CAS 109-85-3) | 1 | 322 $^1$H NMR (400 MHz, DMSO-d$_6$) δ ppm 3.26-3.36 (m, 7 H) 7.82-7.87 (m, 1 H) 8.06-8.13 (m, 2 H) 8.24-8.31 (m, 2 H) 8.37-8.42 (m, 1 H) 8.68 (s, 1 H) 9.02 (s, 1 H) |
| 45 | 4-{7-[(2S)-2-methylpyrrolidine-1-carbonyl]-[1,2,4]triazolo[1,5-a]pyridin-5-yl}benzonitrile | 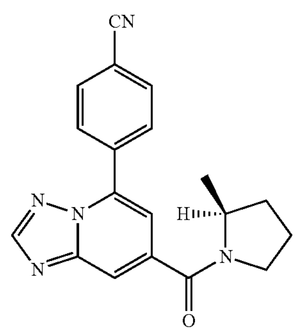 [SMILES: C[C@H]1CCCN1C(=O)c1cc(-c2ccc(C#N)cc2)n2ncnc2c1] | (S)-2-methylpyrrolidine 4-methylbenzenesulfonate (CAS 1212353-38-2) | 1 | 332 $^1$H NMR (400 MHz, DMSO-d$_6$) δ ppm 1.27-1.35 (m, 3 H) 1.54-1.65 (m, 1 H) 1.68-1.80 (m, 1 H) 1.86-1.97 (m, 1 H) 2.05-2.17 (m, 1 H) 3.40-3.65 (m, 2 H) 4.05-4.26 (m, 1 H) 7.54 (s, 1 H) 8.02-8.11 (m, 3 H) 8.21-8.31 (m, 2H) 8.64 (s, 1 H) |
| 46 | 4-[7-(3-methylpyrrolidine-1-carbonyl)-[1,2,4]triazolo[1,5-a]pyridin-5-yl]benzonitrile | 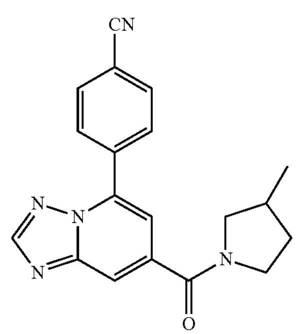 [SMILES: CC1CCN(C(=O)c2cc(-c3ccc(C#N)cc3)n3ncnc3c2)C1] | 3-methylpyrrolidine (CAS 34375-89-8) | 1 | 332 $^1$H NMR (400 MHz, DMSO-d$_6$) δ ppm 0.93-1.13 (m, 3 H) 1.44-1.61 (m, 1 H) 1.94-2.12 (m, 1 H) 2.18-2.38 (m, 1 H) 3.01-3.20 (m, 1 H) 3.44-3.76 (m, 3 H) 7.53-7.59 (m, 1 H) 8.03-8.13 (m, 3 H) 8.22-8.30 (m, 2 H) 8.65 (s, 1 H) |

-continued

| Ex. No. | Compound name | Structure | Starting Amine | Method | MS ES⁺ | ¹H NMR data δ ppm |
|---|---|---|---|---|---|---|
| 47 | 5-(4-cyanophenyl)-N-(3-methoxyphenyl)-[1,2,4]triazolo[1,5-a]pyridine-7-carboxamide | 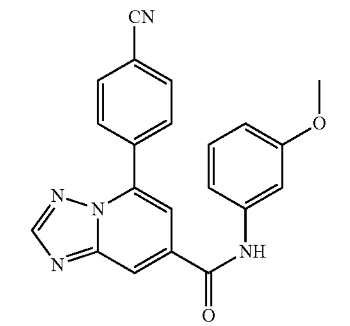 [SMILES: COc1cccc(NC(=O)c2cc(-c3ccc(C#N)cc3)n3ncnc3c2)c1] | 3-methoxy-aniline (CAS 536-90-3) | 2 | 370 | $^1$H NMR (300 MHz, DMSO-d$_6$) δ ppm 3.74 (s, 3 H) 6.72 (d, J = 8 Hz, 1 H) 7.25-7.30 (m, 1 H) 7.37-7.39 (m, 1 H) 7.46 (s, 1H) 7.89 (s, 1H) 8.08 (d, J = 9 Hz, 2 H) 8.27 (d, J = 9 Hz, 2 H) 8.54 (s, 1H) 8.70 (s, 1 H) 10.57 (br s, 1 H) |
| 48 | N-[2-(3-chlorophenyl)ethyl]-5-(4-cyanophenyl)-[1,2,4]triazolo[1,5-a]pyridine-7-carboxamide | 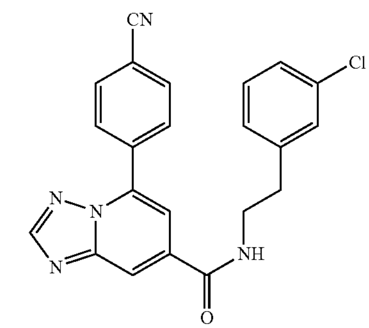 [SMILES: N#Cc1ccc(-c2cc(C(=O)NCCc3cccc(Cl)c3)cc3ncnn23)cc1] | 2-(3-chlorophenyl)ethan-1-amine (CAS 13078-79-0) | 2 | 402 | $^1$H NMR (300 MHz, DMSO-d$_6$) δ ppm 2.85-2.90 (m, 2 H) 3.52-3.58 (m, 2 H) 7.30-7.19 (m, 3 H) 7.33 (s, 1 H) 7.75 (s, 1 H) 8.06 (d, J = 8 Hz, 2 H) 8.22 (d, J = 8 Hz, 2 H) 8.30 (s, 1 H) 8.65 (s, 1 H) 9.00 (br. s, 1 H) |
| 49 | N-[2-(4-chlorophenyl)ethyl]-5-(4-cyanophenyl)-[1,2,4]triazolo[1,5-a]pyridine-7-carboxamide | 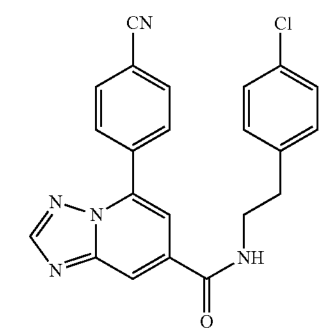 [SMILES: N#Cc1ccc(-c2cc(C(=O)NCCc3ccc(Cl)cc3)cc3ncnn23)cc1] | 2-(4-chlorophenyl)ethan-1-amine (CAS 156-41-2) | 2 | 402 | $^1$H NMR (300 MHz, DMSO-d$_6$) δ ppm 2.84-2.88 (m, 2 H), 3.50-3.56 (m, 2 H), 7.25-7.35 (m, 4 H), 7.75 (s, 1 H) 8.06 (d, J = 8 Hz, 2 H), 8.22 (d, J = 8 Hz, 2 H), 8.30 (s, 1 H), 8.65 (s, 1 H) 9.00 (br. s, 1 H) |
| 50 | 5-(4-cyanophenyl)-N-[2-(3-methoxyphenyl)ethyl]-[1,2,4]triazolo[1,5-a]pyridine-7-carboxamide | 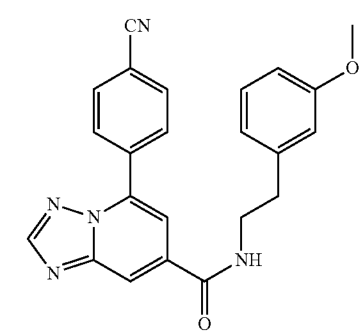 [SMILES: COc1cccc(CCNC(=O)c2cc(-c3ccc(C#N)cc3)n3ncnc3c2)c1] | 2-(3-methoxyphenyl)ethan-1-amine (CAS 2039-67-0) | 2 | 398 | $^1$H NMR (300 MHz, DMSO-d$_6$) δ ppm 2.77-2.89 (m, 2 H) 3.45-3.58 (m, 2 H) 3.69 (s, 3 H) 6.68-6.88 (m, 3 H) 7.12-7.26 (m, 1 H) 7.77 (s, 1 H) 8.07 (d, J = 8.26 Hz, 2 H) 8.22 (d, J = 8.26 Hz, 2 H) 8.31 (s, 1 H) 8.61-8.69 (m, 1 H) 9.01 (br. s., 1 H) |

-continued

| Ex. No. | Compound name | Structure | Starting Amine | Method | MS ES+ | ¹H NMR data δ ppm |
|---|---|---|---|---|---|---|
| 51 | N-(3-chlorophenyl)-5-(4-cyanophenyl)-[1,2,4]triazolo[1,5-a]pyridine-7-carboxamide | 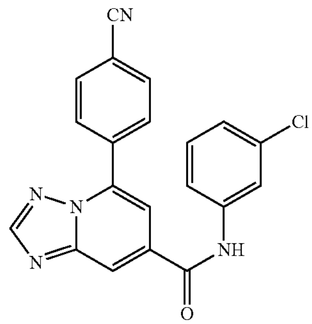 [SMILES: N#Cc1ccc(-c2cc(C(=O)Nc3cccc(Cl)c3)cc3ncnn23)cc1] | 3-chloroaniline (CAS 108-42-9) | 2 | 374 | ¹H NMR (300 MHz, DMSO-d₆) δ ppm 7.19-7.22 (m, 1 H) 7.39-7.44 (m, 1 H) 7.72 (m, 1 H) 7.88 (s, 1 H), 7.96 (s, 1 H) 8.08 (d, J = 8 Hz, 2 H), 8.26 (d, J = 8 Hz, 2 H), 8.54 (s, 1 H), 8.71 (s, 1 H) 10.74 (br s, 1 H) |
| 52 | N-(4-chlorophenyl)-5-(4-cyanophenyl)-[1,2,4]triazolo[1,5-a]pyridine-7-carboxamide | 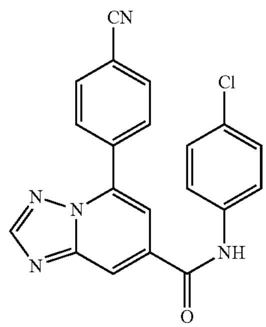 [SMILES: N#Cc1ccc(-c2cc(C(=O)Nc3ccc(Cl)cc3)cc3ncnn23)cc1] | 4-chloroaniline (CAS 106-47-8) | 2 | 374 | ¹H NMR (300 MHz, DMSO-d₆) δ ppm 7.42-7.45 (m, 2 H) 7.82 (m, 2 H) 7.87 (s, 1 H) 8.08 (d, J = 8 Hz, 2 H) 8.26 (d, J = 8 Hz, 2 H) 8.52 (s, 1 H) 8.70 (s, 1 H) 10.71 (br. s, 1 H) |
| 53 | 5-(4-cyanophenyl)-N-(6-methylpyridazin-3-yl)-[1,2,4]triazolo[1,5-a]pyridine-7-carboxamide | 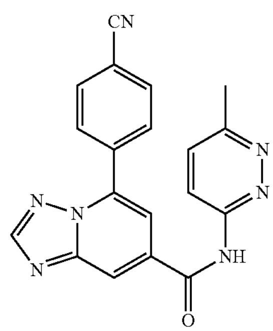 [SMILES: Cc1ccc(NC(=O)c2cc(-c3ccc(C#N)cc3)n3ncnc3c2)nn1] | 6-methyl-pyridazin-3-amine (CAS 18591-82-7) | 2 | 356 | ¹H NMR (300 MHz, DMSO-d₆) δ ppm 2.60 (s, 3 H) 7.64-7.67 (m, 1 H) 8.04 (s, 1 H) 8.08 (d, J = 8 Hz, 2 H) 8.32 (d, J = 8 Hz, 2 H) 8.58-8.59 (m, 2 H) 8.71 (s, 1 H) 11.87 (br. s, 1 H) |
| 54 | 5-(4-cyanophenyl)-N-(2-methylpyrimidin-5-yl)-[1,2,4]triazolo[1,5-a]pyridine-7-carboxamide | 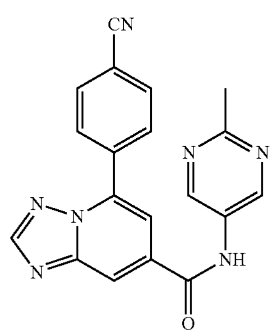 [SMILES: Cc1ncc(NC(=O)c2cc(-c3ccc(C#N)cc3)n3ncnc3c2)cn1] | 2-methyl-pyrimidin-5-amine (CAS 39889-94-6) | 2 | 356 | ¹H NMR (300 MHz, DMSO-d₆) δ ppm 2.59 (s, 3 H) 7.90 (s, 1 H) 8.08 (d, J = 9 Hz, 2 H) 8.26 (d, J = 9 Hz, 2 H), 8.56-8.57 (m, 2 H) 8.72 (s, 1 H) 9.06 (s, 1 H) 10.91 (s, 1 H) |

-continued

| Ex. No. | Compound name | Structure | Starting Amine | Method | MS ES+ | $^1$H NMR data δ ppm |
|---|---|---|---|---|---|---|
| 55 | N-[(3-chlorophenyl)methyl]-5-(4-cyanophenyl)-[1,2,4]triazolo[1,5-a]pyridine-7-carboxamide | 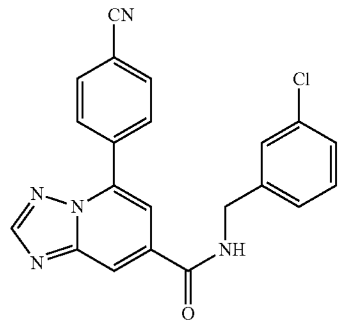 [SMILES: N#Cc1ccc(-c2cc(C(=O)NCc3cccc(Cl)c3)cc3ncnn23)cc1] | (3-chlorophenyl)methanamine (CAS 4152-90-3) | 2 | 388 | $^1$H NMR (300 MHz, DMSO-d$_6$) δ ppm 4.53 (d, J = 5.97 Hz, 2 H) 7.23-7.45 (m, 4 H) 7.85 (s, 1 H) 8.06 (d, J = 8.26 Hz, 2 H), 8.24 (d, J = 8.26 Hz, 2 H) 8.41 (s, 1 H) 8.67 (s, 1 H) 9.46-9.59 (m, 1 H) |
| 56 | N-[(4-chlorophenyl)methyl]-5-(4-cyanophenyl)-[1,2,4]triazolo[1,5-a]pyridine-7-carboxamide | 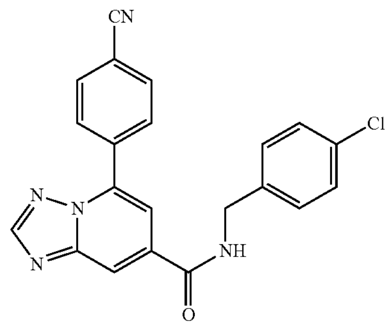 [SMILES: N#Cc1ccc(-c2cc(C(=O)NCc3ccc(Cl)cc3)cc3ncnn23)cc1] | (4-chlorophenyl)methanamine (CAS 104-86-9) | 2 | 388 | $^1$H NMR (300 MHz, DMSO-d$_6$) δ ppm 4.51 (d, J = 6 Hz, 2 H) 7.37 (app. s, 4 H) 7.83 (s, 1 H) 8.07 (d, J = 8 Hz, 2 H) 8.23 (d, J = 8 Hz, 2 H) 8.39 (s, 1 H) 8.66 (s, 1 H) 9.50 (br. s, 1 H) |
| 57 | 5-(4-cyanophenyl)-N-[(3-methoxyphenyl)methyl]-[1,2,4]triazolo[1,5-a]pyridine-7-carboxamide | 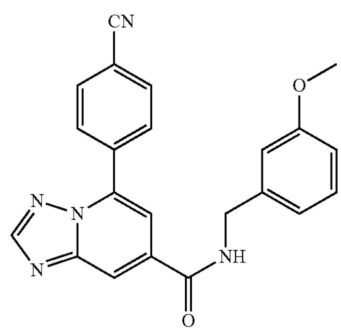 [SMILES: COc1cccc(CNC(=O)c2cc(-c3ccc(C#N)cc3)n3ncnc3c2)c1] | (3-methoxyphenyl)methanamine (CAS 5071-96-5) | 2 | 384 | $^1$H NMR (300 MHz, DMSO-d$_6$) δ ppm 3.71 (s, 3 H) 4.50 (d, J = 6 Hz, 2 H) 6.81 (d, J = 9 Hz, 1 H) 6.91 (d, J = 7 Hz, 2 H) 7.23 (t, J = 8 Hz, 1 H) 7.85 (s, 1 H) 8.06 (d, J = 8 Hz, 2 H) 8.24 (d, J = 8 Hz, 2 H) 8.40 (s, 1 H) 8.66 (s, 1 H) 9.45 (s, 1 H) |
| 58 | 5-(4-cyanophenyl)-[1,2,4]triazolo[1,5-a]pyridine-7-carboxamide | 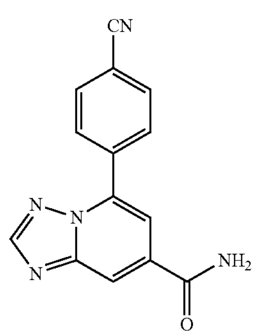 [SMILES: N#Cc1ccc(-c2cc(C(N)=O)cc3ncnn23)cc1] | ammonium chloride (CAS 12125-02-9) | 2 | 264 | $^1$H NMR (300 MHz, DMSO-d$_6$) δ ppm 7.74-7.92 (m, 2 H), 8.06 (d, J = 8.26 Hz, 2 H), 8.23 (d, J = 8.26 Hz, 2 H), 8.38 (br. s., 2 H), 8.65 (s, 1 H) |

| Ex. No. | Compound name | Structure | Starting Amine | Method | MS ES+ | 1H NMR data δ ppm |
|---|---|---|---|---|---|---|
| 59 | 5-(4-cyanophenyl)-N-methyl-[1,2,4]triazolo[1,5-a]pyridine-7-carboxamide | 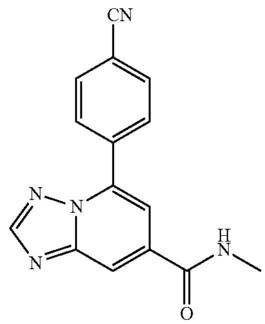 [SMILES: CNC(=O)c1cc(-c2ccc(C#N)cc2)n2ncnc2c1] | methylamine (CAS 74-89-5) | 2 | 278 | 1H NMR (300 MHz, DMSO-d6) δ ppm 2.83 (d, J = 4 Hz, 3 H) 7.79 (s, 1 H) 8.06 (d, J = 8 Hz, 2 H) 8.23 (d, J = 8 Hz, 2 H) 8.31 (s, 1 H) 8.65 (s, 1 H) 8.90 (br s, 1 H) |
| 60 | N-butyl-5-(4-cyanophenyl)-[1,2,4]triazolo[1,5-a]pyridine-7-carboxamide | 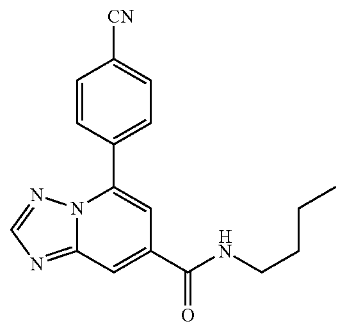 [SMILES: CCCCNC(=O)c1cc(-c2ccc(C#N)cc2)n2ncnc2c1] | butan-1-amine (CAS 109-73-9) | 2 | 320 | 1H NMR (300 MHz, DMSO-d6) δ ppm 0.88 (m, 3 H) 1.29-1.39 (m, 2 H) 1.48-1.55 (m, 2 H), 3.32-3.41 (m, 2 H) 7.79 (s, 1 H) 8.06 (d, J = 8 Hz, 2 H) 8.23 (d, J = 8 Hz, 2 H) 8.34 (s, 1 H) 8.65 (s, 1 H) 8.87 (br. s, 1 H) |
| 61 | 5-(4-cyanophenyl)-N-[(1-methyl-1H-imidazol-4-yl)methyl]-[1,2,4]triazolo[1,5-a]pyridine-7- | 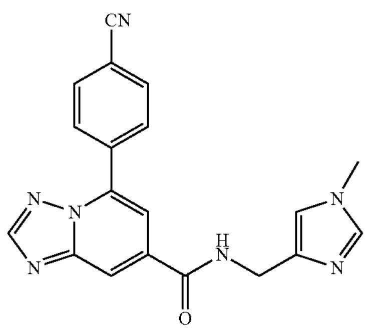 [SMILES: Cn1cnc(CNC(=O)c2cc(-c3ccc(C#N)cc3)n3ncnc3c2)c1] | (1-methyl-1H-imidazol-4-yl) methanamine (CAS 486414-83-9) | 2 | 358 | 1H NMR (300 MHz, DMSO-d6) δ ppm 4.36 (d, J = 6 Hz, 2 H) 3.57 (s, 3 H) 7.01 (s, 1 H) 7.48 (s, 1 H) 7.85 (s, 1 H) 8.06 (d, J =9 Hz, 2 H) 8.24 (d, J = 9 Hz, 2 H) 8.36 (s, 1 H) 8.65 (s, 1 H) 9.30 (br. s, 1 H) |
| 62 | 5-(4-cyanophenyl)-N-[(1-methyl-1H-pyrazol-4-yl)methyl]-[1,2,4]triazolo]1,5-a]pyridine-7-carboxamide | 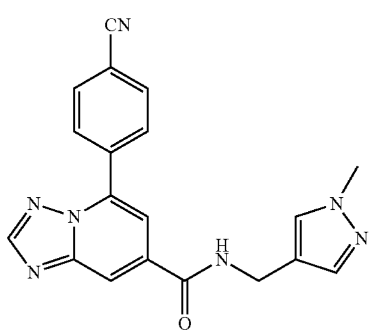 [SMILES: Cn1cc(CNC(=O)c2cc(-c3ccc(C#N)cc3)n3ncnc3c2)cn1] | (1-methyl-1H-pyrazol-4-yl) methanamine (CAS 400877-05-6) | 2 | 358 | 1H NMR (300 MHz, DMSO-d6) δ ppm 3.76 (s, 3 H) 4.34 (m, 2 H) 7.37 (s, 1 H) 7.63 (s, 1 H) 7.81 (s, 1 H) 8.06 (d, J = 8 Hz, 2 H) 8.23 (d, J = 8 Hz, 2 H) 8.35 (s, 1 H) 8.65 (s, 1 H) 9.25 (br s, 1H) |

| Ex. No. | Compound name | Structure | Starting Amine | Method | MS ES⁺ | ¹H NMR data δ ppm |
|---|---|---|---|---|---|---|
| 63 | tert-butyl 3-({[5-(4-cyanophenyl)-[1,2,4]triazolo[1,5-a]pyridin-7-yl]formamido}methyl)azetidine-1-carboxylate | 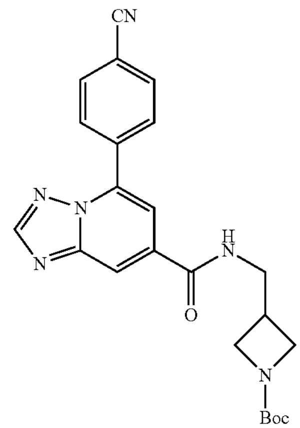 [SMILES: CC(C)(C)OC(=O)N1CC(CNC(=O)c2cc(-c3ccc(C#N)cc3)n3ncnc3c2)C1] | tert-butyl 3-(aminomethyl)azetidine-1-carboxylate (CAS 325775-44-8) | 2 | 433 | ¹H NMR (300 MHz, DMSO-d₆) δ ppm 1.32 (s, 9 H) 2.75 (br. s, 1 H) 3.48-3.52 (m, 2 H) 3.58-3.65 (m, 2 H) 3.84-3.92 (m, 2 H) 7.77 (s, 1 H) 8.07 (d, J = 8 Hz, 2 H) 8.23 (d, J = 8 Hz, 2 H) 8.35 (s, 1 H) 8.66 (s, 1 H) 9.03 (br s, 1 H) |
| 64 | 5-(4-cyanophenyl)-N-[2-(morpholin-4-yl)ethyl]-[1,2,4]triazolo[1,5-a]pyridine-7-carboxamide | 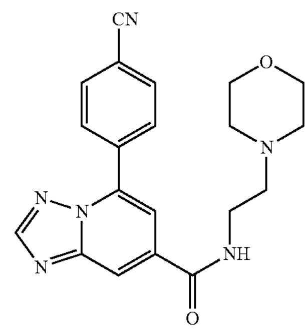 [SMILES: N#Cc1ccc(-c2cc(C(=O)NCCN3CCOCC3)cc3ncnn23)cc1] | 2-(morpholin-4-yl)ethan-1-amine (CAS 2038-03-1) | 2 | 377 | ¹H NMR (300 MHz, DMSO-d₆) δ ppm 2.47-2.48 (m, 2 H) 3.25-3.35 (m, 6 H) 3.50-3.56 (m, 2 H) 4.78-4.82 (m, 2 H) 7.78 (d, J = 2 Hz, 1 H) 8.07 (d, J = 8 Hz, 2 H) 8.22 (d, J = 8 Hz, 2 H) 8.34 (d, J = 2 Hz, 1 H) 8.65 (s, 1 H) 8.86-8.90 (m, 1 H) |
| 65 | 5-(4-cyanophenyl)-N-[2-(4-methylpiperazin-1-yl)ethyl]-[1,2,4]triazolo[1,5-a]pyridine-7-carboxamide | 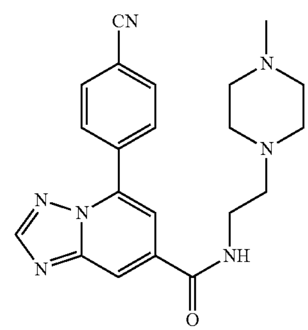 [SMILES: CN1CCN(CCNC(=O)c2cc(-c3ccc(C#N)cc3)n3ncnc3c2)CC1] | 2-(4-methylpiperazin-1-yl)ethan-1-amine (CAS 934-98-5) | 2 | 390 | ¹H NMR (300 MHz, DMSO-d₆) δ ppm 1.07-1.25 (m, 4 H) 1.43-1.50 (m, 2 H) 1.62-1.66 (m, 2 H) 1.73-1.81 (m, 2 H) 2.08 (s, 3 H) 2.68-2.71 (m, 2 H) 7.78 (s, 1 H) 8.06 (d, J = 8 Hz, 2 H), 8.23 (d, J = 8 Hz, 2 H), 8.33 (s, 1 H) 8.64 (s, 1 H) 8.85-8.87 (m, 1 H) |
| 66 | 5-(4-cyanophenyl)-N-(propan-2-yl)-[1,2,4]triazolo[1,5-a]pyridine-7-carboxamide | 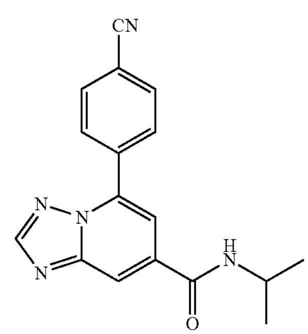 [SMILES: CC(C)NC(=O)c1cc(-c2ccc(C#N)cc2)n2ncnc2c1] | propan-2-amine (CAS 75-31-0) | 2 | 306 | ¹H NMR (300 MHz, DMSO-d₆) δ ppm 1.19 (m, 6 H) 4.06-4.18 (m, 1 H) 7.79 (s, 1 H) 8.06 (d, J = 8 Hz, 2 H), 8.23 (d, J = 8 Hz, 2 H) 8.36 (s, 1 H) 8.64 (s, 1 H) 8.64-8.68 (m, 1 H) |

| Ex. No. | Compound name | Structure | Starting Amine | Method | MS ES+ | ¹H NMR data δ ppm |
|---|---|---|---|---|---|---|
| 67 | 5-(4-cyanophenyl)-N-(cyclopropylmethyl)-[1,2,4]triazolo[1,5-a]pyridine-7-carboxamide | 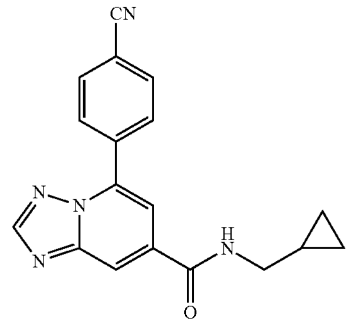 [SMILES: N#Cc1ccc(-c2cc(C(=O)NCC3CC3)cc3ncnn23)cc1] | Cyclopropyl-methan-amine (CAS 2516-47-4) | 2 | 318 | ¹H NMR (300 MHz, DMSO-d₆) δ ppm 0.11-0.28 (m, 2 H) 0.36-0.50 (m, 2 H) 0.96-1.13 (m, 1 H) 3.11-3.25 (m, 2 H) 7.75-7.83 (m, 1 H) 8.06 (d, J = 8.72 Hz, 2 H) 8.18-8.29 (m, 2 H) 8.31-8.42 (m, 1 H) 8.65 (s, 1 H) 8.98-9.11 (m, 1H) |
| 68 | 5-(4-cyanophenyl)-N-(oxetan-3-yl)-[1,2,4]triazolo[1,5-a]pyridine-7-carboxamide | 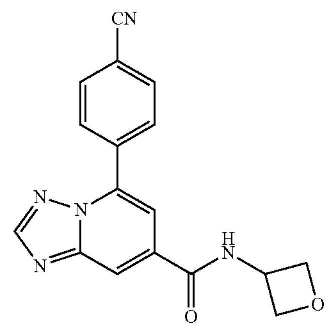 [SMILES: N#Cc1ccc(-c2cc(C(=O)NC3COC3)cc3ncnn23)cc1] | oxetan-3-amine (CAS 21635-88-1) | 2 | 320 | ¹H NMR (300 MHz, DMSO-d₆) δ ppm 4.58-4.62 (m, 2 H) 4.77-4.82 (m, 2 H) 5.01-5.08 (m, 1 H) 7.82 (s, 1 H) 8.07 (d, J = 8 Hz, 2 H) 8.23 (d, J = 8 Hz, 2 H) 8.40 (s, 1 H) 8.67 (s, 1 H) 9.53 (d, J = 6 Hz, 1 H) |
| 69 | 5-(4-cyanophenyl)-N-(oxetan-3-ylmethyl)-[1,2,4]triazolo[1,5-a]pyridine-7-carboxamide | 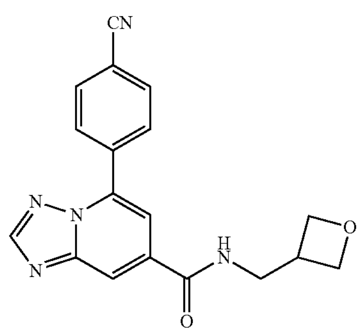 [SMILES: N#Cc1ccc(-c2cc(C(=O)NCC3COC3)cc3ncnn23)cc1] | oxetan-3-ylmethan-amine (CAS 6246-05-5) | 2 | 334 | ¹H NMR (300 MHz, DMSO-d₆) δ ppm 3.13-3.22 (m, 1 H) 3.59 (m, 2 H) 4.32-4.36 (m, 2 H) 4.60-4.65 (m, 2 H) 7.77 (s, 1 H) 8.07 (d, J = 8 Hz, 2 H), 8.22 (d, J = 8 Hz, 2 H) 8.35 (s, 1 H) 8.65 (s, 1 H) 9.00-9.06 (m, 1 H) |
| 70 | 5-(4-cyanophenyl)-N-(1-methylazetidin-3-yl)-[1,2,4]triazolo[1,5-a]pyridine-7-carboxamide | 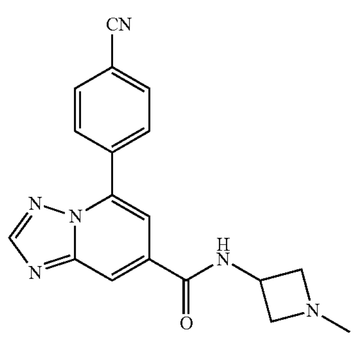 [SMILES: CN1CC(NC(=O)c2cc(-c3ccc(C#N)cc3)n3ncnc3c2)C1] | 1-methyl-azetidin-3-amine (CAS 959957-92-7) | 2 | 333 | ¹H NMR (300 MHz, DMSO-d₆) δ ppm 2.23 (s, 3 H) 2.98 (t, J = 7 Hz, 2 H) 3.57 (t, J = 7 Hz, 2 H) 4.42-4.49 (m, 1 H) 7.80 (s, 1 H) 8.07 (d, J = 8 Hz, 2 H) 8.23 (d, J = 8 Hz, 2 H) 8.38 (s, 1 H) 8.66 (s, 1 H) 9.20-9.22 (m, 1 H) |

| Ex. No. | Compound name | Structure | Starting Amine | Method | MS ES+ ¹H NMR data δ ppm |
|---|---|---|---|---|---|
| 71 | 5-(4-cyanophenyl)-N-(2-hydroxyethyl)-[1,2,4]triazolo[1,5-a]pyridine-7-carboxamide | 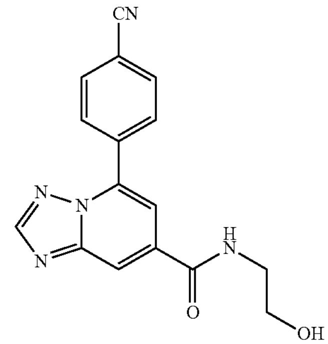 [SMILES: N#Cc1ccc(-c2cc(C(=O)NCCO)cc3ncnn23)cc1] | 2-amino-ethan-1-ol (CAS 141-43-5) | 2 | 308 ¹H NMR (300 MHz, DMSO-d₆) δ ppm 3.33-3.40 (m, 2 H) 3.50-3.56 (m, 2 H) 4.79 (m, 1 H) 7.82 (s, 1 H) 8.06 (d, J = 8 Hz, 2 H) 8.24 (d, J = 8 Hz, 2 H) 8.36 (s, 1 H) 8.65 (s, 1 H) 8.92-8.95 (m, 1 H) |

The following Examples 72 to 99 were prepared by the procedure described below.

An amine (0.548 mmol) was added to a stirred suspension of 4-(5-chloro-[1,2,4]triazolo[1,5-a]pyrimidin-7-yl)benzonitrile (Intermediate 9, 0.1 g, 0.274 mmol) in EtOH (1 mL) under nitrogen. The reaction was heated to 150° C. for 30 min. The reaction mixture was concentrated, diluted with water (20 mL) and extracted with DCM (×3). The organic phases were combined and concentrated. The crude product was loaded onto a cation exchange cartridge which was washed with MeOH then the product was eluted with 2M methanolic ammonia. Concentration in vacuo followed by purification by chromatography on basic silica (eluting with 0-10% MeOH in EtOAc) afforded the title compound.

| Ex. No. | Compound name | Structure | Starting Amine | MS ES+ ¹H NMR data δ ppm |
|---|---|---|---|---|
| 72 | 4-(5-{[2-(dimethylamino)ethyl]amino}-[1,2,4]triazolo[1,5-a]pyrimidin-7-yl)benzonitrile | 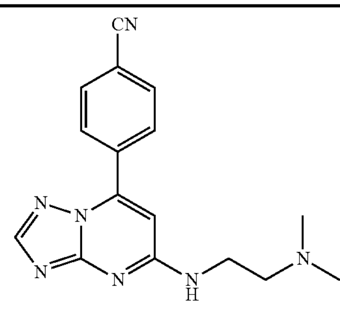 | N,N-dimethyl-ethane-1,2-diamine (CAS 108-00-9) | 308 ¹H NMR (400 MHz, DMSO-d₆) δ ppm 2.21 (s, 6 H) 2.43-2.50 (m, 2 H) 3.45-3.55 (m, 2 H) 6.76 (s, 1 H) 7.83-7.92 (m, 1 H) 8.03-8.10 (m, 2 H) 8.11-8.19 (m, 3 H) |
| 73 | 4-{5-[3-(dimethylamino)pyrrolidin-1-yl]-[1,2,4]triazolo[1,5-a]pyrimidin-7-yl}benzonitrile | 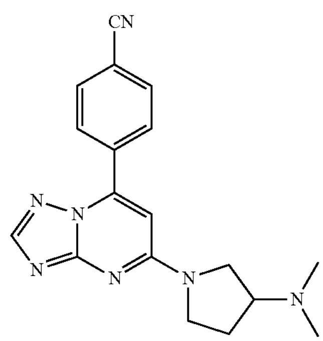 [SMILES: CN(C)C1CCN(c2cc(-c3ccc(C#N)cc3)n3ncnc3n2)C1] | N,N-dimethyl-pyrrolidin-3-amine (CAS 69478-75-7) | 334 ¹H NMR (400 MHz, DMSO-d₆) δ ppm 1.74-1.98 (m, 1 H) 2.23 (s, 6 H) 2.49-2.55 (m, 2H) 2.75-2.90 (m, 1 H) 3.45-3.62 (m, 1 H) 3.77-3.95 (m, 2 H) 6.78-6.93 (m, 1 H) 8.04-8.12 (m, 2 H) 8.21 (s, 1 H) 8.24-8.32 (m, 2 H) |

-continued

| Ex. No. | Compound name | Structure | Starting Amine | MS ES+ | ¹H NMR data δ ppm |
|---|---|---|---|---|---|
| 74 | 1-[7-(4-cyanophenyl)-[1,2,4]triazolo[1,5-a]pyrimidin-5-yl]-N-methylpyrrolidine-2-carboxamide | 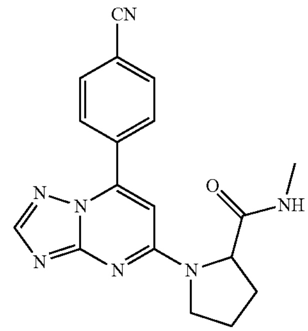 [SMILES: CNC(=O)C1CCCN1c1cc(-c2ccc(C#N)cc2)n2ncnc2n1] | N-methyl-pyrrolidine-2-carboxamide (CAS 137693-34-6) | 348 | ¹H NMR (400 MHz, DMSO-d$_6$) δ ppm 1.91-2.08 (m, 4 H) 2.57-2.63 (m, 3 H) 3.56-3.71 (m, 1 H) 3.74-3.87 (m, 1 H) 4.58-4.66 (m, 1 H) 6.91 (br. s., 1 H) 7.86-7.98 (m, 1 H) 8.05-8.14 (m, 2 H) 8.20-8.31 (m, 3 H) |
| 75 | 4-{5-[(2S)-2-(pyrrolidin-1-ylmethyl)pyrrolidin-1-yl]-[1,2,4]triazolo[1,5-a]pyrimidin-7-yl}benzonitrile | 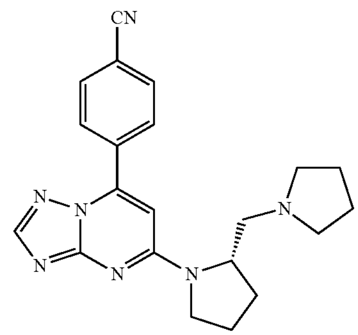 [SMILES: N#Cc1ccc(-c2cc(N3CCC[C@H]3CN3CCCC3)nc3ncnn23)cc1] | (2S)-2-(pyrrolidin-1-ylmethyl)pyrrolidine (CAS 51207-66-0) | 374 | ¹H NMR (400 MHz, DMSO-d$_6$) δ ppm 1.60-1.75 (m, 4 H) 1.91-2.15 (m, 4 H) 2.53-2.69 (m, 6 H) 3.45-3.73 (m, 2 H) 4.27-4.55 (m, 1H) 6.74-6.91 (m, 1 H) 8.06-8.12 (m, 2 H) 8.17-8.30 (m, 3 H) |
| 76 | 4-{5-[3-(pyrrolidin-1-yl)piperidin-1-yl]-[1,2,4]triazolo[1,5-a]pyrimidin-7-yl}benzonitrile | 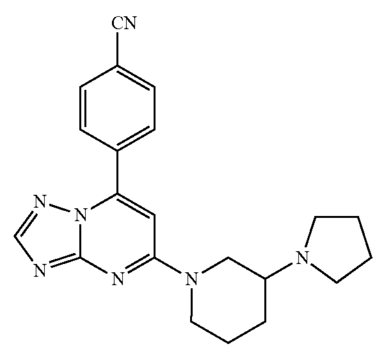 [SMILES: N#Cc1ccc(-c2cc(N3CCCC(N4CCCC4)C3)nc3ncnn23)cc1] | 3-(pyrroldin-1-yl)piperidine (CAS 144243-28-7) | 374 | ¹H NMR (400 MHz, DMSO-d$_6$) δ ppm 1.41-1.60 (m, 2 H) 1.62-1.72 (m, 4 H) 1.74-1.82 (m, 1 H) 1.92-2.05 (m, 1 H) 2.13-2.23 (m, 1 H) 2.56-2.70 (m, 4 H) 3.12-3.26 (m, 2 H) 4.16-4.60 (m, 2 H) 7.17 (s, 1 H) 8.03-8.13 (m, 2 H) 8.18-8.29 (m, 3 H) |
| 77 | 4-{5-[(1-methylpiperidin-4-yl)amino]-[1,2,4]triazolo[1,5-a]pyrimidin-7-yl}benzonitrile | 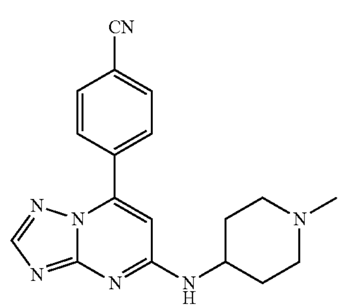 [SMILES: CN1CCC(Nc2cc(-c3ccc(C#N)cc3)n3ncnc3n2)CC1] | 1-methyl-piperidin-4-amine (CAS 41838-46-4) | 334 | ¹H NMR (400 MHz, DMSO-d$_6$) δ ppm 1.44-1.59 (m, 2 H) 1.94 (d, J = 11 Hz, 2 H) 1.99-2.13 (m, 2 H) 2.19 (s, 3 H) 2.70-2.81 (m, 2 H) 3.81-3.96 (m, 1 H) 6.62 (s, 1 H) 7.86-7.96 (m, 1 H) 8.01-8.20 (m, 5 H) |

-continued

| Ex. No. | Compound name | Structure | Starting Amine | MS ES+ / $^1$H NMR data δ ppm |
|---|---|---|---|---|
| 78 | 4-{5-[(1-methylpiperidin-3-yl)amino]-[1,2,4]triazolo[1,5-a]pyrimidin-7-yl}benzonitrile | 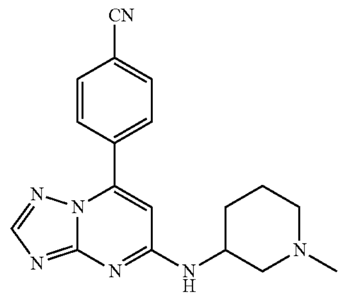 [SMILES: CN1CCCC(Nc2cc(-c3ccc(C#N)cc3)n3ncnc3n2)C1] | 1-methyl-piperidin-3-amine (CAS 42389-57-1) | 334 $^1$H NMR (400 MHz, DMSO-d$_6$) δ ppm 1.30-1.45 (m, 1 H) 1.50-1.64 (m, 1 H) 1.68-1.86 (m, 2H) 1.94-2.15 (m, 2 H) 2.19 (s, 3 H) 2.40-2.50 (m, 1 H) 2.71-2.84 (m, 1 H) 4.06-4.20 (m, 1 H) 6.73 (s, 1 H) 7.84-7.93 (m, 1 H) 8.03-8.19 (m, 5 H) |
| 79 | 4-{5-[(1-acetylpiperidin-3-yl)amino]-[1,2,4]triazolo[1,5-a]pyrimidin-7-yl}benzonitrile | 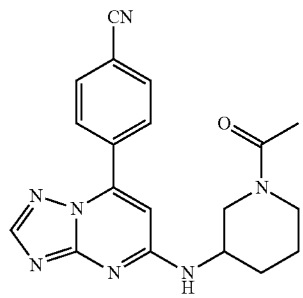 [SMILES: CC(=O)N1CCCC(Nc2cc(-c3ccc(C#N)cc3)n3ncnc3n2)C1] | 1-(3-amino-piperidin-1-yl)ethan-1-one (CAS 1018680-22-2) | 362 $^1$H NMR (300 MHz, DMSO-d$_6$) δ ppm 1.41-1.86 (m, 3 H) 1.92-2.09 (m, 4 H) 2.83-3.00 (m, 1 H) 3.56-3.89 (m, 2 H) 3.94-4.23 (m, 2 H) 6.63-6.80 (m, 1 H) 7.87-8.25 (m, 6 H) |
| 80 | 4-(5-{[(1-methylpiperidin-4-yl)methyl]amino}-[1,2,4]triazolo[1,5-a]pyrimidin-7-yl)benzonitrile | 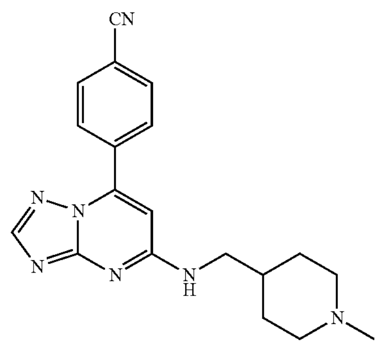 [SMILES: CN1CCC(CNc2cc(-c3ccc(C#N)cc3)n3ncnc3n2)CC1] | (1-methyl-piperidin-4-yl)methanamine (CAS 7149-42-0) | 348 $^1$H NMR (300 MHz, DMSO-d$_6$) δ ppm 1.12-1.35 (m, 3 H) 1.50-1.91 (m, 5 H) 2.15 (s, 3 H) 2.69-2.83 (m, 3 H) 6.66 (s, 1 H) 7.95-8.20 (m, 6 H) |
| 81 | 4-(5-{[2-(2-oxopyrrolidin-1-yl)ethyl]amino}-[1,2,4]triazolo[1,5-a]pyrimidin-7-yl)benzonitrile | 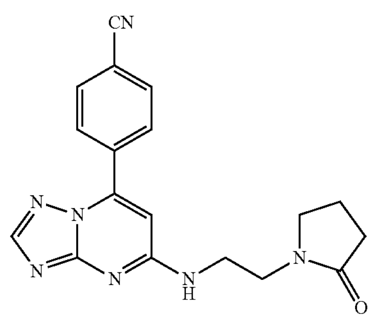 [SMILES: N#Cc1ccc(-c2cc(NCCN3CCCC3=O)nc3ncnn23)cc1] | 1-(2-aminoethyl)pyrrolidin-2-one (CAS 24935-08-8) | 348 $^1$H NMR (300 MHz, DMSO-d$_6$) δ ppm 1.84-1.99 (m, 2 H) 2.12-2.25 (m, 2 H) 3.39-3.50 (m, 4 H) 3.52-3.64 (m, 2 H) 6.64 (br. s, 1 H) 7.95-8.25 (m, 6 H) |
| 82 | 4-[5-(dimethylamino)-[1,2,4]triazolo[1,5-a]pyrimidin-7-yl]benzonitrile | 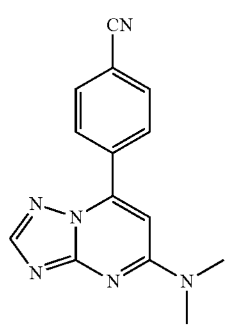 [SMILES: CN(C)c1cc(-c2ccc(C#N)cc2)n2ncnc2n1] | dimethylamine (CAS 124-40-3) | 265 $^1$H NMR (300 MHz, DMSO-d$_6$) δ ppm 3.31 (s, 6 H) 7.00 (s, 1 H) 8.04-8.13 (m, 2 H) 8.18-8.31 (m, 3 H) |

| Ex. No. | Compound name | Structure | Starting Amine | MS ES+ | 1H NMR data δ ppm |
|---|---|---|---|---|---|
| 83 | 4-[5-(pyrrolidin-1-yl)-[1,2,4]triazolo[1,5-a]pyrimidin-7-yl]benzonitrile | 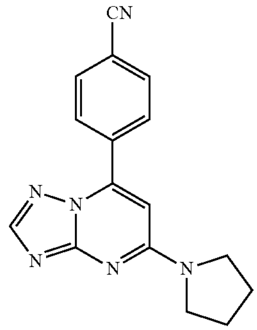 [SMILES: N#Cc1ccc(-c2cc(N3CCCC3)nc3ncnn23)cc1] | pyrrolidine (CAS 123-75-1) | 291 | 1H NMR (400 MHz, DMSO-d$_6$) δ ppm 1.89-2.11 (m, 4 H) 3.54-3.68 (m, 4 H) 6.82 (s, 1 H) 8.04-8.13 (m, 2 H) 8.20 (s, 1 H) 8.23-8.31 (m, 2 H) |
| 84 | 4-{5-[(cyclopropylmethyl)amino]-[1,2,4]triazolo[1,5-a]pyrimidin-7-yl}benzonitrile | 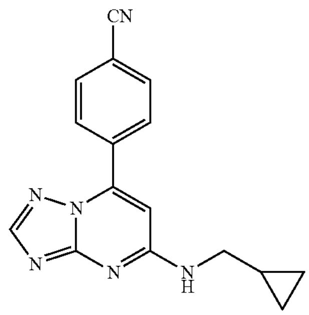 | cyclopropyl-methanamine (CAS 2516-47-4) | 291 | 1H NMR 400 MHz, DMSO-d$_6$) δ ppm 0.23-0.32 (m, 2 H) 0.46-0.55 (m, 2 H) 1.04-1.17 (m, 1 H) 3.22-3.31 (m, 2 H) 6.67 (s, 1 H) 8.00-8.19 (m, 6 H) |
| 85 | 4-{5-[(cyclopropylmethyl)(methyl)amino]-[1,2,4]triazolo[1,5-a]pyrimidin-7-yl}benzonitrile | 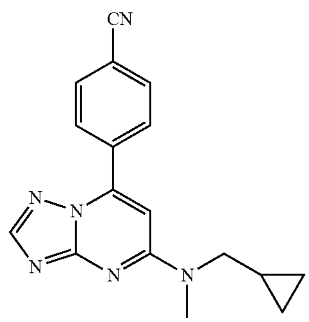 [SMILES: CN(CC1CC1)c1cc(-c2ccc(C#N)cc2)n2ncnc2n1] | (cyclopropyl-methyl)(methyl)amine (CAS 18977-45-2) | 305 | 1H NMR(300 MHz, DMSO-d$_6$) δ ppm 0.29-0.39 (m, 2 H) 0.44-0.54 (m, 2 H) 1.04-1.21 (m, 1 H) 3.25 (s, 3 H) 3.54-3.64 (m, 2 H) 7.01 (br. s, 1 H) 8.03-8.11 (m, 2 H) 8.17-8.30 (m, 3 H) |
| 86 | 4-(5-{[2-(pyrrolidin-1-yl)ethyl]amino}-[1,2,4]triazolo[1,5-a]pyrimidin-7-yl)benzonitrile | 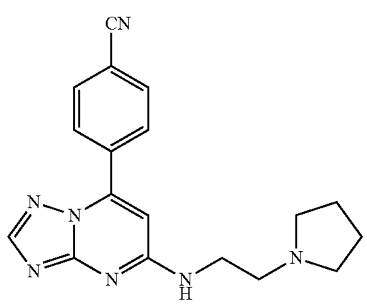 [SMILES: N#Cc1ccc(-c2cc(NCCN3CCCC3)nc3ncnn23)cc1] | 2-(pyrrolidin-1-yl)ethan-1-amine (CAS 7154-73-6) | 334 | 1H NMR (300 MHz, DMSO-d$_6$) δ ppm 1.66-1.79 (m, 4 H) 2.55-2.62 (m, 4 H) 2.67-2.77 (m, 2 H) 3.51-3.64 (m, 2 H) 6.74 (s, 1 H) 7.90-8.20 (m, 6 H) |

-continued

| Ex. No. | Compound name | Structure | Starting Amine | MS ES+ / $^1$H NMR data δ ppm |
|---|---|---|---|---|
| 87 | 4-(5-{[2-(dimethylamino)ethyl](methyl)amino[1,2,4]triazolo[1,5-a]pyrimidin-7-yl)benzonitrile | 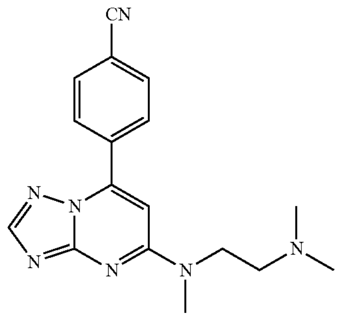 [SMILES: CN(C)CCN(C)c1cc(-c2ccc(C#N)cc2)n2ncnc2n1] | [2-(dimethylamino)ethyl](methyl)amine (CAS 4543-96-8) | 322 $^1$H NMR (400 MHz, DMSO-d$_6$) δ ppm 2.23 (s, 6 H) 2.51-2.56 (obsc., 2 H) 3.21 (s, 3 H) 3.76-3.85 (m, 2 H) 6.91-7.06 (m, 1 H) 8.03-8.14 (m, 2 H) 8.15-8.33 (m, 3 H) |
| 88 | 4-(5-{[3-(dimethylamino)propyl]amino}-[1,2,4]triazolo[1,5-a]pyrimidin-7-yl)benzonitrile | 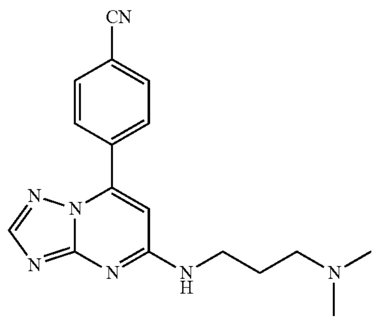 [SMILES: CN(C)CCCNc1cc(-c2ccc(C#N)cc2)n2ncnc2n1] | (3-aminopropyl)dimethylamine (CAS 109-55-7) | 322 $^1$H NMR (400 MHz, DMSO-d ) δppm 1.69-1.81 (m, 2 H) 2.20 (s, 6 H) 2.32-2.41 (m, 2 H) 3.38-3.48 (m, 2 H) 6.64 (s, 1 H) 7.95-8.23 (m, 6 H) |
| 89 | 4-[5-(2-methylpyrrolidin-1-yl)-[1,2,4]triazolo[1,5-a]pyrimidin-7-yl]benzonitrile | 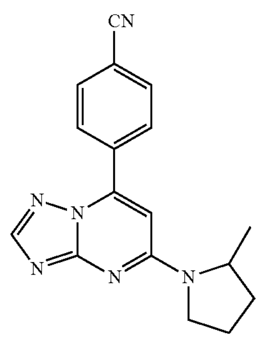 [SMILES: CC1CCCN1c1cc(-c2ccc(C#N)cc2)n2ncnc2n1] | 2-methylpyrrolidine (CAS 765-38-8) | 305 $^1$H NMR (400 MHz, DMSO-d$_6$) δ ppm 1.15-1.33 (m, 3 H) 1.68-1.81 (m, 1 H) 1.95-2.17 (m, 3 H) 3.47-3.57 (m, 1 H) 3.66-3.76 (m, 1 H) 4.33-4.46 (m, 1 H) 6.80 (br. s., 1 H) 8.05-8.12 (m, 2 H) 8.19 (s, 1 H) 8.23-8.31 (m, 2 H) |
| 90 | 4-[5-(3-methylpyrrolidin-1-yl)-[1,2,4]triazolo[1,5-a]pyrimidin-7-yl]benzonitrile | 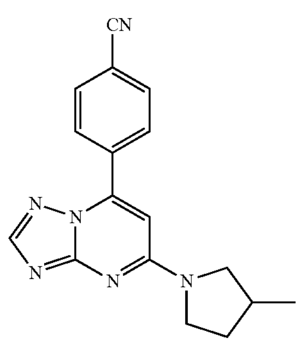 [SMILES: CC1CCN(c2cc(-c3ccc(C#N)cc3)n3ncnc3n2)C1] | 3-methylpyrrolidine (CAS 34375-89-8) | 305 $^1$H NMR (400 MHz, DMSO-d$_6$) δ ppm 1.06-1.14 (m, 3 H) 1.55-1.74 (m, 1 H) 2.07-2.22 (m, 1 H) 2.30-2.46 (m, 1 H) 3.07-3.20 (m, 1 H) 3.48-3.62 (m, 1 H) 3.70-3.88 (m, 2 H) 6.81 (s, 1 H) 8.04-8.12 (m, 2 H) 8.20 (s, 1 H) 8.24-8.32 (m, 2 H) |

| Ex. No. | Compound name | Structure | Starting Amine | MS ES+ / 1H NMR data δ ppm |
|---|---|---|---|---|
| 91 | 4-[5-(2,5-dimethylpyrrolidin-1-yl)-[1,2,4]triazolo[1,5-a]pyrimidin-7-yl]benzonitrile | 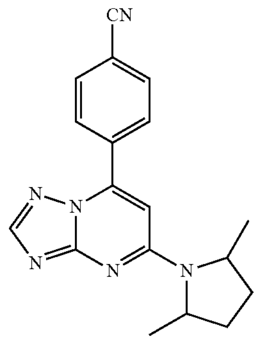 [SMILES: CC1CCC(C)N1c1cc(-c2ccc(C#N)cc2)n2ncnc2n1] | 2,5-dimethylpyrrolidine (CAS 3378-71-0) | 319 1H NMR (400 MHz, DMSO-d6) δ ppm 1.28-1.41 (m, 6 H) 1.72-1.86 (m, 2 H) 2.04-2.19 (m, 2 H) 4.24-4.37 (m, 2 H) 6.77 (s, 1 H) 8.03-8.11 (m, 2H) 8.18 (s, 1 H) 8.22-8.28 (m, 2 H) |
| 92 | 4-[5-(3,3-dimethylpyrrolidin-1-yl)-[1,2,4]triazolo[1,5-a]pyrimidin-7-yl]benzonitrile | 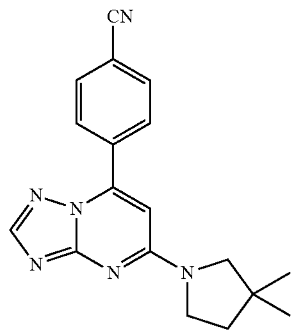 [SMILES: CC1(C)CCN(c2cc(-c3ccc(C#N)cc3)n3ncnc3n2)C1] | 3,3-dimethylpyrrolidine (CAS 3437-30-7) | 319 1H NMR (400 MHz, DMSO-d6) δ ppm 1.13 (s, 6 H) 1.75-1.90 (m, 2 H) 3.40 (s, 2 H) 3.65-3.74 (m, 2 H) 6.80 (s, 1 H) 8.04-8.13 (m, 2 H) 8.20 (s, 1 H) 8.24-8.33 (m, 2 H) |
| 93 | 4-[5-(2-cyclopropylpyrrolidin-1-yl)-[1,2,4]triazolo[1,5-a]pyrimidin-7-yl]benzonitrile | 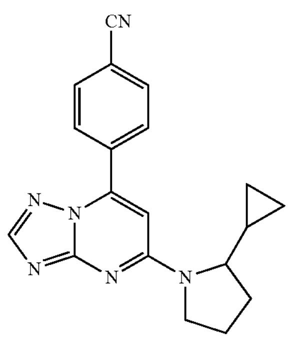 [SMILES: N#Cc1ccc(-c2cc(N3CCCC3C3CC3)nc3ncnn23)cc1] | 2-cyclopropylpyrrolidine (CAS 383127-81-2) | 331 1H NMR (400 MHz, DMSO-d6) δ ppm 0.17-0.90 (m, 4 H) 0.99-1.17 (m, 1 H) 1.76-2.24 (m, 4 H) 3.44-3.80 (m, 2 H) 4.03-4.21 (m, 1 H) 6.74-7.01 (m, 1 H) 8.05-8.13 (m, 2 H) 8.17-8.29 (m, 3 H) |
| 94 | 4-{5-[2-(2-methylpropyl)pyrrolidin-1-yl]-[1,2,4]triazolo[1,5-a]pyrimidin-7-yl}benzonitrile | 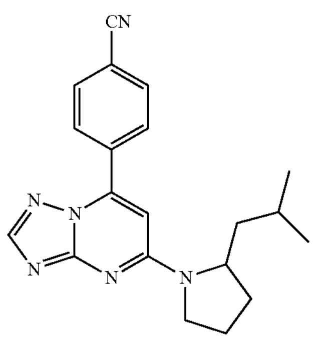 [SMILES: CC(C)CC1CCCN1c1cc(-c2ccc(C#N)cc2)n2ncnc2n1] | 2-(2-methylpropyl)pyrrolidine (CAS 124602-03-5) | 347 1H NMR (400 MHz, DMSO-d6) δ ppm 0.87-1.08 (m, 6 H) 1.18-1.51 (m, 1 H) 1.61-2.15 (m, 6 H) 3.44-3.73 (m, 2 H) 4.15-4.47 (m, 1 H) 6.52-6.82 (m, 1 H) 8.03-8.13 (m, 2 H) 8.15-8.30 (m, 3 H) |

-continued

| Ex. No. | Compound name | Structure | Starting Amine | MS ES⁺ ¹H NMR data δ ppm |
|---|---|---|---|---|
| 95 | 4-{5-[(3-methylbutyl)amino]-[1,2,4]triazolo[1,5-a]pyrimidin-7-yl}benzonitrile | 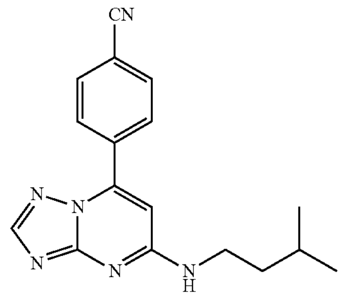 | 3-methylbutan-1-amine (CAS 107-85-7) | 307 ¹H NMR (400 MHz, DMSO-d₆) δ ppm 0.86-0.99 (m, 6 H) 1.44-1.56 (m, 2 H) 1.62-1.78 (m, 1 H) 3.37-3.49 (m, 2 H) 6.62 (s, 1 H) 7.93 (s, 1 H) 8.02-8.20 (m, 5 H) |
| 96 | 4-[5-(cyclopropylamino)-[1,2,4]triazolo[1,5-a]pyrimidin-7-yl]benzonitrile | 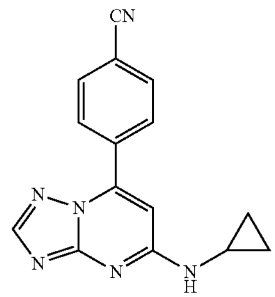 [SMILES: N#Cc1ccc(-c2cc(NC3CC3)nc3ncnn23)cc1] | cyclopropan-amine (CAS 765-30-0) | 277 ¹H NMR (400 MHz, DMSO-d₆) δ ppm 0.47-0.61 (m, 2 H) 0.77-0.87 (m, 2 H) 2.77-2.94 (m, 1 H) 6.56 (s, 1 H) 8.02-8.25 (m, 6 H) |
| 97 | 4-{5-[3-(2-methylpropyl)pyrrolidin-1-yl]-[1,2,4]triazolo[1,5-a]pyrimidin-7-yl}benzonitrile | 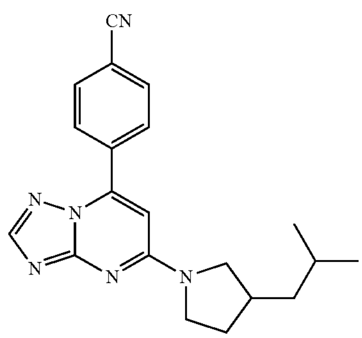 [SMILES: CC(C)CC1CCN(c2cc(-c3ccc(C#N)cc3)n3ncnc3n2)C1] | 3-(2-methylpropyl)pyrrolidine (CAS 959238-03-0) | 347 ¹H NMR (400 MHz, DMSO-d₆) δ ppm 0.87-0.99(m, 6H) 1.28-1.39 (m, 2 H) 1.52-1.74 (m, 2 H) 2.07-2.23 (m, 1 H) 2.26-2.45 (m, 1 H) 3.03-3.16 (m, 1 H) 3.42-3.58 (m, 1 H) 3.69-3.91 (m, 2 H) 6.77-6.87 (m, 1 H) 8.04-8.11 (m, 2 H) 8.19 (s, 1 H) 8.22-8.31 (m, 2 H) |
| 98 | 4-(5-{7-azaspiro[3.5]nonan-7-yl}-[1,2,4]triazolo[1,5-a]pyrimidin-7-yl)benzonitrile | 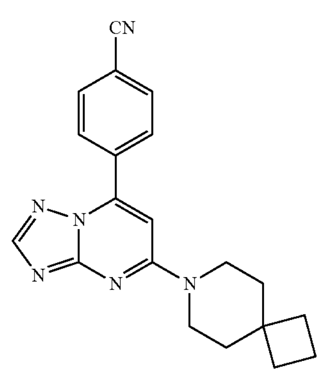 [SMILES: N#Cc1ccc(-c2cc(N3CCC4(CCC4)CC3)nc3ncnn23)cc1] | 7-azaspiro[3.5]nonane (CAS 766-34-7) | 345 ¹H NMR (400 MHz, DMSO-d₆) δ ppm 1.57-1.66 (m, 4 H) 1.76-1.85 (m, 4 H) 1.85-1.97 (m, 2 H) 3.66-3.80 (m, 4 H) 7.17 (s, 1 H) 8.03-8.11 (m, 2H) 8.17-8.29 (m, 3 H) |

| Ex. No. | Compound name | Structure | Starting Amine | MS ES+ | 1H NMR data δ ppm |
|---|---|---|---|---|---|
| 99 | 4-{5-[cyclopropyl(methyl)amino]-[1,2,4]triazolo[1,5-a]pyrimidin-7-yl}benzonitrile | 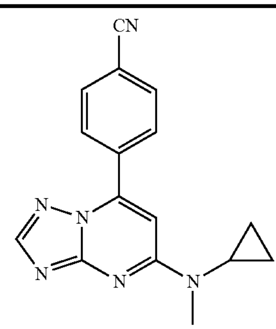 | N-methylcyclopropanamine (CAS 5163-20-2) | 291 | 1H NMR (400 MHz, DMSO-d6) δ ppm 0.76-0.89 (m, 2 H) 0.97-1.06 (m, 2 H) 2.87-2.98 (m, 1 H) 3.19 (s, 3 H) 7.17 (s, 1 H) 8.02-8.15 (m, 2 H) 8.18-8.32 (m, 3 H) |

Example 100: 4-{7-Amino-[1,2,4]triazolo[1,5-a]pyridin-5-yl}benzonitrile

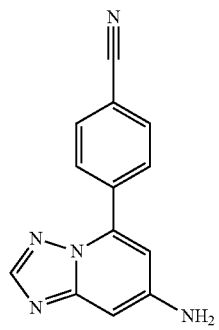 [SMILES: N#Cc1ccc(-c2cc(N)cc3ncnn23)cc1]

A suspension of 5-(4-cyanophenyl)-[1,2,4]triazolo[1,5-a]pyridine-7-carboxylic acid (Example 41, 0.40 g, 1.514 mmol) and TEA (0.422 ml, 3.03 mmol) in dry THF (10 mL) was treated with DPPA (0.391 mL, 1.817 mmol). The reaction mixture was stirred at rt under nitrogen for 4 days. Water (0.082 mL, 4.54 mmol) was added and the reaction mixture heated in a sealed tube at 80° C. for 2 h and then at 100° C. for 12 h. The reaction mixture was diluted with brine and extracted thrice with EtOAc. The combined organics were washed with water, dried (phase separator) and evaporated to dryness. The crude product was purified by reverse phase preparative HPLC eluted with acetonitrile/water (with 0.1% formic acid) to afford the title compound.

1H NMR (400 MHz, DMSO-d6) δ ppm 6.23 (s, 2H) 6.59-6.65 (m, 1H) 6.77-6.83 (m, 1H) 7.98-8.06 (m, 2H) 8.07-8.15 (m, 3H)

MS ES+: 236

The following Examples 101 to 145 were made by one of the procedures described below.

Procedure 1:

A primary amine (2.65 mmol) and TEA (0.369 ml, 2.65 mmol) was added to a stirred suspension of an aryl halide (0.530 mmol) in NMP (2 mL) under nitrogen. The reaction was heated to 180° C. for 2 h. The reaction mixture was diluted in water, extracted into DCM, separated and dried using a phase separator and concentrated in vacuo. The crude material was purified by flash chromatography (0-40% EtOAc in petrol on basic silica) to afford the title compound.

Procedure 2:

A suspension of Pd2(dba)3 (0.01 g, 9.82 μmol), Cs2CO3 (0.128 g, 0.393 mmol), dicyclohexyl(2',4',6'-triisopropyl-[1,1'-biphenyl]-2-yl)phosphine (0.010 g, 0.020 mmol), an aryl halide (0.196 mmol) and an amine (0.393 mmol) in dioxane (1 mL) was heated in a microwave at 110° C. for 1 h and then heated at reflux for 16 h. The reaction was poured into water and extracted with DCM. The organic phase was collected, dried (phase separator) and concentrated in vacuo. The resulting residue was purified by flash chromatography (0-100% EtOAc in petrol on basic silica) to afford the title compound.

Procedure 3:

A suspension of an aryl halide (0.294 mmol), Pd(OAc)2 (0.005 g, 0.024 mmol), [1,1'-binaphthalen]-2-yldi-tert-butylphosphine (0.011 g, 0.029 mmol), Cs2CO3 (0.192 g, 0.589 mmol) and an alcohol (0.441 mmol) in toluene (1.5 mL) was degassed and back-filled with N2 twice. The reaction was heated to 80° C. for 4 h. The reaction mixture was poured into water and extracted with DCM. The organic phase was collected, dried (phase separator) and concentrated in vacuo. The resulting residue was purified by flash chromatography (0-100% EtOAc in petrol). The resulting residue was further purified by reverse phase preparative HPLC eluted with acetonitrile/water (with 0.1% ammonia) to afford the title compound.

Procedure 4:

A microwave vial was charged with an aryl halide (0.393 mmol), dicyclohexyl(2',4',6'-triisopropyl-[1,1'-biphenyl]-2-yl)phosphine (0.009 g, 0.020 mmol), Pd2(dba)3 (0.036 g, 0.039 mmol), Cs2CO3 (0.384 g, 1.178 mmol) and a carboxamide (0.471 mmol). The vial was sealed then de-gassed and back-filled with N2 three times. Dioxane (2 mL) was added and the reaction was heated in a microwave at 120° C. for 30 min. The reaction was diluted with EtOAc and washed twice with water. The organic phase was collected, dried (phase separator) and concentrated in vacuo. The resulting residue was purified by flash chromatography (0-100% EtOAc in petrol on SiO2). The resulting residue was further purified by flash chromatography (0-100% EtOAc in petrol on basic silica).

| Ex. No. | Compound name | Structure | Starting aryl halide | Starting amine/alcohol or amide | Method | MS ES+ | 1H NMR data δ ppm |
|---|---|---|---|---|---|---|---|
| 101 | 4-{7-[(cyclopropyl-methyl)amino]-[1,2,4]triazolo[1,5-a]pyridin-5-yl}benzonitrile | 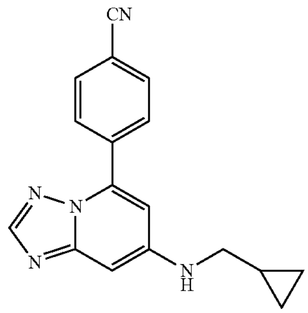 [SMILES: N#Cc1ccc(-c2cc(NCC3CC3)cc3ncnn23)cc1] | 4-(7-chloro-[1,2,4]triazolo[1,5-a]pyridin-5-yl)benzonitrile (Intermediate 8) | cyclopropyl-methanamine (CAS 2516-47-4) | 1 | 290 | 1H NMR (400 MHz, DMSO-d6) δ ppm 0.26 (s, 2 H) 0.49-0.56 (m, 2 H) 1.04-1.15 (m, 1 H) 2.96-3.07 (m, 2 H) 6.48-6.58 (m, 1 H) 6.78-6.90 (m, 2 H) 7.99-8.06 (m, 2 H) 8.07-8.14 (m, 3 H) |
| 102 | 4-{7-(2-methoxyethyl)amino}-[1,2,4]triazolo[1,5-a]pyridin-5-yl}benzonitrile | 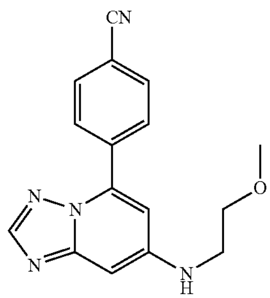 [SMILES: COCCNc1cc(-c2ccc(C#N)cc2)n2ncnc2c1] | 4-(7-chloro-[1,2,4]triazolo[1,5-a]pyridin-5-yl)benzonitrile (Intermediate 8) | 2-methoxyethan-1-amine (CAS 109-85-3) | 2 | 294 | 1H NMR (400 MHz, DCM-d2) δ ppm 3.37-3.52 (m, 5 H) 3.65-3.75 (m, 2 H) 4.92 (s, 1 H) 6.58-6.78 (m, 2 H) 7.80-7.90 (m, 2 H) 8.02-8.09 (m, 2 H) 8.12 (s, 1 H) |
| 103 | 4-[7-(ethylamino)-[1,2,4]triazolo[1,5-a]pyridin-5-yl]benzonitrile | 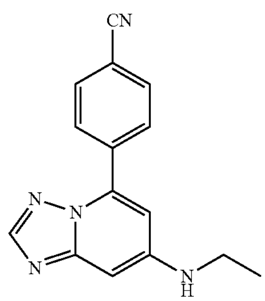 [SMILES: CCNc1cc(-c2ccc(C#N)cc2)n2ncnc2c1] | 4-(7-chloro-[1,2,4]triazolo[1,5-a]pyridin-5-yl)benzonitrile (Intermediate 8) | ethanamine (CAS 75-04-7) | 2 | 264 | 1H NMR (400 MHz, CD2Cl2) δ ppm 1.31-1.39 (m, 3 H) 3.34-3.41 (m, 2 H) 5.12-5.21 (m, 1 H) 6.69-6.74 (m, 1 H) 6.93-6.98 (m, 1 H) 7.80-7.88 (m, 2 H) 7.89-7.97 (m, 2 H) 8.33 (s, 1 H) |
| 104 | 4-{7-[(oxan-4-ylmethyl)amino]-[1,2,4]triazolo[1,5-a]pyridin-5-yl}benzonitrile | 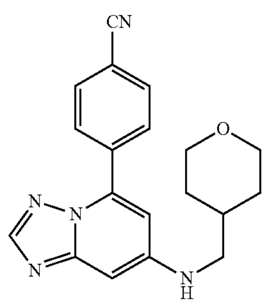 [SMILES: N#Cc1ccc(-c2cc(NCC3CCOCC3)cc3ncnn23)cc1] | 4-(7-chloro-[1,2,4]triazolo[1,5-a]pyridin-5-yl)benzonitrile (Intermediate 8) | oxan-4-ylmethan-amine (CAS 130290-79-8) | 2 | 334 | 1H NMR (400 MHz, DMSO-d6) δ ppm 1.17-1.38 (m, 2 H) 1.65-1.75 (m, 2 H) 1.81-1.95 (m, 1 H) 3.03-3.10 (m, 2 H) 3.26-3.31 (m, 2 H) 3.82-3.95 (m, 2 H) 6.54-6.62 (m, 1 H) 6.78-6.89 (m, 2 H) 7.99-8.06 (m, 2 H) 8.08-8.15 (m, 3 H) |
| 105 | 4-{7-[(oxolan-3-ylmethyl)amino]-[1,2,4]triazolo[1,5-a]pyridin-5-yl}benzonitrile | 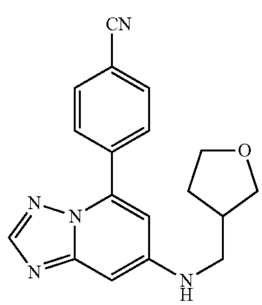 [SMILES: N#Cc1ccc(-c2cc(NCC3CCOC3)cc3ncnn23)cc1] | 4-(7-chloro-[1,2,4]triazolo[1,5-a]pyridin-5-yl)benzonitrile (Intermediate 8) | oxolan-3-ylmethan-amine (CAS 165253-31-6) | 2 | 320 | 1H NMR (400 MHz, DMSO-d6) δ ppm 1.57-1.70 (m, 1 H) 1.97-2.07 (m, 1 H) 2.53-2.59 (m, 1 H) 3.05-3.21 (m, 2 H) 3.43 3.54 (m, 1 H) 3.61-3.70 (m, 1 H) 3.73-3.85 (m, 2 H) 6.57-6.62 (m, 1 H) 6.80-6.90 (m, 2 H) 7.99-8.07 (m, 2 H) 8.09-8.17 (m, 3 H) |

-continued

| Ex. No. | Compound name | Structure | Starting aryl halide | Starting amine/alcohol or amide | Method | MS ES+ | ¹H NMR data δ ppm |
|---|---|---|---|---|---|---|---|
| 106 | 4-{7-[(2,2-difluoroethyl)amino]-[1,2,4]triazolo[1,5-a]pyridin-5-yl}benzonitrile | 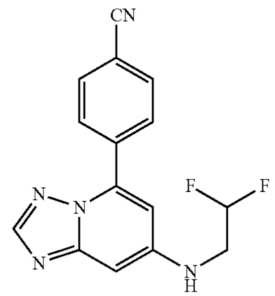 [SMILES: N#Cc1ccc(-c2cc(NCC(F)F)cc3ncnn23)cc1] | 4-(7-chloro-[1,2,4]triazolo[1,5-a]pyridin-5-yl)benzonitrile (Intermediate 8) | 2,2-difluoroethan-1-amine (CAS 430-67-1) | 2 | 300 | ¹H NMR (400 MHz, DMSO-d₆) δ ppm 3.65-3.79 (m, 2 H) 6.06-6.37 (m, 1 H) 6.78-6.85 (m, 1 H) 6.91-6.97 (m, 1 H) 6.99-7.08 (m, 1 H) 8.01-8.06 (m, 2 H) 8.10-8.15 (m, 2 H) 8.17 (s, 1H) |
| 107 | 4-{7-[(oxetan-3-ylmethyl)amino]-[1,2,4]triazolo[1,5-a]pyridin-5-yl}benzonitrile | 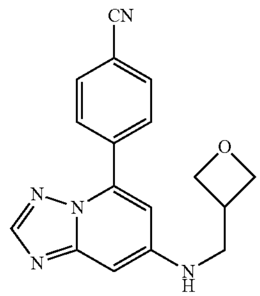 [SMILES: N#Cc1ccc(-c2cc(NCC3COC3)cc3ncnn23)cc1] | 4-(7-chloro-[1,2,4]triazolo[1,5-a]pyridin-5-yl)benzonitrile (Intermediate 8) | oxetan-3-ylmethan-amine (CAS 6246-05-5) | 2 | 306 | ¹H NMR (400 MHz, DMSO-d₆) δ ppm 3.22-3.29 (m, 1 H) 3.44-3.50 (m, 2 H) 4.31-4.39 (m, 2 H) 4.66-4.76 (m, 2 H) 6.59-6.64 (m, 1 H) 6.79-6.81 (m, 1 H) 6.85-6.90 (m, 1 H) 8.00-8.07 (m, 2 H) 8.08-8.18 (m, 3 H) |
| 108 | 4-{7-[(3,3,3-trifluoropropyl)amino]-[1,2,4]triazolo[1,5-a]pyridin-5-yl}benzonitrile | 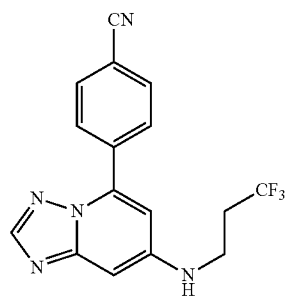 [SMILES: N#Cc1ccc(-c2cc(NCCC(F)(F)F)cc3ncnn23)cc1] | 4-(7-chloro-[1,2,4]triazolo[1,5-a]pyridin-5-yl)benzonitrile (Intermediate 8) | 3,3,3-trifluoro-propan-1-amine (CAS 460-39-9) (Intermediate 8) | 2 | 332 | ¹H NMR (400 MHz, DMSO-d₆) δ ppm 2.55-2.69 (m, 2 H) 3.42-3.52 (m, 2 H) 6.61-6.68 (m, 1 H) 6.82-6.86 (m, 1 H) 6.87-6.95 (m, 1 H) 7.99-8.07 (m, 2 H) 8.08-8.14 (m, 2 H) 8.16 (s, 1H) |
| 109 | 4-(7-{[3-(morpholin-4-yl)propyl]amino}-[1,2,4]triazolo[1,5-a]pyridin-5-yl)benzonitrile | 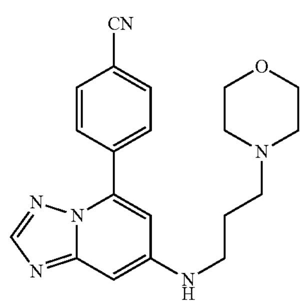 [SMILES: N#Cc1ccc(-c2cc(NCCCN3CCOCC3)cc3ncnn23)cc1] | 4-(7-chloro-[1,2,4]triazolo[1,5-a]pyridin-5-yl)benzonitrile (Intermediate 8) | 3-(morpholin-4-yl)propan-1-amine (CAS 123-00-2) | 2 | 363 | ¹H NMR (400 MHz, DCM-d₂) δ ppm 1.87-2.16 (m, 2 H) 2.77 (br. s., 6 H) 3.38 (br. s., 2 H) 3.87 (br. s., 4 H) 6.04-6.40 (m, 1 H) 6.56 (s, 2 H) 7.81 (d, J = 8.34 Hz, 2 H) 7.98-8.09 (m, 3 H) |
| 110 | 4-{7-[(2-hydroxy-2-methylpropyl)amino]-[1,2,4]triazolo[1,5-a]pyridin-5-yl}benzonitrile | 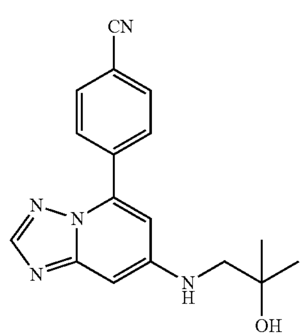 [SMILES: CC(C)(O)CNc1cc(-c2ccc(C#N)cc2)n2ncnc2c1] | 4-(7-chloro-[1,2,4]triazolo[1,5-a]pyridin-5-yl)benzonitrile (Intermediate 8) | 1-amino-2-methylpropan-2-ol (CAS 2854-16-2) | 2 | 308 | ¹H NMR (400 MHz, Methanol-d₄) δ ppm 1.26-1.38 (m, 6 H) 3.21-3.25 (m, 2 H) 6.61-6.68 (m, 1 H) 6.91-6.95 (m, 1 H) 7.87-7.97 (m, 2 H) 8.08-8.14 (m, 3 H) |

| Ex. No. | Compound name | Structure | Starting aryl halide | Starting amine/alcohol or amide | Method | MS ES+ | ¹H NMR data δ ppm |
|---|---|---|---|---|---|---|---|
| 111 | 4-{7-[(3-methoxypropyl)amino]-[1,2,4]triazolo[1,5-a]pyridin-5-yl}benzonitrile | 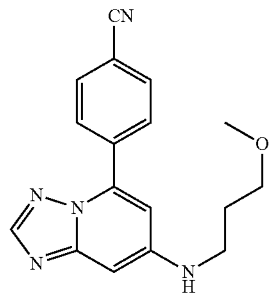 [SMILES: COCCCNc1cc(-c2ccc(C#N)cc2)n2ncnc2c1] | 4-(7-chloro-[1,2,4]triazolo[1,5-a]pyridin-5-yl)benzonitrile (Intermediate 8) | 3-methoxy-propan-1-amine (CAS 5332-73-0) | 2 | 308 | ¹H NMR (400 MHz, Methanol-d₄) δ ppm 1.88-2.04 (m, 2 H) 3.38 (s, 3 H) 3.51-3.59 (m, 2 H) 3.3 (obsc., 2H) 6.53-6.58 (m, 1 H) 6.76-6.84 (m, 1 H) 7.86-7.96 (m, 2 H) 8.05-8.16 (m, 3 H) |
| 112 | 4-{7-[(oxolan-2-ylmethyl)amino]-[1,2,4]triazolo[1,5-a]pyridin-5-yl}benzonitrile | 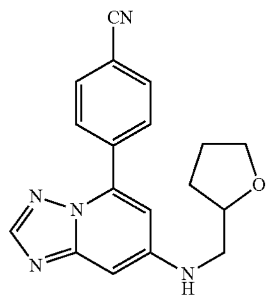 [SMILES: N#Cc1ccc(-c2cc(NCC3CCCO3)cc3ncnn23)cc1] | 4-(7-chloro-[1,2,4]triazolo[1,5-a]pyridin-5-yl)benzonitrile (Intermediate 8) | oxolan-2-ylmethan-amine (CAS 4795-29-3) | 2 | 320 | ¹H NMR (400 MHz, DCM-d₂) δ ppm 1.62-1.78 (m, 1 H) 1.92-2.01 (m, 2 H) 2.08-2.20 (m, 1 H) 3.17-3.27 (m, 1 H) 3.36-3.49 (m, 1 H) 3.76-3.86 (m, 1 H) 3.88-3.98 (m, 1 H) 4.14-4.26 (m, 1 H) 4.97-5.11 (m, 1 H) 6.64-6.71 (m, 1 H) 6.74-6.80 (m, 1 H) 7.81-7.91 (m, 2 H) 8.00-8.09 (m, 2 H) 8.16 (s, 1 H) |
| 113 | 4-(7-{[2-(dimethylamino)ethyl]amino}-[1,2,4]triazolo[1,5-a]pyridin-5-yl)benzonitrile | 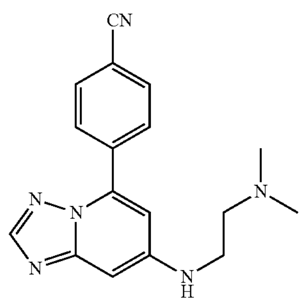 [SMILES: CN(C)CCNc1cc(-c2ccc(C#N)cc2)n2ncnc2c1] | 4-(7-chloro-[1,2,4]triazolo[1,5-a]pyridin-5-yl)benzonitrile (Intermediate 8) | (2-aminoethyl)dimethylamine (CAS 108-00-9) | 2 | 307 | ¹H NMR (400 MHz, DCM-d₂) δ ppm 2.55 (br. s., 5 H) 2.97 (br. s., 2 H) 3.41 (br. s., 2 H) 5.75-6.25 (br.s., 1 H) 5.96-6.28 (m, 1 H) 6.61 (br. s., 1 H) 6.74 (s, 1 H) 7.85 (d, J = 8.59 Hz, 2 H) 8.03-8.17 (m, 3 H) |
| 114 | 4-[7-(benzylamino)-[1,2,4]triazolo[1,5-a]pyridin-5-yl]benzonitrile | 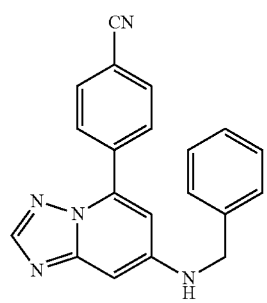 [SMILES: N#Cc1ccc(-c2cc(NCc3ccccc3)cc3ncnn23)cc1] | 4-(7-chloro-[1,2,4]triazolo[1,5-a]pyridin-5-yl)benzonitrile (Intermediate 8) | benzylamine (CAS 100-46-9) | 2 | 326 | ¹H NMR (300 MHz, DCM-d₂) δ ppm 4.49 (s, 2 H) 6.66 (s, 1 H) 6.83 (s, 1 H) 7.27-7.47 (m, 6 H) 7.79-7.88 (m, 2 H) 7.94-8.02 (m, 2 H) 8.16 (s, 1 H) |
| 115 | 4-(7-{[(2-fluorophenyl)methyl]amino}-[1,2,4]triazolo[1,5-a]pyridin-5-yl)benzonitrile | 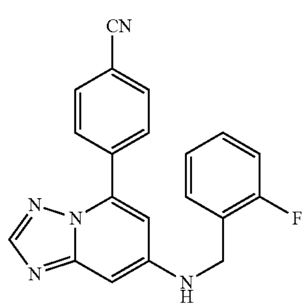 [SMILES: N#Cc1ccc(-c2cc(NCc3ccccc3F)cc3ncnn23)cc1] | 4-(7-chloro-[1,2,4]triazolo[1,5-a]pyridin-5-yl)benzonitrile (Intermediate 8) | (2-fluorophenyl)methanamine (CAS 88-99-6) | 2 | 344 | ¹H NMR (400 MHz, DCM-d₂) δ ppm 4.44-4.64 (m, 2 H) 4.84-5.01 (m, 1 H) 6.53-6.65 (m, 1 H) 6.67-6.76 (m, 1 H) 7.11-7.27 (m, 2 H) 7.31-7.50 (m, 2 H) 7.75-7.91 (m, 2 H) 7.99-8.17 (m, 3 H) |

| Ex. No. | Compound name | Structure | Starting aryl halide | Starting amine/alcohol or amide | Method | MS ES+ | ¹H NMR data δ ppm |
|---|---|---|---|---|---|---|---|
| 116 | 4-(7-{[(3-fluorophenyl)methyl]amino}-[1,2,4]triazolo[1,5-a]pyridin-5-yl)benzonitrile | 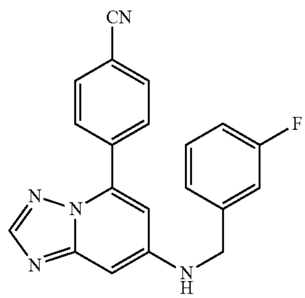 [SMILES: N#Cc1ccc(-c2cc(NCc3cccc(F)c3)cc3ncnn23)cc1] | 4-(7-chloro-[1,2,4]triazolo[1,5-a]pyridin-5-yl)benzonitrile (Intermediate 8) | (3-fluorophenyl)methanamine (CAS 100-82-3) | 2 | 344 | ¹H NMR (400 MHz, DCM-d₂) δ ppm 4.49-4.57 (m, 2 H) 5.64-5.86 (m, 1 H) 6.71 (s, 1 H) 6.83-6.92 (m, 1 H) 6.99-7.06 (m, 1 H) 7.08-7.14 (m, 1 H) 7.17-7.23 (m, 1 H) 7.33-7.41 (m, 1 H) 7.79-7.86 (m, 2 H) 7.94-7.99 (m, 2 H) 8.21 (s, 1 H) |
| 117 | 4-(7-{[(4-fluorophenyl)methyl]amino}-[1,2,4]triazolo[1,5-a]pyridin-5-yl)benzonitrile | 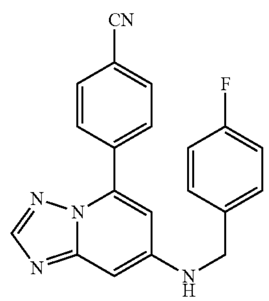 [SMILES: N#Cc1ccc(-c2cc(NCc3ccc(F)cc3)cc3ncnn23)cc1] | 4-(7-chloro-[1,2,4]triazolo[1,5-a]pyridin-5-yl)benzonitrile (Intermediate 8) | (4-fluorophenyl)methanamine (CAS 140-75-0) | 2 | 344 | ¹H NMR (400 MHz, DCM-d₂) δ ppm 4.40-4.50 (m, 2 H) 4.75-4.89 (m, 1 H) 6.52-6.65 (m, 2 H) 7.02-7.13 (m, 2 H) 7.33-7.43 (m, 2 H) 7.75-7.86 (m, 2 H) 7.95-8.08 (m, 3 H) |
| 118 | 4-[7-(cyclopropylmethoxy)-[1,2,4]triazolo[1,5-a]pyridin-5-yl]benzonitrile | 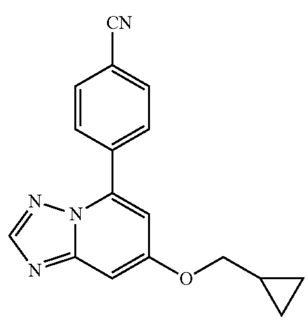 [SMILES: N#Cc1ccc(-c2cc(OCC3CC3)cc3ncnn23)cc1] | 4-(7-chloro-[1,2,4]triazolo[1,5-a]pyridin-5-yl)benzonitrile (Intermediate 8) | cyclopropyl-methanol (CAS 2516-33-8) | 3 | 291 | ¹H NMR (400 MHz, DCM-d₂) δ ppm 0.38-0.51 (m, 2 H) 0.67-0.80 (m, 2 H) 1.32-1.44 (m, 1 H) 3.96-4.08 (m, 2 H) 6.90-7.00 (m, 1 H) 7.04-7.16 (m, 1 H) 7.82-7.92 (m, 2 H) 8.06-8.17 (m, 2 H) 8.26 (s, 1 H) |
| 119 | 4-[7-(benzyloxy)-[1,2,4]triazolo[1,5-a]pyridin-5-yl]benzonitrile | 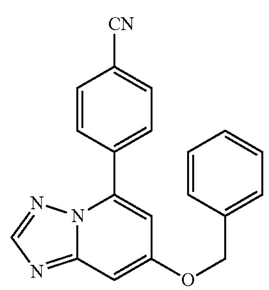 [SMILES: N#Cc1ccc(-c2cc(OCc3ccccc3)cc3ncnn23)cc1] | 4-(7-chloro-[1,2,4]triazolo[1,5-a]pyridin-5-yl)benzonitrile (Intermediate 8) | phenyl-methanol (CAS 100-51-6) | 3 | 291 | ¹H NMR (400 MHz, DCM-d₂) δ ppm 0.38-0.51 (m, 2 H) 0.67-0.80 (m, 2 H) 1.32-1.44 (m, 1 H) 3.96-4.08 (m, 2 H) 6.90-7.00 (m, 1 H) 7.04-7.16 (m, 1 H) 7.82-7.92 (m, 2 H) 8.06-8.17 (m, 2 H) 8.26 (s, 1 H) |
| 120 | tert-butyl N-[5-(4-cyanophenyl)-[1,2,4]triazolo[1,5-a]pyridin-7-yl]carbamate | 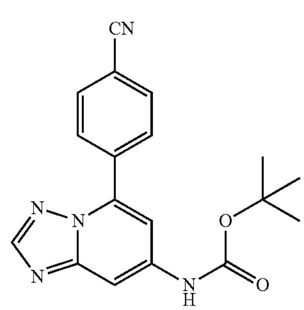 [SMILES: CC(C)(C)OC(=O)Nc1cc(-c2ccc(C#N)cc2)n2ncnc2c1] | 4-(7-chloro-[1,2,4]triazolo[1,5-a]pyridin-5-yl)benzonitrile (Intermediate 8) | tert-butyl carbamate (CAS 4248-19-5) | 4 | 280 (M-ᵗBu) | ¹H NMR (400 MHz, DMSO-d₆) δ ppm 1.53 (s, 9 H) 7.41-7.53 (m, 1 H) 7.88-8.00 (m, 1 H) 8.02-8.17 (m, 4 H) 8.39 (s, 1 H) 10.08 (s, 1H) |

| Ex. No. | Compound name | Structure | Starting aryl halide | Starting amine/alcohol or amide | Method | MS ES+ | ¹H NMR data δ ppm |
|---|---|---|---|---|---|---|---|
| 121 | N-[5-(4-cyanophenyl)-[1,2,4]triazolo[1,5-a]pyridin-7-yl]acetamide | 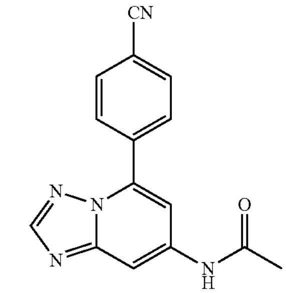 [SMILES: CC(=O)Nc1cc(-c2ccc(C#N)cc2)n2ncnc2c1] | 4-(7-chloro-[1,2,4]triazolo[1,5-a]pyridin-5-yl)benzonitrile (Intermediate 8) | acetamide (CAS 30-35-5) | 4 | 278 | ¹H NMR 300 MHz, DMSO-d₆) δ ppm 2.16 (s, 3 H) 7.44 (s, 1 H) 8.02-8.27 (m, 5 H) 8.43 (s, 1 H) 10.57 (s, 1 H) |
| 122 | N-[5-(4-cyanophenyl)-[1,2,4]triazolo[1,5-a]pyridin-7-yl]cyclopropane-carboxamide | 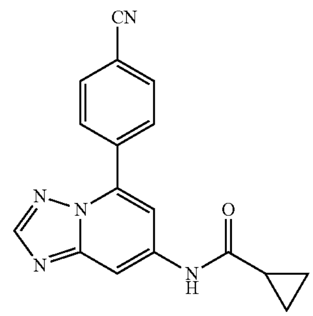 [SMILES: N#Cc1ccc(-c2cc(NC(=O)C3CC3)cc3ncnn23)cc1] | 4-(7-chloro-[1,2,4]triazolo[1,5-a]pyridin-5-yl)benzonitrile (Intermediate 8) | cyclopropyl-carboxamide (CAS 6228-73-5) | 4 | 304 | ¹H NMR (300 MHz, DMSO-d₆) δ ppm 0.81-0.98 (m, 4 H) 1.78-1.94 (m, 1 H) 7.49 (s, 1 H) 8.03-8.12 (m, 2 H) 8.14-8.25 (m, 3 H) 8.42 (s, 1 H) 10.84 (s, 1 H) |
| 123 | N-[5-(4-cyanophenyl)-[1,2,4]triazolo[1,5-a]pyridin-7-yl]benzamide | 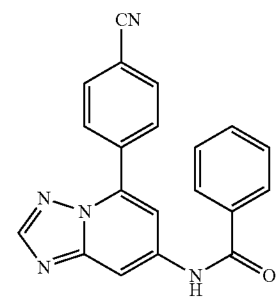 [SMILES: N#Cc1ccc(-c2cc(NC(=O)c3ccccc3)cc3ncnn23)cc1] | 4-(7-chloro-[1,2,4]triazolo[1,5-a]pyridin-5-yl)benzonitrile (Intermediate 8) | benzamide (CAS 55-21-0) | 4 | 340 | ¹H NMR (300 MHz, DMSO-d₆) δ ppm 7.56-7.69 (m, 3 H) 7.82 (s, 1 H) 7.99-8.05 (m, 2 H) 8.07-8.15 (m, 2 H) 8.18-8.26 (m, 2 H) 8.42-8.51 (m, 2 H) 10.80 (s, 1 H) |
| 124 | tert-butyl N-[5-(4-cyano-3-fluorophenyl)-[1,2,4]triazolo[1,5-a]pyridin-7-yl]carbamate | 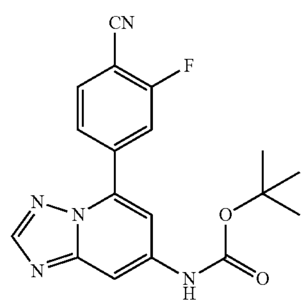 [SMILES: CC(C)(C)OC(=O)Nc1cc(-c2ccc(C#N)c(F)c2)n2ncnc2c1] | 4-(7-chloro-[1,2,4]triazolo[1,5-a]pyridin-5-yl)benzonitrile (Intermediate 10) | tert-butyl carbamate (CAS 4248-19-5) | 4 | 354 | ¹H NMR (400 MHz, CDCl₃) δ ppm 1.49 (s, 9 H) 7.02 (br. s., 1 H) 7.52-7.63 (m, 2 H) 7.70-7.76 (m, 1 H) 7.78-7.85 (m, 1 H) 7.86-7.93 (m, 1 H) 8.22 (s, 1 H) |
| 125 | 2-fluoro-4-{7-[(oxetan-3-ylmethyl)amino]-[1,2,4]triazolo[1,5-a]pyridin-5-yl}benzonitrile | 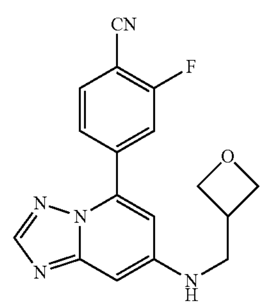 [SMILES: N#Cc1ccc(-c2cc(NCC3COC3)cc3ncnn23)cc1F] | 4-(7-chloro-[1,2,4]triazolo[1,5-a]pyridin-5-yl)benzonitrile (Intermediate 10) | oxetan-3-ylmethan-amine (CAS 6246-05-5) | 2 | 324 | ¹H NMR (400 MHz, DMSO-d₆) δ ppm 3.21-3.30 (m, 1 H) 3.43-3.54 (m, 2 H) 4.30-4.40 (m, 2 H) 4.64-4.74 (m, 2 H) 6.65 (s, 1 H) 6.81-6.94 (m, 2 H) 7.91-8.00 (m, 1 H) 8.08-8.21 (m, 3 H) |

| Ex. No. | Compound name | Structure | Starting aryl halide | Starting amine/alcohol or amide | Method | MS ES+ | ¹H NMR data δ ppm |
|---|---|---|---|---|---|---|---|
| 126 | 2-fluoro-4-{7-[(3,3,3-trifluoropropyl)-amino][1,2,4]triazolo-[1,5-a]pyridin-5-yl}benzonitrile | 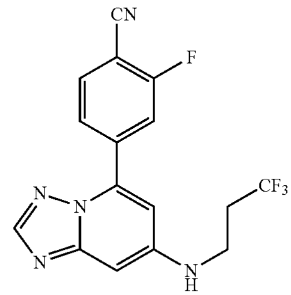 [SMILES: N#Cc1ccc(-c2cc(NCCC(F)(F)F)cc3ncnn23)cc1F] | 4-(7-chloro-[1,2,4]triazolo[1,5-a]pyridin-5-yl)benzonitrile (Intermediate 10) | 3,3,3-trifluoro-propan-1-amine (CAS 460-39-9) | 2 | 350 | ¹H NMR (400 MHz, Methanol-d₄) δ ppm 2.52-2.67 (m, 2 H) 3.47-3.59 (m, 2 H) 6.58 (s, 1 H) 6.85 (s, 1 H) 7.85-7.97 (m, 2 H) 8.00-8.08 (m, 1 H) 8.14 (s, 1 H) |
| 127 | 2-fluoro-4-(7-{[(3-methyloxetan-3-yl)methyl]amino}-[1,2,4]triazolo[1,5-a]pyridin-5-yl)benzonitrile | 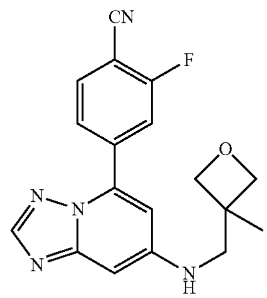 [SMILES: CC1(CNc2cc(-c3ccc(C#N)c(F)c3)n3ncnc3c2)COC1] | 4-(7-chloro-[1,2,4]triazolo[1,5-a]pyridin-5-yl)benzonitrile (Intermediate 10) | 3-methyloxetan-3-yl)methanamine (CAS 153209-97-3) | 2 | 338 | ¹H NMR (400 MHz, DMSO-d₆) δ ppm 1.37 (s, 3 H) 3.39 (d, J = 6 Hz, 2 H) 4.29 (d, J = 6 Hz, 2 H) 4.45 (d, J = 6 Hz, 2 H) 6.70 (d, J = 2 Hz, 1 H) 6.80 (m, 1 H) 7.00 (d, J = 2 Hz, 1 H) 7.89-8.02 (m, 1 H) 8.06-8.22 (m, 3 H) |
| 128 | 2-fluoro-4-(7-{[(3-phenyloxetan-3-yl)methyl]amino}-[1,2,4]triazolo[1,5-a]pyridin-5-yl)benzonitrile | 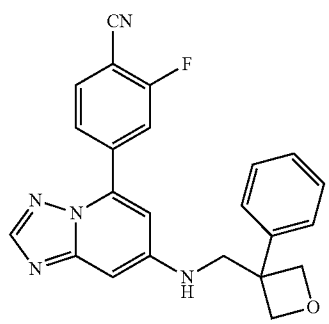 [SMILES: N#Cc1ccc(-c2cc(NCC3(c4ccccc4)COC3)cc3ncnn23)cc1F] | 4-(7-chloro-[1,2,4]triazolo[1,5-a]pyridin-5-yl)benzonitrile (Intermediate 10) | (3-phenyloxetan-3-yl)methanamine (CAS 497239-45-9) | 2 | 400 | ¹H NMR (400 MHz, DMSO-d₆) δ ppm 3.78 (d, J = 6 Hz, 2 H) 4.71-4.87 (m, 4 H) 6.55 (d, J = 2 Hz, 1 H) 6.75-6.84 (m, 1 H) 6.88 (d, J = 2 Hz, 1 H) 7.15-7.39 (m, 5 H) 7.84-7.95 (m, 1 H) 8.01-8.15 (m, 3 H) |
| 129 | 4-{7-[2-(dimethylamino)ethoxy]-[1,2,4]triazolo[1,5-a]pyridin-5-yl}-2-fluorobenzonitrile | 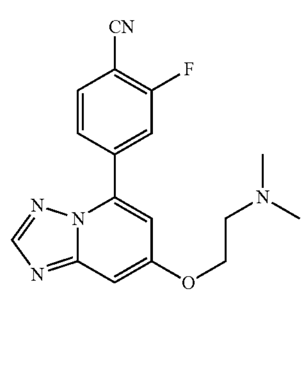 [SMILES: CN(C)CCOc1cc(-c2ccc(C#N)c(F)c2)n2ncnc2c1] | 4-(7-chloro-[1,2,4]triazolo[1,5-a]pyridin-5-yl)benzonitrile (Intermediate 10) | 2-(dimethylamino)ethanol (CAS 108-01-0) | 3 | 326 | ¹H NMR (300 MHz, DMSO-d₆) δ ppm 2.14-2.31 (m, 6 H) 2.62-2.77 (m, 2 H) 4.21-4.36 (m, 2 H) 7.21-7.36 (m, 1 H) 7.38-7.49 (m, 1 H) 8.05-8.18 (m, 2 H) 8.21-8.34 (m, 1 H) 8.36-8.49 (m, 1 H) |

| Ex. No. | Compound name | Structure | Starting aryl halide | Starting amine/alcohol or amide | Method | MS ES+ | ¹H NMR data δ ppm |
|---|---|---|---|---|---|---|---|
| 130 | 2-fluoro-4-{7-[2-(pyrrolidin-1-yl)ethoxy]-[1,2,4]triazolo[1,5-a]pyridin-5-yl}benzonitrile | 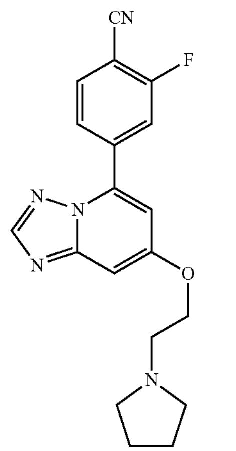 [SMILES: N#Cc1ccc(-c2cc(OCCN3CCCC3)cc3ncnn23)cc1F] | 4-(7-chloro-[1,2,4]triazolo[1,5-a]pyridin-5-yl)benzonitrile (Intermediate 10) | 2-(pyrrolidin-1-yl)ethan-1-ol (CAS 2955-88-6) | 3 | 352 | ¹H NMR (300 MHz, DMSO-d₆) δ ppm 1.58-1.79 (m, 4 H) 2.53-2.60 (m, 4 H) 2.81-2.95 (m, 2 H) 4.23-4.35 (m, 2 H) 7.29 (s, 1 H) 7.39 (s, 1 H) 8.08-8.17 (m, 2 H) 8.21-8.29 (m, 1 H) 8.41 (s, 1 H) |
| 131 | 2-fluoro-4-[7-oxolan-2-ylmethoxy)-[1,2,4]triazolo[1,5-a]pyridin-5-yl]benzonitrile | 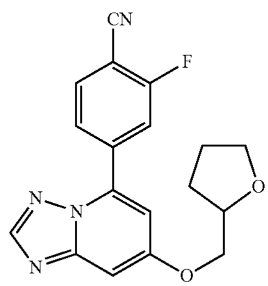 [SMILES: N#Cc1ccc(-c2cc(OCC3CCCO3)cc3ncnn23)cc1F] | 4-(7-chloro-[1,2,4]triazolo[1,5-a]pyridin-5-yl)benzonitrile (Intermediate 10) | (oxolan-2-ylmethanol (CAS 97-99-4) | 3 | 339 | ¹H NMR (300 MHz, DMSO-d₆) δ ppm 1.63-2.17 (m, 4 H) 3.65-3.89 (m, 2 H) 4.07-4.34 (m, 3 H) 7.23-7.34 (m, 1 H) 7.36-7.45 (m, 1 H) 8.08-8.19 (m, 2 H) 8.23-8.31 (m, 1 H) 8.38-8.48 (m, 1 H) |
| 132 | 2-fluoro-4-{7-[2-(2-oxopyrrolidin-1-yl)ethoxy]-[1,2,4]triazolo[1,5-a]pyridin-5-yl}benzonitrile | 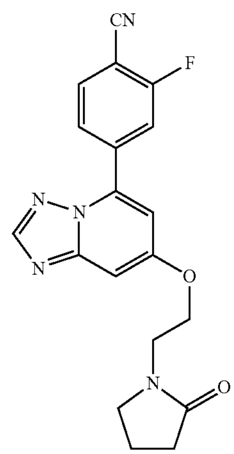 [SMILES: N#Cc1ccc(-c2cc(OCCN3CCCC3=O)cc3ncnn23)cc1F] | 4-(7-chloro-[1,2,4]triazolo[1,5-a]pyridin-5-yl)benzonitrile (Intermediate 10) | 1-(2-hydroxyethyl)pyrrolidin-2-one (CAS 3445-11-2) | 3 | 366 | ¹H NMR (300 MHz, DMSO-d₆) δ ppm 1.86-2.02 (m, 2 H) 2.17-2.30 (m, 2 H) 3.45-3.56 (m, 2 H) 3.59-3.69 (m, 2 H) 4.26-4.38 (m, 2 H) 7.25-7.34 (m, 1 H) 7.40-7.47 (m, 1 H) 8.09-8.19 (m, 2 H) 8.23-8.33 (m, 1 H) 8.42 (s, 1 H) |
| 133 | 2-fluoro-4-[7-oxolan-3-ylmethoxy)-[1,2,4]triazolo[1,5-a]pyridin-5-yl]benzonitrile | 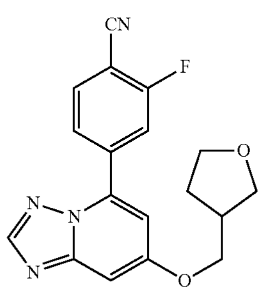 [SMILES: N#Cc1ccc(-c2cc(OCC3CCOC3)cc3ncnn23)cc1F] | 4-(7-chloro-[1,2,4]triazolo[1,5-a]pyridin-5-yl)benzonitrile (Intermediate 10) | (oxolan-3-ylmethanol (CAS 15833-61-1) | 3 | 339 | ¹H NMR (300 MHz, DMSO-d₆) δ ppm 1.60-1.82 (m, 1 H) 1.97-2.16 (m, 1 H) 2.66-2.82 (m, 1 H) 3.52-3.90 (m, 4 H) 4.05-4.25 (m, 2 H) 7.28 (s, 1 H) 7.41 (s, 1 H) 8.07-8.18 (m, 2 H) 8.25 (m, 1 H) 8.36-8.47 (m, 1 H) |

-continued

| Ex. No. | Compound name | Structure | Starting aryl halide | Starting amine/alcohol or amide | Method | MS ES+ | ¹H NMR data δ ppm |
|---|---|---|---|---|---|---|---|
| 134 | 2-fluoro-4-[7-(2-oxopyrrolidin-1-yl)-[1,2,4]triazolo[1,5-a]pyridin-5-yl]benzonitrile | 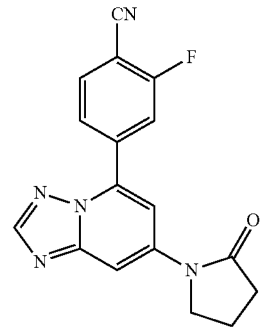 [SMILES: N#Cc1ccc(-c2cc(N3CCCC3=O)cc3ncnn23)cc1F] | 4-(7-chloro-[1,2,4]triazolo[1,5-a]pyridin-5-yl)benzonitrile (Intermediate 10) | pyrrolidin-2-one (CAS 616-45-5) | 4 | 322 | ¹H NMR (400 MHz DCM-d₂) δ ppm 2.05-2.24 (m, 2 H) 2.63 (t, J = 8 Hz, 2 H) 4.03 (t, J = 7 Hz, 2 H) 8.00-8.11 (m, 3 H) 8.14-8.31 (m, 2 H) 8.52 (s, 1 H) |
| 135 | 2-fluoro-4-[7-(2-oxo-1,3-oxazolidin-3-yl)-[1,2,4]triazolo[1,5-a]pyridin-5-yl]benzonitrile | 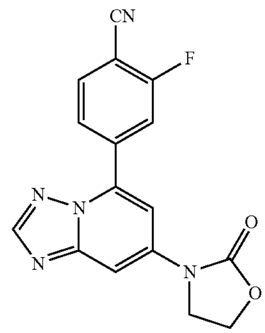 [SMILES: N#Cc1ccc(-c2cc(N3CCOC3=O)cc3ncnn23)cc1F] | 4-(7-chloro-[1,2,4]triazolo[1,5-a]pyridin-5-yl)benzonitrile (Intermediate 10) | 1,3-oxazolidin-2-one (CAS 497-25-6) | 4 | 324 | ¹H NMR (400 MHz DMSO-d₆) δ ppm 4.20-4.31 (m, 2 H) 4.50-4.62 (m, 2 H) 7.89 (d, J = 2 Hz, 1 H) 7.99 (d, J = 2 Hz, 1 H) 8.04-8.07 (m, 1 H) 8.14-8.28 (m, 2 H) 8.52 (s, 1 H) |
| 136 | N-[5-(4-cyano-3-fluorophenyl)-[1,2,4]triazolo[1,5-a]pyridin-7-yl]-N-methylacetamide | 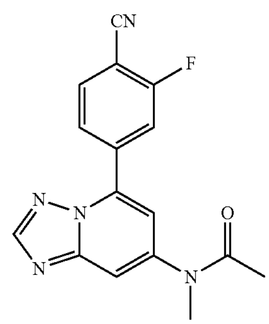 [SMILES: CC(=O)N(C)c1cc(-c2ccc(C#N)c(F)c2)n2ncnc2c1] | 4-(7-chloro-[1,2,4]triazolo[1,5-a]pyridin-5-yl)benzonitrile (Intermediate 10) | N-methylacetamide (CAS 76-16-3) | 4 | 310 | ¹H NMR (400 MHz DCM-d₂) δ ppm 2.19 (s, 3 H) 3.44 (s, 3 H) 7.43 (s, 1 H) 7.74 (d, J = 2 Hz, 1 H) 7.83-7.90 (m, 2 H) 7.97-8.00 (m, 1 H) 8.45 (s, 1 H) |
| 137 | 2-fluoro-4-[7-(morpholin-4-yl)-[1,2,4]triazolo[1,5-a]pyridin-5-yl]benzonitrile | 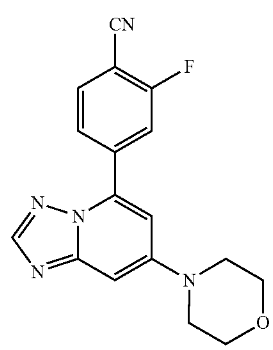 [SMILES: N#Cc1ccc(-c2cc(N3CCOCC3)cc3ncnn23)cc1F] | 4-(7-chloro-[1,2,4]triazolo[1,5-a]pyridin-5-yl)benzonitrile (Intermediate 10) | morpholine (CAS 110-91-8) | 2 | 324 | ¹H NMR (300 MHz, DMSO-d₆) δ ppm 3.37-3.50 (m, 4 H) 3.69-3.88 (m, 4 H) 7.06 (s, 1 H) 7.38 (s, 1 H) 8.08-8.37 (m, 4 H) |

-continued

| Ex. No. | Compound name | Structure | Starting aryl halide | Starting amine/alcohol or amide | Method | MS ES+ | $^1$H NMR data δ ppm |
|---|---|---|---|---|---|---|---|
| 138 | 2-fluoro-4-[7-(3-methoxyazetidin-1-yl)-[1,2,4]triazolo[1,5-a]pyridin-5-yl]benzonitrile | 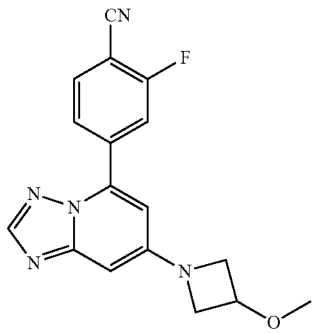 [SMILES: COC1CN(c2cc(-c3ccc(C#N)c(F)c3)n3ncnc3c2)C1] | 4-(7-chloro-[1,2,4]triazolo[1,5-a]pyridin-5-yl)benzonitrile (Intermediate 10) | 3-methoxy-azetidine (CAS 110925-17-2) | 2 | 324 | $^1$H NMR (300 MHz, DMSO-d$_6$) δ ppm 3.25-3.30 (m, 3 H) 3.81-3.93 (m, 2 H) 4.19-4.31 (m, 2 H) 4.34-4.43 (m, 1 H) 6.51-6.59 (m, 1 H) 6.79-6.86 (m, 1 H) 8.03-8.30 (m, 4 H) |
| 139 | N-[5-(4-cyano-3-fluorophenyl)-[1,2,4]triazolo[1,5-a]pyridin-7-yl]acetamide | 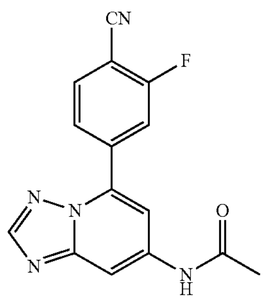 [SMILES: CC(=O)Nc1cc(-c2ccc(C#N)c(F)c2)n2ncnc2c1] | 4-(7-chloro-[1,2,4]triazolo[1,5-a]pyridin-5-yl)benzonitrile (Intermediate 10) | acetamide (CAS 30-35-5) | 4 | 296 | $^1$H NMR (400 MHz, DMSO-d$_6$) δ ppm 2.16 (s, 3 H) 7.41-7.52 (m, 1 H) 7.92-8.04 (m, 1 H) 8.11-8.28 (m, 3 H) 8.46 (s, 1 H) 10.59 (s, 1 H) |
| 140 | 4-[7-(3-methoxyazetidin-1-yl)-[1,2,4]triazolo[1,5-a]pyridin-5-yl]benzonitrile | 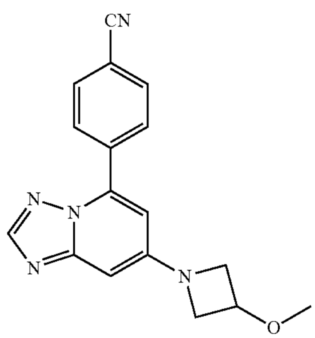 [SMILES: COC1CN(c2cc(-c3ccc(C#N)cc3)n3ncnc3c2)C1] | 4-(7-chloro-[1,2,4]triazolo[1,5-a]pyridin-5-yl)benzonitrile (Intermediate 8) | 3-methoxy-azetidine (CAS 110925-17-2) | 2 | 306 | $^1$H NMR (400 MHz, DMSO-d$_6$) δ ppm 3.28 (s, 3 H) 3.82-3.94 (m, 2 H) 4.21-4.31 (m, 2 H) 4.33-4.45 (m, 1 H) 6.48-6.55 (m, 1 H) 6.68-6.76 (m, 1 H) 8.04 (d, J = 8 Hz, 2 H) 8.15-8.25 (m, 3 H) |
| 141 | 4-(7-{2-oxa-6-azaspiro[3.3]heptan-6-yl}-[1,2,4]triazolo[1,5-a]pyridin-5-yl)benzonitrile | 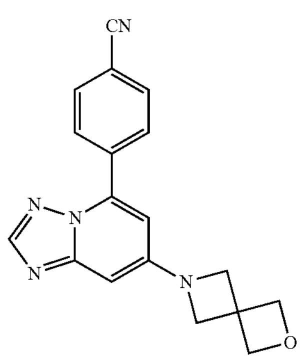 [SMILES: N#Cc1ccc(-c2cc(N3CC4(COC4)C3)cc3ncnn23)cc1] | 4-(7-chloro-[1,2,4]triazolo[1,5-a]pyridin-5-yl)benzonitrile (Intermediate 8) | 2-oxa-6-azaspiro[3.3]heptane (CAS 174-78-7) | 2 | 318 | $^1$H NMR (400 MHz, DMSO-d$_6$) δ ppm 4.22 (s, 4 H) 4.75 (s, 4 H) 6.49-6.57 (m, 1 H) 6.68-6.77 (m, 1 H) 8.04 (d, J = 9 Hz, 2 H) 8.13-8.24 (m, 3 H) |

| Ex. No. | Compound name | Structure | Starting aryl halide | Starting amine/alcohol or amide | Method | MS ES+ | 1H NMR data δ ppm |
|---|---|---|---|---|---|---|---|
| 142 | N-[5-(4-cyano-2-methylphenyl)-[1,2,4]triazolo[1,5-a]pyridin-7-yl]acetamide | 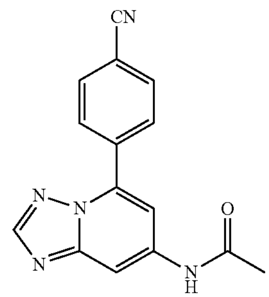 [SMILES: CC(=O)Nc1cc(-c2ccc(C#N)cc2)n2ncnc2c1] | 4-{7-chloro-[1,2,4]triazolo[1,5-a]pyridin-5-yl}-3-methyl-benzonitrile (Intermediate 24) | acetamide (CAS 30-35-5) | 4 | 292 | 1H NMR (400 MHz, DMSO-d6) δ ppm 2.11 (s, 3 H) 2.15 (s, 3 H) 7.20 (d, J = 2 Hz, 1 H) 7.67 (d, J = 8 Hz, 1 H) 7.86 (d, J = 8 Hz, 1 H) 7.94 (s, 1 H) 8.23 (d, J = 2 Hz, 1 H) 8.35 (s, 1 H) 10.56 (s, 1 H) |
| 143 | tert-butyl 4-[5-(4-cyanophenyl)-[1,2,4]triazolo[1,5-a]pyridin-7-yl]piperazine-1-carboxylate | 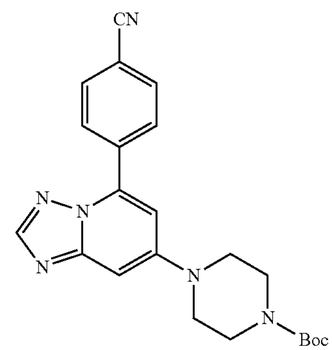 [SMILES: CC(C)(C)OC(=O)N1CCN(c2cc(-c3ccc(C#N)cc3)n3ncnc3c2)CC1] | 4-(7-chloro-[1,2,4]triazolo[1,5-a]pyridin-5-yl)benzonitrile (Intermediate 8) | tert-butyl piperazine-1-carboxylate (CAS 57260-71-6) | 2 | 405 | 1H NMR (400 MHz, DMSO-d6) δ ppm 1.44 (s, 9 H) 3.46 (m, 8 H) 7.03 (d, J = 3 Hz, 1 H) 7.28 (d, J = 3 Hz, 1 H) 8.05 (d, J = 8 Hz, 2 H) 8.21 (d, J = 8 Hz, 2 H) 8.27 (s, 1 H) |
| 144 | tert-butyl 6-[5-(4-cyanophenyl)-[1,2,4]triazolo[1,5-a]pyridin-7-yl]-2,6-diazaspiro[3.3]heptane-2-carboxylate | 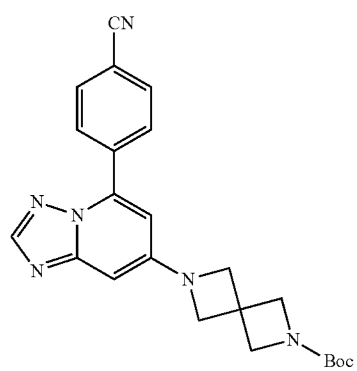 [SMILES: CC(C)(C)OC(=O)N1CC2(C1)CN(c1cc(-c3ccc(C#N)cc3)n3ncnc3c1)C2] | 4-(7-chloro-[1,2,4]triazolo[1,5-a]pyridin-5-yl)benzonitrile (Intermediate 8) | tert-butyl 2,6-diazaspiro[3.3]heptane-2-carboxylate (CAS 1041026-70-3) | 2 | 417 | 1H NMR (400 MHz, DMSO-d6) δ ppm 1.39 (s, 9 H) 4.01-4.08 (m, 4 H) 4.17 (s, 4 H), 6.52 (d, J = 2 Hz, 1 H) 6.71 (d, J = 2 Hz, 1 H) 8.04 (d, J = 9 Hz, 2 H) 8.12-8.24 (m, 3 H) |
| 145 | methyl N-[5-(4-cyano-2-methylphenyl)-[1,2,4]triazolo[1,5-a]pyridin-7-yl]carbamate | 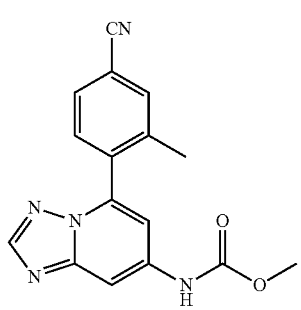 [SMILES: COC(=O)Nc1cc(-c2ccc(C#N)cc2C)n2ncnc2c1] | 4-{7-chloro-[1,2,4]triazolo[1,5-a]pyridin-5-yl}-3-methyl-benzonitrile | methyl carbamate (CAS 598-55-0) (Intermediate 24) | 2 | 308 | 1H NMR (400 MHz, DMSO-d6) δ ppm 2.11 (s, 3 H) 3.32 (s, 3 H) 7.14 (d, J = 2 Hz, 1 H) 7.66 (d, J = 8 Hz, 1 H) 7.86 (d, J = 8 Hz, 1 H) 7.94 (s, 1 H) 8.00 (d, J = 2 Hz, 1 H) 8.34 (s, 1 H) 10.39 (s, 1 H) |

Example 146: 4-{7-Amino-[1,2,4]triazolo[1,5-a]pyridin-5-yl}-2-fluorobenzonitrile

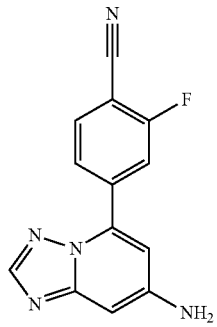 [SMILES: N#Cc1ccc(-c2cc(N)cc3ncnn23)cc1F]

To a stirred suspension of tert-butyl (5-(4-cyano-3-fluorophenyl)-[1,2,4]triazolo[1,5-a]pyridin-7-yl)carbamate (Intermediate 11, 0.318 g, 0.900 mmol) in DCM (4 mL) was added TFA (1 mL). The reaction was stirred at room temperature for 1.5 h. The reaction was heated to reflux overnight. The reaction mixture was removed from heat and allowed to cool to room temperature. The reaction was diluted in DCM and basified with sat. aq. NaHCO$_3$. The DCM layer was removed and the aqueous phase was extracted with DCM (2×). The organic phases were combined and concentrated to dryness in vacuo to yield the title compound.

$^1$H NMR (400 MHz, DMSO-d$_6$) δ ppm 6.27 (br. s, 2H) 6.64 (d, J=2 Hz, 1H) 6.86 (d, J=2 Hz, 1H) 7.90-7.98 (m, 1H) 8.06-8.21 (m, 3H)

MS ES$^+$: 254

Example 147: 4-{6-Fluoro-[1,2,4]triazolo[1,5-a]pyridin-5-yl}benzonitrile

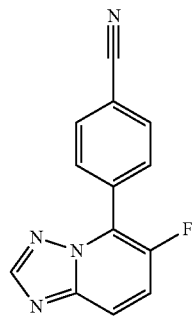 [SMILES: N#Cc1ccc(-c2c(F)ccc3ncnn23)cc1]

A solution of (E)-N-(6-(4-cyanophenyl)-5-fluoropyridin-2-yl)-N'-hydroxyformimidamide (Intermediate 12, 0.085 g, 0.332 mmol) in THF (2 mL) was treated with TFAA (0.094 mL, 0.663 mmol). The reaction was heated to 40° C. for 1 h. The reaction was basified with NaHCO$_3$ (sat. aq) and extracted with DCM. The organic phase was collected, dried (phase separator) and concentrated in vacuo. The resulting residue was purified by flash chromatography (0-100% EtOAc in petrol on basic silica) to afford the title compound.

$^1$H NMR (400 MHz, DMSO-d$_6$) δ ppm 7.92-8.00 (m, 1H) 8.01-8.13 (m, 5H) 8.55 (s, 1H)

MS ES$^+$: 239

Example 148: N-[5-(4-Cyano-3-fluorophenyl)-[1,2,4]triazolo[1,5-a]pyridin-7-yl]cyclopropanesulfonamide

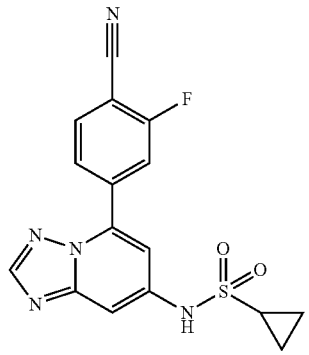 [SMILES: N#Cc1ccc(-c2cc(NS(=O)(=O)C3CC3)cc3ncnn23)cc1F]

A suspension of K$_2$CO$_3$ (0.456 g, 3.30 mmol), 5-(di-tert-butylphosphino)-1',3',5'-triphenyl-1'H-1,4'-bipyrazole (0.223 g, 0.440 mmol), [(cinnamyl)PdCl]$_2$ (0.064 g, 0.110 mmol), cyclopropanesulfonamide (CAS 154350-29-5, 0.400 g, 3.30 mmol) and 4-(7-chloro-[1,2,4]triazolo[1,5-a]pyridin-5-yl)-2-fluorobenzonitrile (Intermediate 10, 0.300 g, 1.100 mmol) in dioxane (4 mL) was heated to 95° C. for 0.5 h under an inert atmosphere. The reaction was diluted with brine, extracted into EtOAc, dried (phase separator) and concentrated in vacuo. The crude product was purified by column chromatography on silica, eluted with 0-100% EtOAc/petrol followed by 0-20% MeOH/EtOAc. The product was further purified by reverse phase preparative HPLC eluted with acetonitrile/water (with 0.1% ammonia) to afford the title compound.

$^1$H NMR (400 MHz, DMSO-d$_6$) δ ppm 1.04 (m, 4H) 2.99 (s, 1H) 7.23 (s, 1H) 7.53 (s., 1H) 7.98 (m, 1H) 8.15-8.23 (m, 2H) 8.45 (s, 1H) 10.72 (s, 1H)

MS ES$^+$: 358

Example 149: N-[5-(4-cyano-3-fluorophenyl)-[1,2,4]triazolo[1,5-a]pyridin-7-yl]benzenesulfonamide

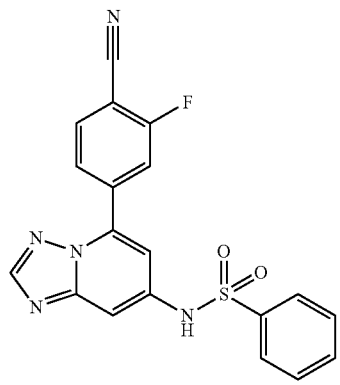 [SMILES: N#Cc1ccc(-c2cc(NS(=O)(=O)c3ccccc3)cc3ncnn23)cc1F]

Prepared as described for N-[5-(4-cyano-3-fluorophenyl)-[1,2,4]triazolo[1,5-a]pyridin-7-yl]cyclopropanesulfonamide (Example 148) from 4-(7-chloro-[1,2,4]triazolo[1,5-a]pyridin-5-yl)-2-fluorobenzonitrile (Intermediate 10) and benzenesulfonamide to afford the title compound.

$^1$H NMR (400 MHz, DMSO-d$_6$) δ ppm 7.07 (s, 1H) 7.24 (s, 1H) 7.57 (m, 3H) 7.91 (m, 3H) 8.08-8.17 (m, 2H) 8.31 (s, 1H)
MS ES$^+$: 394

Example 150: 3-[5-(4-Cyano-3-fluorophenyl)-[1,2,4]triazolo[1,5-a]pyridin-7-yl]-1-phenylurea

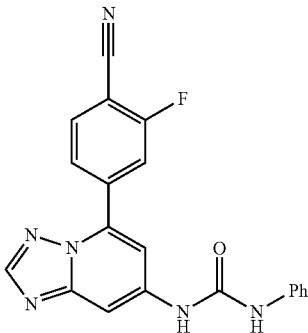 [SMILES: N#Cc1ccc(-c2cc(NC(=O)Nc3ccccc3)cc3ncnn23)cc1F]

To a solution of 4-(7-amino-[1,2,4]triazolo[1,5-a]pyridin-5-yl)-2-fluorobenzonitrile (Intermediate 10, 0.100 g, 0.395 mmol) and DIPEA (0.345 mL, 1.974 mmol) in DMF (1.5 mL) was added isocyanatobenzene (CAS 103-71-9, 0.129 mL, 1.185 mmol). The reaction was stirred at rt for 2.5 h. The reaction was diluted with brine, extracted into EtOAc, washed with brine, dried (phase separator) and concentrated in vacuo. The crude product was purified by reverse phase preparative HPLC eluted with acetonitrile/water (with 0.1% ammonia) to afford the title compound.

$^1$H NMR (400 MHz, DMSO-d$_6$) δ ppm 7.04 (m, 1H) 7.33 (m, 2H) 7.50 (m, 3H) 8.03 (m, 2H) 8.11-8.31 (m, 2H) 8.42 (s, 1H) 9.07 (s, 1H) 9.38 (s, 1H)
MS ES$^+$: 373

The following Examples 151 to 175 were made by one of the procedures described below.

Procedure 1:

A solution of a primary amine (0.227 mmol), TEA (0.158 mL, 1.136 mmol) and the appropriate acid chloride (0.227 mmol) in DMF (2 mL) were stirred at rt overnight more TEA (0.158 mL, 1.136 mmol) and acid chloride (0.454 mmol) was added and the reaction was stirred for a further 2 h. The reaction was poured into water and extracted with DCM. The organic was collected, dried (phase separator) and concentrated in vacuo. The resulting residue was purified by reverse phase preparative HPLC eluted with acetonitrile/water (with 0.1% ammonia) to afford the title compound.

Procedure 2:

A solution of a primary amine (0.345 mmol), TEA (0.144 mL, 1.036 mmol) and a carboxylic acid in DMF (2 mL) were treated with N-propylphosphonic acid anhydride, cyclic trimer (50% in DMF) (0.407 mL, 0.690 mmol) and heated to 40° C. overnight. The reaction was cooled to rt, poured into water extracted with EtOAc, washed with brine, dried (phase separator) and concentrated in vacuo. The resulting residues were purified by preparative HPLC (acetonitrile/0.05% formic acid in water) to afford the title compound.

| Ex. No. | Compound name | Structure | Starting amine | Starting acid chloride/ carboxylic acid | Method | MS ES$^+$ $^1$H NMR data δ ppm |
|---|---|---|---|---|---|---|
| 151 | N-[5-(4-cyanophenyl)-[1,2,4]triazolo[1,5-a]pyridin-7-yl]-3-methoxy-propanamide | 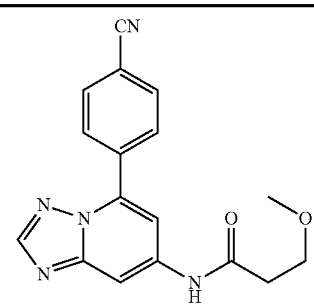 | 4-(7-amino-[1,2,4]triazolo[1,5-a]pyridin-5-yl)benzonitrile (Example 100) | 3-methoxy-propanoic acid (CAS 2544-06-1) | 2 | 322 $^1$H NMR (400 MHz, DMSO-d$_6$) δ ppm 2.62-2.72 (m, 2 H) 3.27 (s, 3 H) 3.62-3.73 (m, 2 H) 7.42-7.50 (m, 1 H) 8.03-8.09 (m, 2 H) 8.12-8.20 (m, 2 H) 8.22-8.26 (m, 1 H) 8.44 (s, 1 H) 10.59 (s, 1 H) |
| 152 | N-[5-(4-cyanophenyl)-[1,2,4]triazolo[1,5-a]pyridin-7-yl]-2-phenylacetamide | 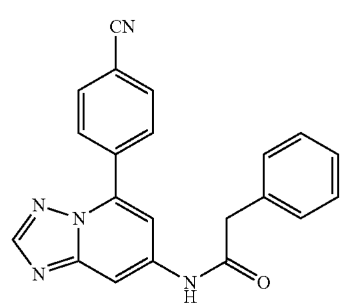 [SMILES: N#Cc1ccc(-c2cc(NC(=O)Cc3ccccc3)cc3ncnn23)cc1] | 4-(7-amino-[1,2,4]triazolo[1,5-a]pyridin-5-yl)benzonitrile (Example 100) | 2-phenylacetyl chloride (CAS 103-80-0) | 1 | 354 $^1$H NMR (400 MHz, DMSO-d$_6$) δ ppm 3.76 (s, 2 H) 7.23-7.41 (m, 5 H) 7.45-7.54 (m, 1 H) 8.02-8.11 (m, 2 H) 8.14-8.18 (m, 2 H) 8.20-8.26 (m, 1 H) 8.43 (s, 1 H) 10.80 (s, 1 H) |

-continued

| Ex. No. | Compound name | Structure | Starting amine | Starting acid chloride/ carboxylic acid | Method | MS ES+ | 1H NMR data δ ppm |
|---|---|---|---|---|---|---|---|
| 153 | N-[5-(4-cyano-fluorophenyl)-[1,2,4]triazolo[1,5-a]pyridin-7-yl]-3,3,3-trifluoro-propanamide | 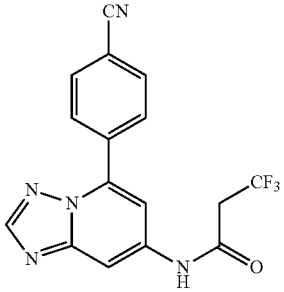 [SMILES: N#Cc1ccc(-c2cc(NC(=O)CC(F)(F)F)cc3ncnn23)cc1] | 4-(7-amino-[1,2,4]triazolo[1,5-a]pyridin-5-yl)benzonitrile (Example 100) | 3,3,3-trifluoro-propanoyl chloride (CAS 41463-83-6) | 2 | 364 | 1H NMR (300 MHz, DMSO-d6) δ ppm 3.56-3.77 (m, 2 H) 7.47 (s, 1 H) 7.95-8.05 (m, 1 H) 8.12-8.30 (m, 3 H) 8.50 (s, 1 H) 10.97 (s, 1 H) |
| 154 | N-[5-(4-cyano-3-fluorophenyl)-[1,2,4]triazolo[1,5-a]pyridin-7-yl]-2-methoxyacetamide | 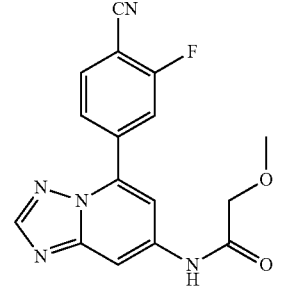 [SMILES: COCC(=O)Nc1cc(-c2ccc(C#N)c(F)c2)n2ncnc2c1] | 4-(7-amino-[1,2,4]triazolo[1,5-a]pyridin-5-yl)-2-fluorobenzonitrile (Example 146) | 2-methoxyacetyl chloride (CAS 38870-89-2) | 1 | 326 | 1H NMR (300 MHz, DMSO-d6) δ ppm 3.43 (s, 3 H) 4.12 (s, 2 H) 7.69-7.87 (m, 1 H) 8.97-8.07 (m, 1 H) 8.13-8.28 (m, 2 H) 8.36 (s, 1 H) 8.48 (s, 1 H) 10.37 (s, 1 H) |
| 155 | N-[5-(4-cyano-3-fluorophenyl)-[1,2,4]triazolo[1,5-a]pyridin-7-yl]cyclobutane-carboxamide | 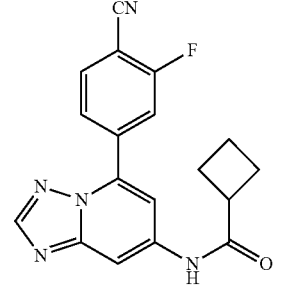 | 4-(7-amino-[1,2,4]triazolo[1,5-a]pyridin-5-yl)-2-fluorobenzonitrile (Example 146) | cyclobutane-carbonyl chloride (CAS 5006-22-4) | 1 | 336 | 1H NMR (300 MHz, DMSO-d6) δ ppm 1.73-2.08 (m, 2 H) 2.12-2.37 (m, 4 H) 3.11-3.22 (m, 1 H) 7.44-7.62 (m, 1 H) 7.95-8.02 (m, 1 H) 8.12-8.35 (m, 3 H) 8.45 (s, 1 H) 10.35 (s, 1 H) |
| 156 | N-[5-(4-cyano-3-fluorophenyl)-[1,2,4]triazolo[1,5-a]pyridin-7-yl]-2-(oxan-4-yl)acetamide | 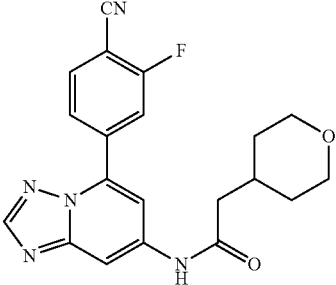 [SMILES: N#Cc1ccc(-c2cc(NC(=O)CC3CCOCC3)cc3ncnn23)cc1F] | 4-(7-amino-[1,2,4]triazolo[1,5-a]pyridin-5-yl)-2-fluorobenzonitrile (Example 146) | 2-(oxan-4-yl)acetic acid (CAS 85064-61-5) | 1 | 380 | 1H NMR (300 MHz, DMSO-d6) δ ppm 1.15-1.41 (m, 2 H) 1.55-1.67 (m, 2 H) 1.95-2.10 (m, 1 H) 2.29-2.39 (m, 2 H) 3.31-3.40 (m, 2 H) 3.74-3.93 (m, 2 H) 7.50 (s, 1 H) 7.93-8.05 (m, 1 H) 8.12-8.28 (m, 3 H) 8.45 (s, 1 H) 10.56 (s, 1 H) |
| 157 | N-[5-(4-cyano-3-fluorophenyl)-[1,2,4]triazolo[1,5-a]pyridin-7-yl]-2-methyl-cyclopropane-1-carboxamide | 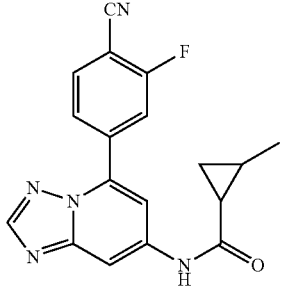 [SMILES: CC1CC1C(=O)Nc1cc(-c2ccc(C#N)c(F)c2)n2ncnc2c1] | 4-(7-amino-[1,2,4]triazolo[1,5-a]pyridin-5-yl)-2-fluorobenzonitrile (Example 146) | 2-methyl-cyclopropane-1-carboxylic acid (CAS 29555-02-0) | 2 | 336 | 1H NMR (300 MHz, DMSO-d6) δ ppm 0.68-0.87 (m, 1 H) 1.05-1.21 (m, 4 H) 1.25-1.48 (m, 1 H) 1.50-1.67 (m, 1 H) 7.53 (s, 1 H) 7.93-8.07 (m, 1 H) 8.08-8.28 (m, 3 H) 8.39-8.55 (m, 1 H) 10.79 (s, 1 H) |

-continued

| Ex. No. | Compound name | Structure | Starting amine | Starting acid chloride/ carboxylic acid | Method | MS ES+ | ¹H NMR data δ ppm |
|---|---|---|---|---|---|---|---|
| 158 | N-[5-(4-cyano-3-fluorophenyl)-[1,2,4]triazolo[1,5-a]pyridin-7-yl]-2-(piperidin-1-yl)acetamide | 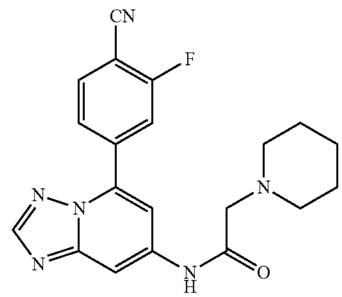 [SMILES: N#Cc1ccc(-c2cc(NC(=O)CN3CCCCC3)cc3ncnn23)cc1F] | 4-(7-amino-[1,2,4]triazolo[1,5-a]pyridin-5-yl)-2-fluorobenzonitrile (Example 146) | 2-(piperidin-1-yl)acetic acid (CAS 3235-67-4) | 2 | 379 | ¹H NMR (300 MHz, DMSO-d₆) δ ppm 1.36-1.50 (m, 2 H) 1.54-1.70 (m, 4 H) 2.40-2.50 (obsc., 4H) 3.18 (s, 2 H) 7.75 (s, 1 H) 7.93-8.06 (m, 1 H) 8.15-8.28 (m, 2 H) 8.38 (s, 1 H) 8.47 (s, 1 H) 10.23 (s, 1 H) |
| 159 | (2S)-N-[5-(4-cyano-3-fluorophenyl)-[1,2,4]triazolo[1,5-a]pyridin-7-yl]oxolane-2-carboxamide | 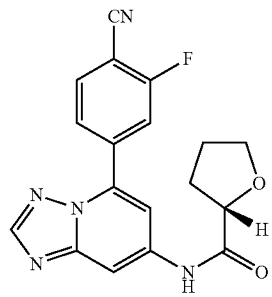 [SMILES: N#Cc1ccc(-c2cc(NC(=O)[C@@H]3CCCO3)cc3ncnn23)cc1F] | 4-(7-amino-[1,2,4]triazolo[1,5-a]pyridin-5-yl)-2-fluorobenzonitrile (Example 146) | (2S)-oxolane-2-carboxylic acid (CAS 87392-07-2) | 2 | 352 | ¹H NMR (300 MHz, DMSO-d₆) δ ppm 1.80-1.95 (m, 2 H) 1.98-2.16 (m, 1 H) 2.19-2.36 (m, 1 H) 3.83-3.95 (m, 1 H) 3.97-4.14 (m, 1 H) 4.44-4.57 (m, 1 H) 7.87 (s, 1 H) 8.00-8.10 (m, 1 H) 8.14-8.30 (m, 2 H) 8.40 (s, 1 H) 8.46-8.53 (m, 1 H) 10.27 (s, 1 H) |
| 160 | (2R)-N-[5-(4-cyano-3-fluorophenyl)-[1,2,4]triazolo[1,5-a]pyridin-7-yl]oxolane-2-carboxamide | 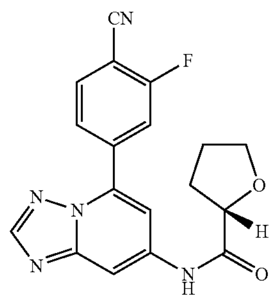 [SMILES: N#Cc1ccc(-c2cc(NC(=O)[C@@H]3CCCO3)cc3ncnn23)cc1F] | 4-(7-amino-[1,2,4]triazolo[1,5-a]pyridin-5-yl)-2-fluorobenzonitrile (Example 146) | (2R)-oxolane-2-carboxylic acid (CAS 87392-05-0) | 2 | 352 | ¹H NMR (300 MHz, DMSO-d₆) δ ppm 1.80-1.95 (m, 2 H) 1.98-2.13 (m, 1 H) 2.20-2.35 (m, 1 H) 3.82-3.95 (m, 1 H) 3.96-4.10 (m, 1 H) 4.42-4.59 (m, 1 H) 7.88 (s, 1 H) 7.98-8.06 (m, 1 H) 8.11-8.32 (m, 2 H) 8.35-8.54 (m, 2 H) 10.27 (s, 1 H) |
| 161 | N-[5-(4-cyano-3-fluorophenyl)-[1,2,4]triazolo[1,5-a]pyridin-7-yl]-2-(dimethylamino)acetamide | 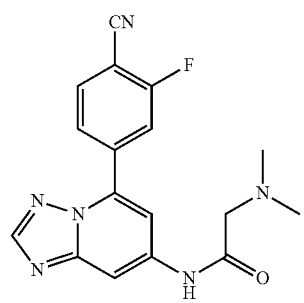 [SMILES: CN(C)CC(=O)Nc1cc(-c2ccc(C#N)c(F)c2)n2ncnc2c1] | 4-(7-amino-[1,2,4]triazolo[1,5-a]pyridin-5-yl)-2-fluorobenzonitrile (Example 146) | 2-(dimethylamino)acetic acid (CAS 1118-68-9) | 2 | 339 | ¹H NMR (300 MHz, DMSO-d₆) δ ppm 2.25-2.35 (m, 6 H) 3.13-3.22 (m, 2 H) 7.82 (s, 1 H) 7.99-8.09 (m, 1 H) 8.13-8.27 (m, 2 H) 8.38 (s, 1 H) 8.43-8.50 (m, 1 H) 10.35 (s, 1 H) |
| 162 | N-[5-(4-cyano-3-fluorophenyl)-[1,2,4]triazolo[1,5-a]pyridin-7-yl]oxolane-3-carboxamide | 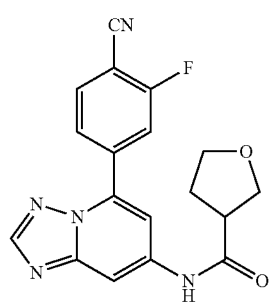 [SMILES: N#Cc1ccc(-c2cc(NC(=O)C3CCOC3)cc3ncnn23)cc1F] | 4-(7-amino-[1,2,4]triazolo[1,5-a]pyridin-5-yl)-2-fluorobenzonitrile (Example 146) | oxolane-3-carboxylic acid (CAS 89364-31-8) | 2 | 352 | ¹H NMR (300 MHz, DMSO-d₆) δ ppm 2.01-2.23 (m, 2 H) 3.14-3.28 (m, 1 H) 3.66-3.87 (m, 3 H) 3.90-4.02 (m, 1 H) 7.54 (s, 1 H) 7.93-8.06 (m, 1 H) 8.10-8.32 (m, 3 H) 8.39-8.53 (m, 1 H) 10.66 (s, 1 H) |

-continued

| Ex. No. | Compound name | Structure | Starting amine | Starting acid chloride/ carboxylic acid | Method | MS ES+ | 1H NMR data δ ppm |
|---|---|---|---|---|---|---|---|
| 163 | N-[5-(4-cyano-3-fluorophenyl)-[1,2,4]triazolo[1,5-a]pyridin-7-yl]-1-methyl-cyclopropane-1-carboxamide | 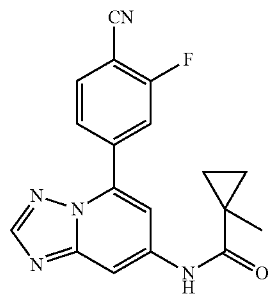 [SMILES: CC1(C(=O)Nc2cc(-c3ccc(C#N)c(F)c3)n3ncnc3c2)CC1] | 4-(7-amino-[1,2,4]triazolo[1,5-a]pyridin-5-yl)-2-fluorobenzonitrile (Example 146) | 1-methyl-cyclopropane-1-carboxylic acid (CAS 6914-76-7) | 2 | 336 | 1H NMR (300 MHz, DMSO-d6) δ ppm 0.70-0.80 (m, 2 H) 1.14-1.25 (m, 2 H) 1.46 (s, 3 H) 7.82 (s, 1 H) 8.03 (d, J = 8 Hz, 1 H) 8.10-8.28 (m, 2 H) 8.34 (s, 1 H) 8.43-8.50 (m, 1 H) 9.68 (s, 1 H) |
| 164 | N-[5-(4-cyano-3-fluorophenyl)-[1,2,4]triazolo[1,5-a]pyridin-7-yl]oxane-3-carboxamide | 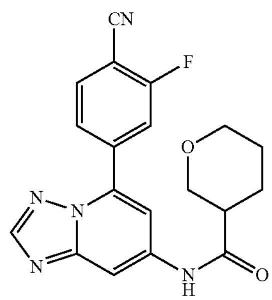 [SMILES: N#Cc1ccc(-c2cc(NC(=O)C3CCCOC3)cc3ncnn23)cc1F] | 4-(7-amino-[1,2,4]triazolo[1,5-a]pyridin-5-yl)-2-fluorobenzonitrile (Example 146) | oxane-3-carboxylic acid (CAS 873397-34-3) | 2 | 366 | 1H NMR (300 MHz, DMSO-d6) δ ppm 1.40-1.88 (m, 4 H) 1.95-2.12 (m, 1 H) 2.64-2.77 (m, 1 H) 3.40-3.53 (m, 1 H) 3.76-3.92 (m, 1 H) 3.97-4.08 (m, 1 H) 7.53 (s, 1 H) 7.92-8.02 (m, 1 H) 8.10-8.25 (m, 3 H) 8.42-8.50 (m, 1 H) 10.59 (s, 1 H) |
| 165 | N-[5-(4-cyano-3-fluorophenyl)-[1,2,4]triazolo[1,5-a]pyridin-7-yl]-4-methyloxane-4-carboxamide | 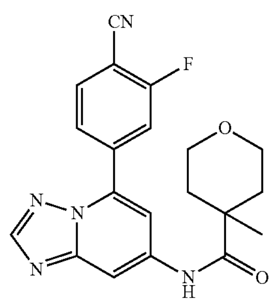 [SMILES: CC1(C(=O)Nc2cc(-c3ccc(C#N)c(F)c3)n3ncnc3c2)CCOCC1] | 4-(7-amino-[1,2,4]triazolo[1,5-a]pyridin-5-yl)-2-fluorobenzonitrile (Example 146) | 4-methyloxane-4-carboxylic acid (CAS 233276-38-5) | 2 | 380 | 1H NMR (400 MHz, DMSO-d6) δ ppm 1.33-1.54 (m, 7 H) 1.67 (s, 1 H) 2.10-2.24 (m, 1 H) 3.47-3.59 (m, 1 H) 3.86 (m, 1 H) 7.97 (m, 1 H) 8.04 (m, 1 H) 8.13-8.27 (m, 2 H) 8.43 (m, 1 H) 8.48 (s, 1 H) 10.38 (s, 1 H) |
| 166 | N-[5-(4-cyano-3-fluorophenyl)-[1,2,4]triazolo[1,5-a]pyridin-7-yl]-3-methyloxetane-3-carboxamide | 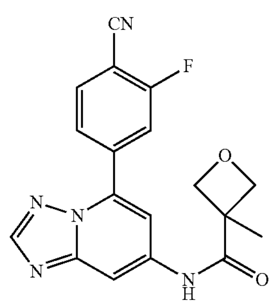 [SMILES: CC1(C(=O)Nc2cc(-c3ccc(C#N)c(F)c3)n3ncnc3c2)COC1] | 4-(7-amino-[1,2,4]triazolo[1,5-a]pyridin-5-yl)-2-fluorobenzonitrile (Example 146) | 3-methyloxetane-3-carboxylic acid (CAS 28562-86-7) | 2 | 352 | 1H NMR (400 MHz, DMSO-d6) δ ppm 1.66 (s, 3 H) 4.41 (m, 2 H) 4.88 (m, 2 H) 7.58 (m, 1 H) 8.02 (m, 1 H) 8.12-8.25 (m, 2 H) 8.32 (m, 1 H) 8.49 (s, 1 H) 10.38 (s, 1 H) |
| 167 | N-[5-(4-cyano-3-fluorophenyl)-[1,2,4]triazolo[1,5-a]pyridin-7-yl]oxetane-3-carboxamide | 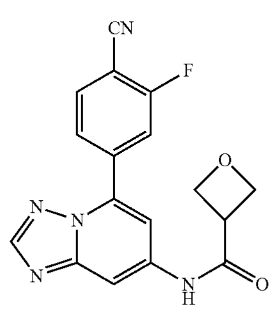 [SMILES: N#Cc1ccc(-c2cc(NC(=O)C3COC3)cc3ncnn23)cc1F] | 4-(7-amino-[1,2,4]triazolo[1,5-a]pyridin-5-yl)-2-fluorobenzonitrile (Example 146) | oxetane-3-carboxylic acid (CAS 114012-41-8) | 2 | 338 | 1H NMR (400 MHz, DCM-d2) δ ppm 4.16 (s, 1 H) 4.94 (m, 4H) 7.85-7.96 (m, 2 H) 8.02 (m, 1 H) 8.22-8.32 (m, 2 H) 8.49 (s, 1 H) 9.32-9.50 (m, 1 H) |

-continued

| Ex. No. | Compound name | Structure | Starting amine | Starting acid chloride/ carboxylic acid | Method | MS ES+ | ¹H NMR data δ ppm |
|---|---|---|---|---|---|---|---|
| 168 | N-[5-(4-cyano-3-fluorophenyl)-[1,2,4]triazolo[1,5-a]pyridin-7-yl]-2,2-difluoro-cyclopropane-1-carboxamide | 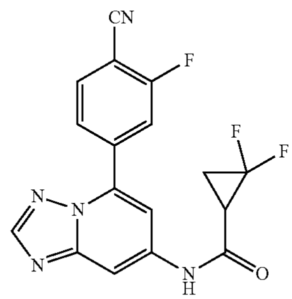 [SMILES: N#Cc1ccc(-c2cc(NC(=O)C3CC3(F)F)cc3ncnn23)cc1F] | 4-(7-amino-[1,2,4]triazolo[1,5-a]pyridin-5-yl)-2-fluorobenzonitrile (Example 146) | 2,2-difluoro-cyclopropane-1-carboxylic acid (CAS 107873-03-0) | 2 | 358 | ¹H NMR (400 MHz, Methanol-d₄) δ ppm 1.87-1.99 (m, 1 H) 2.14-2.24 (m, 1 H) 2.79 (m, 1 H) 7.58 (m, 1 H) 7.97-8.02 (m, 2 H) 8.15 (m, 1 H) 8.29 (m, 1 H) 8.40 (s, 1 H) |
| 169 | N-[5-(4-cyano-3-fluorophenyl)-[1,2,4]triazolo[1,5-a]pyridin-7-yl]-2-cyclopropyl-acetamide | 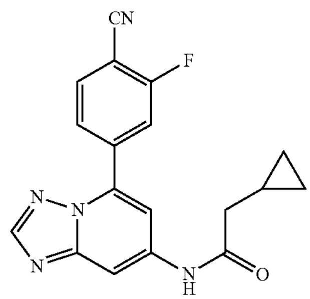 [SMILES: N#Cc1ccc(-c2cc(NC(=O)CC3CC3)cc3ncnn23)cc1F] | 4-(7-amino-[1,2,4]triazolo[1,5-a]pyridin-5-yl)-2-fluorobenzonitrile (Example 146) | 2-cyclopropyl-acetic acid (CAS 5239-82-7) | 2 | 336 | ¹H NMR (400 MHz, DCM-d₂) δ ppm 0.37 (m, 2 H) 0.66-0.78 (m, 2 H) 1.11-1.25 (m, 1 H) 2.49 (m, 2 H) 7.83-7.91 (m, 1 H) 7.91-7.97(m, 1 H) 8.02 (m, 1 H) 8.09 (s, 1 H) 8.25 (m, 1 H) 8.44 (s, 1 H) 9.10 (m, 1 H) |
| 170 | N-[5-(4-cyano-3-fluorophenyl)-[1,2,4]triazolo[1,5-a]pyridin-7-yl]-2-methoxy-2-methyl-propanamide | 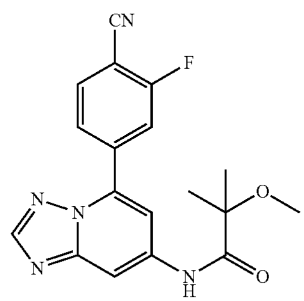 [SMILES: COC(C)(C)C(=O)Nc1cc(-c2ccc(C#N)c(F)c2)n2ncnc2c1] | 4-(7-amino-[1,2,4]triazolo[1,5-a]pyridin-5-yl)-2-fluorobenzonitrile (Example 146) | 2-methoxy-2-methyl-propanoic acid (CAS 13836-62-9) | 2 | 354 | ¹H NMR (400 MHz, DCM-d₂) δ ppm 1.52 (s, 6 H) 3.43 (s, 3 H) 7.64 (m, 1 H) 7.82-7.90 (m, 1 H) 7.95 (m, 1 H) 8.05 (m, 1 H) 8.16 (m, 1 H) 8.34 (s, 1 H) 9.00 (m, 1 H) |
| 171 | 1-cyano-N-[5-(4-cyano-3-fluorophenyl)-[1,2,4]triazolo[1,5-a]pyridin-7-yl]cyclopropane-1-carboxamide | 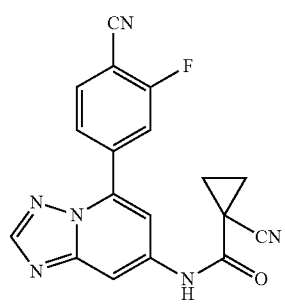 [SMILES: N#Cc1ccc(-c2cc(NC(=O)C3(C#N)CC3)cc3ncnn23)cc1F] | 4-(7-amino-[1,2,4]triazolo[1,5-a]pyridin-5-yl)-2-fluorobenzonitrile (Example 146) | 1-cyano-cyclopropane-1-carboxylic acid (CAS 6914-79-0) | 2 | 347 | ¹H NMR (400 MHz, DMSO-d₆) δ ppm 1.72-1.85 (m, 4 H) 7.72-7.83 (m, 1 H) 7.95-8.09 (m, 1 H) 8.14-8.29 (m, 3 H) 8.51 (s, 1 H) 10.58 (s, 1 H) |
| 172 | N-[5-(4-cyano-3-fluorophenyl)-[1,2,4]triazolo[1,5-a]pyridin-7-yl]-3-fluorocyclobutane-1-carboxamide | 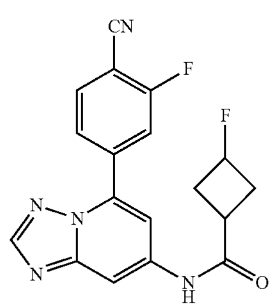 [SMILES: N#Cc1ccc(-c2cc(NC(=O)C3CC(F)C3)cc3ncnn23)cc1F] | 4-(7-amino-[1,2,4]triazolo[1,5-a]pyridin-5-yl)-2-fluorobenzonitrile (Example 146) | 3-fluoro-cyclobutane-1-carboxylic acid (CAS 122665-96-7) | 2 | 354 | ¹H NMR (400 MHz, DMSO-d₆) δ ppm 2.52-2.72 (obsc., m, 4 H) 3.25-3.35 (obsc., m, 1 H) 5.12-5.38 (m, 1 H) 7.46-7.59 (m, 1 H) 7.94-8.05 (m, 1 H) 8.11-8.31 (m, 3 H) 8.47 (s, 1 H) 10.62 (s, 1 H) |

-continued

| Ex. No. | Compound name | Structure | Starting amine | Starting acid chloride/ carboxylic acid | Method | MS ES+ 1H NMR data δ ppm |
|---|---|---|---|---|---|---|
| 173 | N-[5-(4-cyano-3-fluorophenyl)-[1,2,4]triazolo[1,5-a]pyridin-7-yl]-2-(oxetan-3-yl)acetamide | 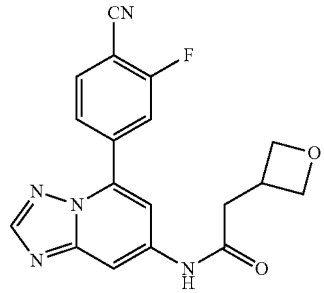 [SMILES: N#Cc1ccc(-c2cc(NC(=O)CC3COC3)cc3ncnn23)cc1F] | 4-(7-amino-[1,2,4]triazolo[1,5-a]pyridin-5-yl)-2-fluorobenzonitrile (Example 146) | 2-(oxetan-3-yl)acetic acid (CAS 1310381-54-4) | 2 | 352 1H NMR (400 MHz, DMSO-d6) δ ppm 2.87 (d, J = 8 Hz, 2 H), 3.32-3.40 (m, 1 H), 4.29-4.47 (m, 2 H) 4.67-4.77 (m, 2 H) 7.45-7.56 (m, 1 H) 7.94-8.02 (m, 1 H) 8.13-8.26 (m, 3 H) 8.46 (s, 1 H) 10.64 (s, 1 H) |
| 174 | N-[5-(4-cyano-3-fluorophenyl)-[1,2,4]triazolo[1,5-a]pyridin-7-yl]cyclopropane-carboxamide | 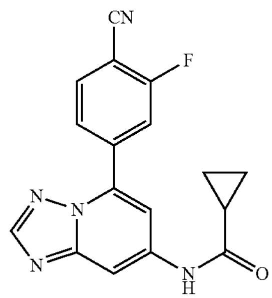 [SMILES: N#Cc1ccc(-c2cc(NC(=O)C3CC3)cc3ncnn23)cc1F] | 4-(7-amino-[1,2,4]triazolo[1,5-a]pyridin-5-yl)-2-fluorobenzonitrile (Example 146) | cyclopropane carboxylic acid (CAS 1759-53-1) | 2 | 322 1H NMR (400 MHz, DMSO-d6) δ ppm 0.81-0.99 (m, 4 H) 1.77-1.93 (m, 1 H) 7.54 (s, 1 H) 7.92-8.04 (m, 1 H) 8.13-8.24 (m, 3 H) 8.45 (s, 1 H) 10.85 (s, 1 H) |
| 175 | N-[5-(4-cyano-2-methylphenyl)-[1,2,4]triazolo[1,5-a]pyridin-7-yl]-3,3,3-trifluoro-propanamide | 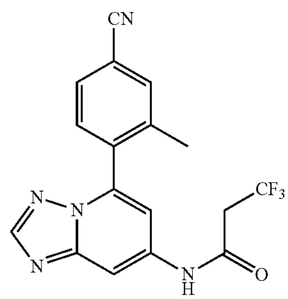 [SMILES: Cc1cc(C#N)ccc1-c1cc(NC(=O)CC(F)(F)F)cc2ncnn12] | 4-{7-amino-[1,2,4]triazolo[1,5-a]pyridin-7-yl}-methylbenzonitrile (Example 209) | 3,3,3-trifluoro-propanoyl chloride (CAS 41463-83-6) | 1 | 360 1H NMR (400 MHz, DMSO-d6) δ ppm 2.12 (s, 3 H) 3.58-3.74 (m, 2 H) 7.20 (d, J = 2 Hz, 1 H) 7.69 (d, J = 8 Hz, 1 H) 7.87 (d, J = 8 Hz, 1 H) 7.95 (s, 1 H) 8.21 (d, J = 2 Hz, 1 H) 8.40 (s, 1 H) 10.94 (s, 1 H) |

Example 176: 4-[7-(Benzylsulfanyl)-[1,2,4]triazolo[1,5-a]pyridin-5-yl]benzonitrile

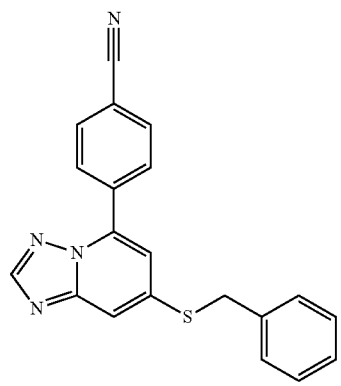 [SMILES: N#Cc1ccc(-c2cc(SCc3ccccc3)cc3ncnn23)cc1]

A solution of phenylmethanethiol (CAS 100-53-8, 0.232 ml, 1.963 mmol) in DMF (5 ml) was treated with NaH (60% wt dispersed in mineral oil, 0.079 g, 1.963 mmol). The reaction was stirred at rt for 15 min. A solution of 4-{7-chloro-[1,2,4]triazolo[1,5-a]pyridin-5-yl}benzonitrile (Intermediate 8) (0.5 g, 1.963 mmol) in DMF (5 ml) was then added and the reaction was stirred at rt for 1.5 h. The reaction was diluted with EtOAc, washed with water followed by brine, dried (phase separator) and concentrated in vacuo. The resulting residue was purified by flash chromatography (0-100% EtOAc in petrol) to afford the title compound.

1H NMR (300 MHz, DMSO-d6) δ ppm 4.52 (s, 2H) 7.14-7.44 (m, 4H) 7.46-7.54 (m, 2H) 7.74-7.83 (m, 1H) 7.99-8.10 (m, 2H) 8.16-8.28 (m, 2H) 8.46 (s, 1H)

MS ES+: 343

Example 177: 5-(4-Cyanophenyl)-N-(cyclopropylmethyl)-[1,2,4]triazolo[1,5-a]pyridine-7-sulfonamide

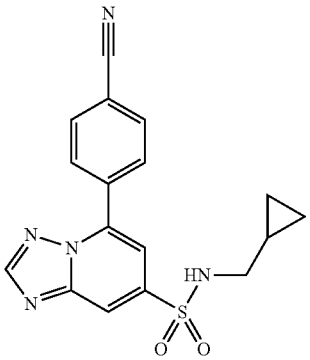 [SMILES: N#Cc1ccc(-c2cc(S(=O)(=O)NCC3CC3)cc3ncnn23)cc1]

To a suspension of 4-[7-(benzylsulfanyl)-[1,2,4]triazolo[1,5-a]pyridin-5-yl]benzonitrile (Example 176) (100 mg, 0.292 mmol) in AcOH (3 mL) and water (1.5 mL) was added NCS (156 mg, 1.168 mmol). The reaction was stirred at rt overnight. The reaction was concentrated in vacuo. The crude sulfonyl chloride intermediate was taken up in DCM (5 mL) and cyclopropylmethanamine (CAS 2516-47-4, 0.101 mL, 1.168 mmol) was added and the reaction was stirred at rt for 30 min. The reaction was diluted with DCM, washed with water, dried (phase separator) and concentrated in vacuo. The resulting residue was purified by reverse phase preparative HPLC eluted with acetonitrile/water (with 0.1% ammonia) to afford the title compound.

$^1$H NMR (300 MHz, DMSO-$d_6$) δ ppm 0.05-0.19 (m, 2H) 0.28-0.47 (m, 2H) 0.77-0.98 (m, 1H) 2.76-2.89 (m, 2H) 7.68-7.83 (m, 1H) 8.07-8.32 (m, 5H) 8.72-8.85 (m, 1H)
MS ES$^+$: 354

Example 178: 5-(4-Cyanophenyl)-N-[2-(dimethylamino)ethyl]-[1,2,4]triazolo[1,5-a]pyridine-7-sulfonamide

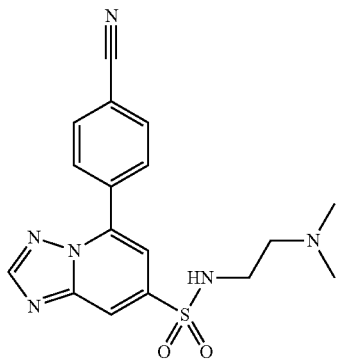 [SMILES: CN(C)CCNS(=O)(=O)c1cc(-c2ccc(C#N)cc2)n2ncnc2c1]

Prepared as described for 5-(4-cyanophenyl)-N-(cyclopropylmethyl)-[1,2,4]triazolo[1,5-a]pyridine-7-sulfonamide (Example 177) from 4-[7-(benzylsulfanyl)-[1,2,4]triazolo[1,5-a]pyridin-5-yl]benzonitrile (Example 176) and N,N-dimethylethane-1,2-diamine (CAS 108-00-9) to afford the title compound.

$^1$H NMR (300 MHz, DMSO-$d_6$) δ ppm 2.02 (s, 6H) 2.21-2.37 (m, 2H) 2.83-3.06 (m, 2H) 7.67-7.82 (m, 1H) 7.88-8.46 (m, 6H) 8.70-8.92 (m, 1H)
MS ES$^+$: 371

Example 179: 5-(4-Cyanophenyl)-N-[2-(dimethylamino)ethyl]-[1,2,4]triazolo[1,5-a]pyridine-7-sulfonamide

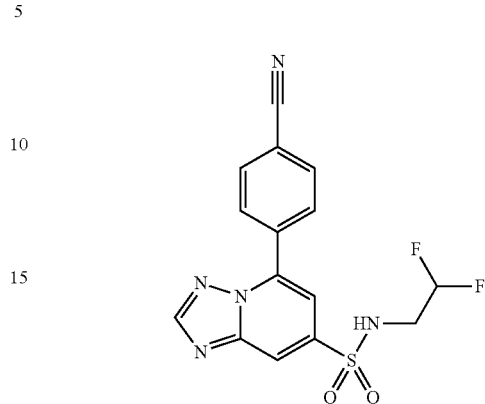

Prepared as described for 5-(4-cyanophenyl)-N-(cyclopropylmethyl)-[1,2,4]triazolo[1,5-a]pyridine-7-sulfonamide (Example 177) from 4-[7-(benzylsulfanyl)-[1,2,4]triazolo[1,5-a]pyridin-5-yl]benzonitrile (Example 176) and 2,2-difluoroethan-1-amine (CAS 430-67-1) to afford the title compound.

$^1$H NMR (300 MHz, DMSO-$d_6$) δ ppm 3.23-3.42 (m, 2H) 5.83-6.33 (m, 1H) 7.65-7.81 (m, 1H) 8.03-8.42 (m, 5H) 8.55 (s, 1H) 8.72-8.87 (m, 1H)
MS ES$^+$: 364

Example 180: 2-(Azetidin-1-yl)-N-[5-(4-cyanophenyl)-[1,2,4]triazolo[1,5-a]pyridin-7-yl]acetamide

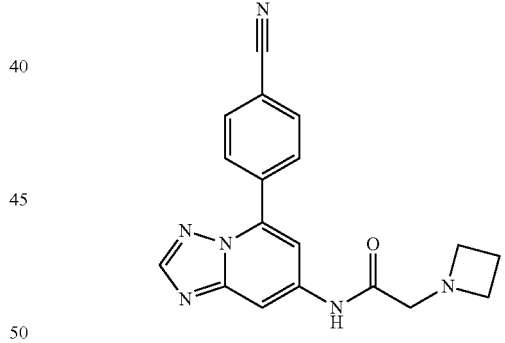

To a solution of 2-chloro-N-(5-(4-cyanophenyl)-[1,2,4]triazolo[1,5-a]pyridin-7-yl)acetamide (Intermediate 13) (70 mg, 0.225 mmol) and TEA (0.047 ml, 0.337 mmol) in DMF (1 mL) was added azetidine (CAS 503-29-7, 0.018 ml, 0.269 mmol). The reaction was stirred at room temperature for 1 h. The reaction was diluted with EtOAc and washed with sat. NaHCO$_3$ solution. The organic phase was collected, dried (phase separator) and concentrated in vacuo. The crude product was loaded onto a strong-cation exchange cartridge (SCX-2), washed with MeOH and eluted with 2M ammonia/MeOH solution. The eluent was concentrated in vacuo to give the title compound.

$^1$H NMR (400 MHz, DCM-$d_2$) δ ppm 2.10-2.27 (m, 2H) 3.28 (s, 2H) 3.38-3.53 (m, 4H) 7.41-7.53 (m, 1H) 7.85 (d, J=8 Hz, 2H) 8.07-8.19 (m, 3H) 8.26 (s, 1H) 9.55 (s, 1H)
MS ES$^+$: 333

Example 181: 4-{7-Amino-6-fluoro-[1,2,4]triazolo[1,5-a]pyridin-5-yl}benzonitrile

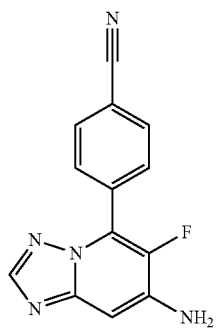 [SMILES: N#Cc1ccc(-c2c(F)c(N)cc3ncnn23)cc1]

A solution of 5-(4-cyanophenyl)-6-fluoro-[1,2,4]triazolo[1,5-a]pyridine-7-carboxylic acid (Intermediate 14, 0.080 g, 0.283 mmol), DPPA (0.061 mL, 0.283 mmol), TEA (0.059 mL, 0.425 mmol) and water (5.11 µL, 0.283 mmol) in toluene (1 mL) was heated to 90° C. for 30 min. The reaction was concentrated in vacuo and was purified by reverse phase preparative HPLC eluting with acetonitrile/water (with 0.1% ammonia) to afford the title compound.

$^1$H NMR (400 MHz, DMSO-$d_6$) ppm 6.46 (s, 2H) 6.77-6.84 (m, 1H) 7.94-8.02 (m, 2H) 8.04-8.09 (m, 2H) 8.12 (s, 1H)

MS ES$^+$: 254

Example 182: 5-(4-Ethynylphenyl)-[1,2,4]triazolo[1,5-a]pyridine

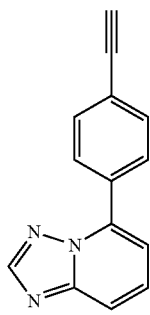 [SMILES: C#Cc1ccc(-c2cccc3ncnn23)cc1]

To a vial containing 5-(tributylstannyl)-[1,2,4]triazolo[1,5-a]pyridine (Intermediate 4, 0.1 g, 0.245 mmol), copper (I) iodide (2.333 mg, 0.012 mmol) and tetrakis(triphenylphosphine)palladium(0) (0.014 g, 0.012 mmol) in THF (1 mL) was added [2-(4-iodophenyl)ethynyl]trimethylsilane (0.081 g, 0.269 mmol). The vial was degassed and purged with nitrogen, sealed and irradiated in a microwave at 120° C. for 20 mins. To the stirred reaction mixture was added sodium hydroxide (1.0 M, 1.0 mL, 1.0 mmol). The reaction mixture was stirred at room temperature for 15 min. The reaction mixture was diluted in water and extracted into DCM using a phase separator cartridge. The aq/precipitated solid phase was further extracted with DCM/EtOH (9:1). The aqueous was removed from the settled solid layer by pipette and the solid was added to the organic phase and the organics were concentrated in vacuo into DMSO for purification by reverse phase preparative HPLC eluted with acetonitrile/water (with 0.1% ammonia) to afford the title compound.

$^1$H NMR (400 MHz, DMSO-$d_6$) δ ppm 4.40 (s, 1H) 7.40-7.48 (m, 1H) 7.69 (d, J=8 Hz, 2H) 7.76-7.84 (m, 1H) 7.88-7.92 (m, 1H) 8.06 (d, J=8 Hz, 2H) 8.56 (s, 1H)

MS ES$^+$: 220

The following Examples 183 to 194 were prepared using the general procedure below.

A mixture of an amine (0.6 mmol) and 4-(7-formyl-[1,2,4]triazolo[1,5-a]pyridin-5-yl)benzonitrile (Intermediate 15, 0.1 g, 0.4 mmol) and acetic acid (0.8 mL) was stirred in dimethylacetamide (3 mL) at RT until the corresponding imine had formed by tlc. STAB (0.171 g, 0.8 mmol) was added and the reaction mixture was stirred overnight. Once the amine had formed, water was added and stirring was continued for 15 min. The reaction mixture was concentrated the DMA removed using azeotropic distillation from water. The residue was extracted with EtOAc, washed with water and brine and was then dried over MgSO$_4$ and concentrated in vacuo. The residue was purified by reverse phase preparative HPLC.

| Ex. No. | Compound name | Structure | Starting amine | MS ES$^+$ | $^1$H NMR data δ ppm |
|---|---|---|---|---|---|
| 183 | 4-(7-{[(propan-2-yl)amino]methyl}-[1,2,4]triazolo[1,5-a]pyridin-5-yl)benzonitrile | 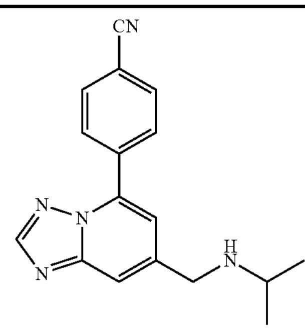 | isopropylamine (CAS 75-31-0) | 292 | $^1$H NMR (400 MHz, Methanol-$d_4$) δ ppm 1.37 (d, J = 6 Hz, 6 H) 2.86-2.89 (m, 1 H) 3.97 (s, 2 H) 7.47 (d, J = 1 Hz, 1 H) 7.80-7.81 (m, 1 H) 7.90-7.93 (m, 2 H) 8.20-8.22 (m, 2 H) 8.41 (s, 1 H) |

-continued

| Ex. No. | Compound name | Structure | Starting amine | MS ES+ 1H NMR data δ ppm |
|---|---|---|---|---|
| 184 | 4-(7-{[(2,2,2-trifluoroethyl)amino]methyl}-[1,2,4]triazolo[1,5-a]pyridin-5-yl)benzonitrile | 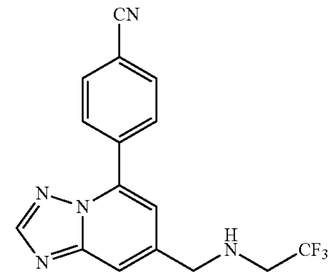 [SMILES: N#Cc1ccc(-c2cc(CNCC(F)(F)F)cc3ncnn23)cc1] | 2,2,2-trifluoroethan-1-amine (CAS 753-90-2) | 332 1H NMR (300 MHz, DMSO-d6) δ ppm 3.31 (d, J = 10 Hz, 2 H) 3.44 (s, 1 H) 4.00 (s, 2 H) 7.49 (s, 1 H) 7.84 (s, 1 H) 8.04-8.06 (m, 2 H) 8.19-8.22 (m, 2 H) 8.51 (s, 1 H) |
| 185 | 4-(7-{[(oxetan-3-yl)amino]methyl}-[1,2,4]triazolo[1,5-a]pyridin-5-yl)benzonitrile | 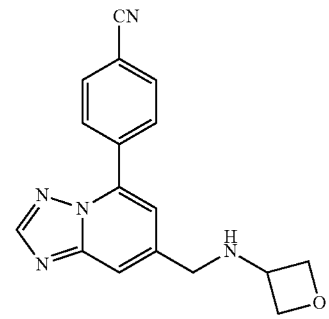 [SMILES: N#Cc1ccc(-c2cc(CNC3COC3)cc3ncnn23)cc1] | oxetan-3-amine (CAS 21635-88-1) | 306 1H NMR (300 MHz, Methanol-d4) δ ppm 3.91 (s, 2 H) 4.05-4.11 (m, 1 H) 4.51-4.53 (m, 2 H) 4.76-4.78 (m, 2 H) 7.45 (s, 1 H) 7.81 (s, 1 H) 7.91 (d, J = 8 Hz, 2 H) 8.20 (d, J = 8 Hz, 2 H) 8.41 (s, 1 H) |
| 186 | 4-(7-{[(oxetan-3-ylmethyl)amino]methyl}-[1,2,4]triazolo[1,5-a]pyridin-5-yl)benzonitrile | 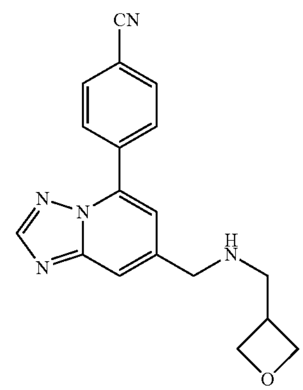 [SMILES: N#Cc1ccc(-c2cc(CNCC3COC3)cc3ncnn23)cc1] | oxetan-3-ylmethanamine (CAS 6246-05-5) | 320 1H NMR (300 MHz, Methanol-d4) δ ppm 3.00-3.02 (m, 1 H) 3.22-3.30 (m, 2 H) 3.97 (s, 2 H) 4.49-4.51 (m, 2 H) 4.77-4.79 (m, 2 H) 7.45 (s, 1 H) 7.81 (s, 1 H) 7.91 (d, J = 8 Hz, 2 H) 8.20 (d, J = 8 Hz, 2 H) 8.41 (s, 1 H) |
| 187 | 4-(7-{[(2,2-difluoroethyl)amino]methyl}-[1,2,4]triazolo[1,5-a]pyridin-5-yl)benzonitrile | 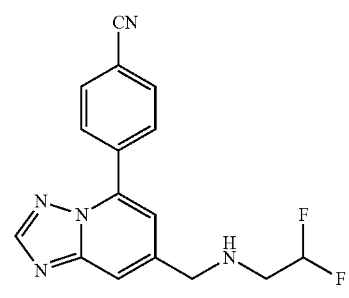 [SMILES: N#Cc1ccc(-c2cc(CNCC(F)F)cc3ncnn23)cc1] | 2,2-difluoroethan-1-amine (CAS 430-67-1) | 314 1H NMR (300 MHz, Methanol-d4) δ ppm 3.00 (m, 2 H) 3.4-3.7 (br. s, 1 H) 4.04 (s, 2 H) 5.75-6.13 (m, 1 H) 7.45 (s, 1 H) 7.81 (s, 1 H) 7.92 (d, J = 8 Hz, 2 H) 8.21 (d, J = 8 Hz, 2 H) 8.42 (s, 1 H) |
| 188 | 4-[7-({[(3-chlorophenyl)methyl]amino}methyl)-[1,2,4]triazolo[1,5-c]pyridin-5-yl]benzonitrile | 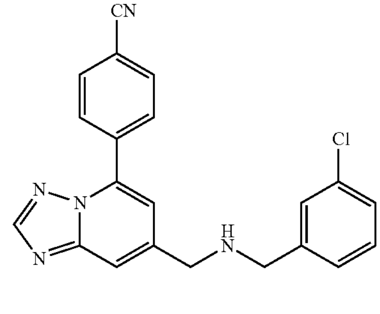 [SMILES: N#Cc1ccc(-c2cc(CNCc3cccc(Cl)c3)cc3ncnn23)cc1] | (3-chlorophenyl)methanamine (CAS 4152-90-3) | 374 1H NMR (300 MHz, DMSO-d6) δ ppm 3.12 (s, 1 H) 3.72 (s, 2 H) 3.85 (s, 2 H) 7.23-7.32 (m, 3 H) 7.41 (s, 1 H) 7.47 (s, 1 H) 7.81 (s, 1 H) 8.04 (d, J = 8 Hz, 2 H) 8.21 (d, J = 8 Hz, 2 H) 8.48 (s, 1 H) |

-continued

| Ex. No. | Compound name | Structure | Starting amine | MS ES+ $^1$H NMR data δ ppm |
|---|---|---|---|---|
| 189 | 4-(7-{[(cyclopropylmethyl)amino]methyl}-[1,2,4]triazolo[1,5-a]pyridin-5-yl)benzonitrile | 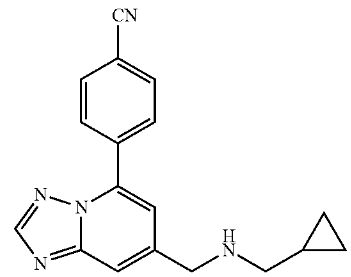 [SMILES: N#Cc1ccc(-c2cc(CNCC3CC3)cc3ncnn23)cc1] | cyclopropyl-methanamine (CAS 2516-47-4) | 304 $^1$H NMR (300 MHz, Methanol-$d_4$) δ ppm 0.15-0.24 (m, 2 H) 0.50-0.56 (m, 2 H) 0.97-1.05 (m, 1 H) 2.55 (d, J = 7 Hz, 2 H) 4.03 (s, 2 H) 7.48 (s, 1 H) 7.81 (s, 1 H) 7.92 (d, J = 8 Hz, 2 H) 8.21 (d, J = 8 Hz, 2 H) 8.42 (s, 1 H) |
| 190 | 4-[7-({[(3-methoxyphenyl)methyl]amino}methyl)-[1,2,4]triazolo[1,5-a]pyridin-5-yl]benzonitrile | 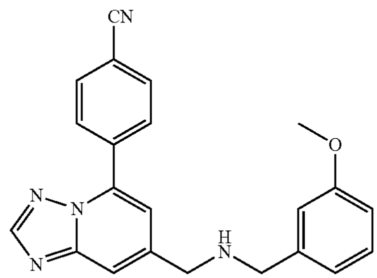 [SMILES: COc1cccc(CNCc2cc(-c3ccc(C#N)cc3)n3ncnc3c2)c1] | (3-methoxyphenyl)methanamine (CAS 5071-96-5) | 370 $^1$H NMR (300 MHz, DMSO-$d_6$) δ ppm 2.90-3.10 (br. s, 1 H) 3.70 (app. s, 5 H) 3.85 (s, 2 H) 6.74 (d, J = 8 Hz, 1 H) 6.89 (d, J = 9 Hz, 1 H) 6.0 (br. s, 1 H) 7.18 (t, J = 8 Hz, 1 H) 7.47 (s, 1 H) 7.81 (s, 1 H) 8.04 (d, J = 8 Hz, 2 H) 8.21 (d, J = 8 Hz, 2 H) 8.48 (s, 1 H) |
| 191 | 4-{7-[(3-methoxyazetidin-1-yl)methyl]-[1,2,4]triazolo[1,5-a]pyridin-5-yl}benzonitrile | 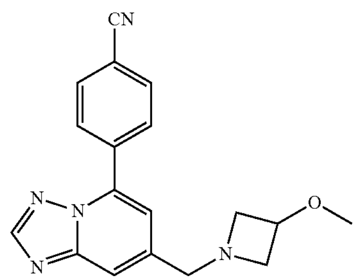 [SMILES: COC1CN(Cc2cc(-c3ccc(C#N)cc3)n3ncnc3c2)C1] | 3-methoxyazetidine (CAS 110925-17-2) | 320 $^1$H NMR (300 MHz, Methanol-$d_4$) δ ppm 2.93-2.95 (m, 2 H) 3.13 (s, 3 H) 3.55-3.57 (m, 2 H) 3.71 (s, 2 H) 3.95-4.02 (m, 1 H) 7.34 (s, 1 H) 7.74 (s, 1 H) 7.91 (d, J = 8 Hz, 2 H) 8.20 (d, J = 8 Hz, 2 H) 8.49 (s, 1 H) |
| 192 | 4-(7-{[(oxolan-3-yl)amino]methyl}-[1,2,4]triazolo[1,5-a]pyridin-5-yl)benzonitrile | 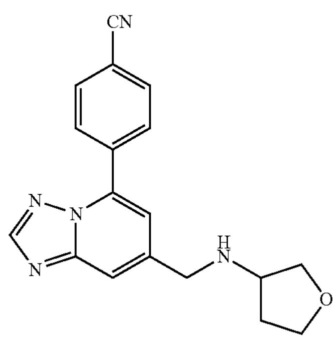 [SMILES: N#Cc1ccc(-c2cc(CNC3CCOC3)cc3ncnn23)cc1] | oxolan-3-amine (CAS 88675-24-5) | 320 $^1$H NMR (300 MHz, Methanol-$d_4$) δ ppm 1.79-1.90 (m, 1 H) 2.1-2.2 (m, 1 H) 3.44-3.50 (m, 1 H) 3.62-3.98 (m, 6 H) 7.47 (s, 1 H) 7.81 (s, 1 H) 7.91 (d, J = 8 Hz, 2 H) 8.20 (d, J = 8 Hz, 2 H) 8.41 (s, 1 H) |
| 193 | 4-(7-{[(oxolan-3-ylmethyl)amino]methyl}-[1,2,4]triazolo[1,5-a]pyridin-5-yl)benzonitrile | 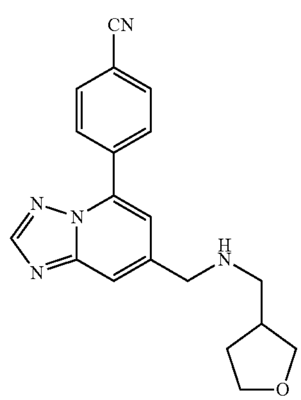 [SMILES: N#Cc1ccc(-c2cc(CNCC3CCOC3)cc3ncnn23)cc1] | oxolan-3-ylmethanamine (CAS 165253-31-6) | 334 $^1$H NMR (300 MHz, Methanol-$d_4$) δ ppm 1.55-1.67 (m, 1 H) 2.02-2.13 (m, 1 H) 2.38-2.52 (m, 1 H) 2.58-2.70 (m, 2 H) 3.28-3.30 (m, 1 H) 3.44-3.52 (m, 1 H) 3.66-3.98 (m, 4 H) 7.46 (s, 1 H) 7.80 (s, 1 H) 7.91 (d, J = 8 Hz, 2 H) 8.20 (d, J = 8 Hz, 2 H) 8.41 (s, 1 H) |

| Ex. No. | Compound name | Structure | Starting amine | MS ES+ 1H NMR data δ ppm |
|---|---|---|---|---|
| 194 | 4-{7-[(cyclopropylamino)methyl]-[1,2,4]triazolo[1,5-a]pyridin-5-yl}benzonitrile | 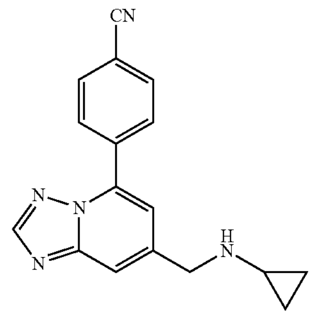 [SMILES: N#Cc1ccc(-c2cc(CNC3CC3)cc3ncnn23)cc1] | cyclopropan-amine(CAS 765-30-0) | 290 1H NMR (300 MHz, DMSO-d6) δ ppm 0.25-0.34 (m, 4 H) 2.00-2.10 (m, 1 H) 3.00-3.10 (s, 1 H) 3.88 (s, 2 H) 7.47 (s, 1 H) 7.78 (s, 1 H) 8.04 (d, J = 8 Hz, 2 H) 8.19 (d, J = 8 Hz, 2 H) 8.47 (s, 1 H) |

Examples 195 to 200 were prepared using one of the following procedures.

Procedure 1:

Step 1:

An alcohol (2.7 mmol) in toluene was added drop wise to a stirred solution of 20% phosgene in toluene (2 mL, 3.6 mmol) at 0° C. The reaction mixture was allowed to warm to room temperature over 20 h. The solvent was removed by evaporation under reduced pressure to afford the corresponding chloroformate intermediate which was used without further purification.

Step 2:

The above chloroformate (0.142 g, 1 mmol) was added to a stirred solution of 4-(7-amino-[1,2,4]triazolo[1,5-a]pyridin-5-yl)-2-fluorobenzonitrile (Example 146, 0.2 g, 0.8 mmol) and TEA (0.2 g, 2 mmol) in dry DMF (2 mL) at 0° C. and then allowed to stir at room temperature for 3 h. The reaction mixture was poured into EtOAc and was washed with 2M HCl. The organic layer was dried over sodium sulphate and concentrated under reduced pressure. The resulting residue was purified by flash chromatography on silica, eluting with EtOAc followed by an additional purification using reverse phase preparative HPLC to afford the title compounds.

Procedure 2:

Step 1:

An alcohol (8.7 mmol) in toluene (5 mL) was added drop wise to a stirred solution of 20% phosgene in toluene (6.2 mL, 11.7 mmol) at 0° C. to give the hydrochloride salt of the chloroformate as a white precipitate. After 10 min, this was filtered off and added to 28% ammonium hydroxide (6 mL, 17.4 mmol). Sodium hydroxide (2M, 10 mL, 20 mmol) was added to basify the mixture which was extracted with EtOAc. The organic phase was dried over sodium sulphate and evaporated to give the corresponding crude carbamate intermediate which was used without further purification.

Step 2:

A stirred suspension of 4-(7-chloro-[1,2,4]triazolo[1,5-a]pyridin-5-yl)-2-fluorobenzonitrile (Intermediate 8, 0.1 g, 0.29 mmol), a carbamate (1.47 mmol), Cs₂CO₃ (0.191 g, 0.6 mmol), Pd₂(dba)₃ (0.012 g, 1.5 μmol) and X-Phos (0.014 g, 2.9 μmol) in degassed dioxane (10 mL) was heated at 120° C. for 1 h. The reaction mixture was cooled and concentrated in vacuo. The residue was shaken with EtOAc and water, then filtered, and the organic phase was concentrated. The compounds was purified using Flash chromatography on silica, eluting with EtOAc then with 1%-5% (2M NH₃ in MeOH) in EtOAc followed by reverse-phase preparative HPLC gave the title compounds.

Procedure 3:

Step 1:

Ethyl carbamate (1.0 g, 11.2 mmol), an alcohol (11.2 mmol) aluminium triisopropoxide (0.25 g, 1.2 mmol) and 60% sodium hydride in oil (0.1 g, 2.5 mmol) were mixed at room temperature and then heated to 105° C. for 2 h. The mixture was cooled and diluted in wet IPA. The solution was adsorbed onto a 5 g SCX-2 cartridge and was washed with MeOH. Subsequent elution with 17% ammonia in MeOH (20 mL) gave the corresponding carbamate intermediate which was used without further purification.

Step 2:

A stirred suspension of 4-(7-chloro-[1,2,4]triazolo[1,5-a]pyridin-5-yl)-2-fluorobenzonitrile (Intermediate 8, 0.1 g, 0.29 mmol), a carbamate (1.47 mmol), Cs₂CO₃ (0.191 g, 0.6 mmol), Pd₂(dba)₃ (0.012 g, 1.5 μmol) and X-Phos (0.014 g, 2.9 μmol) in degassed dioxane (10 mL) was heated at 120° C. for 1 h. The reaction mixture was cooled and concentrated in vacuo. The residue was shaken with EtOAc and water and then filtered, and the organic phase was concentrated. The compound was purified using flash chromatography on silica, eluting with EtOAc then with 1%-5% (2M NH₃ in MeOH) in EtOAc followed by reverse-phase preparative HPLC gave the title compounds.

| Ex. No. | Compound name | Structure | Starting material | Method | MS ES+ | ¹H NMR data δ ppm |
|---|---|---|---|---|---|---|
| 195 | cyclopropylmethyl N-[5-(4-cyano-3-fluorophenyl)-[1,2,4]triazolo[1,5-a]pyridin-7-yl]carbamate | 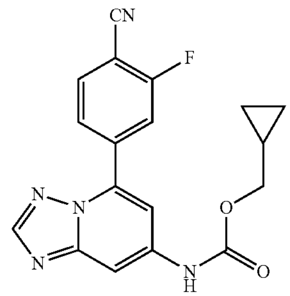 [SMILES: N#Cc1ccc(-c2cc(NC(=O)OCC3CC3)cc3ncnn23)cc1F] | cyclopropyl-methanol (CAS 2516-3-8) | 1 | 352 | ¹H NMR (300 MHz, DMSO-d₆) δ ppm 0.29-0.32 (m, 2 H) 0.50-0.54 (m, 2 H) 1.12-1.22 (m, 1 H) 3.98 (d, J = 7 Hz, 2 H) 7.42 (s, 1 H) 7.93-7.96 (m, 2 H) 8.12-8.20 (m, 2 H) 8.40 (s, 1 H) 10.45 (s, 1 H) |
| 196 | 2-methoxyethyl N-[5-(4-cyano-3-fluorophenyl)-[1,2,4]triazolo[1,5-a]pyridin-7-yl]carbamate | 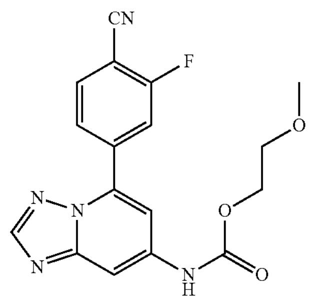 [SMILES: COCCOC(=O)Nc1cc(-c2ccc(C#N)c(F)c2)n2ncnc2c1] | 2-methoxy-ethanol (CAS 109-86-4) | 1 | 356 | ¹H NMR (400 MHz, DMSO-d₆) δ ppm 3.26 (s, 3 H) 3.57-3.58 (m, 2 H) 4.24-4.25 (m, 2 H) 7.41 (s, 1 H) 7.92-7.94 m, 2 H) 8.10-8.13 (m, 2 H) 8.40 (s, 1 H) 10.50 (s, 1 H) |
| 197 | 1-methylpiperidin-4-yl N-[5-(4-cyano-3 -fluorophenyl)-[1,2,4]triazolo[1,5-a]pyridin-7-yl]carbamate | 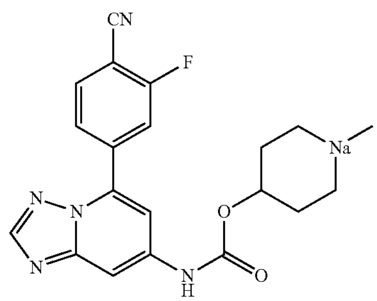 | N-methyl 4-hydroxy piperidine (CAS 106-52-5) | 2 | 395 | ¹H NMR (300 MHz, CDCl₃) δ ppm 1.69-1.85 (m, 4 H) 2.15-2.30 (m, 2 H) 2.30 (s, 3 H) 2.63-2.77 (m, 2 H) 4.82-4.85 (m, 1 H) 7.37 (s, 1 H) 7.62 (s, 1 H) 7.68-7.73 (m, 1 H) 7.76-7.79 (m, 1 H) 7.88 (m, 1 H) 7.90-8.00 (m, 1 H) 8.30 (s, 1 H) |
| 198 | 3-(dimethylamino)propyl N-[5-(4-cyano-3-fluorophenyl)-[1,2,4]triazolo[1,5-a]pyridin-7-yl]carbamate | 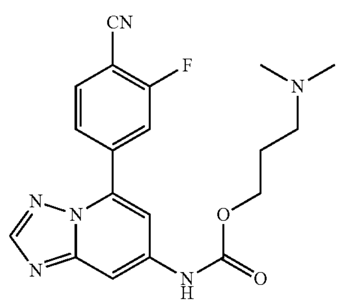 [SMILES: CN(C)CCCOC(=O)Nc1cc(-c2ccc(C#N)c(F)c2)n2ncnc2c1] | 3-(dimethyl-amino)propan-1-ol (CAS 3179-63-3) | 3 | 383 | ¹H NMR (300 MHz, CDCl₃) δ ppm 1.90 (m, 2 H) 2.27 (s, 6 H) 2.45 (t, J = 7 Hz, 2 H) 4.29 (t, J = 6 Hz, 2 H) 7.70 (s, 1 H) 7.73 (s, 1 H) 7.76-7.83 (m, 1 H) 7.85-7.90 (m, 1 H) 7.95-7.98 (m, 1 H) 8.30 (s, 1 H) 8.50 (s, 1 H) |
| 199 | 2-(dimethylamino)ethyl N-[5-(4-cyano-3-fluorophenyl)-[1,2,4]triazolo[1,5-a]pyridin-7-yl]carbamate | 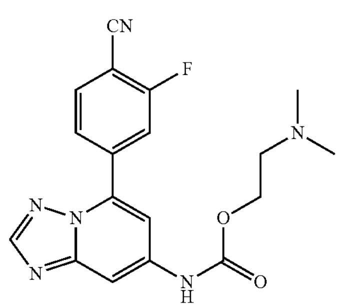 [SMILES: CN(C)CCOC(=O)Nc1cc(-c2ccc(C#N)c(F)c2)n2ncnc2c1] | 3-(dimethyl-amino)ethan-1-ol (CAS 108-01-0) | 3 | 369 | ¹H NMR (300 MHz, CDCl₃) δ ppm 2.34 (s, 6 H) 2.67 (t, J = 5 Hz, 2 H) 4.37 (t, J = 5 Hz, 2 H) 7.39 (d, J = 2 Hz, 1 H) 7.70 (d, J = 2 Hz, 1 H) 7.74-7.80 (m, 1 H) 7.80-7.85 (m, 1 H) 7.87-7.90 (m, 1 H) 8.20 (s, 1 H) 8.76 (s, 1 H) |

| Ex. No. | Compound name | Structure | Starting material | Method | MS ¹H NMR data ES⁺ δ ppm |
|---|---|---|---|---|---|
| 200 | oxolan-3-yl N-[5-(4-cyano-3-fluorophenyl)-[1,2,4]triazolo[1,5-a]pyridin-7-yl]carbamate | 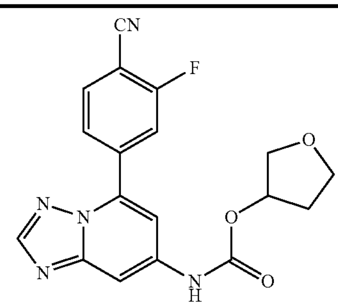 | oxolan-3-ol (CAS 453-20-3) | 3 | 368 ¹H NMR (400 MHz, CDCl₃) δ ppm 2.10-2.19 (m, 1 H) 2.23-2.38 (m, 1 H) 3.83-4.08 (m, 4 H) 5.38-5.50 (m, 1 H) 7.58-7.84 (m, 4 H) 7.85 - 7.91 (m, 1 H) 7.96 (d, J = 10 Hz, 1 H) 8.31 (s, 1 H) |

Examples 201 to 208 were prepared using any of the following procedures:

Procedure 1:

A suspension of [1,2,4]triazolo[1,5-a]pyrimidine (Intermediate 16, 0.1 g, 0.647 mmol), a boronic acid (0.841 mmol), PdCl₂.dppf (37 mg, 45.3 µmol) and Na₂CO₃ (0.206 g, 1.94 mmol) in degassed dioxane (4 mL) and water (3 mL) was heated at 100° C. for 3 h. After cooling to room temperature the reaction mixture was filtered through a pad of filter agent, and the filtrate was absorbed on silica and purified by flash chromatography on silica eluting with 1:1 EtOAc—heptanes then EtOAc to afford the title compounds.

Procedure 2:

A stirred suspension of an aryl bromide (0.841 mmol), bis(pinacolato)diboron (0.214 g, 0.841 mmol), potassium acetate (0.191 g, 1.94 mmol) and PdCl₂.dppf (37 mg, 45.3 µmol) in degassed dioxane (4 mL) was heated at 80° C. under argon for 1.5 h. A solution of [1,2,4]triazolo[1,5-a]pyrimidine (Intermediate 16, 0.100 g, 0.647 mmol) in dioxane (3 mL) was then added via syringe followed by K₂CO₃ (0.268 g, 1.94 mmol) in water (3 mL) and the temperature was increased to 90° C. for 3 h. The reaction mixture was cooled, filtered through filter agent, and absorbed on silica and purified by flash chromatography on silica eluting with 1:1 EtOAc—heptanes then EtOAc to afford the title compounds.

| Ex. No. | Compound name | Structure | Starting material | Method | MS ¹H NMR data ES⁺ δ ppm |
|---|---|---|---|---|---|
| 201 | 2-fluoro-4-{[1,2,4]triazolo[1,5-a]pyrimidin-7-yl}benzonitrile | 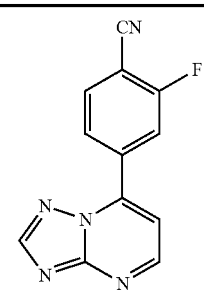 | (4-cyano-3-fluorophenyl)boronic acid (CAS 843663-18-3) | 1 | 240 ¹H NMR (300 MHz, DMSO-d₆) δ ppm 7.74-7.75 (m, 1 H) 8.20-8.22 (m, 2 H) 8.33-8.37 (m, 1 H) 8.76 (s, 1 H) 9.00-9.02 (m, 1 H) |
| 202 | 2,6-difluoro-4-{[1,2,4]triazolo[1,5-a]pyrimidin-7-yl}benzonitrile | 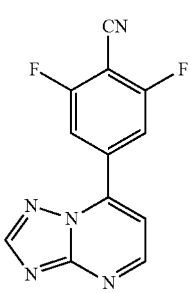 [SMILES: N#Cc1c(F)cc(-c2ccnc3ncnn23)cc1F] | 4-bromo-2,6-difluorobenzonitrile (CAS 123843-67-4) | 2 | 258 ¹H NMR (300 MHz, DMSO-d₆) δ ppm 7.78-7.79 (m, 1 H) 8.26-8.29 (m, 2 H) 8.78 (s, 1 H) 9.03-9.05 (m, 1 H) |

-continued

| Ex. No. | Compound name | Structure | Starting material | Method | MS ES+ | ¹H NMR data δ ppm |
|---|---|---|---|---|---|---|
| 203 | 3-fluoro-4-{[1,2,4]triazolo[1,5-a]pyrimidin-7-yl}benzonitrile | 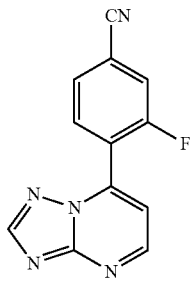 [SMILES: N#Cc1ccc(-c2ccnc3ncnn23)c(F)c1] | (4-cyano-2-fluorophenyl) boronic acid (CAS 1150114-77-4) | 1 | 240 | ¹H NMR (300 MHz, DMSO-d₆) δ ppm 7.61-7.63 (m, 1 H) 7.95-7.99 (m, 1 H) 8.06-8.11 (m, 1 H) 8.17-8.21 (m, 1 H) 8.70 (s, 1 H) 9.00-9.02 (m, 1 H) |
| 204 | 3-methyl-4-{[1,2,4]triazolo[1,5-a]pyrimidin-7-yl}benzonitrile | 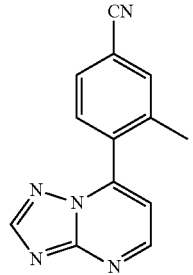 [SMILES: Cc1cc(C#N)ccc1-c1ccnc2ncnn12] | (4-cyano-2-methylphenyl) boronic acid (CAS 126747-14-6) | 1 | 236 | ¹H NMR (300 MHz, DMSO-d₆) δ ppm 2.14 (s, 3 H) 7.45-7.47 (m, 1 H) 7.71-7.73 (m, 1 H) 7.87-7.89 (m, 1 H) 7.96 (s, 1 H) 8.65 (s, 1 H) 8.97-8.99 (m, 1 H) |
| 205 | 3-chloro-4-{[1,2,4]triazolo[1,5-a]pyrimidin-7-yl}benzonitrile | 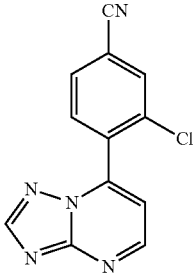 [SMILES: N#Cc1ccc(-c2ccnc3ncnn23)c(Cl)c1] | (4-cyano-2-chlorophenyl) boronic acid (CAS 677743-50-9) | 1 | 256 | ¹H NMR (300 MHz, DMSO-d₆) δ ppm 7.56-7.58 (m, 1 H) 7.92-7.95 (m, 1 H) 8.08-8.11 (m, 1 H) 8.36-8.37 (m, 1 H) 8.68 (s, 1 H) 9.02-9.04 (m, 1 H) |
| 206 | 3-fluoro-5-{[1,2,4]triazolo[1,5-a]pyrimidin-7-yl}pyridine-2-carbonitrile | 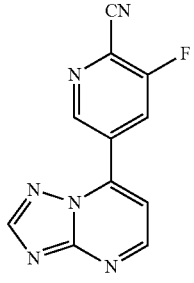 [SMILES: N#Cc1ncc(-c2ccnc3ncnn23)cc1F] | 5-bromo-3-fluoropyridine-2-carbonitrile (CAS 886373-28-0) | 2 | 241 | ¹H NMR (300 MHz, DMSO-d₆) δ ppm 7.86 (d, J = 5 Hz, 1 H) 8.80 (s, 1 H) 8.85-8.95 (m, 1 H) 9.06 (d, J = 5 Hz, 1 H) 9.35 (s, 1 H) |
| 207 | 2,3-difluoro-4-{[1,2,4]triazolo[1,5-a]pyrimidin-7-yl}benzonitrile | 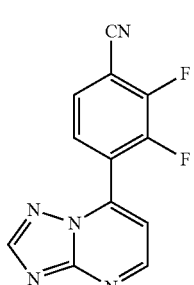 | 4-bromo-2,3-difluorobenzonitrile (CAS 126163-58-4) | 2 | 258 | ¹H NMR (300 MHz, DMSO-d₆) δ ppm 7.65 (d, J = 4 Hz, 1 H) 7.84-7.97 (m, 1 H) 8.00-8.13 (m, 1 H) 8.67-8.77 (m, 1 H) 9.04 (d, J = 5 Hz, 1H) |

| Ex. No. | Compound name | Structure | Starting material | Method | MS ES+ | ¹H NMR data δ ppm |
|---|---|---|---|---|---|---|
| 208 | 2-fluoro-5-methyl-4-{[1,2,4]triazolo[1,5-a]pyrimidin-7-yl}benzonitrile | 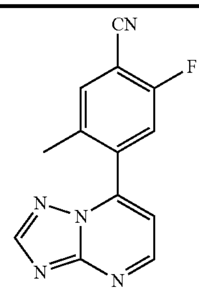 | 4-bromo-2-fluoro-5-methylbenzonitrile (CAS 916792-13-7) | 2 | 254 | ¹H NMR (300 MHz, DMSO-d₆) δ ppm 2.11 (s, 3 H) 7.49-7.50 (m, 1 H) 7.79-7.82 (m, 1 H) 8.05-8.07 (m, 1 H) 8.67 (s, 1 H) 8.99-9.01 (m, 1 H) |

Example 209: 4-{7-Amino-[1,2,4]triazolo[1,5-a]pyridin-5-yl}-3-methylbenzonitrile

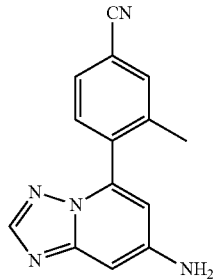 [SMILES: Cc1cc(C#N)ccc1-c1cc(N)cc2ncnn12]

Example 210: 4-{7-Amino-[1,2,4]triazolo[1,5-a]pyridin-5-yl}-3-fluorobenzonitrile

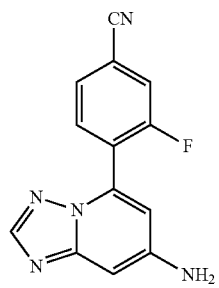 [SMILES: N#Cc1ccc(-c2cc(N)cc3ncnn23)c(F)c1]

Step 1:

A suspension of tert-butyl (5-chloro-[1,2,4]triazolo[1,5-a]pyridin-7-yl)carbamate (Intermediate 17, 0.2 g, 0.744 mmol), (4-cyano-2-methylphenyl)boronic acid (CAS 126747-14-6,120 mg, 0.744 mmol), PdCl₂(dppf) (54.5 mg, 0.074 mmol) and Na₂CO₃ (0.158 g, 1.489 mmol) in dioxane (2 mL) and water (0.4 mL) was flushed with N₂ and heated to 100° C. for 2 h. The reaction was cooled to rt and partitioned between EtOAc and water. The organic phase was collected, washed with brine, dried (phase separator) and concentrated in vacuo. The resulting residue was purified by flash chromatography (0-100% EtOAc in petrol on basic silica) to afford tert-butyl (5-(4-cyano-2-methylphenyl)-[1,2,4]triazolo[1,5-a]pyridin-7-yl)carbamate.

¹H NMR (400 MHz, DMSO-d₆) δ ppm 1.52 (s, 9H), 2.10 (s, 3H), 7.15-7.23 (m, 1H), 7.61-7.74 (m, 1H), 7.82-7.90 (m, 1H), 7.92-8.02 (m, 2H), 8.31 (s, 1H), 10.10 (s, 1H)

MS ES+: 294 (M-$^t$Bu)

Step 2:

A solution of tert-butyl (5-(4-cyano-2-methylphenyl)-[1,2,4]triazolo[1,5-a]pyridin-7-yl)carbamate (0.194 g, 0.555 mmol) and HCl (4M in dioxane, 0.694 ml, 2.78 mmol) in dioxane (5 mL) was heated to 50° C. for 2 h. The reaction was concentrated in vacuo and the resulting residue was purified by SCX-2, loading and washing with MeOH and eluting with 2M NH₃ in MeOH. The resulting residue was purified by reverse phase preparative HPLC eluting with acetonitrile/water (with 0.1% ammonia) to afford the title compound.

¹H NMR (400 MHz, DCM-d₂) δ ppm 2.18 (s, 3H) 4.39 (br. s., 2H) 6.35-6.45 (m, 1H) 6.80-6.85 (m, 1H) 7.42-7.51 (m, 1H) 7.59-7.69 (m, 2H) 8.01 (s, 1H)

MS ES+: 250

Prepared as described for 4-(7-amino-[1,2,4]triazolo[1,5-a]pyridin-5-yl)-3-methylbenzonitrile Example 209 from tert-butyl (5-chloro-[1,2,4]triazolo[1,5-a]pyridin-7-yl)carbamate (Intermediate 17) and (4-cyano-2-fluorophenyl)boronic acid (CAS 1150114-77-4) to afford the title compound.

¹H NMR (400 MHz, DMSO-d₆) δ ppm 6.29 (s, 2H) 6.61-6.74 (m, 2H) 7.84-7.98 (m, 2H) 8.01-8.15 (m, 2H)

MS ES+: 254

Example 211: 4,6-Dimethyl-5-{[1,2,4]triazolo[1,5-a]pyridin-5-yl}pyrimidine-2-carbonitrile

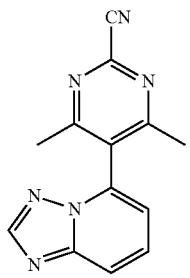 [SMILES: Cc1nc(C#N)nc(C)c1-c1cccc2ncnn12]

Step 1:

To a stirred solution of 5-bromo-4,6-dimethylpyrimidine (CAS 157335-97-2, 1 g, 5.35 mmol) in DCM (10 mL) was added m-CPBA (1.107 g, 6.42 mmol). The reaction mixture was stirred at room temperature for 4 h. Additional m-CPBA (0.368 g, 2.14 mmol, 0.4 eq) was added and the reaction was stirred at rt overnight. The reaction mixture was absorbed onto filter agent and purified by flash chromatography (0-100% EtOAc in petrol on SiO$_2$) to afford 5-bromo-4,6-dimethylpyrimidine 1-oxide.

$^1$H NMR (400 MHz, DMSO-d$_6$) δ ppm 2.53 (s, 3H) 2.56 (s, 3H) 8.98 (s, 1H)

MS ES$^+$: 203

Step 2:

A sealed vial containing 5-(tributylstannyl)-[1,2,4]triazolo[1,5-a]pyridine (Intermediate 4, 0.300 g, 0.735 mmol), copper (I) iodide (7.00 mg, 0.037 mmol), tetrakis(triphenylphosphine)palladium(0) (0.042 g, 0.037 mmol) and 5-bromo-4,6-dimethylpyrimidine 1-oxide (0.179 g, 0.882 mmol) dissolved in NMP (4 mL) was irradiated in a microwave at 100° C. for 80 mins. The reaction was heated thermally at 110° C. overnight. The reaction was diluted in DCM and water and the organic phase was separated using a phase separation cartridge. The aqueous was further extracted with DCM and the combined organics were absorbed onto filter agent and purified by flash chromatography (0-100% EtOAc/MeOH (9:1) in petrol on basic silica) to afford 5-([1,2,4]triazolo[1,5-a]pyridin-5-yl)-4,6-dimethylpyrimidine 1-oxide.

MS ES$^+$: 242

Step 3:

To a stirred solution of 5-([1,2,4]triazolo[1,5-a]pyridin-5-yl)-4,6-dimethylpyrimidine 1-oxide (42 mg, 0.174 mmol) and TEA (0.049 ml, 0.348 mmol) in acetonitrile (1 mL) was added TMS-CN (0.070 ml, 0.522 mmol). The reaction vial was purged with nitrogen, sealed and heated at 110° C. for 1 h. The reaction was diluted with DCM and water. The organic phase was separated and the aqueous was further extracted with DCM. The combined organic phases were concentrated in vacuo and purified by reverse phase preparative HPLC eluting with acetonitrile/water (with 0.1% ammonia) to afford the title compound.

$^1$H NMR (400 MHz, CD$_3$CN) δ ppm 2.26 (s, 6H) 7.12-7.25 (m, 1H) 7.71-7.80 (m, 1H) 7.88-7.96 (m, 1H) 8.33 (s, 1H)

MS ES$^+$: 251

Example 212: 5-{7-Amino-[1,2,4]triazolo[1,5-a]pyridin-5-yl}-6-methylpyridine-2-carbonitrile

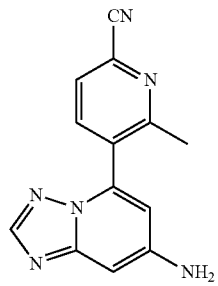 [SMILES: Cc1nc(C#N)ccc1-c1cc(N)cc2ncnn12]

Step 1:

A solution of tert-butyl (5-chloro-[1,2,4]triazolo[1,5-a]pyridin-7-yl)carbamate (Intermediate 17, 0.38 g, 1.414 mmol), 1,1,1,2,2,2-hexabutyldistannane (1.504 ml, 2.83 mmol), TEA (9.86 ml, 70.7 mmol) and tetrakis(triphenylphosphine)palladium(0) (0.490 g, 0.424 mmol) in dioxane (10 mL) was heated to 110° C. for 36 h. The reaction was concentrated in vacuo and the resulting residue was purified by flash chromatography (0-100% EtOAc in petrol on basic silica) to afford tert-butyl (5-(tributylstannyl)-[1,2,4]triazolo[1,5-a]pyridin-7-yl)carbamate.

MS ES$^+$: 525

Step 2:

A suspension of tert-butyl (5-(tributylstannyl)-[1,2,4]triazolo[1,5-a]pyridin-7-yl)carbamate (190 mg, 0.363 mmol), 5-bromo-6-methylpyridine-2-carbonitrile (CAS 1173897-86-3, 71.5 mg, 0.363 mmol), tetrakis(triphenylphosphine)palladium(0) (42.0 mg, 0.036 mmol) and copper (I) iodide (6.91 mg, 0.036 mmol) in NMP (2 mL) was flushed with N$_2$ and heated in a microwave at 100° C. for 20 min. The reaction was passed through a 10% K$_2$CO$_3$ and basic silica column eluting with EtOAc. The appropriate fractions were collected and concentrated in vacuo to afford the crude product in residual NMP. The product was used without further purification.

MS ES$^+$: 295 (M-$^t$Bu)

Step 3:

A solution of tert-butyl (5-(6-cyano-2-methylpyridin-3-yl)-[1,2,4]triazolo[1,5-a]pyridin-7-yl)carbamate (127 mg, 0.362 mmol) and HCl (4M in dioxane, 1 mL, 4.00 mmol) was heated to 50° C. for 24 h. The reaction was concentrated in vacuo and the resulting residue was purified by SCX-2, loading and washing with MeOH then eluting with 2M NH$_3$ in MeOH. The resulting residue was purified by reverse phase preparative HPLC eluted with acetonitrile/water (with 0.1% ammonia) to afford the title compound.

$^1$H NMR (400 MHz, Methanol-d$_4$) δ ppm 2.41 (s, 3H) 6.65-6.70 (m, 1H) 6.72-6.77 (m, 1H) 7.86-7.93 (m, 1H) 7.98-8.13 (m, 2H)

MS ES$^+$=251

Example 213: 5-(4-Chloro-3-methoxyphenyl)-[1,2,4]triazolo[1,5-a]pyridine

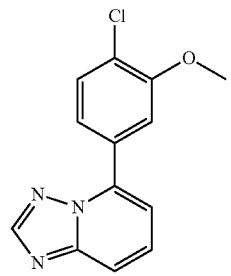 [SMILES: COc1cc(-c2cccc3ncnn23)ccc1Cl]

Step 1:

A microwave vial containing 5-bromo-[1,2,4]triazolo[1,5-a]pyridine (CAS 143329-58-2, 0.100 g, 0.505 mmol), tetrakis(triphenylphosphine)palladium (0) (0.029 g, 0.025 mmol), sodium carbonate (0.107 g, 1.010 mmol) and 2-chloro-5-(tetramethyl-1,3,2-dioxaborolan-2-yl)phenol (CAS 1443151-85-6, 0.141 g, 0.555 mmol) in dioxane (2 mL) and water (0.5 mL) was degassed and irradiated in a microwave at 100° C. for 20 mins. The reaction was filtered through celite and the filter cake was washed with MeOH and DMSO. The filtrtae was combined and concnetrated in vacuo to give a DMSO solution from which the crude product was purified by reverse phase preparative HPLC eluted with acetonitrile/water (with 0.1% ammonia) to afford 5-([1,2,4]triazolo[1,5-a]pyridin-5-yl)-2-chlorophenol
$^1$H NMR (400 MHz, DMSO-d$_6$) δ ppm 7.26-7.45 (m, 2H) 7.53 (d, J=8 Hz, 1H) 7.68 (d, J=2 Hz, 1H) 7.72-7.81 (m, 1H) 7.88 (d, J=8 Hz, 1H) 8.55 (s, 1H) 9.65 (br. s., 1H)

MS ES$^+$: 246

Step 2:

To a stirred suspension of 5-([1,2,4]triazolo[1,5-a]pyridin-5-yl)-2-chlorophenol (0.050 g, 0.204 mmol) in NMP (1 mL) was added sodium hydride (60% dispersion in mineral oil, 4.88 mg, 0.122 mmol). After a couple of minutes the reaction mixture had solubilised and iodomethane (0.016 mL, 0.254 mmol) was added. After 1 h additional sodium hydride (60% dispersion in mineral oil, 4.88 mg, 0.122 mmol) and iodomethane (0.016 mL, 0.254 mmol) was added and the reaction stirred for a further 80 min. The reaction was quenched with NaHCO$_3$ (5 mL) and extracted twice with DCM. The organic phases were combined and concentrated in vacuo. The resulting residue was purified by reverse phase preparative HPLC eluting with acetonitrile/water (with 0.1% ammonia) to afford the title compound.

$^1$H NMR (400 MHz, DMSO-d$_6$) δ ppm 3.95 (s, 3H) 7.47 (d, J=7 Hz, 1H) 7.63 (s, 2H) 7.73-7.84 (m, 2H) 7.86-7.95 (m, 1H) 8.56 (s, 1H)

MS ES$^+$: 260

Example 214: 2-Fluoro-4-{6-fluoro-[1,2,4]triazolo[1,5-a]pyridin-5-yl}benzonitrile

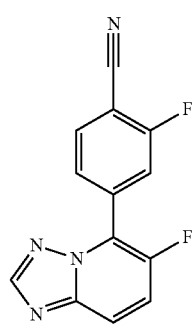 [SMILES: N#Cc1ccc(-c2c(F)ccc3ncnn23)cc1F]

A solution of 6-fluoro-5-iodo-[1,2,4]triazolo[1,5-a]pyridine (Intermediate 18, 0.095 g, 0.361 mmol), PdCl$_2$(dppf) (0.026 g, 0.036 mmol), Na$_2$CO$_3$ (0.115 g, 1.084 mmol) and (4-cyano-3-fluorophenyl)boronic acid (CAS 843663-18-3) in dioxane (1.0 mL) and water (0.2 mL) was heated to 100° C. in a microwave for 1 h. The reaction was diluted with EtOAc, washed with water, dried (phase separator) and concentrated in vacuo. The resulting residue was purified by reverse phase preparative HPLC eluted with acetonitrile/water (with 0.1% ammonia) to afford the title compound.

$^1$H NMR (400 MHz, Methanol-d$_4$) δ ppm 7.84-7.91 (m, 2H) 7.92-8.05 (m, 3H) 8.48 (s, 1H)

MS ES$^+$: 257

Example 215: 4-{6-Fluoro-[1,2,4]triazolo[1,5-a]pyridin-5-yl}-3-methylbenzonitrile

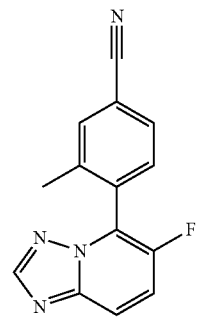 [SMILES: Cc1cc(C#N)ccc1-c1c(F)ccc2ncnn12]

Prepared as described for 2-fluoro-4-{6-fluoro-[1,2,4]triazolo[1,5-a]pyridin-5-yl}benzonitrile (Example 214) from 6-fluoro-5-iodo-[1,2,4]triazolo[1,5-a]pyridine (Intermediate 18) and (4-cyano-2-methylphenyl)boronic acid (CAS 126747-14-6) to afford the title compound.

$^1$H NMR (400 MHz, Methanol-d$_4$) δ ppm 2.20 (s, 3H) 7.63-7.70 (m, 1H) 7.75-7.81 (m, 1H) 7.86-7.93 (m, 2H) 7.93-8.00 (m, 1H) 8.44 (s, 1H)

MS ES$^+$: 253

Example 216: 3-Fluoro-4-{6-fluoro-[1,2,4]triazolo[1,5-a]pyridin-5-yl}benzonitrile

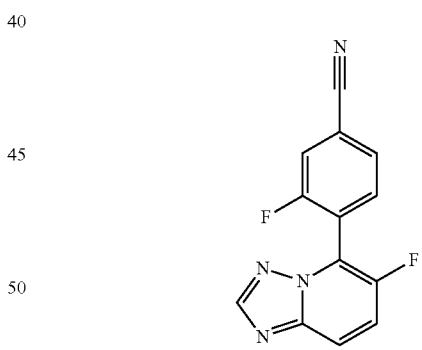

Prepared as described for 2-fluoro-4-{6-fluoro-[1,2,4]triazolo[1,5-a]pyridin-5-yl}benzonitrile (Example 214) from 6-fluoro-5-iodo-[1,2,4]triazolo[1,5-a]pyridine (Intermediate 18) and (4-cyano-2-fluorophenyl)boronic acid (CAS 1150114-77-4) to afford the title compound.

$^1$H NMR (400 MHz, DCM-d$_2$) δ ppm 7.53-7.72 (m, 3H) 7.80-7.93 (m, 2H) 8.33 (s, 1H)

MS ES$^+$: 257

Example 217: 4-{5-Amino-[1,2,4]triazolo[1,5-a]pyrimidin-7-yl}benzonitrile

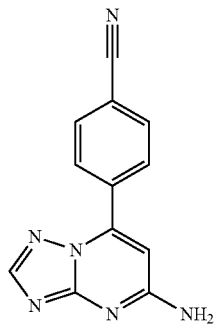 [SMILES: N#Cc1ccc(-c2cc(N)nc3ncnn23)cc1]

Step 1:
A solution of tert-butyl carbamate (0.928 g, 7.92 mmol) in DMF (10 mL) was treated with NaH (60% in mineral oil, 0.317 g, 7.92 mmol) and stirred at rt for 10 min. This was added to a solution of 4-(5-chloro-[1,2,4]triazolo[1,5-a]pyrimidin-7-yl)benzonitrile (Intermediate 9, 1.35 g, 5.28 mmol) in DMF (10 mL) and the reaction was stirred at rt for 3 days. The reaction was partitioned between EtOAc and water. The organic phase was collected, dried (phase separator) and concentrated in vacuo. The resulting residue was purified by flash chromatography (0-100% EtOAc in petrol on basic silica) to afford tert-butyl (7-(4-cyanophenyl)-[1,2,4]triazolo[1,5-a]pyrimidin-5-yl)carbamate.
MS ES+: 281 (M-$^t$Bu)

Step 2:
A solution of tert-butyl (7-(4-cyanophenyl)-[1,2,4]triazolo[1,5-a]pyrimidin-5-yl)carbamate (650 mg, 1.933 mmol) and HCl (4M solution in dioxane, 4 mL, 16.00 mmol) in dioxane (6 mL) was heated to 50° C. overnight. The reaction was concentrated in vacuo and the resulting residue was triturated with MeOH. The resulting precipitate was filtered and the filtrate was concentrated in vacuo and the resulting residue was purified by flash chromatography (0-100% EtOAc in petrol then 0-25% MeOH in EtOAc on basic silica). The product was further purified by flash chromatography (0-20% MeOH in EtOAc on basic silica) to afford the title compound.
$^1$H NMR (400 MHz, DMSO-d$_6$) δ ppm 6.63 (s, 1H) 7.41 (s, 2H) 8.03-8.11 (m, 2H) 8.13-8.21 (m, 3H)
MS ES+:237

Example 218: 4-{7-Hydroxy-[1,2,4]triazolo[1,5-a]pyridin-5-yl}benzonitrile

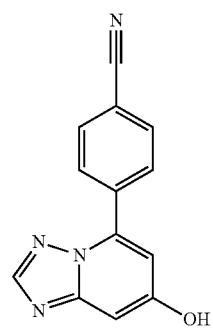 [SMILES: N#Cc1ccc(-c2cc(O)cc3ncnn23)cc1]

A reaction vial was charged with 4-(7-chloro-[1,2,4]triazolo[1,5-a]pyridin-5-yl)benzonitrile (Intermediate 8, 0.15 g, 0.589 mmol), KOH (0.036 g, 0.648 mmol), Pd$_2$(dba)$_3$ (0.022 g, 0.024 mmol) and di-tert-butyl(2',4',6'-triisopropyl-[1,1'-biphenyl]-2-yl)phosphine (CAS 564483-19-8, 0.020 g, 0.047 mmol). 1,4-dioxane (0.5 mL) and water (0.5 mL) was added and the vial was purged with argon, sealed and heated at 100° C. in a heating block for 2 h. The reaction was removed from heat and partitioned between EtOAc and water. The resulting emulsion/precipitate in the aqueous layer was filtered and combined with organic extract, dissolved in DMSO and purified by reverse phase preparative HPLC eluted with acetonitrile/water (with 0.1% formic acid) to afford the title compound.
$^1$H NMR (400 MHz, DMSO-d$_6$) δ ppm 6.99 (s, 2H) 8.04 (d, J=8 Hz, 2H) 8.17 (d, J=8 Hz, 2H) 8.29 (s, 1H) 10.75-11.75 (br. s, 1H)
MS ES+: 237

Example 219: 2-Fluoro-4-{7-hydroxy-[1,2,4]triazolo[1,5-a]pyridin-5-yl}benzonitrile

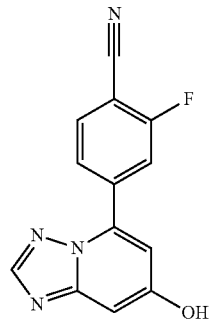 [SMILES: N#Cc1ccc(-c2cc(O)cc3ncnn23)cc1F]

Prepared as described for 4-{7-hydroxy-[1,2,4]triazolo[1,5-a]pyridin-5-yl}benzonitrile (Example 218) from 4-(7-chloro-[1,2,4]triazolo[1,5-a]pyridin-5-yl)benzonitrile (Intermediate 10).
$^1$H NMR (400 MHz, DMSO-d$_6$) δ ppm 6.98-7.10 (m, 2H) 8.00-8.08 (m, 1H) 8.09-8.16 (m, 1H) 8.18-8.25 (m, 1H) 8.32 (s, 1H) 10.5-12.0 (br. s, 1H)
MS ES+: 255

Example 220: 4-{7-Amino-[1,2,4]triazolo[1,5-a]pyridin-5-yl}-2-fluoro-5-methylbenzonitrile

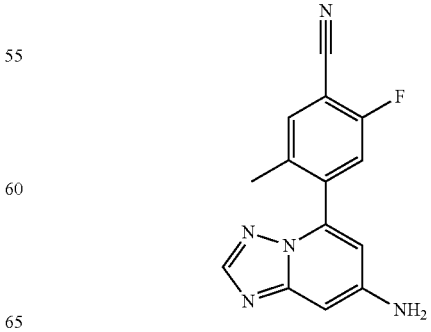

Step 1:

An oven-dried microwave vial was charged with 4-bromo-2-fluoro-5-methylbenzonitrile (CAS 916792-13-7, 0.20 g, 0.934 mmol) and purged with argon. THF (0.5 mL) was added and the vial was cooled in dry-ice/acetone (−78° C.) then isopropylmagnesium lithium chloride (1.3M solution in THF, 0.791 mL, 1.028 mmol) was added, and the vial was transferred to an ice bath for 40 min. Zinc chloride (1.9M in 2-methylTHF solution, 0.5 mL, 0.950 mmol) was added. A separate oven-dried flask was charged with 5,7-dichloro-[1,2,4]triazolo[1,5-a]pyridine (Intermediate 2, 0.141 g, 0.748 mmol) and tetrakis(triphenylphosphine)palladium (0) (0.027 g, 0.023 mmol), then purged with argon. After 30 min THF (5 mL) was added and the Grignard/organozinc solution was added via syringe and the mixture was heated to 50° C. for 2.5 h. The mixture was cooled to rt and concentrated in vacuo and the resulting residue was partitioned between EtOAc and sat. aq. potassium sodium tartrate solution. The organic was washed with brine. The aqueous was further extracted with EtOAc. The combined organics were dried (MgSO$_4$) and concentrated in vacuo. The resulting residue was purified by flash chromatography (0-50% EtOAc in petrol on SiO$_2$) to afford 4-(7-chloro-[1,2,4]triazolo[1,5-a]pyridin-5-yl)-2-fluoro-5-methylbenzonitrile.

$^1$H NMR (400 MHz, DMSO-d$_6$) δ ppm 2.09 (s, 3H) 7.50 (d, J=2 Hz, 1H) 7.79 (d, J=10 Hz, 1H) 8.04 (d, J=7 Hz, 1H) 8.25 (d, J=2 Hz, 1H) 8.55 (s, 1H)

MS ES$^+$: 287

Step 2:

4-(7-Chloro-[1,2,4]triazolo[1,5-a]pyridin-5-yl)-2-fluoro-5-methylbenzonitrile (0.149 g, 0.520 mmol), Xantphos (0.030 g, 0.052 mmol), Cs$_2$CO$_3$ (0.339 g, 1.039 mmol) and Pd$_2$(dba)$_3$ (0.024 g, 0.026 mmol) were placed in a flask which was then purged with argon and dioxane (5 mL) was added. The mixture was sparged with argon for 5 min then benzophenone imine (CAS 1013-88-3, 0.1 mL, 0.596 mmol) was added, and sparging was continued for a further 5 min before the mixture was heated to 90° C. for 7 h. The mixture was cooled to rt and diluted with diethyl ether and filtered through a phase separator cartridge. The solid residue was rinsed with further ether and the filtrate was concentrated to give the crude product as an oil. This was purified by flash chromatography (0-60% EtOAc in petrol on SiO$_2$) to afford 4-(7-((diphenylmethylene)amino)-[1,2,4]triazolo[1,5-a]pyridin-5-yl)-2-fluoro-5-methylbenzonitrile.

$^1$H NMR (400 MHz, Methanol-d$_4$) δ ppm 1.93 (s, 3H) 6.70 (d, J=2 Hz, 1H) 7.16 (d, J=2 Hz, 1H) 7.27-7.61 (m, 9H) 7.71-7.89 (m, 3H) 8.25 (s, 1H)

MS ES$^+$: 432

Step 3:

4-(7-((Diphenylmethylene)amino)-[1,2,4]triazolo[1,5-a]pyridin-5-yl)-2-fluoro-5-methylbenzonitrile (173 mg, 0.401 mmol) was dissolved in THF (5 mL). HCl (2M aq., 1 mL, 2.000 mmol) was added and the mixture was stirred under argon for 1.5 h. The mixture was concentrated in vacuo to remove THF and the material was partitioned between sat. (aq) K$_2$CO$_3$ solution and EtOAc. The aqueous was separated and the organic phase containing solid precipitate was filtered through a phase separator, the solid was washed with water and EtOAc. The filtered organic phase was washed with brine and dried (MgSO$_4$). The extraction process was repeated on the solid and the extracts were combined and concentrated. The resulting residue was purified by flash chromatography (0-10% MeOH in DCM on basic silica) to afford the title compound.

$^1$H NMR (400 MHz, Methanol-d$_4$) δ ppm 2.15 (s, 3H) 6.62 (d, J=2 Hz, 1H) 6.72 (d, J=2 Hz, 1H) 7.46 (d, J=9 Hz, 1H) 7.78 (d, J=6 Hz, 1H) 8.05 (s, 1H)

MS ES$^+$: 268

Example 221: 4-{[1,2,4]Triazolo[1,5-a]pyridin-5-yl}piperazine-1-carbonitrile

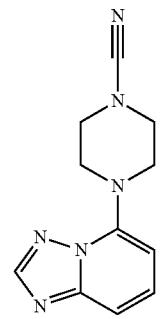

To a stirred solution of 5-(piperazin-1-yl)-[1,2,4]triazolo[1,5-a]pyridine (Intermediate 19, 0.100 g, 0.492 mmol) in DCM (1 mL) was added NaHCO$_3$ (0.083 g, 0.984 mmol) in water (0.5 mL). The biphasic mixture was stirred rapidly and to it was added cyanic bromide [3.0M in DCM] (0.197 mL, 0.590 mmol). The reaction was stirred at rt for 2 h. The reaction mixture was diluted in water and extracted twice with DCM. The organics were combined, dried (phase separator) and concentrated in vacuo. The crude product was purified by reverse phase preparative HPLC eluted with acetonitrile/water (with 0.1% ammonia) to afford the title compound.

$^1$H NMR (400 MHz, DMSO-d$_6$) δ ppm 3.41-3.59 (m, 8H) 6.63 (d, J=8 Hz, 1H) 7.48 (d, J=8 Hz, 1H) 7.59-7.68 (m, 1H) 8.48 (s, 1H)

MS ES$^+$: 229

Example 222: 3,5-Difluoro-4-{[1,2,4]triazolo[1,5-a]pyridin-5-yl}benzonitrile

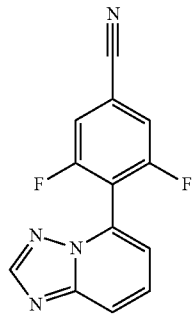 [SMILES: N#Cc1cc(F)c(-c2cccc3ncnn23)c(F)c1]

A sealed vial containing 5-(trimethyl stannyl)-[1,2,4]triazolo[1,5-a]pyridine (Intermediate 20, 0.15 g, 0.532 mmol), copper (I) iodide (0.005 g, 0.027 mmol), tetrakis(triphenylphosphine)palladium(0) (0.031 g, 0.027 mmol) and 4-bromo-3,5-difluorobenzonitrile (CAS 123688-59-5, 0.128 g, 0.585 mmol) dissolved in NMP (2 mL) was irradiated in a microwave at 100° C. for 20 mins. The reaction mixture was treated with (aq) KF solution (10 wt %) with stirring for 1 h. The mixture was diluted in EtOAc, filtered through filter agent and washed with water then brine. The solvent was removed in vacuo and the crude product was purified by reverse phase preparative HPLC eluted with acetonitrile/water (with 0.1% ammonia) to afford the title compound.

$^1$H NMR (400 MHz, CD$_3$CN) δ ppm 7.29 (d, J=7 Hz, 1H) 7.56-7.65 (m, 2H) 7.67-7.75 (m, 1H) 7.84-7.91 (m, 1H) 8.30 (s, 1H)

MS ES$^+$: 257

Example 223: 2-Fluoro-3-methyl-4-{[1,2,4]triazolo[1,5-a]pyridin-5-yl}benzonitrile

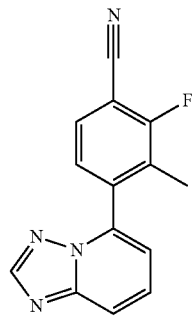 [SMILES: Cc1c(-c2cccc3ncnn23)ccc(C#N)c1F]

Prepared as described for 3,5-difluoro-4-{[1,2,4]triazolo[1,5-a]pyridin-5-yl}benzonitrile Example 222 from 5-(trimethyl stannyl)-[1,2,4]triazolo[1,5-a]pyridine (Intermediate 20) and 4-bromo-2-fluoro-3-methylbenzonitrile (CAS 1114546-30-3).

$^1$H NMR (400 MHz, CD$_3$CN) δ ppm 2.05 (d, J=2 Hz, 3H) 7.12 (d, J=7 Hz, 1H) 7.42 (d, J=8 Hz, 1H) 7.66-7.80 (m, 2H) 7.83-7.90 (m, 1H) 8.31 (s, 1H)

MS ES$^+$: 253

Example 224: 4-[7-(Methoxymethyl)-[1,2,4]triazolo[1,5-a]pyridin-5-yl]benzonitrile

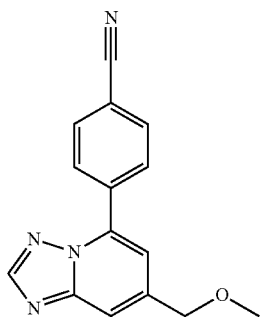 [SMILES: COCc1cc(-c2ccc(C#N)cc2)n2ncnc2c1]

To a solution of 4-(7-(hydroxymethyl)-[1,2,4]triazolo[1,5-a]pyridin-5-yl)benzonitrile (Example 39, 0.107 g, 0.428 mmol) in dry THF (2.5 mL) under nitrogen was added sodium hydride, 60% wt. in mineral oil (0.026 g, 0.641 mmol). After 10 min iodomethane (0.040 mL, 0.641 mmol) was added and the reaction was stirred at rt under nitrogen for 3 days. The reaction mixture was partitioned between water and EtOAc and separated. The aqueous was further extracted with EtOAc. The combined organics were dried (phase separator) and evaporated to dryness. The crude was purified by reverse phase preparative HPLC (basic acetonitrile/water method) to afford the title compound $^1$H NMR (400 MHz, DMSO-d$_6$) δ ppm 3.41 (s, 3H) 4.64 (s, 2H) 7.37-7.46 (m, 1H) 7.83 (s, 1H) 8.07 (d, J=8 Hz, 2H) 8.23 (d, J=8 Hz, 2H) 8.55 (s, 1H)

MS ES$^+$: 265

Example 225: N-{[5-(4-Cyanophenyl)-[1,2,4]triazolo[1,5-a]pyridin-7-yl]methyl}acetamide

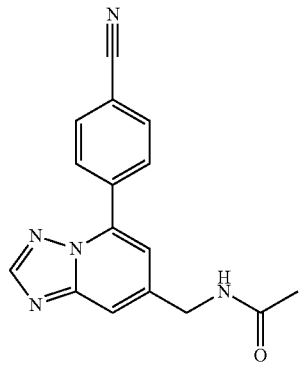 [SMILES: CC(=O)NCc1cc(-c2ccc(C#N)cc2)n2ncnc2c1]

A solution of 4-(7-(aminomethyl)-[1,2,4]triazolo[1,5-a]pyridin-5-yl)benzonitrile (Intermediate 21, 0.040 g, 0.160 mmol) and TEA (0.067 mL, 0.481 mmol) in DCM (2.0 mL) was treated with acetyl chloride (0.034 mL, 0.481 mmol) and stirred at rt for 1 h. The reaction mixture was applied to a Strata cartridge primed with DCM. Elution with 0.5 M NH$_3$ in EtOH gave the crude product which was further purified by reverse phase preparative HPLC (basic acetonitrile/water method) to afford the title compound.

$^1$H NMR (400 MHz, DMSO-d$_6$) δ ppm 1.95 (s, 3H) 4.47 (d, J=6 Hz, 2H) 7.41 (s, 1H) 7.72 (s, 1H) 8.08 (d, J=8 Hz, 2H) 8.22 (d, J=9 Hz, 2H) 8.53 (s, 2H)

MS ES$^+$: 292

Example 226: N-{[5-(4-Cyanophenyl)-[1,2,4]triazolo[1,5-a]pyridin-7-yl]methyl}cyclopropanecarboxamide

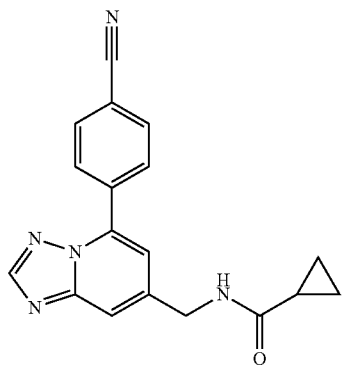 [SMILES: N#Cc1ccc(-c2cc(CNC(=O)C3CC3)cc3ncnn23)cc1]

Prepared as described for N-{[5-(4-cyanophenyl)-[1,2,4]triazolo[1,5-a]pyridin-7-yl]methyl}acetamide Example 225 from Intermediate 21 and cyclopropyl carbonyl chloride (CAS 4023-34-1).

¹H NMR (400 MHz, Methanol-d₄) δ ppm 0.78-0.98 (m, 4H) 1.66-1.80 (m, 1H) 4.61 (s, 2H) 7.34-7.42 (m, 1H) 7.71 (s, 1H) 7.95 (d, J=8 Hz, 2H) 8.21 (d, J=9 Hz, 2H) 8.44 (s, 1H)

MS ES⁺: 318

Example 227: 4-{6-Amino-[1,2,4]triazolo[1,5-a]pyridin-5-yl}benzonitrile

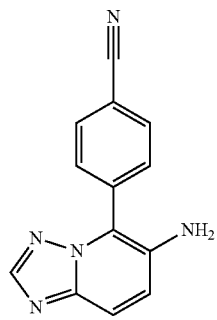 [SMILES: N#Cc1ccc(-c2c(N)ccc3ncnn23)cc1]

Step 1:
A suspension of 6-bromo-[1,2,4]triazolo[1,5-a]pyridine (CAS 356560-80-0, 0.5 g, 2.52 mmol), tert-butyl carbamate (CAS 4248-19-5, 0.592 g, 5.05 mmol), Pd₂(dba)₃ (0.185 g, 0.202 mmol), Cs₂CO₃ (1.645 g, 5.05 mmol) and Xantphos (0.234 g, 0.404 mmol) in dioxane (8.5 mL) was degassed and refilled with argon twice. The reaction was heated to 100° C. for 40 h. The reaction was cooled and partitioned between EtOAc and water. The organic was collected, dried (phase separator) and concentrated in vacuo. The resulting residue was purified by flash chromatography (0-70% EtOAc in petrol on basic silica) to afford tert-butyl [1,2,4]triazolo[1,5-a]pyridin-6-yl carbamate.

¹H NMR (400 MHz, DCM-d₂) δ ppm 1.57 (s, 9H) 6.57-6.71 (m, 1H) 7.34-7.40 (m, 1H) 7.70-7.78 (m, 1H) 8.31 (s, 1H) 9.14-9.25 (m, 1H)

MS ES⁺: 179 (M-ᵗBu)

Step 2:
A solution of tert-butyl [1,2,4]triazolo[1,5-a]pyridin-6-yl carbamate (250 mg, 1.067 mmol) and NBS (190 mg, 1.067 mmol) in acetic acid (3.5 mL) was heated in a microwave at 100° C. for 20 min. The reaction was quenched and basified with NaHCO₃ and extracted twice with EtOAc. The organic was collected, dried (phase separator) and concentrated in vacuo. The resulting residue was purified by flash chromatography (0-100% EtOAc in petrol on basic silica) to afford 5-bromo-[1,2,4]triazolo[1,5-a]pyridin-6-amine.

MS ES⁺: 213

Step 3:
A suspension of 5-bromo-[1,2,4]triazolo[1,5-a]pyridin-6-amine (0.073 g, 0.343 mmol), (4-cyanophenyl)boronic acid (CAS 126747-14-6, 0.055 g, 0.377 mmol), PdCl₂(dppf) (0.025 g, 0.034 mmol) and Na₂CO₃ (0.073 g, 0.685 mmol) in dioxane (1 mL) and water (0.2 mL) was heated in a microwave at 100° C. for 1 h. The reaction was diluted with EtOAc, washed with water, dried (phase separator) and concentrated in vacuo. The resulting residue was purified by reverse phase preparative HPLC eluted with acetonitrile/water (with 0.1% ammonia) to afford the title compound.

¹H NMR (400 MHz, DMSO-d₆) δ ppm 5.17 (s, 2H) 7.38 (d, J=10 Hz, 1H) 7.67 (d, J=10 Hz, 1H) 7.83 (d, J=8 Hz, 2H) 8.01 (d, J=8 Hz, 2H) 8.14 (s, 1H)

MS ES⁺: 236

Example 228: 4-{7-Amino-[1,2,4]triazolo[1,5-a]pyridin-5-yl}-2-fluoro-3-methylbenzonitrile hydrochloride

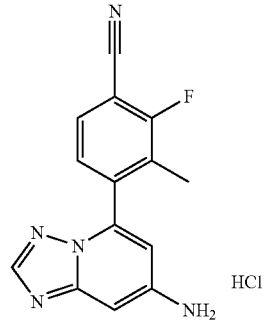 [SMILES: Cc1c(-c2cc(N)cc3ncnn23)ccc(C#N)c1F ; Cl]

Prepared as described for Example 2209 (4-{7-amino-[1,2,4]triazolo[1,5-a]pyridin-5-yl}-2-fluoro-5-methylbenzonitrile) from 5,7-dichloro-[1,2,4]triazolo[1,5-a]pyridine (Intermediate 2) and 4-bromo-2-fluoro-3-methylbenzonitrile (CAS 1114546-30-3) without free basing the title compound.

¹H NMR (400 MHz, DMSO-d₆) δ ppm 2.08 (d, J=2 Hz, 3H) 6.77-6.85 (m, 2H) 7.22 (s, 2H) 7.48-7.58 (m, 1H) 7.93-8.03 (m, 1H) 8.76 (s, 1H)

MS ES⁺: 268

Example 229: 5-{6-Fluoro-[1,2,4]triazolo[1,5-a]pyridin-5-yl}-6-methylpyridine-2-carbonitrile

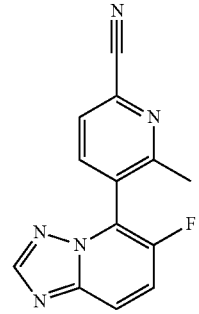 [SMILES: Cc1nc(C#N)ccc1-c1c(F)ccc2ncnn12]

Step 1:
A suspension of 6-fluoro-5-iodo-[1,2,4]triazolo[1,5-a]pyridine (Intermediate 18, 0.2 g, 0.760 mmol), (2-methylpyridin-3-yl)boronic acid (CAS 899436-71-6, 0.125 g, 0.913 mmol), PdCl₂(dppf) (0.056 g, 0.076 mmol) and Na₂CO₃ (0.161 g, 1.521 mmol) in dioxane (2 mL) and water (0.5 mL) was heated to 100° C. for 0.5 h. The reaction was partitioned between EtOAc and water. The organic phase was collected, washed with brine, dried (phase separator) and concentrated in vacuo. The resulting residue was purified by flash chromatography (0-100% EtOAc in petrol on basic silica) to afford 6-fluoro-5-(2-methylpyridin-3-yl)-[1,2,4]triazolo[1,5-a]pyridine.

MS ES⁺: 229

Step 2:

A solution of 6-fluoro-5-(2-methylpyridin-3-yl)-[1,2,4]triazolo[1,5-a]pyridine (0.103 g, 0.451 mmol) and m-CPBA (0.117 g, 0.677 mmol) in DCM (5 mL) was stirred at rt for 36 h. The reaction was diluted with DCM, washed with bicarb, dried (phase separator) and concentrated in vacuo to afford crude 3-(6-fluoro-[1,2,4]triazolo[1,5-a]pyridin-5-yl)-2-methylpyridine 1-oxide that was used directly in the next reaction.

MS ES+: 245

Step 3:

A solution of 3-(6-fluoro-[1,2,4]triazolo[1,5-a]pyridin-5-yl)-2-methylpyridine 1-oxide (0.055 g, 0.225 mmol), TMS-CN (0.091 mL, 0.676 mmol) and TEA (0.063 mL, 0.450 mmol) in acetonitrile (2 mL) was heated to 110° C. for 3 days. The reaction was cooled to rt and partitioned between DCM and water. The aqueous was further extracted with DCM. The organic phases were combined, dried (phase separator) and concentrated in vacuo. The resulting residue was purified by reverse phase preparative HPLC eluted with acetonitrile/water (with 0.1% ammonia) to afford the title compound.

$^1$H NMR (400 MHz, DMSO-$d_6$) δ ppm 2.35 (s, 3H) 7.95-8.07 (m, 1H) 8.10-8.22 (m, 2H) 8.32 (d, J=8 Hz, 1H) 8.56 (s, 1H)

MS ES+: 254

Example 230: 4-[7-(Piperazin-1-yl)-[1,2,4]triazolo[1,5-a]pyridin-5-yl]benzonitrile

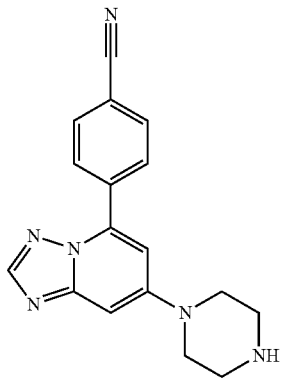 [SMILES: N#Cc1ccc(-c2cc(N3CCNCC3)cc3ncnn23)cc1]

Step 1:

A mixture of 4-(7-chloro-[1,2,4]triazolo[1,5-a]pyridin-5-yl)benzonitrile (Intermediate 8, 0.223 g, 0.876 mmol), tert-butyl piperazine-1-carboxylate (CAS 57260-71-6, 0.326 g, 1.751 mmol), X-Phos (0.042 g, 0.088 mmol), Pd$_2$(dba)$_3$ (0.040 g, 0.044 mmol) and Cs$_2$CO$_3$ (0.571 g, 1.751 mmol) was degassed (vacuum/nitrogen cycles) and heated in a sealed tube at 130° C. for 4 h. The reaction was diluted with EtOAc and filtered through Celite. The filtrate was washed with sat. sodium bicarbonate then brine, dried (phase separator) and concentrated in vacuo. The crude product was purified by flash chromatography (0-100% EtOAc in petrol on SiO$_2$) to afford tert-butyl 4-(5-(4-cyanophenyl)-[1,2,4]triazolo[1,5-a]pyridin-7-yl)piperazine-1-carboxylate.

MS ES+: 405

Step 2:

A mixture of tert-butyl 4-(5-(4-cyanophenyl)-[1,2,4]triazolo[1,5-a]pyridin-7-yl)piperazine-1-carboxylate (0.192 g, 0.475 mmol), HCl, 4M in dioxane (0.593 mL, 2.374 mmol) and EtOH 1 mL was stirred at rt for 28 h. The reaction mixture was concentrated in vacuo, diluted with sat. (aq) NaHCO$_3$ and extracted twice with DCM. The organics were combined, dried (phase separator) and concentrated in vacuo. The crude material was purified by SCX-2, loading and washing with 5% EtOH/DCM and eluting using 2M NH$_3$ solution in MeOH. The resulting residue was purified by reverse phase preparative HPLC eluted with acetonitrile/water (with 0.1% ammonia) to afford the title compound.

$^1$H NMR (400 MHz, DMSO-$d_6$) δ ppm 3.15-3.27 (m, 4H) 3.56-3.78 (m, 4H) 7.16 (d, J=2 Hz, 1H) 7.33 (d, J=3 Hz, 1H) 8.06 (d, J=8 Hz, 2H) 8.22 (d, J=9 Hz, 2H) 8.31 (s, 1H) 9.31 (br. s., 1H)

MS ES+: 305

Example 231: 4-[7-(4-Acetylpiperazin-1-yl)-[1,2,4]triazolo[1,5-a]pyridin-5-yl]benzonitrile

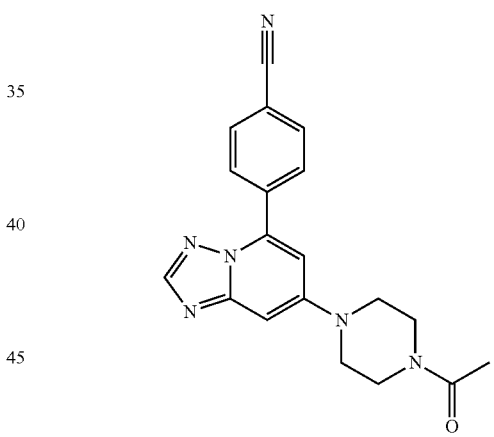

A solution of 4-(7-(piperazin-1-yl)-[1,2,4]triazolo[1,5-a]pyridin-5-yl)benzonitrile (Example 230, 0.095 g, 0.312 mmol) and TEA (0.087 mL, 0.624 mmol) in dry DCM (3.121 mL) under nitrogen was treated with acetyl chloride (0.044 mL, 0.624 mmol). The reaction was stirred at rt for 18 h. The reaction was applied to a Strata cartridge and eluted first with EtOH, then 1:1 2M NH$_3$ in MeOH/EtOH. Both eluents contained product and were combined, concentrated and purified by reverse phase preparative HPLC (basic acetonitrile/water method) to afford the title compound.

$^1$H NMR (400 MHz, CD$_3$CN) δ ppm 2.09 (s, 3H) 3.35-3.50 (m, 4H) 3.62-3.74 (m, 4H) 6.94 (d, J=3 Hz, 1H) 7.07 (d, J=2 Hz, 1H) 7.92 (d, J=8 Hz, 2H) 8.11-8.17 (m, 3H)

MS ES+: 347

183

Example 232: 4-{7-[(2,3-Dihydroxypropyl)amino]-[1,2,4]triazolo[1,5-a]pyridin-5-yl}-3-methylbenzonitrile

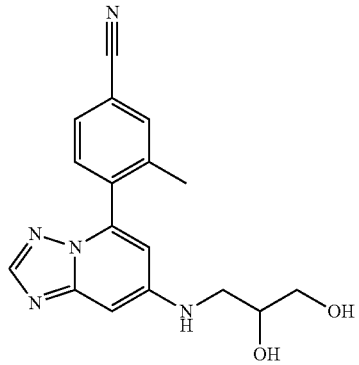 [SMILES: Cc1cc(C#N)ccc1-c1cc(NCC(O)CO)cc2ncnn12]

Step 1:

To a reaction vial containing 4-(7-chloro-[1,2,4]triazolo[1,5-a]pyridin-5-yl)-3-methylbenzonitrile (Intermediate 24, 0.100 g, 0.372 mmol), Pd$_2$(dba)$_3$ (0.017 g, 0.019 mmol), dicyclohexyl(2',4',6'-triisopropyl-[1,1'-biphenyl]-2-yl)phosphine (0.018 g, 0.037 mmol) and Cs$_2$CO$_3$ (0.243 g, 0.744 mmol) in dioxane (2 mL) was added (2,2-dimethyl-1,3-dioxolan-4-yl)methanamine (CAS 22195-47-7, 0.146 g, 1.116 mmol). The reaction vial was degassed with nitrogen for 5 mins and was then heated in a sealed tube at 110° C. under a nitrogen atmosphere for 19 h. The reaction was allowed to cool and absorbed onto filter agent. The crude product was purified by flash chromatography (0-100% EtOAc in petrol on basic silica) to afford 4-(7-(((2,2-dimethyl-1,3-dioxolan-4-yl)methyl)amino)-[1,2,4]triazolo[1,5-a]pyridin-5-yl)-3-methylbenzonitrile.

MS ES$^+$: 364

Step 2:

To a stirred solution of 4-(7-(((2,2-dimethyl-1,3-dioxolan-4-yl)methyl)amino)-[1,2,4]triazolo[1,5-a]pyridin-5-yl)-3-methylbenzonitrile (0.133 g, 0.366 mmol) in MeOH (3 mL)/water (0.5 mL) was added p-toluenesulfonic acid monohydrate (0.017 g, 0.091 mmol). The reaction was stirred at rt for 40 min and heated to 100° C. for 65 h. HCl (1.18 S.G., 37%, 0.301 mL, 3.66 mmol) was added and the reaction was stirred at room temperature for 1 h. The reaction mixture was treated with aq. NaOH (10%, 2 mL) until basic (pH~12). Saturated aq. NaHCO$_3$ (~3 mL) was added until pH~9. The solvent was removed in vacuo and the resulting residue was taken up in DMSO (4 mL). The suspension was subjected to sonication in an ultrasound bath and was then filtered. The resulting filtrate was purified by reverse phase preparative HPLC eluted with acetonitrile/water (with 0.1% ammonia) to afford the title compound.

$^1$H NMR (400 MHz, DMSO-d$_6$) δ ppm 2.12 (s, 3H) 2.98-3.11 (m, 1H) 3.27-3.35 (obsc., m, 1H) 3.36-3.49 (m, 2H) 3.66-3.77 (m, 1H) 4.61-4.75 (m, 1H) 4.88-4.95 (m, 1H) 6.56 (d, J=2 Hz, 1H) 6.65 (d, J=2 Hz, 1H) 6.72-6.79 (m, 1H) 7.60 (d, J=8 Hz, 1H) 7.82 (d, J=8 Hz, 1H) 7.90 (s, 1H) 8.03 (s, 1H)

MS ES$^+$: 324

184

Example 233: N-[5-(4-Cyano-3-fluoro-2-methylphenyl)-[1,2,4]triazolo[1,5-a]pyridin-7-yl]acetamide

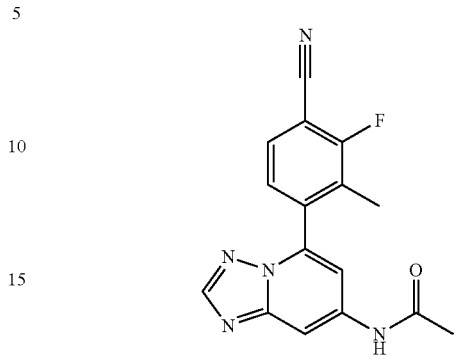

A suspension of 4-(7-amino-[1,2,4]triazolo[1,5-a]pyridin-5-yl)-2-fluoro-3-methylbenzonitrile hydrochloride (Example 228, 96 mg, 0.316 mmol) in DCM (5 mL) and pyridine (0.5 mL, 6.18 mmol) was cooled in ice. Acetyl chloride (0.034 mL, 0.474 mmol) was added drop wise. The reaction was allowed to warm to rt and was stirred for 17 h. The mixture was concentrated in vacuo then 2N HCl (6 mL) was added. The residue was partitioned between EtOAc and water. The aqueous was further extracted with EtOAc. The combined organic phases were washed with sat. (aq.) sodium bicarbonate solution followed by brine, dried (MgSO$_4$) and concentrated in vacuo. The resulting residue was recrystallized from a minimal amount of EtOH to afford the title compound.

$^1$H NMR (400 MHz, DMSO-d$_6$) δ ppm 1.97-2.09 (m, 3H) 2.16 (s, 3H) 7.26 (d, J=2 Hz, 1H) 7.51-7.61 (m, 1H) 7.92-8.03 (m, 1H) 8.25 (d, J=2 Hz, 1H) 8.37 (s, 1H) 10.59 (s, 1H)

MS ES$^+$: 310

Example 234: 4-{7-Chloro-[1,2,4]triazolo[1,5-a]pyridin-5-yl}-2,3-difluorobenzonitrile

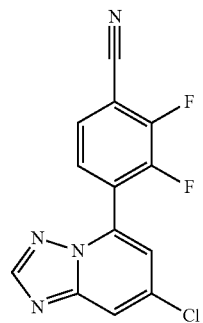 [SMILES: N#Cc1ccc(-c2cc(Cl)cc3ncnn23)c(F)c1F]

An oven-dried flask was allowed to cool under N$_2$ then charged with 4-bromo-2,3-difluorobenzonitrile (CAS: 126163-58-4, 0.488 g, 2.239 mmol) and flushed with nitrogen. THF (1 mL) was added and the solution was cooled in an ice/salt mixture. Isopropylmagnesium lithium chloride (THF solution) (1.894 mL, 2.462 mmol) was added slowly. The reaction was stirred at −15° C. for a further 45 min. Zinc chloride was added. An oven-dried microwave tube was allowed to cool under nitrogen then charged with 5,7- dichloro-[1,2,4]triazolo[1,5-a]pyridine (Intermediate 2, 379 mg, 2.015 mmol) and tetrakis(triphenylphosphine)palladium(0) (0.065 g, 0.056 mmol) and purged again with nitrogen. THF (5 mL) was added. The solution was transferred via syringe to the first flask, leaving behind the small amount of insoluble material. The mixture was then heated to 50° C. for 5 h. The reaction was cooled to rt and concentrated in vacuo. The resulting residue was partitioned between EtOAc and sat. aq. potassium sodium tartrate solution. The organic phase was washed with brine and dried (MgSO$_4$) and concentrated in vacuo. The resulting residue was purified by flash chromatography (0-40% EtOAc in petrol on SiO$_2$) to afford the title compound.

$^1$H NMR (400 MHz, DMSO-d$_6$) δ ppm 7.68 (d, J=2 Hz, 1H) 7.82-7.93 (m, 1H) 8.00-8.09 (m, 1H) 8.31 (d, J=2 Hz, 1H) 8.60 (s, 1H)

MS ES$^+$: 291

Example 235: 4-{7-Chloro-[1,2,4]triazolo[1,5-a]pyridin-5-yl}-2-fluoro-5-methylbenzonitrile

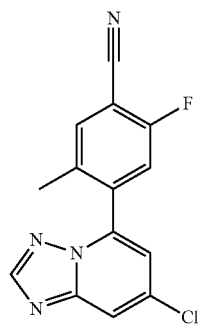 [SMILES: Cc1cc(C#N)c(F)cc1-c1cc(Cl)cc2ncnn12]

Prepared as described for Example 234 (4-{7-chloro-[1,2,4]triazolo[1,5-a]pyridin-5-yl}-2,3-difluorobenzonitrile) from 5,7-dichloro-[1,2,4]triazolo[1,5-a]pyridine (Intermediate 2) and 4-bromo-2-fluoro-5-methylbenzonitrile (CAS 916792-13-7).

$^1$H NMR (400 MHz, DMSO-d$_6$) δ ppm 2.09 (s, 3H) 7.50 (d, J=2 Hz, 1H) 7.75-7.83 (m, 1H) 8.00-8.07 (m, 1H) 8.24 (d, J=2 Hz, 1H) 8.55 (s, 1H)

MS ES$^+$: 287

Example 236: N-[5-(4-Cyano-3-fluorophenyl)-[1,2,4]triazolo[1,5-a]pyridin-7-yl]formamide

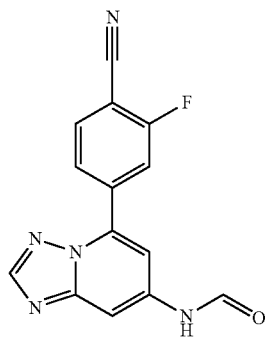 [SMILES: N#Cc1ccc(-c2cc(NC=O)cc3ncnn23)cc1F]

To stirring acetic anhydride (0.324 mL, 3.44 mmol) was added formic acid (0.161 mL, 4.19 mmol) drop wise. The mixture was heated at 60° C. in a sealed vial for 2 h. The reaction mixture was cooled in ice and to the stirred mixture was added 4-(7-amino-[1,2,4]triazolo[1,5-a]pyridin-5-yl)-2-fluorobenzonitrile (Example 146, 0.100 g, 0.395 mmol) as a suspension in THF (2 mL). The reaction vial was sealed and heated at 60° C. for 18 h. The reaction was allowed to cool to rt and was poured onto saturated (aq) NaHCO$_3$ and was then filtered. The crude product was purified by reverse phase preparative HPLC eluted with acetonitrile/water (with 0.1% formic acid) to afford the title compound.

$^1$H NMR (400 MHz, DMSO-d$_6$) δ ppm 7.49 (d, J=2 Hz, 1H) 7.95-8.25 (m, 4H) 8.45-8.55 (m, 2H) 10.6-10.9 (br. m, 1H)

MS ES$^+$: 282

Example 237: 6-Amino-5-{[1,2,4]triazolo[1,5-a]pyridin-5-yl}pyridine-2-carbonitrile

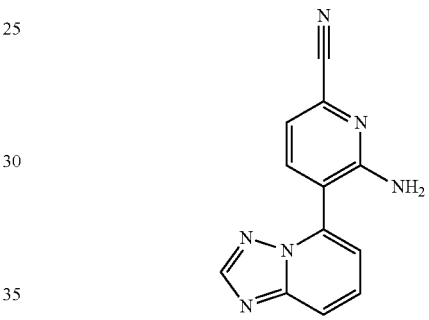

Step 1:

To a sealed vial containing copper (I) iodide (0.004 g, 0.019 mmol), tetrakis(triphenylphosphine)palladium(0) (0.022 g, 0.019 mmol) and 6-chloro-3-iodopyridin-2-amine (CAS 800402-06-6, 0.096 g, 0.377 mmol) under nitrogen was added a solution of 5-(tributylstannyl)-[1,2,4]triazolo[1,5-a]pyridine (Intermediate 4, 0.150 g, 0.367 mmol) in NMP (2 mL). The reaction mixture was irradiated in a microwave at 100° C. for 20 min. The reaction mixture was purified by reverse phase preparative HPLC eluted with acetonitrile/water (with 0.1% ammonia) to afford 3-([1,2,4]triazolo[1,5-a]pyridin-5-yl)-6-chloropyridin-2-amine.

MS ES$^+$: 246

Step 2:

A solution/suspension of 3-([1,2,4]triazolo[1,5-a]pyridin-5-yl)-6-chloropyridin-2-amine (0.044 g, 0.179 mmol), dicyanozinc (0.021 g, 0.179 mmol), zinc (0.001 g, 0.021 mmol), dppf (0.008 g, 0.014 mmol) and Pd$_2$(dba)$_3$ (0.006 mg, 7.16 μmol) in DMA (4 mL) was irradiated in a microwave at 120° C. for 30 mins then at 150° C. for 60 min. The reaction mixture was filtered through a PTFE frit (0.2 M porosity) and was purified by reverse phase preparative HPLC eluted with acetonitrile/water (with 0.1% ammonia) to afford the title compound.

$^1$H NMR (400 MHz, DMSO-d$_6$) δ ppm 6.53 (s, 2H) 7.21-7.30 (m, 2H) 7.70-7.80 (m, 2H) 7.89-7.95 (m, 1H) 8.46 (s, 1H)

MS ES$^+$: 237

Example 238: N-[5-(4-Cyano-2-methylphenyl)-[1,2,4]triazolo[1,5-a]pyridin-7-yl]-2-hydroxyacetamide

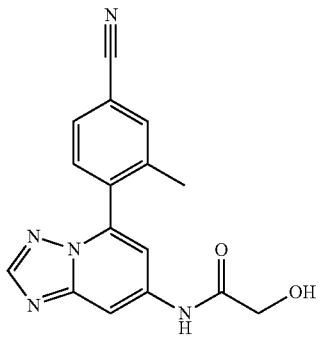 [SMILES: Cc1cc(C#N)ccc1-c1cc(NC(=O)CO)cc2ncnn12]

To a stirred solution of 2-chloro-2-oxoethyl acetate (CAS 13831-31-7, 0.086 ml, 0.802 mmol) in NMP (2 ml) was added 4-(7-amino-[1,2,4]triazolo[1,5-a]pyridin-5-yl)-3-methylbenzonitrile (Example 209, 0.100 g, 0.401 mmol) and pyridine (0.130 mL, 1.605 mmol). The reaction was stirred at room temperature for 18 h. The reaction mixture was concentrated in vacuo (to remove excess pyridine) and loaded onto a pre-equilibrated SCX-2 cartridge. This was washed with MeOH and eluted with 2M NH$_3$ in MeOH. The crude product was purified by reverse phase preparative HPLC eluted with acetonitrile/water (with 0.1% formic acid) to afford the title compound.

$^1$H NMR (400 MHz, DMSO-d$_6$) δ ppm 2.13 (s, 3H), 4.10 (d, J=3 Hz, 2H), 5.87 (s, 1H), 7.55 (d, J=2 Hz, 1H), 7.68 (d, J=8 Hz, 1H), 7.86 (d, J=8 Hz, 1H), 7.94 (s, 1H), 8.32-8.44 (m, 2H), 10.35 (s, 1H)

MS ES$^+$: 308

Example 239: N-[5-(4-Cyano-2-methylphenyl)-[1,2,4]triazolo[1,5-a]pyridin-7-yl]-3,3,3-trifluoro-2-hydroxypropanamide

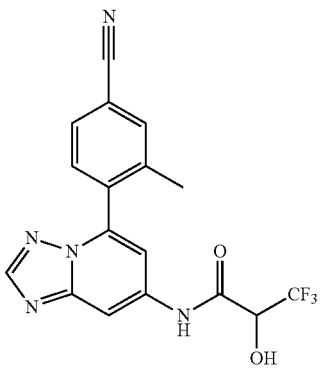 [SMILES: Cc1cc(C#N)ccc1-c1cc(NC(=O)C(O)C(F)(F)F)cc2ncnn12]

To a stirred solution of 3,3,3-trifluoro-2-hydroxypropanoic acid (CAS 684-07-1, 0.116 g, 0.802 mmol) in anhydrous THF (2 mL) was added triphosgene (0.286 g, 0.963 mmol). The reaction was stirred under nitrogen at room temperature for 30 mins. To the reaction mixture was added activated charcoal (0.005 g, 0.401 mmol) and the reaction was stirred for a further 1.5 h. The reaction mixture was evaporated to dryness and the residue was taken up in NMP (1.5 mL) and was passed through a PTFE filter into a stirred solution of 4-(7-amino-[1,2,4]triazolo[1,5-a]pyridin-5-yl)-3-methylbenzonitrile (Example 209, 0.100 g, 0.401 mmol) dissolved in NMP (0.5 mL). The reaction mixture was stirred at room temperature for 2 h. The reaction mixture was then heated in a microwave at 70° C. for 60 mins. MeOH (3 mL) was added and the reaction was concentrated in vacuo. The crude product was purified by reverse phase preparative HPLC eluted with acetonitrile/water (with 0.1% ammonia) to afford the title compound.

$^1$H NMR (400 MHz, DMSO-d$_6$) δ ppm 2.13 (s, 3H), 4.82-4.98 (m, 1H), 7.58 (d, J=2 Hz, 1H), 7.69 (d, J=8 Hz, 1H), 7.74 (d, J=7 Hz, 1H), 7.87 (d, J=8 Hz, 1H), 7.95 (s, 1H), 8.34-8.43 (m, 2H), 10.75 (s, 1H)

MS ES$^+$: 376

Example 240: N-[5-(4-Cyano-2-methylphenyl)-[1,2,4]triazolo[1,5-a]pyridin-7-yl]-2-hydroxy-2-methylpropanamide

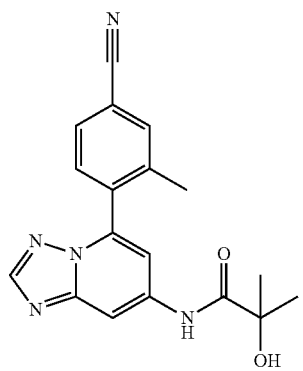 [SMILES: Cc1cc(C#N)ccc1-c1cc(NC(=O)C(C)(C)O)cc2ncnn12]

Step 1:

To a stirred solution of 1-chloro-2-methyl-1-oxopropan-2-yl acetate (CAS 40635-66-3, 0.115 ml, 0.802 mmol) in NMP (2 mL) was added 4-(7-amino-[1,2,4]triazolo[1,5-a]pyridin-5-yl)-3-methylbenzonitrile (Example 209, 0.100 g, 0.401 mmol) and pyridine (0.130 mL, 1.605 mmol). The reaction was stirred at room temperature for 45 mins. More 1-chloro-2-methyl-1-oxopropan-2-yl acetate (CAS 40635-66-3, 0.115 mL, 0.802 mmol) was added and the reaction was stirred at rt for 1 h. The crude reaction was purified directly by column chromatography (0-100% EtOAc in petrol on basic silica) to afford 1-((5-(4-cyano-2-methylphenyl)-[1,2,4]triazolo[1,5-a]pyridin-7-yl)amino)-2-methyl-1-oxopropan-2-yl acetate.

MS ES$^+$: 378

Step 2:

To a stirred solution of 1-((5-(4-cyano-2-methylphenyl)-[1,2,4]triazolo[1,5-a]pyridin-7-yl)amino)-2-methyl-1-oxopropan-2-yl acetate (0.092 g, 0.244 mmol) in THF (1.5 mL) and water (0.5 mL) was added lithium hydroxide (0.012 g, 0.488 mmol). The reaction was stirred at rt for 1.25 h. The pH of the reaction was adjusted to ~5 with aq. HCl (10%, ~2 mL) and concentrated in vacuo. The residue was taken up in DMSO (2 mL), filtered and purified by reverse phase HPLC eluted with acetonitrile/water (with 0.1% ammonia) to afford the title compound.

$^1$H NMR: (400 MHz, CD$_3$CN) δ ppm 1.46 (s, 6H), 2.15 (s, 3H), 3.94 (s, 1H), 7.26 (d, J=2 Hz, 1H), 7.56 (d, J=8 Hz, 1H), 7.71 (d, J=8 Hz, 1H), 7.76 (s, 1H), 8.19 (s, 1H), 8.31 (d, J=2 Hz, 1H), 9.34 (s, 1H)

MS ES+: 336

Example 241: N-[5-(6-Cyano-2-methylpyridin-3-yl)-[1,2,4]triazolo[1,5-a]pyridin-7-yl]acetamide

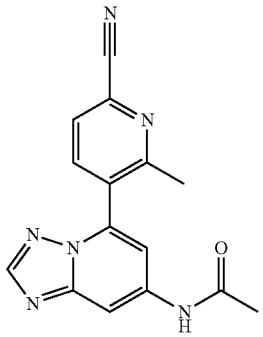 [SMILES: CC(=O)Nc1cc(-c2ccc(C#N)nc2C)n2ncnc2c1]

In 2×20 ml sealed vials a mixture of 5-{7-chloro-[1,2,4]triazolo[1,5-a]pyridin-5-yl}-6-methylpyridine-2-carbonitrile (Example 20, 2.38 g, 8.82 mmol), acetamide (CAS 30-35-5, 1.043 g, 17.65 mmol), Cs$_2$CO$_3$ (5.75 g, 17.65 mmol), Pd$_2$(dba)$_3$ (0.323 g, 0.353 mmol) and dicyclohexyl(2',4',6'-triisopropyl-[1,1'-biphenyl]-2-yl)phosphine (0.337 g, 0.706 mmol) in dioxane (29 mL) was degassed (vacuum/nitrogen cycles) and heated in a sand bath at 130° C. for 4 h. Pd$_2$(dba)$_3$ (0.300 g) and X-Phos (0.300 g) were added, the reaction was degassed and heated at 130° C. for 1 h. The reaction was filtered through celite and partitioned between 2:1 EtOAc/THF and water. The layers were separated and the aqueous extracted further with EtOAc. The combined organics were washed with brine, dried (phase separator) and evaporated to dryness. The crude product was purified by flash chromatography (40-100% EtOAc in petrol then 0-5% MeOH in EtOAc on basic silica). The resulting residue was purified by reverse phase HPLC eluted with acetonitrile/water (with 0.1% ammonia) to afford the title compound.

$^1$H NMR (400 MHz, DMSO-d$_6$) δ ppm 2.16 (s, 3H), 2.33 (s, 3H), 7.29 (d, J=2 Hz, 1H), 8.07-8.13 (m, 1H), 8.17-8.24 (m, 1H), 8.26 (d, J=2 Hz, 1H), 8.39 (s, 1H), 10.61 (s, 1H)

MS ES+: 293

Example 242: tert-Butyl N-[5-(4-cyano-2-fluorophenyl)-[1,2,4]triazolo[1,5-a]pyridin-7-yl]carbamate

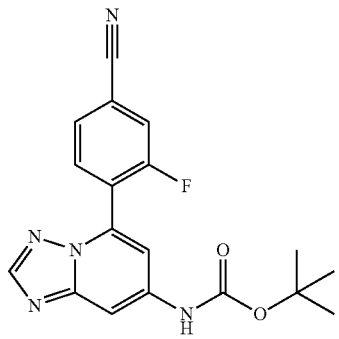 [SMILES: CC(C)(C)OC(=O)Nc1cc(-c2ccc(C#N)cc2F)n2ncnc2c1]

Step 1:

Prepared as described for 4-{7-chloro-[1,2,4]triazolo[1,5-a]pyridin-5-yl}benzonitrile (Intermediate 8) from 5,7-dichloro-[1,2,4]triazolo[1,5-a]pyridine (Intermediate 2) and (4-cyano-2-fluorophenyl)boronic acid (CAS 1150114-77-4) to afford 4-{7-chloro-[1,2,4]triazolo[1,5-a]pyridin-5-yl}-3-fluorobenzonitrile.

MS ES+: 273

Step 2:

Prepared as described for tert-butyl N-[5-(4-cyano-3-fluorophenyl)-[1,2,4]triazolo[1,5-a]pyridin-7-yl]carbamate (Intermediate 11) from 4-{7-chloro-[1,2,4]triazolo[1,5-a]pyridin-5-yl}-3-fluorobenzonitrile to afford the title compound.

$^1$H NMR (300 MHz, CD$_2$Cl$_2$) δ ppm 1.58 (s, 9H), 7.08 (br. s, 1H), 7.44 (s, 1H), 7.59-7.65 (m, 1H), 7.66-7.73 (m, 1H), 7.84-7.97 (m, 2H), 8.25 (s, 1H)

MS ES+: 354

Example 243: N-[5-(4-Cyano-3-fluorophenyl)-[1,2,4]triazolo[1,5-a]pyridin-7-yl]oxetane-2-carboxamide

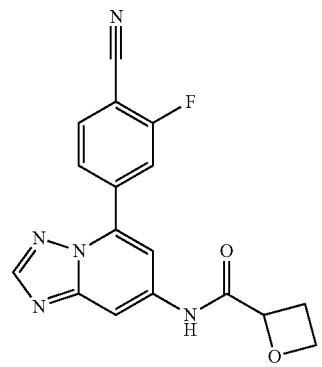 [SMILES: N#Cc1ccc(-c2cc(NC(=O)C3CCO3)cc3ncnn23)cc1F]

A solution of 4-(7-amino-[1,2,4]triazolo[1,5-a]pyridin-5-yl)-2-fluorobenzonitrile (Example 146, 0.100 g, 0.395 mmol), TEA (0.110 mL, 0.790 mmol), HATU (0.180 g, 0.474 mmol) and oxetane-2-carboxylic acid (CAS 864373-47-7, 0.048 g, 0.474 mmol) in NMP (2 mL) was stirred at room temperature for 18 h. More oxetane-2-carboxylic acid (CAS 864373-47-7, 0.048 g, 0.474 mmol) and HATU (0.075 g, 0.197 mmol) were added and the reaction was stirred at room temperature for a further 18 h. More oxetane-3-carboxylic acid (CAS 864373-47-7, 0.048 g, 0.474 mmol) and HATU (0.075 g, 0.197 mmol) were added and the reaction was stirred at room temperature for a further 18 h. The reaction mixture was quenched with (aq.) saturated NaHCO$_3$ and extracted into DCM. The crude product was purified by reverse phase preparative HPLC eluted with acetonitrile/water (with 0.1% formic acid) to afford the title compound.

$^1$H NMR (400 MHz, DMSO-d$_6$) δ ppm 2.61-2.75 (m, 1H), 2.98-3.11 (m, 1H), 4.62-4.76 (m, 2H), 5.13-5.25 (m, 1H), 7.92 (d, J=2 Hz, 1H), 8.01-8.09 (m, 1H), 8.15-8.27 (m, 2H), 8.44 (d, J=2 Hz, 1H), 8.50 (s, 1H), 10.54 (s, 1H)

MS ES+: 338

Example 244: N-[5-(4-Cyano-2-fluorophenyl)-[1,2,4]triazolo[1,5-a]pyridin-7-yl]acetamide

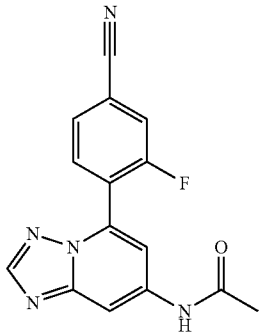 [SMILES: CC(=O)Nc1cc(-c2ccc(C#N)cc2F)n2ncnc2c1]

Prepared as described for Example 242 from 5,7-dichloro-[1,2,4]triazolo[1,5-a]pyridine (Intermediate 2), (4-cyano-2-fluorophenyl)boronic acid (CAS 1150114-77-4) and acetamide (CAS 30-35-5) to afford the title compound.

$^1$H NMR (300 MHz, DMSO-$d_6$) δ ppm 2.15 (s, 3H), 7.39 (s, 1H), 7.91-8.05 (m, 2H), 8.14 (d, J=10 Hz, 1H), 8.25 (s, 1H), 8.38 (s, 1H), 10.61 (br. s., 1H)

MS ES$^+$: 296

Example 245: N-[5-(4-Cyano-2-fluorophenyl)-[1,2,4]triazolo[1,5-a]pyridin-7-yl]cyclopropanecarboxamide

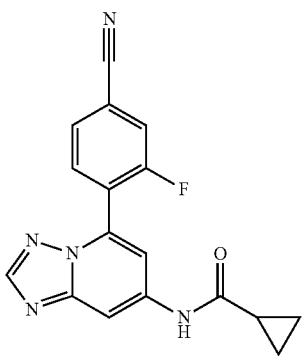

Prepared as described for Example 242 from 5,7-dichloro-[1,2,4]triazolo[1,5-a]pyridine (Intermediate 2), (4-cyano-2-fluorophenyl)boronic acid (CAS 1150114-77-4) and cyclopropanecarboxamide (CAS 6228-73-5) to afford the title compound.

$^1$H NMR (400 MHz, DMSO-$d_6$) δ ppm 0.85-0.96 (m, 4H), 1.80-1.89 (m, 1H), 7.45 (d, J=2 Hz, 1H), 7.92-7.97 (m, 1H), 7.98-8.05 (m, 1H), 8.14 (d, J=10 Hz, 1H), 8.23 (d, J=2 Hz, 1H), 8.38 (s, 1H), 10.88 (s, 1H)

MS ES$^+$: 322

Example 246: 3-Fluoro-4-{7-[(2-methoxyethyl)amino]-[1,2,4]triazolo[1,5-a]pyridin-5-yl}benzonitrile

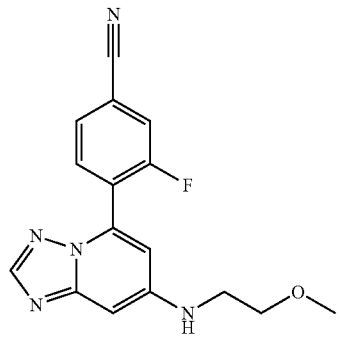 [SMILES: COCCNc1cc(-c2ccc(C#N)cc2F)n2ncnc2c1]

Step 1:
Prepared as described for 4-{7-chloro-[1,2,4]triazolo[1,5-a]pyridin-5-yl}benzonitrile (Intermediate 8) from 5,7-dichloro-[1,2,4]triazolo[1,5-a]pyridine (Intermediate 2) and (4-cyano-2-fluorophenyl)boronic acid (CAS 1150114-77-4) to afford 4-{7-chloro-[1,2,4]triazolo[1,5-a]pyridin-5-yl}-3-fluorobenzonitrile.
MS ES$^+$: 273

Step 2:
A suspension of 4-(7-chloro-[1,2,4]triazolo[1,5-a]pyridin-5-yl)-3-fluorobenzonitrile (0.15 g, 0.550 mmol), 2-methoxyethanamine (CAS 109-85-3, 0.096 ml, 1.100 mmol), Pd$_2$(dba)$_3$ (0.020 g, 0.022 mmol), Cs$_2$CO$_3$ (0.358 g, 1.100 mmol), and dicyclohexyl(4'-ethyl-2',6'-diisopropyl-[1,1'-biphenyl]-2-yl)phosphine (0.005 g, 0.011 mmol) in dioxane (2 mL) was degassed and refilled with N$_2$ two times. The reaction was sealed and heated to reflux for 5 days. The reaction was diluted with EtAOc, washed with water followed by brine, dried (phase separator) and concentrated in vacuo. The resulting residue was purified by flash chromatography (0-100% EtOAc in petrol on basic silica). The residue was further purified by reverse phase preparative HPLC eluted with acetonitrile/water (with 0.1% ammonia) to afford the title compound.

$^1$H NMR (400 MHz, DMSO-$d_6$) δ ppm 3.32-3.39 (m, 5H), 3.53-3.58 (m, 2H), 6.62 (d, J=2 Hz, 1H), 6.81 (d, J=2 Hz, 1H), 6.84-6.90 (m, 1H), 7.87-7.98 (m, 2H), 8.03-8.14 (m, 2H)

MS ES$^+$: 312

Example 247: N-[5-(6-Cyano-4-methylpyridin-3-yl)-[1,2,4]triazolo[1,5-a]pyridin-7-yl]acetamide

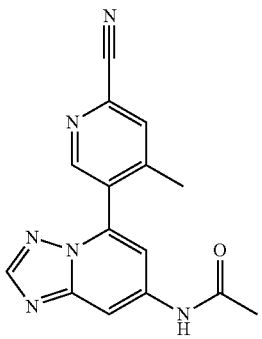 [SMILES: CC(=O)Nc1cc(-c2cnc(C#N)cc2C)n2ncnc2c1]

Step 1:

A suspension of 5-bromo-4-methylpyridine-2-carbonitrile (CAS 886364-86-9, 5.0 g, 25.4 mmol), PdCl$_2$(dppf) (0.928 g, 1.269 mmol), bis(pinacolato)diboron (9.02 g, 35.5 mmol) and potassium acetate (4.98 g, 50.8 mmol) in dry DMSO (34 mL) was degassed (vacuum/nitrogen cycles) and heated under nitrogen at 90° C. for 6 h. The reaction was partitioned between EtOAc and brine and separated. The aqueous was extracted further with EtOAc. The combined organics were washed with brine, dried (phase separator) and concentrated in vacuo. The crude product was purified by flash chromatography (0-30% EtOAc in heptane on SiO$_2$) to afford 4-methyl-5-(tetramethyl-1,3,2-dioxaborolan-2-yl)pyridine-2-carbonitrile.

MS ES$^+$: 245

Step 2:

A mixture of 4-methyl-5-(tetramethyl-1,3,2-dioxaborolan-2-yl)pyridine-2-carbonitrile (0.575 g, 2.356 mmol), 5,7-dichloro-[1,2,4]triazolo[1,5-a]pyridine (Intermediate 2) (0.403 g, 2.141 mmol), sodium carbonate (0.295 g, 2.78 mmol) and PdCl$_2$(dppf) (0.078 g, 0.107 mmol) in dioxane (6 mL) and water (1.2 mL) was heated at reflux under nitrogen for 4 h. The reaction was concentrated in vacuo, diluted with NaHCO$_3$ solution, extracted with DCM, dried (phase separator) and concentrated in vacuo. The crude product was purified by flash chromatography (50-80% EtOAc in petrol on SiO$_2$) to afford 5-{7-chloro-[1,2,4]triazolo[1,5-a]pyridin-5-yl}-4-methylpyridine-2-carbonitrile.

MS ES$^+$: 270

Step 3:

In a sealed vial a mixture of 5-(7-chloro-[1,2,4]triazolo[1,5-a]pyridin-5-yl)-4-methylpicolinonitrile (0.34 g, 1.261 mmol), dicyclohexyl(2',4',6'-triisopropyl-[1,1'-biphenyl]-2-yl)phosphine (0.060 g, 0.126 mmol), Cs$_2$CO$_3$ (0.822 g, 2.52 mmol), acetamide (CAS 30-35-5, 0.149 g, 2.52 mmol) and Pd$_2$(dba)$_3$ (0.058 g, 0.063 mmol) in dioxane (4 mL) was degassed (vacuum/nitrogen cycles) and heated in a sand bath at 130° C. for 4 h. More Pd$_2$(dba)$_3$ (0.050 g), X-Phos (0.050 mg) and acetamide (CAS 30-35-5, 0.100 g, 1.69 mmol) were added and the reaction was heated at 130° C. for 2 h. The reaction was concentrated, diluted with sat. NaHCO$_3$, extracted with DCM, dried (phase separator) and concentrated in vacuo. The crude product was dissolved in hot DMSO (9 mL) and precipitated with water. The filtrate was concentrated to remove the water and purified by reverse phase preparative HPLC eluted with acetonitrile/water (with 0.1% ammonia) to afford the title compound.

$^1$H NMR (400 MHz, DMSO-d$_6$) δ ppm 2.16 (s, 3H) 2.21 (s, 3H) 7.29 (d, J=2 Hz, 1H) 8.20 (s, 1H) 8.28 (d, J=2 Hz, 1H) 8.38 (s, 1H) 8.82 (s, 1H) 10.62 (s, 1H)

MS ES$^+$: 293

Example 248: 5-{7-Amino-[1,2,4]triazolo[1,5-a]pyridin-5-yl}-4-methylpyridine-2-carbonitrile

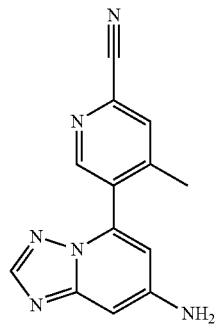 [SMILES: Cc1cc(C#N)ncc1-c1cc(N)cc2ncnn12]

A mixture of N-(5-(6-cyano-4-methylpyridin-3-yl)-[1,2,4]triazolo[1,5-a]pyridin-7-yl)acetamide (Example 247) (0.050 g, 0.171 mmol), 2M HCl (0.257 mL, 0.513 mmol) and ethanol (0.342 mL) was irradiated at 80° C. for 80 mins. The reaction was basified with sat. NaHCO$_3$ solution, extracted with DCM, dried (phase separator) and concentrated in vacuo to afford the title compound.

$^1$H NMR (400 MHz, DMSO-d$_6$) δ ppm 2.19 (s, 3H) 6.31 (s, 2H) 6.62 (d, J=2 Hz, 1H) 6.65 (d, J=2 Hz, 1H) 8.06 (s, 1H) 8.17 (s, 1H) 8.77 (s, 1H)

MS ES$^+$: 251

Example 249: 4-{7-Hydroxy-[1,2,4]triazolo[1,5-a]pyridin-5-yl}-3-methylbenzonitrile

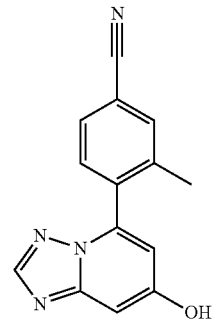 [SMILES: Cc1cc(C#N)ccc1-c1cc(O)cc2ncnn12]

To a solution of KOH (0.034 g, 0.614 mmol) in water (0.500 ml) and 1,4-dioxane (0.5 ml) was added 4-{7-chloro-[1,2,4]triazolo[1,5-a]pyridin-5-yl}-3-methylbenzonitrile (Intermediate 24) (0.15 g, 0.558 mmol), di-tert-butyl(2',4',6'-triisopropyl-3,4,5,6-tetramethyl-[1,1'-biphenyl]-2-yl)phosphine (0.021 g, 0.045 mmol) and Pd$_2$(dba)$_3$ (0.020 g, 0.022 mmol). The vial was purged with nitrogen, sealed and irradiated in a microwave at 100° C. for 60 mins. The reaction mixture was diluted in DMSO (3 mL) and was neutralised (pH-6) with formic acid (0.25 mL). The solution was filtered and concentrated in vacuo and the crude product was purified by reverse phase preparative HPLC eluted with acetonitrile/water (with 0.1% formic acid) to afford the title compound.

$^1$H NMR (400 MHz, DMSO-d$_6$) δ ppm 2.10 (s, 3H), 6.76 (d, J=2 Hz, 1H), 7.01 (d, J=2 Hz, 1H), 7.64 (d, J=8 Hz, 1H), 7.84 (d, J=8 Hz, 1H), 7.92 (s, 1H), 8.23 (s, 1H), 11.06 (br. s, 1H)

MS ES$^+$: 251

Example 250: N-[5-(4-Cyano-2-methylphenyl)-[1,2,4]triazolo[1,5-a]pyridin-7-yl]cyclopropanecarboxamide

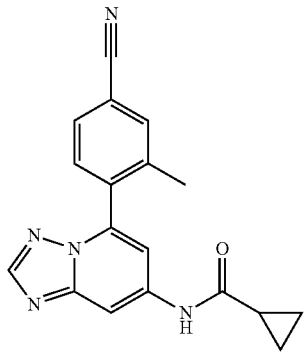 [SMILES: Cc1cc(C#N)ccc1-c1cc(NC(=O)C2CC2)cc2ncnn12]

A solution/suspension of 4-{7-chloro-[1,2,4]triazolo[1,5-a]pyridin-5-yl}-3-methylbenzonitrile (Intermediate 24) (0.2 g, 0.744 mmol), cyclopropanecarboxamide (CAS 6228-73-5, 0.317 g, 3.72 mmol), caesium carbonate (0.485 g, 1.489 mmol), Pd$_2$(dba)$_3$ (0.034 g, 0.037 mmol) and dicyclohexyl(2',4',6'-triisopropyl-[1,1'-biphenyl]-2-yl)phosphine (0.035 g, 0.074 mmol) in dioxane (4 mL) was degassed with nitrogen for 5 mins. The reaction mixture was heated at 110° C. for 1 h. The reaction was removed from heat and allowed to cool to room temperature. The reaction mixture was diluted in DMSO (3 mL), filtered through celite and the filter cake was washed with EtOH (10 mL). The solution was concentrated in vacuo and was purified by reverse phase preparative HPLC eluted with acetonitrile/water (with 0.1% ammonia) to afford the title compound.

$^1$H NMR (400 MHz, DMSO-d$_6$) δ ppm 0.80-0.95 (m, 4H), 1.75-1.88 (m, 1H), 2.11 (s, 3H), 7.25 (d, J=2 Hz, 1H), 7.68 (d, J=8 Hz, 1H), 7.87 (d, J=8 Hz, 1H), 7.94 (s, 1H), 8.22 (d, J=2 Hz, 1H), 8.35 (s, 1H), 10.84 (s, 1H)

MS ES$^+$: 318

Example 251: 5-{7-Hydroxy-[1,2,4]triazolo[1,5-a]pyridin-5-yl}-6-methylpyridine-2-carbonitrile

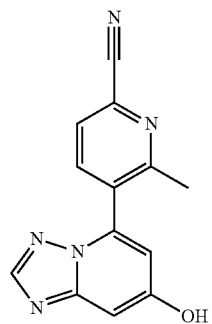 [SMILES: Cc1nc(C#N)ccc1-c1cc(O)cc2ncnn12]

A mixture of 5-{7-chloro-[1,2,4]triazolo[1,5-a]pyridin-5-yl}-6-methylpyridine-2-carbonitrile (Example 20) (0.097 g, 0.360 mmol), KOH (0.022 g, 0.396 mmol), Pd$_2$(dba)$_3$ (0.013 g, 0.014 mmol) and di-tert-butyl(2',4',6'-triisopropyl-3,4,5,6-tetramethyl-[1,1'-biphenyl]-2-yl)phosphine (0.014 g, 0.029 mmol) in dioxane (0.9 mL) and water (0.3 mL) was degassed (vacuum/nitrogen cycles) and heated in a sealed tube at 130° C. for 2 h. The reaction was diluted with EtOAc, washed with water, dried (phase separator) and concentrated in vacuo. The crude was purified by reverse phase preparative HPLC eluted with acetonitrile/water (with 0.1% formic acid) to afford the title compound.

$^1$H NMR (400 MHz, DMSO-d$_6$) δ ppm 2.31 (s, 3H) 6.88 (d, J=2 Hz, 1H) 7.04 (d, J=2 Hz, 1H) 8.04-8.12 (m, 1H) 8.13-8.20 (m, 1H) 8.26 (s, 1H) 11.22 (br. s., 1H)

MS ES$^+$: 252

Example 252: 3-Methyl-4-(7-{2-oxa-6-azaspiro[3.3]heptan-6-yl}-[1,2,4]triazolo[1,5-a]pyridin-5-yl)benzonitrile

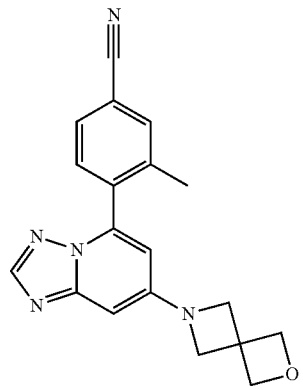 [SMILES: Cc1cc(C#N)ccc1-c1cc(N2CC3(COC3)C2)cc2ncnn12]

A reaction vial 4-{7-chloro-[1,2,4]triazolo[1,5-a]pyridin-5-yl}-3-methylbenzonitrile (Intermediate 24) (0.150 g, 0.558 mmol), 2-oxa-6-azaspiro[3.3]heptane hemioxalate (CAS 174-78-7, 0.121 g, 0.419 mmol), Pd$_2$(dba)$_3$ (0.026 g, 0.028 mmol), dicyclohexyl(2',4',6'-triisopropyl-[1,1'-biphenyl]-2-yl)phosphine (0.027 g, 0.056 mmol) and caesium carbonate (0.546 g, 1.675 mmol) in dioxane (3 mL) was degassed with nitrogen for 5 mins and was then heated in a sealed tube at 120° C. under a nitrogen atmosphere for 20 h. The reaction was cooled to rt, filtered through celite and the filter cake washed with MeOH and DMSO. The filtrate was concentrated in vacuo to remove the MeOH and purified by reverse phase preparative HPLC eluted with acetonitrile/water (with 0.1% formic acid) to afford the title compound.

$^1$H NMR (400 MHz, DMSO-d$_6$) δ ppm 2.09 (s, 3H), 4.19 (s, 4H), 4.74 (s, 4H), 6.51 (s, 2H), 7.60 (d, J=8 Hz, 1H), 7.84 (d, J=8 Hz, 1H), 7.91 (s, 1H), 8.12 (s, 1H)

MS ES$^+$: 332

Example 253: N-[5-(6-Cyano-2-methylpyridin-3-yl)-[1,2,4]triazolo[1,5-a]pyridin-7-yl]cyclopropanecarboxamide

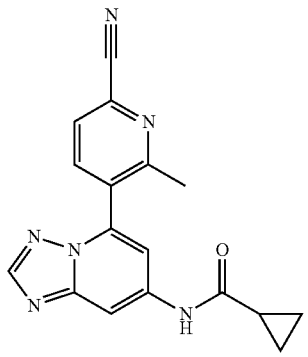 [SMILES: Cc1nc(C#N)ccc1-c1cc(NC(=O)C2CC2)cc2ncnn12]

A suspension of 5-{7-amino-[1,2,4]triazolo[1,5-a]pyridin-5-yl}-6-methylpyridine-2-carbonitrile (Example 212) (0.22 g, 0.879 mmol) in DCM (9 mL) was treated with cyclopropanecarbonyl chloride (CAS 4023-34-1, 0.160 ml, 1.758 mmol) and TEA (0.368 mL, 2.64 mmol) and stirred at room temperature under nitrogen for 3 h. The reaction was concentrated, diluted with EtOAc, washed sequentially with sodium bicarbonate solution, 0.2 M HCl and water, dried (phase separator) and concentrated in vacuo. The crude product was purified by flash chromatography (40-100% EtOAc in petrol on basic silica) to afford the title compound.

$^1$H NMR (400 MHz, DMSO-$d_6$) δ ppm 0.85-0.95 (m, 4H) 1.78-1.90 (m, 1H) 2.33 (s, 3H) 7.34 (d, J=2 Hz, 1H) 8.11 (d, J=8 Hz, 1H) 8.17-8.27 (m, 2H) 8.38 (s, 1H) 10.87 (s, 1H)
MS ES$^+$: 319

Example 254: 4-{5-Amino-[1,2,4]triazolo[1,5-a]pyrimidin-7-yl}-2-fluoro-5-methylbenzonitrile

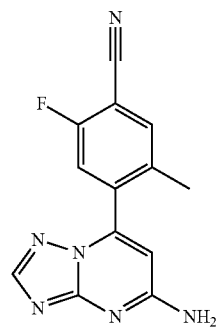 [SMILES: Cc1cc(C#N)c(F)cc1-c1cc(N)nc2ncnn12]

Step 1:
A solution of 4-bromo-2-fluoro-5-methylbenzonitrile (CAS 916792-13-7) (0.500 g, 2.336 mmol) in THF (1.3 ml) under an atmosphere of N$_2$ was cooled to −15° C. Isopropylmagnesium lithium chloride (1.3M in THF) (1.874 mL, 2.437 mmol) was added in a drop wise fashion ensuring the temperature remained below −10° C. The reaction was stirred at ~−15° C. for 30 mins. More isopropylmagnesium lithium chloride (1.3M in THF) (0.170 mL, 1.168 mmol) was added in a dropwise fashion ensuring the temp did not exceed −10° C. and the reaction was stirred at −15° C. for a further 30 mins. A solution of 5,7-dichloro-[1,2,4]triazolo[1,5-a]pyrimidine (CAS 78706-26-0, 0.397 g, 2.102 mmol) in THF (6.50 mL) was added over 2 mins and the reaction was allowed to warm to rt for 3 days. The reaction was quenched with 2M HCl and partitioned between EtAOc and water. The organic was collected, washed with brine, dried (phase separator) and concentrated in vacuo. The resulting residue was purified by flash chromatography (0-100% EtOAc in petrol on SiO$_2$) to afford 4-{5-chloro-[1,2,4]triazolo[1,5-a]pyrimidin-7-yl}-2-fluoro-5-methylbenzonitrile.
MS ES$^+$: 288

Step 2:
A solution of 4-{5-chloro-[1,2,4]triazolo[1,5-a]pyrimidin-7-yl}-2-fluoro-5-methylbenzonitrile (0.130 g, 0.452 mmol), 4-methoxybenzylamine (CAS 2393-23-9, 0.118 ml, 0.904 mmol) and TEA (0.126 mL, 0.904 mmol) in acetonitrile (2 mL) was heated to 70° C. for 2 h. The reaction was concentrated in vacuo and the resulting residue was purified by flash chromatography (0-100% EtOAc in petrol on basic silica) to afford 2-fluoro-4-(5-{[(4-methoxyphenyl)methyl]amino}-[1,2,4]triazolo[1,5-a]pyrimidin-7-yl)-5-methylbenzonitrile.
MS ES$^+$: 389

Step 3:
A solution of 2-fluoro-4-(5-{[(4-methoxyphenyl)methyl]amino}-[1,2,4]triazolo[1,5-a]pyrimidin-7-yl)-5-methylbenzonitrile (0.160 g, 0.412 mmol) and TFA (0.317 mL, 4.12 mmol) in DCM (2 mL) was stirred at rt for 3 days. The reaction was heated to 45° C. for 2 days. The reaction was concentrated in vacuo and the resulting residue was partitioned between EtOAc and sat. bicarb solution. The organic was collected, dried (phase separator) and concentrated in vacuo. The resulting residue was purified by reverse phase preparative HPLC eluted with acetonitrile/water (with 0.1% ammonia) to afford the title compound $^1$H NMR (300 MHz, DMSO-$d_6$) δ ppm 2.14 (s, 3H), 6.40 (s, 1H), 7.46 (s, 2H), 7.78 (d, J=10 Hz, 1H), 8.01 (d, J=7 Hz, 1H), 8.09 (s, 1H)
MS ES$^+$: 269

Example 255: 4-{7-Amino-[1,2,4]triazolo[1,5-a]pyridin-5-yl}-3,5-difluorobenzonitrile

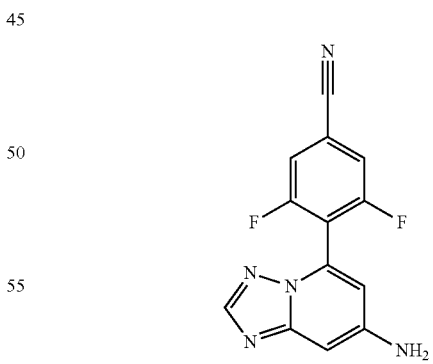

A sealed vial containing tert-butyl (5-(tributylstannyl)-[1,2,4]triazolo[1,5-a]pyridin-7-yl)carbamate (Intermediate 25, 0.3 g, 0.573 mmol), copper(I) iodide (0.005 g, 0.029 mmol), tetrakis(triphenylphosphine)palladium(0) (0.033 g, 0.029 mmol) and 4-bromo-3,5-difluorobenzonitrile (CAS 123688-59-5, 0.137 g, 0.631 mmol) dissolved in NMP (4 mL) was irradiated in a microwave at 100° C. for 80 mins. The reaction mixture was treated with (aq) KF solution (10 wt %, 2 mL) with stirring for 1 h. The mixture was diluted in EtOAc, filtered through celite and washed with water then brine. The organic phase was concentrated in vacuo and was taken up in hydrogen chloride [4.0M solution in 1,4-Dioxane] (4 mL, 16.00 mmol). The reaction was stirred at rt for 3 h. The reaction was concentrated in vacuo and the crude product was purified by reverse phase preparative HPLC eluted with acetonitrile/water (with 0.1% ammonia) to afford the title compound.

$^1$H NMR (400 MHz, DMSO-$d_6$) δ ppm 6.35 (s, 2H), 6.68 (d, J=2 Hz, 1H), 6.79 (d, J=2 Hz, 1H), 8.01-8.12 (m, 3H)

MS ES$^+$: 272

Example 256: 4-{5-[(Cyclopropylmethyl)amino]-[1,2,4]triazolo[1,5-a]pyrimidin-7-yl}-3-methylbenzonitrile

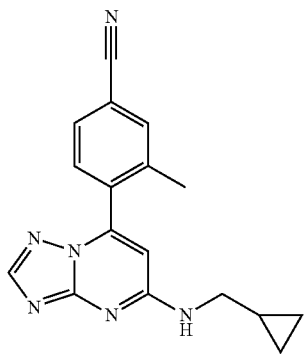 [SMILES: Cc1cc(C#N)ccc1-c1cc(NCC2CC2)nc2ncnn12]

Step 1:

A suspension of 5,7-dichloro-[1,2,4]triazolo[1,5-a]pyrimidine (CAS 78706-26-0) (1 g, 5.29 mmol), (4-cyano-2-methylphenyl)boronic acid (CAS 313546-18-8, 0.852 g, 5.29 mmol), Na$_2$CO$_3$ (0.589 g, 5.56 mmol) and PdCl$_2$(dppf)-CH$_2$Cl$_2$Adduct (0.432 g, 0.529 mmol) in dioxane (30 mL) and water (6 mL) was flushed with N$_2$ and heated to 50° C. for 2 h. The reaction was poured into EtOAc and washed with water. The organic was collected, dried (phase separator) and concentrated in vacuo to afford crude 4-(5-chloro-[1,2,4]triazolo[1,5-a]pyrimidin-7-yl)-3-methylbenzonitrile which was taken directly onto the next step.

MS ES$^+$: 270.2

Step 2:

A solution of 4-(5-chloro-[1,2,4]triazolo[1,5-a]pyrimidin-7-yl)-3-methylbenzonitrile (0.7 g, 2.60 mmol), TEA (0.724 mL, 5.19 mmol) and cyclopropylmethanamine (CAS 2516-47-4, 0.450 ml, 5.19 mmol) in acetonitrile (9 mL) was heated to 70° C. for 1 h. The reaction was concentrated in vacuo and the resulting residue was purified by flash chromatography (0-100% EtOAc in petrol on basic silica). The resulting residue was triturated with EtOAc, filtered and dried to afford the title compound.

$^1$H NMR (300 MHz, CD$_3$CN) δ ppm 0.25-0.38 (m, 2H), 0.47-0.65 (m, 2H), 1.15 (br. s., 1H), 2.23 (s, 3H), 3.27-3.43 (m, 2H), 6.31 (s, 1H), 6.41 (br. s., 1H), 7.57 (d, J=8 Hz, 1H), 7.67-7.79 (m, 2H), 7.97 (s, 1H)

MS ES$^+$: 305

Example 257: 4-{5-Amino-[1,2,4]triazolo[1,5-a]pyrimidin-7-yl}-3-methylbenzonitrile

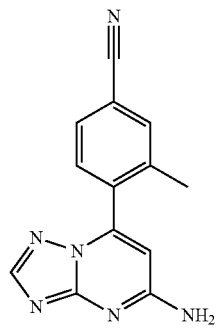 [SMILES: Cc1cc(C#N)ccc1-c1cc(N)nc2ncnn12]

Step 1:

A suspension of 5,7-dichloro-[1,2,4]triazolo[1,5-a]pyrimidine (CAS 78706-26-0, 1 g, 5.29 mmol), (4-cyano-2-methylphenyl)boronic acid (CAS 313546-18-8, 0.852 g, 5.29 mmol), Na$_2$CO$_3$ (0.589 g, 5.56 mmol) and PdCl$_2$(dppf)-CH$_2$Cl$_2$Adduct (0.432 g, 0.529 mmol) in dioxane (30 mL) and water (6 mL) was flushed with N$_2$ and heated to 50° C. for 2 h. The reaction was poured into EtOAc and washed with water. The organic was collected, dried (phase separator) and concentrated in vacuo to afford crude 4-(5-chloro-[1,2,4]triazolo[1,5-a]pyrimidin-7-yl)-3-methylbenzonitrile which was taken directly onto the next step.

MS ES$^+$: 270.2

Step 2:

A solution of 4-(5-chloro-[1,2,4]triazolo[1,5-a]pyrimidin-7-yl)-3-methylbenzonitrile (0.7 g, 2.60 mmol), TEA (0.724 mL, 5.19 mmol) and cyclopropylmethanamine (CAS 2516-47-4, 0.450 mL, 5.19 mmol) in acetonitrile (9 mL) was heated to 70° C. for 1 h. The reaction was concentrated in vacuo and the resulting residue was purified by flash chromatography (0-100% EtOAc in petrol on basic silica) to afford 4-(5-{[(4-methoxyphenyl)methyl]amino}-[1,2,4]triazolo[1,5-a]pyrimidin-7-yl)-3-methylbenzonitrile.

MS ES$^+$: 371

Step 3:

A solution of 4-(5-{[(4-methoxyphenyl)methyl]amino}-[1,2,4]triazolo[1,5-a]pyrimidin-7-yl)-3-methylbenzonitrile (0.8 g, 2.160 mmol) in TFA (2 mL, 26.0 mmol) was heated to 60° C. for 24 h. The reaction was concentrated in vacuo and the resulting residue was partitioned between EtOAc and sat bicarb solution. The organic was collected, dried (phase separator) and concentrated in vacuo. The resulting residue triturated with DCM, filtered and dried. The resulting residue was purified by reverse phase preparative HPLC eluted with acetonitrile/water (with 0.1% ammonia) to afford the title compound.

$^1$H NMR (400 MHz, Methanol-$d_4$) δ ppm 2.27 (s, 3H), 6.47 (s, 1H), 7.63 (d, J=8 Hz, 1H), 7.75 (d, J=8 Hz, 1H), 7.81 (s, 1H), 8.08 (s, 1H)

MS ES$^+$: 251

Example 258: N-[5-(4-Cyano-2-methylphenyl)-[1,2,4]triazolo[1,5-a]pyridin-7-yl]-2,2-difluorocyclopropane-1-carboxamide

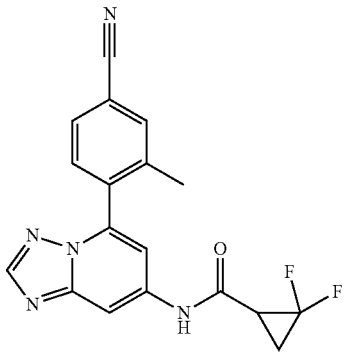 [SMILES: Cc1cc(C#N)ccc1-c1cc(NC(=O)C2CC2(F)F)cc2ncnn12]

A solution 2,2-difluorocyclopropane-1-carboxylic acid (CAS 107873-03-0, 0.256 g, 2.100 mmol), 4-(7-amino-[1,2,4]triazolo[1,5-a]pyridin-5-yl)-3-methylbenzonitrile hydrochloride (the hydrochloride salt of Example 209, 0.500 g, 1.750 mmol) and TEA (0.976 mL, 7.00 mmol) in NMP (4 mL) was treated with N-propylphosphonic acid anhydride, cyclic trimer (50% wt in EtOAc) (2.32 mL, 3.94 mmol) and the reaction was stirred at rt for 2 h. The reaction was diluted with EtOAc, washed with water followed by brine, dried (phase separator) and concentrated in vacuo. The resulting residue was purified by flash chromatography (0-100% EtOAc in petrol on basic silica). The resulting residue was further purified by reverse phase preparative HPLC eluted with acetonitrile/water (with 0.1% ammonia) to afford the title compound.

$^1$H NMR (400 MHz, DMSO-$d_6$) δ ppm 2.02-2.15 (m, 5H), 2.82-2.96 (m, 1H), 7.22 (d, J=2 Hz, 1H), 7.69 (d, J=8 Hz, 1H), 7.87 (d, J=8 Hz, 1H), 7.95 (s, 1H), 8.22 (d, J=2 Hz, 1H), 8.38 (s, 1H), 11.06 (s, 1H)

MS ES$^+$: 354

Example 259: 4-{7-Amino-[1,2,4]triazolo[1,5-a]pyridin-5-yl}-3-chlorobenzonitrile

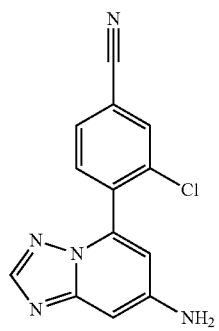 [SMILES: N#Cc1ccc(-c2cc(N)cc3ncnn23)c(Cl)c1]

Step 1:

A suspension of tert-butyl {5-chloro-[1,2,4]triazolo[1,5-a]pyridin-7-yl}carbamate (Intermediate 25, 1 g, 3.72 mmol), (2-chloro-4-cyanophenyl)boronic acid (CAS 677743-50-9, 0.945 g, 5.21 mmol), tetrakis(triphenylphosphine)palladium (0) (0.215 g, 0.186 mmol) and saturated sodium carbonate (3.91 mL, 7.82 mmol) in DME (12 mL) was flushed with N$_2$ and heated to 120° C. for 1 h. The reaction was partitioned between EtOAc and water. The organic was collected, washed with water followed by brine, dried (phase separator) and concentrated in vacuo. The resulting residue was purified by flash chromatography (0-100% EtOAc in petrol on basic silica). The resulting residue was purified by reverse phase flash chromatography (0-100% acetonitrile in water with 0.05% NH$_4$OH on C18) to afford tert-butyl N-[5-(2-chloro-4-cyanophenyl)-[1,2,4]triazolo[1,5-a]pyridin-7-yl]carbamate.

MS ES$^+$: 370

Step 2:

A solution of tert-butyl (5-(2-chloro-4-cyanophenyl)-[1,2,4]triazolo[1,5-a]pyridin-7-yl)carbamate (432 mg, 1.168 mmol) and HCl (4M in dioxane) (2.92 mL, 11.68 mmol) in dioxane (4 mL) was heated to 50° C. for 3 days. The reaction was cooled to rt and concentrated in vacuo. The resulting residue was partitioned between EtOAc and sat bicarb solution. The organic was collected, dried (phase separator) and concentrated in vacuo. The resulting residue was purified by reverse phase preparative HPLC eluted with acetonitrile/water (with 0.1% ammonia) to afford the title compound.

$^1$H NMR (400 MHz, DMSO-$d_6$) δ ppm 6.27 (s, 2H), 6.55-6.67 (m, 2H), 7.84 (d, J=8 Hz, 1H), 7.99-8.06 (m, 2H), 8.29 (d, J=1 Hz, 1H)

MS ES$^+$: 270

Example 260: 4-{7-Amino-[1,2,4]triazolo[1,5-a]pyridin-5-yl}-2,3-difluorobenzonitrile

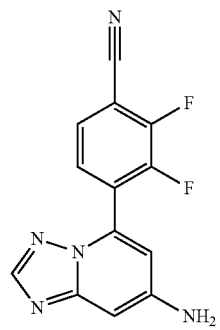 [SMILES: N#Cc1ccc(-c2cc(N)cc3ncnn23)c(F)c1F]

Prepared as described for 4-{7-amino-[1,2,4]triazolo[1,5-a]pyridin-5-yl}-3,5-difluorobenzonitrile (Example 255) from tert-butyl (5-(tributylstannyl)-[1,2,4]triazolo[1,5-a]pyridin-7-yl)carbamate (Intermediate 25) and 4-bromo-2,3-difluorobenzonitrile (CAS 126163-58-4) to afford the title compound.

$^1$H NMR (400 MHz, DMSO-$d_6$) δ ppm 6.34 (s, 2H), 6.66 (d, J=2 Hz, 1H), 6.75 (d, J=2 Hz, 1H), 7.72-7.82 (m, 1H), 7.92-8.01 (m, 1H), 8.08 (s, 1H)

MS ES$^+$: 272

Example 261: N-[5-(2-Chloro-4-cyanophenyl)-[1,2,4]triazolo[1,5-a]pyridin-7-yl]acetamide

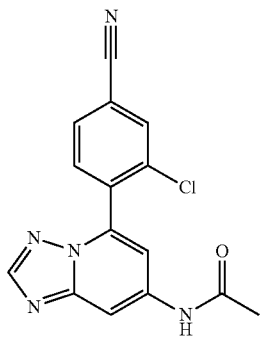

A solution of 4-{7-amino-[1,2,4]triazolo[1,5-a]pyridin-5-yl}-3-chlorobenzonitrile (Example 259, 0.063 g, 0.234 mmol) and TEA (0.065 mL, 0.467 mmol) in DMF (1 mL) was treated with AcCl (0.033 mL, 0.467 mmol). The reaction was stirred at rt for 1 h. More TEA (0.065 mL, 0.467 mmol) and AcCl (0.033 mL, 0.467 mmol) was added and the reaction was stirred at rt for a further 1 h. More TEA (0.185 mL) and AcCl (0.100 mL) was added and the reaction was stirred at rt for a further 1 h. The reaction was diluted with EtOAc and washed three times with water. The organic was collected, dried (phase separator) and concentrated in vacuo. The resulting residue was purified by reverse phase preparative HPLC eluted with acetonitrile/water (with 0.1% ammonia) to afford the title compound.

$^1$H NMR (400 MHz, DMSO-d$_6$) δ ppm 2.16 (s, 3H), 7.30 (d, J=2 Hz, 1H), 7.91 (d, J=8 Hz, 1H), 8.04-8.11 (m, 1H), 8.25 (d, J=2 Hz, 1H), 8.31-8.39 (m, 2H), 10.60 (s, 1H)

MS ES$^+$=312

Example 262: N-[5-(4-Cyano-5-fluoro-2-methylphenyl)-[1,2,4]triazolo[1,5-a]pyridin-7-yl]acetamide

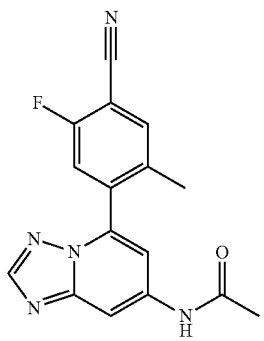 [SMILES: CC(=O)Nc1cc(-c2cc(F)c(C#N)cc2C)n2ncnc2c1]

4-{7-amino-[1,2,4]triazolo[1,5-a]pyridin-5-yl}-2-fluoro-5-methylbenzonitrile (Example 220, 0.333 g, 1.246 mmol) was suspended in DCM (5 mL) and pyridine (0.5 mL, 6.18 mmol) then cooled in ice. AcCl (0.15 mL, 2.110 mmol) was added and the flask was sonicated to attempt to dislodge material from the flask walls. The flask was returned to the ice bath and allowed to stir for 1 h. The mixture was removed from the ice-bath and stirred at rt for 18 h. The reaction was diluted with EtOAc, water and sat bicarb solution. The aqueous was further extracted with more EtOAc. The organics were combined, washed with brine, dried (MgSO$_4$) and concentrated in vacuo. The resulting residue was purified by flash chromatography (0-10% MeOH in DCM on SiO$_2$). The resulting residue was recrystallised from EtOH to afford the title compound.

$^1$H NMR (400 MHz, DMSO-d$_6$) δ ppm 2.08 (s, 3H), 2.16 (s, 3H), 7.24 (d, J=2 Hz, 1H), 7.77 (d, J=10 Hz, 1H), 8.03 (d, J=7 Hz, 1H), 8.24 (d, J=2 Hz, 1H), 8.37 (s, 1H), 10.59 (s, 1H)

MS ES$^+$: 310

3. BIOLOGICAL EFFICACY OF COMPOUNDS OF THE INVENTION

PHD1 Enzyme Assay

The IC$_{50}$ values for the PHD1 enzyme (residues 1-407) were determined by mixing increasing amounts of a compound of the invention with a fixed amount of the enzyme (20 nM final concentration) and peptide substrate (Asp-Leu-Asp-Leu-Glu-Ala-Leu-Ala-Pro-Tyr-Ile-Pro-Ala-Asp-Asp-Asp-Phe-Gln-Leu, 1 μM final concentration) and 2-oxoglutarate (0.5 M final concentration) in an assay buffer comprising 30 mM 2-(N-morpholino)ethanesulfonic acid pH 6.0, 2 mM sodium ascorbate, 100 μM dithiothreitol, 2 mg/ml bovine serum albumin, 60 μg/ml catalase enzyme and 1 μM iron (II) sulphate (FeSO$_4$). The reaction was conducted by pre-incubating the PHD1 enzyme in the presence of a compound of the invention for 60 minutes at room temperature. The activity of the free enzyme was measured by adding the peptide, the 2-oxoglutarate and sodium ascorbate (see above for final concentrations). The assay was quenched by the addition of 30% v/v trichloroacetic acid (final concentration 5%). The amount of product released was measured using a UPLC-MS (Agilent 1290 with an ABSciex 4000qTrap Mass Spectrometer). Data were analysed using the classical isotherm equation for the determination of IC$_{50}$. The IC$_{50}$ values for the compounds of the Examples are shown in Table 1.

Results

TABLE 1

| Ex No. | IC$_{50}$ (nM) | Ex No. | IC$_{50}$ (nM) | Ex No. | IC$_{50}$ (nM) |
|---|---|---|---|---|---|
| 1 | 677 | 2 | 54 | 3 | 34 |
| 4 | 39 | 5 | 10 | 6 | 34 |
| 7 | 50 | 8 | 74 | 9 | 307 |
| 10 | 3890 | 11 | 1874 | 12 | 452 |
| 13 | 829 | 14 | 272 | 15 | 171 |
| 16 | 3941 | 17 | 2156 | 18 | 460 |
| 19 | 665 | 20 | 1955 | 21 | 84 |
| 22 | 1283 | 23 | 67 | 24 | 99 |
| 25 | 56 | 26 | 197 | 27 | 1400 |
| 28 | 93 | 29 | 145 | 30 | 136 |
| 31 | 141 | 32 | 506 | 33 | 6109 |
| 34 | 223 | 35 | 58 | 36 | 67 |
| 37 | 280 | 38 | 543 | 39 | 223 |
| 40 | 323 | 41 | 459 | 42 | 138 |
| 43 | 1840 | 44 | 1760 | 45 | 755 |
| 46 | 1949 | 47 | 470 | 48 | 206 |
| 49 | 366 | 50 | 927 | 51 | 978 |
| 52 | 531 | 53 | 387 | 54 | 730 |
| 55 | 307 | 56 | 167 | 57 | 445 |
| 58 | 145 | 59 | 269 | 60 | 377 |
| 61 | 392 | 62 | 490 | 63 | 714 |
| 64 | 669 | 65 | 551 | 66 | 613 |
| 67 | 103 | 68 | 1885 | 69 | 1114 |
| 70 | 607 | 71 | 904 | 72 | 5086 |
| 73 | 5436 | 74 | 184 | 75 | 2158 |
| 76 | 969 | 77 | 2043 | 78 | 1833 |
| 79 | 275 | 80 | 3000 | 81 | 884 |
| 82 | 11 | 83 | 406 | 84 | 5 |

TABLE 1-continued

| Ex No. | IC$_{50}$ (nM) | Ex No. | IC$_{50}$ (nM) | Ex No. | IC$_{50}$ (nM) |
|---|---|---|---|---|---|
| 85 | 164 | 86 | 2108 | 87 | 119 |
| 88 | 29 | 89 | 360 | 90 | 574 |
| 91 | 2448 | 92 | 792 | 93 | 129 |
| 94 | 238 | 95 | 61 | 96 | 32 |
| 97 | 115 | 98 | 427 | 99 | 435 |
| 100 | 13 | 101 | 9 | 102 | 34 |
| 103 | 25 | 104 | 37 | 105 | 25 |
| 106 | 10 | 107 | 5 | 108 | 9 |
| 109 | 77 | 110 | 166 | 111 | 247 |
| 112 | 20 | 113 | 8 | 114 | 33 |
| 115 | 13 | 116 | 29 | 117 | 5 |
| 118 | 54 | 119 | 49 | 120 | 52 |
| 121 | 8 | 122 | 70 | 123 | 151 |
| 124 | 49 | 125 | 208 | 126 | 53 |
| 127 | 47 | 128 | 215 | 129 | 299 |
| 130 | 139 | 131 | 168 | 132 | 480 |
| 133 | 2300 | 134 | 229 | 135 | 240 |
| 136 | 3223 | 137 | 145 | 138 | 170 |
| 139 | 77 | 140 | 151 | 141 | 115 |
| 142 | 72 | 143 | 437 | 144 | 145 |
| 145 | 66 | 146 | 27 | 147 | 461 |
| 148 | 126 | 149 | 252 | 150 | 12 |
| 151 | 47 | 152 | 42 | 153 | 28 |
| 154 | 490 | 155 | 130 | 156 | 129 |
| 157 | 57 | 158 | 91 | 159 | 147 |
| 160 | 248 | 161 | 123 | 162 | 117 |
| 163 | 88 | 164 | 131 | 165 | 650 |
| 166 | 630 | 167 | 225 | 168 | 218 |
| 169 | 49 | 170 | 3017 | 171 | 58 |
| 172 | 220 | 173 | 63 | 174 | 34 |
| 175 | 143 | 176 | 40 | 177 | 6900 |
| 178 | 4000 | 179 | 3300 | 180 | 79 |
| 181 | 325 | 182 | 5400 | 183 | 1500 |
| 184 | 870 | 185 | 3794 | 186 | 1400 |
| 187 | 1400 | 188 | 800 | 189 | 1300 |
| 190 | 1700 | 191 | 2900 | 192 | 1300 |
| 193 | 4800 | 194 | 2300 | 195 | 14 |
| 196 | 190 | 197 | 53 | 198 | 109 |
| 199 | 111 | 200 | 79 | 201 | 1125 |
| 202 | 4475 | 203 | 1109 | 204 | 468 |
| 205 | 970 | 206 | 3623 | 207 | 2663 |
| 208 | 2531 | 209 | 88 | 210 | 36 |
| 211 | 25 | 212 | 79 | 213 | 7142 |
| 214 | 632 | 215 | 953 | 216 | 997 |
| 217 | 376 | 218 | 233 | 219 | 30 |
| 220 | 73 | 221 | 1796 | 222 | 161 |
| 223 | 52 | 224 | 3093 | 225 | 1647 |
| 226 | 135 | 227 | 774 | 228 | 68 |
| 229 | 3661 | 230 | 925 | 231 | 199 |
| 232 | 74 | 233 | 69 | 234 | 2113 |
| 235 | 1690 | 236 | 65 | 237 | 89 |
| 238 | 96 | 239 | 333 | 240 | 460 |
| 241 | 152 | 242 | 381 | 243 | 1286 |
| 244 | 131 | 245 | 107 | 246 | 65 |
| 247 | 80 | 248 | 35 | 249 | 27 |
| 250 | 88 | 251 | 17 | 252 | 1130 |
| 253 | 216 | 254 | 751 | 255 | 157 |
| 256 | 92 | 257 | 165 | 258 | 152 |
| 259 | 205 | 260 | 29 | 261 | 96 |
| 262 | 108 | | | | |

This application is based on a patent application No. GB 1504565.1 filed in United Kingdom of Great Britain and Northern Ireland, the contents of which are incorporated in full herein.

The invention claimed is:

1. A compound of formula (I)

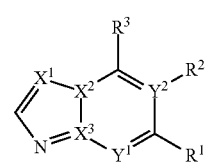

or a pharmaceutically acceptable salt thereof, wherein
$X^1$ represents N; $X^2$ represents N; $X^3$ represents C; $Y^1$ represents CH;
$R^1$ represents hydrogen, halogen, $C_1$-$C_6$ alkyl, $C_3$-$C_6$ cycloalkyl, $C_1$-$C_6$ alkoxy$C_1$-$C_6$ alkyl, $C_1$-$C_6$ hydroxyalkyl, —OR$^4$, —SR$^4$, —C(O)R$^4$, —C(O)OR$^4$, —(CH$_2$)$_m$NHC(O)R$^4$, —(CH$_2$)$_m$NH C(O)OR$^4$, —NHC(O)NHR$^4$, —NHSO$_2$R$^4$, —C(O)NR$^5$R$^6$, —(CH$_2$)$_m$NR$^5$R$^6$, —SO$_2$NR$^5$R$^6$ or a 4- to 9-membered heterocyclyl (unsubstituted, or substituted by at least one substituent independently selected from oxo, $C_1$-$C_6$ alkyl, $C_1$-$C_6$ alkylcarbonyl, $C_1$-$C_6$ alkoxy, $C_3$-$C_6$ cycloalkyl, $C_1$-$C_6$ alkoxycarbonyl, —(CH$_2$)$_p$NR$^7$R$^8$ and C(O)NR$^7$R$^8$);
m is 0 or 1;
p is 0 or 1;
$R^4$ represents hydrogen, $C_1$-$C_6$ alkyl (unsubstituted, or substituted by at least one substituent independently selected from halogen, hydroxyl, $C_1$-$C_6$ haloalkyl, $C_1$-$C_6$ alkoxy, $C_3$-$C_6$ cycloalkyl, $C_6$-$C_{10}$ aryl, NR$^9$R$^{10}$, oxetanyl, oxolanyl and oxanyl), $C_3$-$C_6$ cycloalkyl (unsubstituted, or substituted by at least one substituent independently selected from halogen, cyano and $C_1$-$C_6$ alkyl), $C_6$-$C_{10}$ aryl, or a 4- to 7-membered heterocyclyl (unsubstituted, or substituted by at least one $C_1$-$C_6$ alkyl);
$R^5$ and $R^6$ each independently represent hydrogen, $C_1$-$C_6$ alkyl (unsubstituted, or substituted by at least one substituent independently selected from halogen, hydroxyl, $C_1$-$C_6$ alkoxy, $C_3$-$C_6$ cycloalkyl, NR$^{11}$R$^{12}$, $C_6$-$C_{10}$ aryl, 5- to 10-membered heteroaryl and 4- to 7-membered heterocyclyl, each of the aryl, heteroaryl and heterocyclyl substituents being optionally substituted with at least one substituent independently selected from halogen, oxo, $C_1$-$C_6$ alkyl, $C_1$-$C_6$ alkoxy, $C_1$-$C_6$ alkoxycarbonyl, and phenyl), $C_1$-$C_6$ alkylcarbonyl, $C_3$-$C_6$ cycloalkyl, $C_6$-$C_{10}$ aryl, 5- to 10-membered heteroaryl, 4- to 7-membered heterocyclyl, each of the aryl, heteroaryl and heterocyclyl groups being optionally substituted with at least one substituent independently selected from halogen, $C_1$-$C_6$ alkyl, $C_1$-$C_6$ alkoxy, and $C_1$-$C_6$ alkylcarbonyl,
or $R^5$ and $R^6$ may together with the nitrogen atom to which they are attached form a 4- to 7-membered saturated heterocyclic ring unsubstituted, or substituted by at least one substituent independently selected from halogen, hydroxyl, oxo and $C_1$-$C_6$ alkoxy;
$R^7$ and $R^8$ each independently represent a hydrogen atom or a $C_1$-$C_6$ alkyl or $C_3$-$C_6$ cycloalkyl group, or $R^7$ and $R^8$ may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;

$R^9$ and $R^{10}$ each independently represent a hydrogen atom or a $C_1$-$C_6$ alkyl or $C_3$-$C_6$ cycloalkyl group, or $R^9$ and $R^{10}$ may together with the nitrogen atom to which they are attached form a 4- to 7-membered saturated heterocyclic ring optionally substituted by at least one substituent independently selected from halogen, hydroxyl, oxo and $C_1$-$C_6$ alkoxy;

$R^{11}$ and $R^{12}$ each independently represent a hydrogen atom or a $C_1$-$C_6$ alkyl or $C_3$-$C_6$ cycloalkyl group;

$Y^2$ represents C or N;

when $Y^2$ represents C, $R^2$ represents a hydrogen or halogen atom, or a $C_1$-$C_3$ alkyl or amino group;

when $Y^2$ represents N, $R^2$ is absent;

$R^3$ represents a group of formula (II) to (VIII)

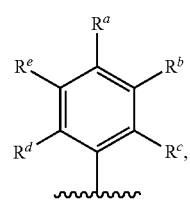  (II)

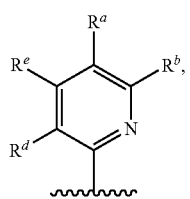  (III)

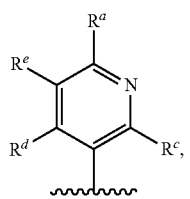  (IV)

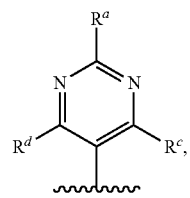  (V)

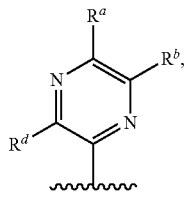  (VI)

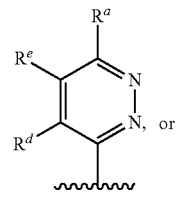  (VII)

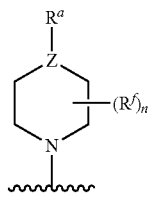  (VIII)

wherein in formulae (II) to (VIII), n is 0 or an integer from 1 to 4, Z represents CH or N, $R^a$ represents halogen, cyano, $C_2$-$C_6$ alkenyl, $C_2$-$C_6$ alkynyl or $C_3$-$C_6$ cycloalkyl, each of $R^b$, $R^c$, $R^d$ and $R^e$ independently represents hydrogen, halogen, $C_1$-$C_6$ alkyl, $C_1$-$C_6$ alkoxy, $C_1$-$C_6$ haloalkyl, $C_3$-$C_6$ cycloalkyl or $NR^{13}R^{14}$, and each $R^f$ independently represents halogen, $C_1$-$C_6$ alkyl, $C_1$-$C_6$ alkoxy, $C_1$-$C_6$ haloalkyl, $C_3$-$C_6$ cycloalkyl or $NR^{13}R^{14}$; and $R^{13}$ and $R^{14}$ each independently represent a hydrogen atom or a $C_1$-$C_6$ alkyl or $C_3$-$C_6$ cycloalkyl group, or $R^{13}$ and $R^{14}$ may together with the nitrogen atom to which they are attached form a 4- to 7-membered saturated heterocyclic ring optionally substituted by at least one substituent independently selected from halogen, hydroxyl, oxo and $C_1$-$C_6$ alkoxy.

2. The compound or pharmaceutically acceptable salt thereof according to claim 1, wherein $R^1$ represents
(i) hydrogen,
(ii) chlorine,
(iii) methyl,
(iv) cyclopropyl,
(v) methoxymethyl,
(vi) hydroxymethyl,
(vii) —$OR^4$,
(viii) —$SR^4$,
(ix) —$C(O)R^4$,
(x) —$C(O)OR^4$,
(xi) —$(CH_2)_m NHC(O)R^4$,
(xii) —$(CH_2)_m NHC(O)OR^4$,
(xiii) —$NHC(O)NHR^4$,
(xiv) —$NHSO_2R^4$,
(xv) —$C(O)NR^5R^6$,
(xvi) —$(CH_2)_m NR^5R^6$,
(xvii) —$SO_2NR^5R^6$, or
(xviii) a 4- to 9-membered heterocyclyl comprising one or two ring heteroatoms independently selected from nitrogen and oxygen which is either unsubstituted or is substituted by one or two substituents independently selected from oxo, $C_1$-$C_4$ alkyl, $C_1$-$C_2$ alkylcarbonyl, $C_1$-$C_2$ alkoxy, cyclopropyl, $C_1$-$C_4$ alkoxycarbonyl, —$(CH_2)_p NR^7R^8$ and $C(O)NR^7R^8$.

3. The compound or pharmaceutically acceptable salt thereof according to claim 1, wherein $R^1$ represents —$(CH_2)_m NHC(O)R^4$ or —$(CH_2)_m NR^5R^6$ and m is 0.

4. The compound or pharmaceutically acceptable salt thereof according to claim 1, wherein $R^4$ represents hydrogen, $C_1$-$C_3$ alkyl (unsubstituted, or substituted by one, two or three substituents independently selected from fluorine, hydroxyl, trifluoromethyl, $C_1$-$C_2$ alkoxy, cyclopropyl, phenyl, $NR^9R^{10}$, oxetanyl, oxolanyl and oxanyl), $C_3$-$C_4$ cycloalkyl (unsubstituted, or substituted by one or two substituents independently selected from fluorine, cyano and $C_1$-$C_2$ alkyl), phenyl, or a 4- to 6-membered heterocyclyl (unsubstituted, or substituted by one or two $C_1$-$C_6$ alkyl groups).

5. The compound or pharmaceutically acceptable salt thereof according to claim 1, wherein $R^5$ and $R^6$ each independently represent
(i) hydrogen,
(ii) $C_1$ to $C_5$ alkyl (unsubstituted, or substituted by one, two, three or four substituents independently selected from fluorine, hydroxyl, methoxy, cyclopropyl, $NR^{11}R^{12}$, phenyl, 5- to 6-membered heteroaryl and 4- to 6-membered heterocyclyl, each of the aryl, heteroaryl and heterocyclyl substituents being optionally substituted with one, two, three, or four substituents independently selected from fluorine, chlorine, oxo, methyl, methoxy, $C_1$-$C_4$ alkoxycarbonyl, and phenyl),
(iii) methylcarbonyl,
(iv) cyclopropyl,
(v) phenyl,
(vi) 5- to 6-membered heteroaryl, or
(vii) 4- to 6-membered heterocyclyl,
each of the aryl, heteroaryl and heterocyclyl groups (groups (v), (vi) and (vii) above) being optionally substituted with one, two, three or four substituents independently selected from methyl, methoxy, and $C_1$-$C_2$ alkylcarbonyl.

6. The compound or pharmaceutically acceptable salt thereof according to claim 1, wherein $R^3$ represents a group of formula (II) or a group of formula (IV).

7. The compound or pharmaceutically acceptable salt thereof according to claim 1, wherein $R^a$ represents cyano.

8. The compound or pharmaceutically acceptable salt thereof according to claim 1, wherein $R^3$ represents a group of formula (II) in which $R^a$ represents cyano, $R^c$ represents methyl, and each of $R^b$, $R^d$ and $R^e$ independently represents hydrogen, fluorine or methyl.

9. The compound or pharmaceutically acceptable salt thereof according to claim 1, which is represented by formula (Ia)

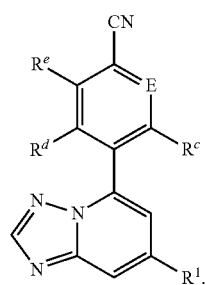

(Ia)

in which $R^1$ represents $NHC(O)R^4$ or $NR^5R^6$;
E is a nitrogen atom or $CR^b$;
$R^b$ and $R^e$ each independently represent a hydrogen or fluorine atom;
$R^c$ and $R^d$ each independently represent a hydrogen, fluorine or chlorine atom or a methyl group;
$R^4$ represents a $C_1$-$C_3$ alkyl or $C_3$-$C_6$ cycloalkyl group; and
$R^5$ and $R^6$ each represent a hydrogen atom.

10. The compound according to claim 1 which is selected from the group of compounds:
5-(2,4-dichlorophenyl)-[1,2,4]triazolo[1,5-a]pyridine;
5-(4-chlorophenyl)-[1,2,4]triazolo[1,5-a]pyridine;
4-{[1,2,4]triazolo [1,5-a]pyridin-5-yl}benzonitrile;
4-{7-methyl-[1,2,4]triazolo[1,5-a]pyridin-5-yl}benzonitrile;
2-fluoro-4-{[1,2,4]triazolo[1,5-a]pyridin-5-yl}benzonitrile;
2,6-difluoro-4-{[1,2,4]triazolo[1,5-a]pyridin-5-yl}benzonitrile;
3-fluoro-4-{[1,2,4]triazolo[1,5-a]pyridin-5-yl}benzonitrile;
3-methyl-4-{[1,2,4]triazolo[1,5-a]pyridin-5-yl}benzonitrile;
5-(4-chloro-2-fluorophenyl)-[1,2,4]triazolo[1,5-a]pyridine;
2-chloro-4-{[1,2,4]triazolo[1,5-a]pyridin-5-yl}benzonitrile;
4-{[1,2,4]triazolo[1,5-a]pyridin-5-yl}-2-(trifluoromethyl)benzonitrile;
5-(4-chloro-3-fluorophenyl)-[1,2,4]triazolo[1,5-a]pyridine;
2-methyl-4-{[1,2,4]triazolo[1,5-a]pyridin-5-yl}benzonitrile;
6-{[1,2,4]triazolo[1,5-a]pyridin-5-yl}pyridine-3-carbonitrile;
5-{[1,2,4]triazolo[1,5-a]pyridin-5-yl}pyridine-2-carbonitrile;
4-{[1,2,4]triazolo[1,5-c]pyrimidin-5-yl}benzonitrile;
2-fluoro-4-{[1,2,4]triazolo[1,5-c]pyrimidin-5-yl}benzonitrile;
4-{6-methyl-[1,2,4]triazolo[1,5-a]pyridin-5-yl}benzonitrile;
2-fluoro-4-{6-methyl-[1,2,4]triazolo[1,5-a]pyridin-5-yl}benzonitrile;
5-{7-chloro-[1,2,4]triazolo[1,5-a]pyridin-5-yl}-6-methylpyridine-2-carbonitrile;
5-{[1,2,4]triazolo[1,5-a]pyridin-5-yl}pyrimidine-2-carbonitrile;
5-{[1,2,4]triazolo[1,5-a]pyridin-5-yl}pyrazine-2-carbonitrile;
2,3-difluoro-4-{[1,2,4]triazolo[1,5-a]pyridin-5-yl}benzonitrile;
3-fluoro-5-{[1,2,4]triazolo[1,5-a]pyridin-5-yl}pyridine-2-carbonitrile;
4-methyl-5-{[1,2,4]triazolo[1,5-a]pyridin-5-yl}pyridine-2-carbonitrile;
3,5-dimethyl-4-{[1,2,4]triazolo [1,5-a]pyridin-5-yl}benzonitrile;
6-{[1,2,4]triazolo[1,5-a]pyridin-5-yl}pyridazine-3-carbonitrile;
6-methyl-5-{[1,2,4]triazolo [1,5-a]pyridin-5-yl}pyridine-2-carbonitrile;
2-fluoro-5-methyl-4-{[1,2,4] triazolo [1,5-a]pyridin-5-yl}benzonitrile;
3-chloro-4-{[1,2,4]triazolo[1,5-a]pyridin-5-yl}benzonitrile;
3-methoxy-4-{[1,2,4]triazolo[1,5-a]pyridin-5-yl}benzonitrile;
5-methyl-6-{[1,2,4]triazolo[1,5-a]pyridin-5-yl}pyridine-3-carbonitrile;
3-ethyl-4-{[1,2,4]triazolo[1,5-a]pyridin-5-yl}benzonitrile;
3-fluoro-5-methyl-4-{[1,2,4]triazolo [1,5-a]pyridin-5-yl}benzonitrile;
3-amino-4-{[1,2,4]triazolo[1,5-a]pyridin-5-yl}benzonitrile;
3-bromo-4-{[1,2,4]triazolo[1,5-a]pyridin-5-yl}benzonitrile;
1-{[1,2,4]triazolo [1,5-a]pyridin-5-yl}piperidine-4-carbonitrile;
4-[7-(hydroxymethyl)-[1,2,4]triazolo[1,5-a]pyridin-5-yl]benzonitrile;

methyl 5-(4-cyanophenyl)-[1,2,4]triazolo[1,5-a]pyridine-7-carboxylate;
5-(4-cyanophenyl)-[1,2,4]triazolo[1,5-a]pyridine-7-carboxylic acid;
4-{7-cyclopropyl-[1,2,4]triazolo[1,5-a]pyridin-5-yl}benzonitrile;
4-[7-(pyrrolidine-1-carbonyl)-[1,2,4]triazolo[1,5-a]pyridin-5-yl]benzonitrile;
5-(4-cyanophenyl)-N-(2-methoxyethyl)-[1,2,4]triazolo[1,5-a]pyridine-7-carboxamide;
4-{7-[(2S)-2-methylpyrrolidine-1-carbonyl]-[1,2,4]triazolo [1,5-a]pyridin-5-yl}benzonitrile;
4-[7-(3-methylpyrrolidine-1-carbonyl)-[1,2,4]triazolo[1,5-a]pyridin-5-yl]benzonitrile;
5-(4-cyanophenyl)-N-(3-methoxyphenyl)-[1,2,4]triazolo[1,5-a]pyridine-7-carboxamide;
N-[2-(3-chlorophenyl)ethyl]-5-(4-cyanophenyl)-[1,2,4]triazolo[1,5-a]pyridine-7-carboxamide;
N-[2-(4-chlorophenyl)ethyl]-5-(4-cyanophenyl)-[1,2,4]triazolo[1,5-a]pyridine-7-carboxamide;
5-(4-cyanophenyl)-N-[2-(3-methoxyphenyl)ethyl]-[1,2,4]triazolo[1,5-a]pyridine-7-carboxamide;
N-(3-chlorophenyl)-5-(4-cyanophenyl)-[1,2,4]triazolo[1,5-a]pyridine-7-carboxamide;
N-(4-chlorophenyl)-5-(4-cyanophenyl)-[1,2,4]triazolo[1,5-a]pyridine-7-carboxamide;
5-(4-cyanophenyl)-N-(6-methylpyridazin-3-yl)-[1,2,4]triazolo[1,5-a]pyridine-7-carboxamide;
5-(4-cyanophenyl)-N-(2-methylpyrimidin-5-yl)-[1,2,4]triazolo[1,5-a]pyridine-7-carboxamide;
N-[(3-chlorophenyl)methyl]-5-(4-cyanophenyl)-[1,2,4]triazolo[1,5-a]pyridine-7-carboxamide;
N-[(4-chlorophenyl)methyl]-5-(4-cyanophenyl)-[1,2,4]triazolo[1,5-a]pyridine-7-carboxamide;
5-(4-cyanophenyl)-N-[(3-methoxyphenyl)methyl]-[1,2,4]triazolo[1,5-a]pyridine-7-carboxamide;
5-(4-cyanophenyl)-[1,2,4]triazolo[1,5-a]pyridine-7-carboxamide;
5-(4-cyanophenyl)-N-methyl-[1,2,4]triazolo[1,5-a]pyridine-7-carboxamide;
N-butyl-5-(4-cyanophenyl)-[1,2,4]triazolo[1,5-a]pyridine-7-carboxamide;
5-(4-cyanophenyl)-N-[(1-methyl-1H-imidazol-4-yl)methyl]-[1,2,4]triazolo[1,5-a]pyridine-7-carboxamide;
5-(4-cyanophenyl)-N-[(1-methyl-1H-pyrazol-4-yl)methyl]-[1,2,4]triazolo[1,5-a]pyridine-7-carboxamide;
tert-butyl 3-({[5-(4-cyanophenyl)-[1,2,4]triazolo[1,5-a]pyridin-7-yl]formamido}methyl)azetidine-1-carboxylate;
5-(4-cyanophenyl)-N-[2-(morpholin-4-yl)ethyl]-[1,2,4]triazolo[1,5-a]pyridine-7-carboxamide;
5-(4-cyanophenyl)-N-[2-(4-methylpiperazin-1-yl)ethyl]-[1,2,4]triazolo[1,5-a]pyridine-7-carboxamide;
5-(4-cyanophenyl)-N-(propan-2-yl)-[1,2,4]triazolo[1,5-a]pyridine-7-carboxamide;
5-(4-cyanophenyl)-N-(cyclopropylmethyl)-[1,2,4]triazolo[1,5-a]pyridine-7-carboxamide;
5-(4-cyanophenyl)-N-(oxetan-3-yl)-[1,2,4]triazolo[1,5-a]pyridine-7-carboxamide;
5-(4-cyanophenyl)-N-(oxetan-3-ylmethyl)-[1,2,4]triazolo[1,5-a]pyridine-7-carboxamide;
5-(4-cyanophenyl)-N-(1-methylazetidin-3-yl)-[1,2,4]triazolo[1,5-a]pyridine-7-carboxamide;
5-(4-cyanophenyl)-N-(2-hydroxyethyl)-[1,2,4]triazolo[1,5-a]pyridine-7-carboxamide;
4-{7-amino-[1,2,4]triazolo[1,5-a]pyridin-5-yl}benzonitrile;
4-{7-[(cyclopropylmethyl)amino]-[1,2,4]triazolo[1,5-a]pyridin-5-yl}benzonitrile;
4-{7-[(2-methoxyethyl)amino]-[1,2,4]triazolo[1,5-a]pyridin-5-yl}benzonitrile;
4-[7-(ethylamino)-[1,2,4]triazolo[1,5-a]pyridin-5-yl]benzonitrile;
4-{7-[(oxan-4-ylmethyl)amino]-[1,2,4]triazolo [1,5-a]pyridin-5-yl}benzonitrile;
4-{7-[(oxolan-3-ylmethyl)amino]-[1,2,4]triazolo[1,5-a]pyridin-5-yl}benzonitrile;
4-{7-[(2,2-difluoroethyl)amino]-[1,2,4]triazolo[1,5-a]pyridin-5-yl}benzonitrile;
4-{7-[(oxetan-3-ylmethyl)amino]-[1,2,4]triazolo[1,5-a]pyridin-5-yl}benzonitrile;
4-{7-[(3,3,3-trifluoropropyl)amino]-[1,2,4]triazolo [1,5-a]pyridin-5-yl}benzonitrile;
4-(7-{[3-(morpholin-4-yl)propyl]amino}-[1,2,4]triazolo[1,5-a]pyridin-5-yl)benzonitrile;
4-{7-[(2-hydroxy-2-methylpropyl)amino]-[1,2,4]triazolo[1,5-a]pyridin-5-yl}benzonitrile;
4-{7-[(3-methoxypropyl)amino]-[1,2,4]triazolo[1,5-a]pyridin-5-yl}benzonitrile;
4-{7-[(oxolan-2-ylmethyl)amino]-[1,2,4]triazolo [1,5-a]pyridin-5-yl}benzonitrile;
4-(7-{[2-(dimethylamino)ethyl]amino}-[1,2,4]triazolo[1,5-a]pyridin-5-yl)benzonitrile;
4-[7-(benzylamino)-[1,2,4]triazolo[1,5-a]pyridin-5-yl]benzonitrile;
4-(7-{[(2-fluorophenyl)methyl]amino}-[1,2,4]triazolo[1,5-a]pyridin-5-yl)benzonitrile;
4-(7-{[(3-fluorophenyl)methyl]amino}-[1,2,4]triazolo[1,5-a]pyridin-5-yl)benzonitrile;
4-(7-{[(4-fluorophenyl)methyl]amino}-[1,2,4]triazolo[1,5-a]pyridin-5-yl)benzonitrile;
4-[7-(cyclopropylmethoxy)-[1,2,4]triazolo[1,5-a]pyridin-5-yl]benzonitrile;
4-[7-(benzyloxy)-[1,2,4]triazolo[1,5-a]pyridin-5-yl]benzonitrile;
tert-butyl N-[5-(4-cyanophenyl)-[1,2,4]triazolo[1,5-a]pyridin-7-yl]carbamate;
N-[5-(4-cyanophenyl)-[1,2,4]triazolo[1,5-a]pyridin-7-yl]acetamide;
N-[5-(4-cyanophenyl)-[1,2,4]triazolo[1,5-a]pyridin-7-yl]cyclopropanecarboxamide;
N-[5-(4-cyanophenyl)-[1,2,4]triazolo[1,5-a]pyridin-7-yl]benzamide;
tert-butyl N-[5-(4-cyano-3-fluorophenyl)-[1,2,4]triazolo[1,5-a]pyridin-7-yl]carbamate;
2-fluoro-4-{7-[(oxetan-3-ylmethyl)amino]-[1,2,4]triazolo[1,5-a]pyridin-5-yl}benzonitrile;
2-fluoro-4-{7-[(3,3,3-trifluoropropyl)amino]-[1,2,4]triazolo[1,5-a]pyridin-5-yl}benzonitrile;
2-fluoro-4-(7-{[(3-methyloxetan-3-yl)methyl]amino}-[1,2,4]triazolo[1,5-a]pyridin-5-yl)benzonitrile;
2-fluoro-4-(7-{[(3-phenyloxetan-3-yl)methyl]amino}-[1,2,4]triazolo [1,5-a]pyridin-5-yl)benzonitrile;
4-{7-[2-(dimethylamino)ethoxy]-[1,2,4]triazolo[1,5-a]pyridin-5-yl}-2-fluorobenzonitrile;
2-fluoro-4-{7-[2-(pyrrolidin-1-yl)ethoxy]-[1,2,4]triazolo[1,5-a]pyridin-5-yl}benzonitrile;
2-fluoro-4-[7-(oxolan-2-ylmethoxy)-[1,2,4]triazolo[1,5-a]pyridin-5-yl]benzonitrile;
2-fluoro-4-{7-[2-(2-oxopyrrolidin-1-yl)ethoxy]-[1,2,4]triazolo[1,5-a]pyridin-5-yl}benzonitrile;
2-fluoro-4-[7-(oxolan-3-ylmethoxy)-[1,2,4]triazolo[1,5-a]pyridin-5-yl]benzonitrile;

2-fluoro-4-[7-(2-oxopyrrolidin-1-yl)-[1,2,4]triazolo[1,5-a]pyridin-5-yl]benzonitrile;
2-fluoro-4-[7-(2-oxo-1,3-oxazolidin-3-yl)-[1,2,4]triazolo[1,5-a]pyridin-5-yl]benzonitrile;
N-[5-(4-cyano-3-fluorophenyl)-[1,2,4]triazolo[1,5-a]pyridin-7-yl]-N-methylacetamide;
2-fluoro-4-[7-(morpholin-4-yl)-[1,2,4]triazolo[1,5-a]pyridin-5-yl]benzonitrile;
2-fluoro-4-[7-(3-methoxyazetidin-1-yl)-[1,2,4]triazolo[1,5-a]pyridin-5-yl]benzonitrile;
N-[5-(4-cyano-3-fluorophenyl)-[1,2,4]triazolo[1,5-a]pyridin-7-yl]acetamide;
4-[7-(3-methoxyazetidin-1-yl)-[1,2,4]triazolo[1,5-a]pyridin-5-yl]benzonitrile;
4-(7-{2-oxa-6-azaspiro[3.3]heptan-6-yl}-[1,2,4]triazolo[1,5-a]pyridin-5-yl)benzonitrile;
N-[5-(4-cyano-2-methylphenyl)-[1,2,4]triazolo[1,5-a]pyridin-7-yl]acetamide;
tert-butyl 4-[5-(4-cyanophenyl)-[1,2,4]triazolo[1,5-a]pyridin-7-yl]piperazine-1-carboxylate;
tert-butyl 6-[5-(4-cyanophenyl)-[1,2,4]triazolo[1,5-a]pyridin-7-yl]-2,6-diazaspiro[3.3]heptane-2-carboxylate;
methyl N-[5-(4-cyano-2-methylphenyl)-[1,2,4]triazolo[1,5-a]pyridin-7-yl]carbamate;
4-{7-amino-[1,2,4]triazolo[1,5-a]pyridin-5-yl}-2-fluorobenzonitrile;
4-{6-fluoro-[1,2,4]triazolo[1,5-a]pyridin-5-yl}benzonitrile;
N-[5-(4-cyano-3-fluorophenyl)-[1,2,4]triazolo[1,5-a]pyridin-7-yl]cyclopropanesulfonamide;
N-[5-(4-cyano-3-fluorophenyl)-[1,2,4]triazolo[1,5-a]pyridin-7-yl]benzenesulfonamide;
3-[5-(4-cyano-3-fluorophenyl)-[1,2,4]triazolo[1,5-a]pyridin-7-yl]-1-phenylurea;
N-[5-(4-cyanophenyl)-[1,2,4]triazolo[1,5-a]pyridin-7-yl]-3-methoxypropanamide;
N-[5-(4-cyanophenyl)-[1,2,4]triazolo[1,5-a]pyridin-7-yl]-2-phenylacetamide;
N-[5-(4-cyano-3-fluorophenyl)-[1,2,4]triazolo[1,5-a]pyridin-7-yl]-3,3,3-trifluoropropanamide;
N-[5-(4-cyano-3-fluorophenyl)-[1,2,4]triazolo[1,5-a]pyridin-7-yl]-2-methoxyacetamide;
N-[5-(4-cyano-3-fluorophenyl)-[1,2,4]triazolo[1,5-a]pyridin-7-yl]cyclobutanecarboxamide;
N-[5-(4-cyano-3-fluorophenyl)-[1,2,4]triazolo[1,5-a]pyridin-7-yl]-2-(oxan-4-yl)acetamide;
N-[5-(4-cyano-3-fluorophenyl)-[1,2,4]triazolo[1,5-a]pyridin-7-yl]-2-methylcyclopropane-1-carboxamide;
N-[5-(4-cyano-3-fluorophenyl)-[1,2,4]triazolo[1,5-a]pyridin-7-yl]-2-(piperidin-1-yl)acetamide;
(2S)-N-[5-(4-cyano-3-fluorophenyl)-[1,2,4]triazolo[1,5-a]pyridin-7-yl]oxolane-2-carboxamide;
(2R)-N-[5-(4-cyano-3-fluorophenyl)-[1,2,4]triazolo[1,5-a]pyridin-7-yl]oxolane-2-carboxamide;
N-[5-(4-cyano-3-fluorophenyl)-[1,2,4]triazolo[1,5-a]pyridin-7-yl]-2-(dimethylamino)acetamide;
N-[5-(4-cyano-3-fluorophenyl)-[1,2,4]triazolo[1,5-a]pyridin-7-yl]oxolane-3-carboxamide;
N-[5-(4-cyano-3-fluorophenyl)-[1,2,4]triazolo[1,5-a]pyridin-7-yl]-1-methylcyclopropane-1-carboxamide;
N-[5-(4-cyano-3-fluorophenyl)-[1,2,4]triazolo[1,5-a]pyridin-7-yl]oxane-3-carboxamide;
N-[5-(4-cyano-3-fluorophenyl)-[1,2,4]triazolo[1,5-a]pyridin-7-yl]-4-methyloxane-4-carboxamide;
N-[5-(4-cyano-3-fluorophenyl)-[1,2,4]triazolo[1,5-a]pyridin-7-yl]-3-methyloxetane-3-carboxamide;
N-[5-(4-cyano-3-fluorophenyl)-[1,2,4]triazolo[1,5-a]pyridin-7-yl]oxetane-3-carboxamide;
N-[5-(4-cyano-3-fluorophenyl)-[1,2,4]triazolo[1,5-a]pyridin-7-yl]-2,2-difluorocyclopropane-1-carboxamide;
N-[5-(4-cyano-3-fluorophenyl)-[1,2,4]triazolo[1,5-a]pyridin-7-yl]-2-cyclopropylacetamide;
N-[5-(4-cyano-3-fluorophenyl)-[1,2,4]triazolo[1,5-a]pyridin-7-yl]-2-methoxy-2-methylpropanamide;
1-cyano-N-[5-(4-cyano-3-fluorophenyl)-[1,2,4]triazolo[1,5-a]pyridin-7-yl]cyclopropane-1-carboxamide;
N-[5-(4-cyano-3-fluorophenyl)-[1,2,4]triazolo[1,5-a]pyridin-7-yl]-3-fluorocyclobutane-1-carboxamide;
N-[5-(4-cyano-3-fluorophenyl)-[1,2,4]triazolo[1,5-a]pyridin-7-yl]-2-(oxetan-3-yl)acetamide;
N-[5-(4-cyano-3-fluorophenyl)-[1,2,4]triazolo[1,5-a]pyridin-7-yl]cyclopropanecarboxamide;
N-[5-(4-cyano-2-methylphenyl)-[1,2,4]triazolo[1,5-a]pyridin-7-yl]-3,3,3-trifluoropropanamide;
4-[7-(benzylsulfanyl)-[1,2,4]triazolo[1,5-a]pyridin-5-yl]benzonitrile;
5-(4-cyanophenyl)-N-(cyclopropylmethyl)-[1,2,4]triazolo[1,5-a]pyridine-7-sulfonamide;
5-(4-cyanophenyl)-N-[2-(dimethylamino)ethyl]-[1,2,4]triazolo[1,5-a]pyridine-7-sulfonamide;
5-(4-cyanophenyl)-N-[2-(dimethylamino)ethyl]-[1,2,4]triazolo[1,5-a]pyridine-7-sulfonamide;
2-(azetidin-1-yl)-N-[5-(4-cyanophenyl)-[1,2,4]triazolo[1,5-a]pyridin-7-yl]acetamide;
4-{7-amino-6-fluoro-[1,2,4]triazolo[1,5-a]pyridin-5-yl}benzonitrile;
5-(4-ethynylphenyl)-[1,2,4]triazolo[1,5-a]pyridine;
4-(7-{[(propan-2-yl)amino]methyl}-[1,2,4]triazolo[1,5-a]pyridin-5-yl)benzonitrile;
4-(7-{[(2,2,2-trifluoroethyl)amino]methyl}-[1,2,4]triazolo[1,5-a]pyridin-5-yl)benzonitrile;
4-(7-{[(oxetan-3-yl)amino]methyl}-[1,2,4]triazolo[1,5-a]pyridin-5-yl)benzonitrile;
4-(7-{[(oxetan-3-ylmethyl)amino]methyl}-[1,2,4]triazolo[1,5-a]pyridin-5-yl)benzonitrile;
4-(7-{[(2,2-difluoroethyl)amino]methyl}-[1,2,4]triazolo[1,5-a]pyridin-5-yl)benzonitrile;
4-[7-({[(3-chlorophenyl)methyl]amino}methyl)-[1,2,4]triazolo[1,5-a]pyridin-5-yl]benzonitrile;
4-(7-{[(cyclopropylmethyl)amino]methyl}-[1,2,4]triazolo[1,5-a]pyridin-5-yl)benzonitrile;
4-[7-({[(3-methoxyphenyl)methyl]amino}methyl)-[1,2,4]triazolo[1,5-a]pyridin-5-yl]benzonitrile;
4-{7-[(3-methoxyazetidin-1-yl)methyl]-[1,2,4]triazolo[1,5-a]pyridin-5-yl}benzonitrile;
4-(7-{[(oxolan-3-yl)amino]methyl}-[1,2,4]triazolo[1,5-a]pyridin-5-yl)benzonitrile;
4-(7-{[(oxolan-3-ylmethyl)amino]methyl}-[1,2,4]triazolo[1,5-a]pyridin-5-yl)benzonitrile;
4-{7-[(cyclopropylamino)methyl]-[1,2,4]triazolo[1,5-a]pyridin-5-yl}benzonitrile;
cyclopropylmethyl N-[5-(4-cyano-3-fluorophenyl)-[1,2,4]triazolo[1,5-a]pyridin-7-yl]carbamate;
2-methoxyethyl N-[5-(4-cyano-3-fluorophenyl)-[1,2,4]triazolo[1,5-a]pyridin-7-yl]carbamate;
1-methylpiperidin-4-yl N-[5-(4-cyano-3-fluorophenyl)-[1,2,4]triazolo[1,5-a]pyridin-7-yl]carbamate;
3-(dimethylamino)propyl N-[5-(4-cyano-3-fluorophenyl)-[1,2,4]triazolo[1,5-a]pyridin-7-yl]carbamate;
2-(dimethylamino)ethyl N-[5-(4-cyano-3-fluorophenyl)-[1,2,4]triazolo[1,5-a]pyridin-7-yl]carbamate;

oxolan-3-yl N-[5-(4-cyano-3-fluorophenyl)-[1,2,4]triazolo[1,5-a]pyridin-7-yl]carbamate;
4-{7-amino-[1,2,4]triazolo[1,5-a]pyridin-5-yl}-3-methylbenzonitrile;
4-{7-amino-[1,2,4]triazolo[1,5-a]pyridin-5-yl}-3-fluorobenzonitrile;
4,6-dimethyl-5-{[1,2,4]triazolo[1,5-a]pyridin-5-yl}pyrimidine-2-carbonitrile;
5-{7-amino-[1,2,4]triazolo[1,5-a]pyridin-5-yl}-6-methylpyridine-2-carbonitrile;
5-(4-chloro-3-methoxyphenyl)-[1,2,4]triazolo[1,5-a]pyridine;
2-fluoro-4-{6-fluoro-[1,2,4]triazolo[1,5-a]pyridin-5-yl}benzonitrile;
4-{6-fluoro-[1,2,4]triazolo[1,5-a]pyridin-5-yl}-3-methylbenzonitrile;
3-fluoro-4-{6-fluoro-[1,2,4]triazolo[1,5-a]pyridin-5-yl}benzonitrile;
4-{7-hydroxy-[1,2,4]triazolo[1,5-a]pyridin-5-yl}benzonitrile;
2-fluoro-4-{7-hydroxy-[1,2,4]triazolo[1,5-a]pyridin-5-yl}benzonitrile;
4-{7-amino-[1,2,4]triazolo[1,5-a]pyridin-5-yl}-2-fluoro-5-methylbenzonitrile;
4-{[1,2,4]triazolo [1,5-a]pyridin-5-yl}piperazine-1-carbonitrile;
3,5-difluoro-4-{[1,2,4]triazolo[1,5-a]pyridin-5-yl}benzonitrile;
2-fluoro-3-methyl-4-{[1,2,4]triazolo[1,5-a]pyridin-5-yl}benzonitrile;
4-[7-(methoxymethyl)-[1,2,4]triazolo[1,5-a]pyridin-5-yl]benzonitrile;
N-{[5-(4-cyanophenyl)-[1,2,4]triazolo [1,5-a]pyridin-7-yl]methyl}acetamide;
N-{[5-(4-cyanophenyl)-[1,2,4]triazolo[1,5-a]pyridin-7-yl]methyl}cyclopropanecarboxamide;
4-{6-amino-[1,2,4]triazolo[1,5-a]pyridin-5-yl}benzonitrile;
4-{7-amino-[1,2,4]triazolo [1,5-a]pyridin-5-yl}-2-fluoro-3-methylbenzonitrile hydrochloride;
5-{6-fluoro-[1,2,4]triazolo[1,5-a]pyridin-5-yl}-6-methylpyridine-2-carbonitrile;
4-[7-(piperazin-1-yl)-[1,2,4]triazolo[1,5-a]pyridin-5-yl]benzonitrile;
4-[7-(4-acetylpiperazin-1-yl)-[1,2,4]triazolo[1,5-a]pyridin-5-yl]benzonitrile;
4-{7-[(2,3-dihydroxypropyl)amino]-[1,2,4]triazolo[1,5-a]pyridin-5-yl}-3-methylbenzonitrile;
N-[5-(4-cyano-3-fluoro-2-methylphenyl)-[1,2,4]triazolo[1,5-a]pyridin-7-yl]acetamide;
4-{7-chloro-[1,2,4]triazolo[1,5-a]pyridin-5-yl}-2,3-difluorobenzonitrile;
4-{7-chloro-[1,2,4]triazolo[1,5-a]pyridin-5-yl}-2-fluoro-5-methylbenzonitrile;
N-[5-(4-cyano-3-fluorophenyl)-[1,2,4]triazolo[1,5-a]pyridin-7-yl]formamide;
6-amino-5-{[1,2,4]triazolo[1,5-a]pyridin-5-yl}pyridine-2-carbonitrile;
N-[5-(4-Cyano-2-methylphenyl)-[1,2,4]triazolo[1,5-a]pyridin-7-yl]-2-hydroxyacetamide;
N-[5-(4-Cyano-2-methylphenyl)-[1,2,4]triazolo[1,5-a]pyridin-7-yl]-3,3,3-trifluoro-2-hydroxypropanamide;
N-[5-(4-Cyano-2-methylphenyl)-[1,2,4]triazolo[1,5-a]pyridin-7-yl]-2-hydroxy-2-methylpropanamide;
N-[5-(6-Cyano-2-methylpyridin-3-yl)-[1,2,4]triazolo[1,5-a]pyridin-7-yl]acetamide;
tert-Butyl N-[5-(4-cyano-2-fluorophenyl)-[1,2,4]triazolo[1,5-a]pyridin-7-yl]carbamate;
N-[5-(4-Cyano-3-fluorophenyl)-[1,2,4]triazolo[1,5-a]pyridin-7-yl]oxetane-2-carboxamide;
N-[5-(4-Cyano-2-fluorophenyl)-[1,2,4]triazolo[1,5-a]pyridin-7-yl]acetamide;
N-[5-(4-Cyano-2-fluorophenyl)-[1,2,4]triazolo[1,5-a]pyridin-7-yl]cyclopropanecarboxamide;
3-Fluoro-4-{7-[(2-methoxyethyl)amino]-[1,2,4]triazolo[1,5-a]pyridin-5-yl}benzonitrile;
N-[5-(6-Cyano-4-methylpyridin-3-yl)-[1,2,4]triazolo[1,5-a]pyridin-7-yl]acetamide;
5-{7-Amino-[1,2,4]triazolo[1,5-a]pyridin-5-yl}-4-methylpyridine-2-carbonitrile;
4-{7-Hydroxy-[1,2,4]triazolo[1,5-a]pyridin-5-yl}-3-methylbenzonitrile;
N-[5-(4-Cyano-2-methylphenyl)-[1,2,4]triazolo[1,5-a]pyridin-7-yl]cyclopropanecarboxamide;
5-{7-Hydroxy-[1,2,4]triazolo[1,5-a]pyridin-5-yl}-6-methylpyridine-2-carbonitrile;
3-Methyl-4-(7-{2-oxa-6-azaspiro[3.3]heptan-6-yl}-[1,2,4]triazolo[1,5-a]pyridin-5-yl)benzonitrile;
N-[5-(6-Cyano-2-methylpyridin-3-yl)-[1,2,4]triazolo[1,5-a]pyridin-7-yl]cyclopropanecarboxamide;
4-{7-Amino-[1,2,4]triazolo[1,5-a]pyridin-5-yl}-3,5-difluorobenzonitrile;
N-[5-(4-Cyano-2-methylphenyl)-[1,2,4]triazolo [1,5-a]pyridin-7-yl]-2,2-difluorocyclopropane-1-carboxamide;
4-{7-Amino-[1,2,4]triazolo[1,5-a]pyridin-5-yl}-3-chlorobenzonitrile;
4-{7-Amino-[1,2,4]triazolo[1,5-a]pyridin-5-yl}-2,3-difluorobenzonitrile;
N-[5-(2-Chloro-4-cyanophenyl)-[1,2,4]triazolo[1,5-a]pyridin-7-yl]acetamide;
N-[5-(4-Cyano-5-fluoro-2-methylphenyl)-[1,2,4]triazolo[1,5-a]pyridin-7-yl]acetamide; and
a pharmaceutically acceptable salt of any one of the aforementioned compounds.

11. A pharmaceutical composition comprising a compound or pharmaceutically acceptable salt thereof as defined in claim 1, and a pharmaceutically acceptable adjuvant, diluent or carrier.

12. A method for inhibiting PHD in a patient, the method comprising administering to the patient a compound or pharmaceutically acceptable salt thereof, as defined in claim 1.

13. A method for treating acute kidney injury, chronic kidney disease, acute decompensated heart failure, heart failure following a heart attack or peripheral artery disease in a patient, the method comprising administering to the patient a compound or pharmaceutically acceptable salt thereof as defined in claim 1.

* * * * *